United States Patent
Itoi

(10) Patent No.: US 10,361,374 B2
(45) Date of Patent: Jul. 23, 2019

(54) AMINE COMPOUND AND ORGANIC LIGHT EMITTING DEVICE INCLUDING THE SAME

(71) Applicant: Samsung Display Co., Ltd., Yongin-si, Gyeonggi-do (KR)

(72) Inventor: Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 15/199,764

(22) Filed: Jun. 30, 2016

(65) Prior Publication Data

US 2017/0170402 A1 Jun. 15, 2017

(30) Foreign Application Priority Data

Dec. 15, 2015 (KR) .................. 10-2015-0179445

(51) Int. Cl.
*H01L 51/00* (2006.01)
*C07C 211/54* (2006.01)
(Continued)

(52) U.S. Cl.
CPC ........ *H01L 51/0061* (2013.01); *C07C 211/54* (2013.01); *C07C 211/58* (2013.01);
(Continued)

(58) Field of Classification Search
None
See application file for complete search history.

(56) References Cited

U.S. PATENT DOCUMENTS

2013/0328021 A1* 12/2013 Lim ................. C07C 211/54 257/40

FOREIGN PATENT DOCUMENTS

JP 2004-315495 A 11/2004
JP 2009-029726 A 2/2009
(Continued)

OTHER PUBLICATIONS

Machine English translation of Lee et al. (KR 10-2012-0118563). Jul. 15, 2017.*
Machine English translation of KR-10-2015-0106668. Dec. 5, 2017.*

*Primary Examiner* — Jay Yang
(74) *Attorney, Agent, or Firm* — Lewis Roca Rothgerber Christie LLP

(57) ABSTRACT

An amine compound represented by Formula 1, and an organic light emitting device including the same:

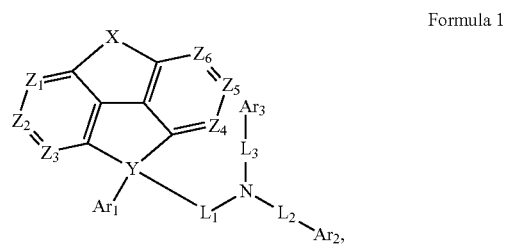

Formula 1 wherein X may be selected from the compounds represented by Formula 2:

Formula 2

(Continued)

-continued

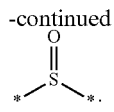

When the amine compound represented by Formula 1 is included in the hole transport region of an organic light emitting device, the organic light emitting device may achieve long lifespan and high efficiency.

18 Claims, 1 Drawing Sheet

(51) Int. Cl.
*C07D 307/91* (2006.01)
*C07D 307/93* (2006.01)
*C07C 211/58* (2006.01)
*C07C 211/61* (2006.01)
*C07D 333/76* (2006.01)
*C07D 409/12* (2006.01)
*C09K 11/00* (2006.01)
*C09K 11/06* (2006.01)
*H01L 51/50* (2006.01)

(52) U.S. Cl.
CPC .......... *C07C 211/61* (2013.01); *C07D 307/91* (2013.01); *C07D 307/93* (2013.01); *C07D 333/76* (2013.01); *C07D 409/12* (2013.01); *C09K 11/00* (2013.01); *C09K 11/06* (2013.01); *H01L 51/006* (2013.01); *H01L 51/0059* (2013.01); *H01L 51/0073* (2013.01); *C07C 2603/18* (2017.05); *C07C 2603/40* (2017.05); *C09K 2211/1014* (2013.01); *C09K 2211/1022* (2013.01); *H01L 51/0054* (2013.01); *H01L 51/0058* (2013.01); *H01L 51/0081* (2013.01); *H01L 51/5056* (2013.01)

(56) References Cited

FOREIGN PATENT DOCUMENTS

| | | | |
|---|---|---|---|
| JP | 2009-267255 A | | 11/2009 |
| JP | 2012-046478 A | | 3/2012 |
| KR | 10-2007-0084110 A | | 8/2007 |
| KR | 10-2012-0118563 | * | 10/2012 |
| KR | 10-1211091 B1 | | 12/2012 |
| KR | 10-2015-0106668 | * | 9/2015 |
| WO | WO 2010/074440 A2 | | 7/2010 |
| WO | WO 2010/137601 A1 | | 12/2010 |
| WO | WO 2015/046955 A1 | | 4/2015 |
| WO | WO 2015/050391 A1 | | 4/2015 |

* cited by examiner

AMINE COMPOUND AND ORGANIC LIGHT EMITTING DEVICE INCLUDING THE SAME

CROSS-REFERENCE TO RELATED APPLICATIONS

This application claims priority to and the benefit of Korean Patent Application No. 10-2015-0179445, filed on Dec. 15, 2015 in the Korean Intellectual Property Office, the entire content of which is incorporated herein by reference.

BACKGROUND

One or more aspects of example embodiments of the present disclosure are related to an amine compound and an organic light emitting device including the same.

Recently, developments are being actively conducted on organic electroluminescent displays as image display apparatuses. An organic light emitting display is a self-luminescent display in which a luminescent material including an organic compound in an emission layer emits light via the recombination of holes and electrons, which are respectively injected from an anode and a cathode into the emission layer. As such, an organic light emitting display is different from a liquid crystal display.

An example organic light emitting device may include an anode, a hole transport layer on the anode, an emission layer on the hole transport layer, an electron transport layer on the emission layer, and a cathode on the electron transport layer. Holes may be injected from the anode, and the injected holes may move through the hole transport layer and may be injected into the emission layer. Electrons may be injected from the cathode, and the injected electrons may move through the electron transport layer and may be injected into the emission layer. The holes and the electrons injected into the emission layer may recombine to produce excitons in the emission layer. The organic light emitting device may thereby emit light via the radiation deactivation (e.g., radiative decay) of the excitons. Configurations of an organic light emitting device are not limited to the above-described configuration, however, and various modifications may be possible.

Decreases in the driving voltage and increases in the emission efficiency and lifespan of organic light emitting devices are required for application of organic light emitting devices to a display. Strategies to attain low driving voltage, high emission efficiency, and long lifespan in an organic light emitting device have included normalization, stabilization, etc. of a hole transport layer, etc. An aromatic amine compound has been developed in the related art as a hole transport material used in the hole transport layer, but some defects related to low charge tolerance and device life remain. Amine derivatives substituted with a heteroaryl group are also available in the related art as materials for increasing the life of an organic light emitting device.

When an organic EL device has low emission efficiency in a blue emission region compared to a red emission region and a green emission region, improvement in emission efficiency is required. In addition, the amine derivatives substituted with a heteroaryl group in the related art may not have sufficient high temperature tolerance in an organic light emitting device, and the development of improved materials is required.

SUMMARY

One or more aspects of example embodiments of the present disclosure are directed toward an amine compound capable of being used in an organic light emitting device with long lifespan and high efficiency.

One or more aspects of example embodiments of the present disclosure are directed toward an organic light emitting device with long lifespan and high efficiency.

One or more example embodiments of the present disclosure provide an amine compound represented by Formula 1:

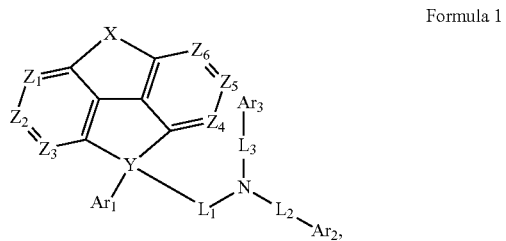

Formula 1 wherein X is selected from the compounds represented by Formula 2:

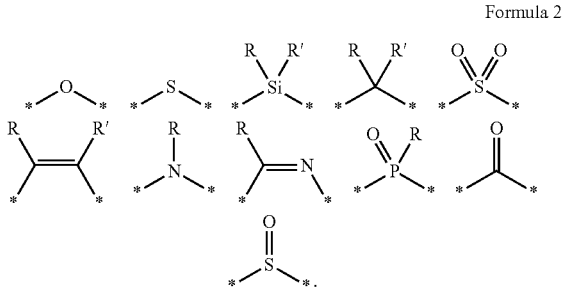

Formula 2

In Formulae 1 and 2,

Y may be carbon (C), silicon (Si), or germanium (Ge), $Z_1$ to $Z_6$ may each independently be CR or N, $Ar_1$ to $Ar_3$ may each independently be hydrogen, deuterium, a halogen atom, a substituted or unsubstituted aryl group having 6 to 30 carbon atoms for forming a ring, a substituted or unsubstituted heteroaryl group having 5 to 30 carbon atoms for forming a ring, an alkyl group having 1 to 20 carbon atoms, or a silyl group having 3 to 20 carbon atoms, $L_1$ to $L_3$ may each independently be a direct linkage, a substituted or unsubstituted arylene group having 6 to 30 carbon atoms for forming a ring, or a substituted or unsubstituted heteroarylene group having 5 to 30 carbon atoms for forming a ring, and R and R' may each independently be hydrogen, deuterium, a substituted or unsubstituted aryl group having 6 to 30 carbon atoms for forming a ring, a substituted or unsubstituted heteroaryl group having 5 to 30 carbon atoms for forming a ring, or an alkyl group having 1 to 20 carbon atoms.

In one embodiment, Formula 1 may be represented by Formula 3:

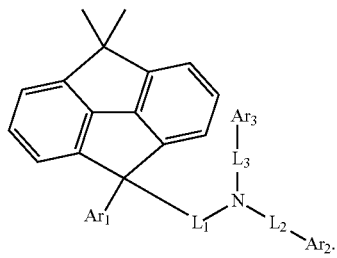

Formula 3

In one embodiment, Formula 1 may be represented by Formula 4:

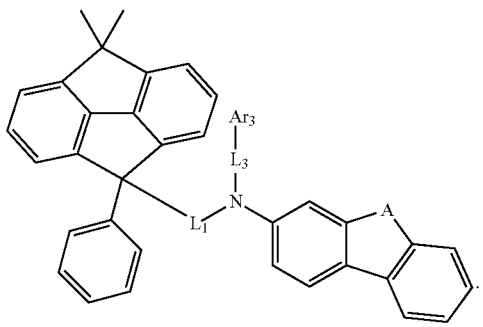

Formula 4

In Formula 4, A may be O, S, or $CR_2R_3$, and $R_2$ and $R_3$ may each independently be hydrogen, deuterium, an alkyl group having 1 to 20 carbon atoms, a substituted or unsubstituted aryl group having 6 to 30 carbon atoms for forming a ring, or a substituted or unsubstituted heteroaryl group having 5 to 30 carbon atoms for forming a ring.

In one embodiment, Formula 1 may be represented by Formula 5:

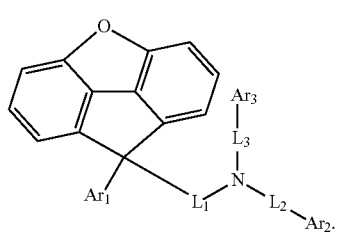

Formula 5

In an embodiment, Formula 1 may be represented by Formula 6:

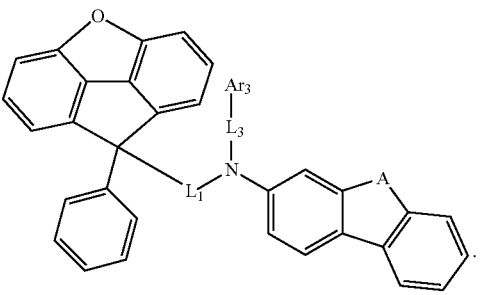

Formula 6

In Formula 6, A may be O, S, or $CR_2R_3$. $R_2$ and $R_3$ may be the same as defined above.

In one embodiment, Formula 1 may be represented by Formula 7:

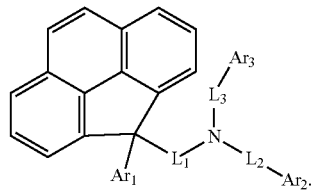

Formula 7

In one embodiment, Formula 1 may be represented by Formula 8:

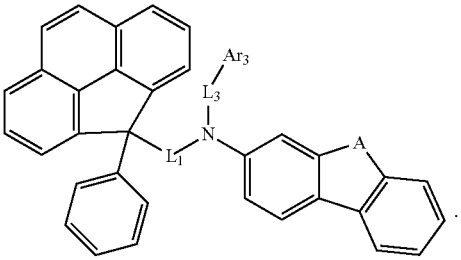

Formula 8

In Formula 8, A may be O, S, or $CR_2R_3$. $R_2$ and $R_3$ may be the same as defined above.

In Formulae 3 to 8, $L_1$ to $L_3$ and $Ar_1$ to $Ar_3$ may each independently be the same as described herein in connection with Formula 1.

In one embodiment, $L_1$ may be a direct linkage, a substituted or unsubstituted divalent phenyl group, or a substituted or unsubstituted divalent biphenyl group.

In one embodiment, $Ar_2$ may be a substituted or unsubstituted phenyl group, a substituted or unsubstituted naphthyl group, a substituted or unsubstituted dibenzofuranyl group, a substituted or unsubstituted dibenzothiophene group, or a substituted or unsubstituted fluorene group.

In one embodiment, $Ar_3$ may be a substituted or unsubstituted phenyl group, a substituted or unsubstituted biphenyl group, or a substituted or unsubstituted naphthyl group.

In one embodiment, Formula 1 may be selected from the compounds represented by Compound Group 1:
Compound Group 1
1
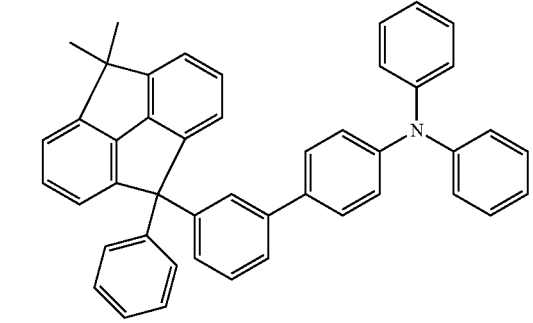
2
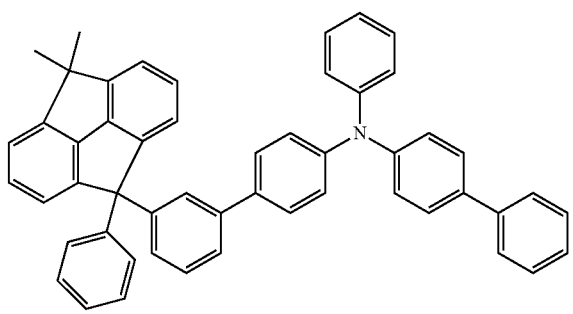
3
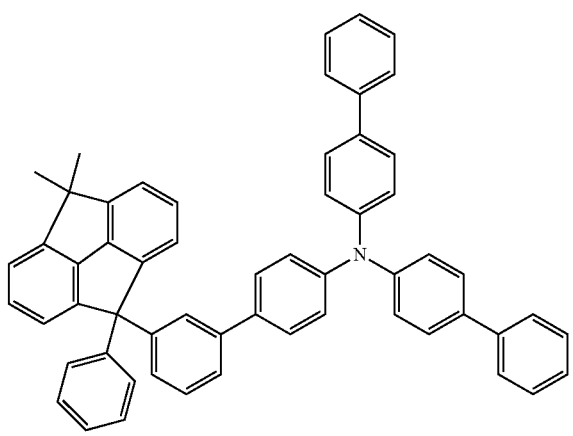
4
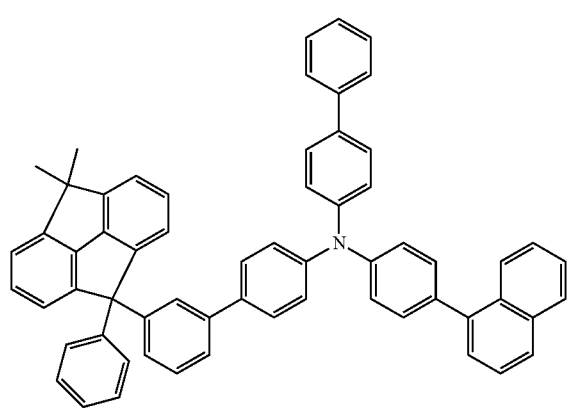
-continued
5
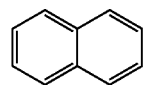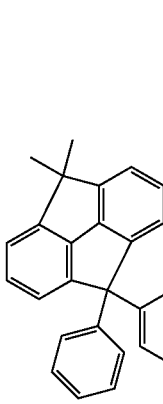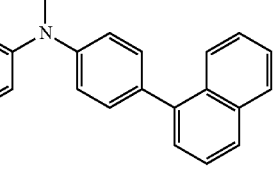
6
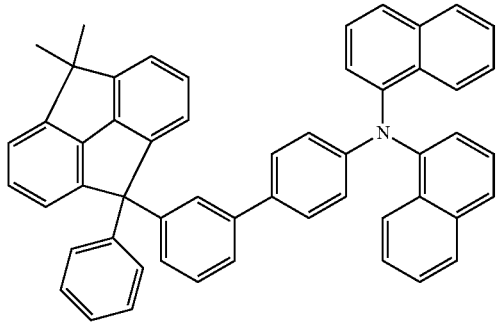
7
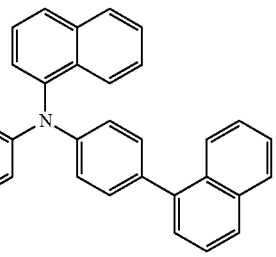
8
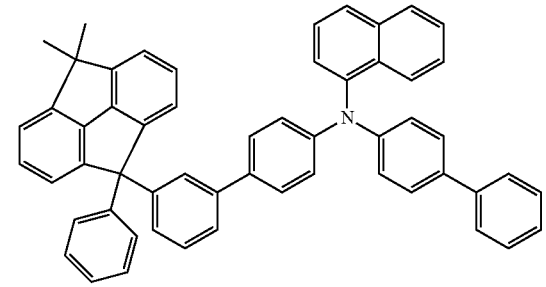

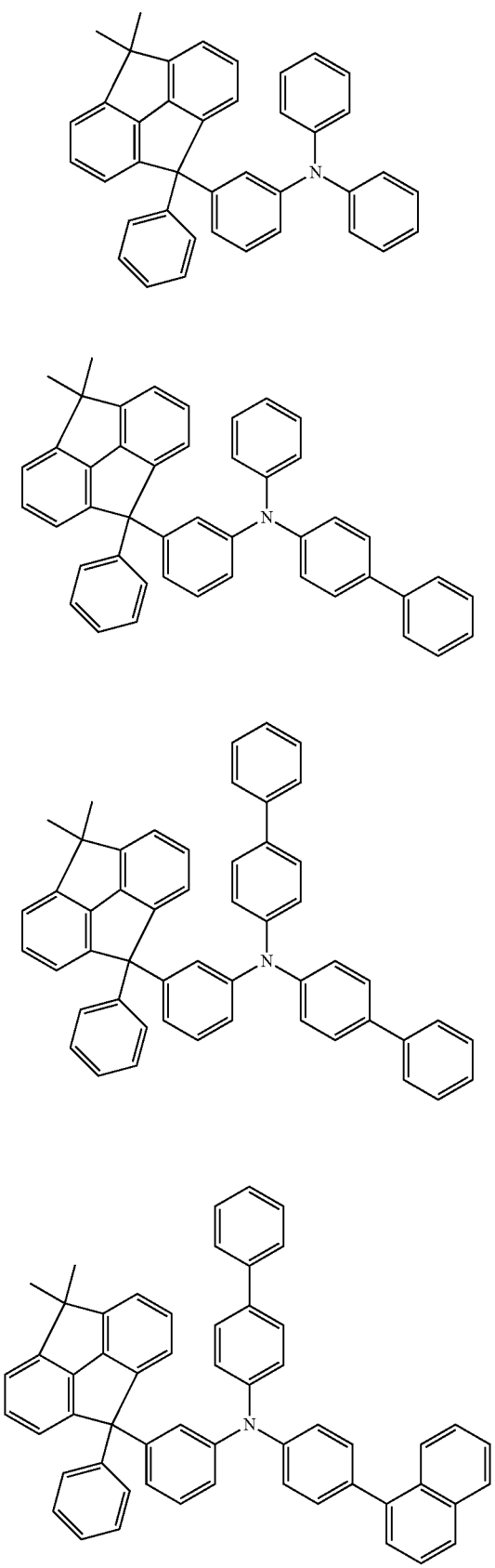
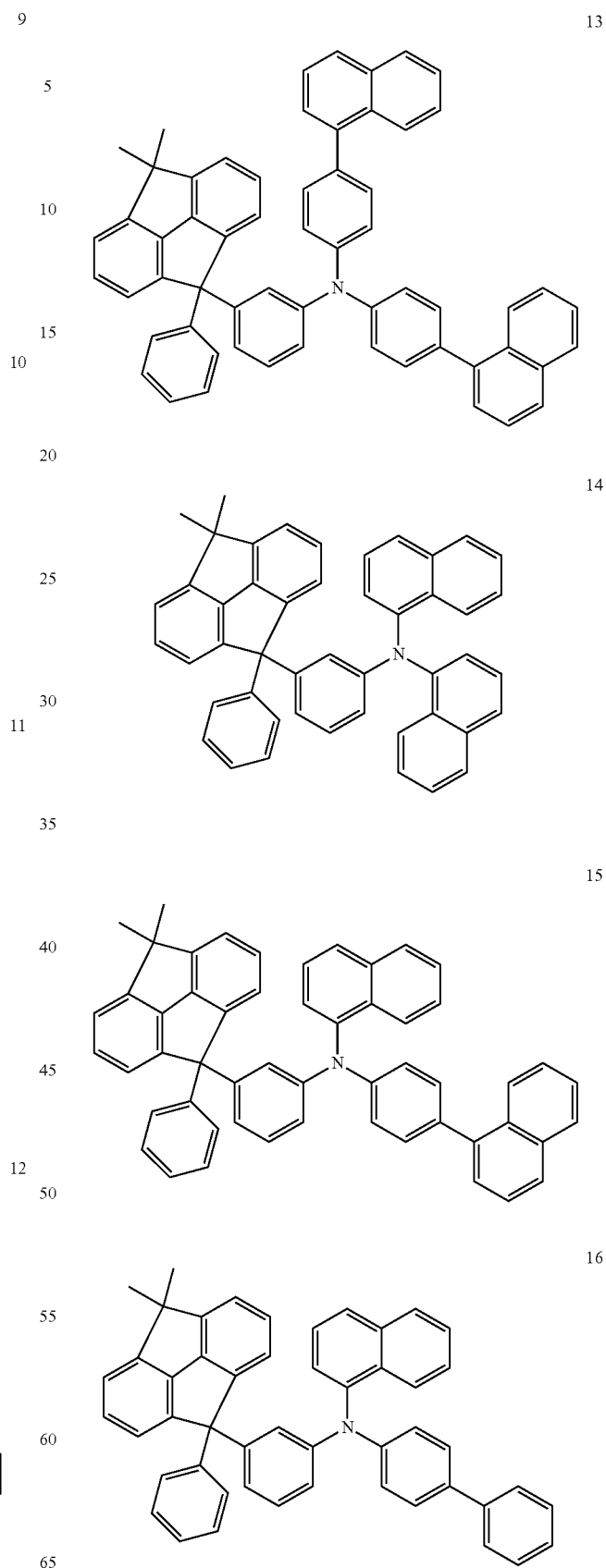

17
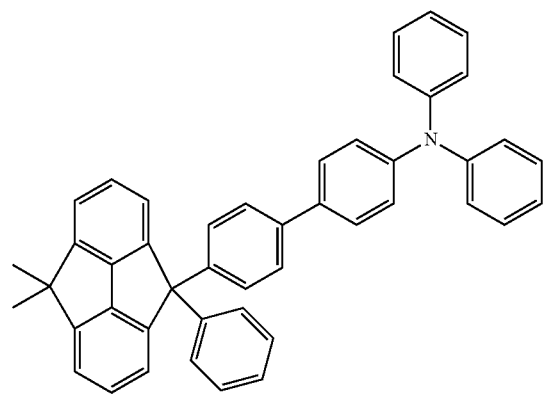
18
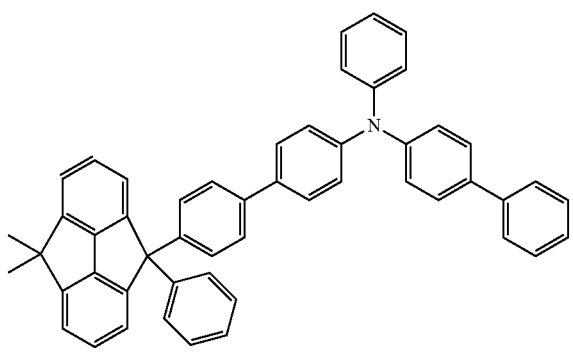
19
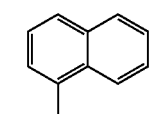
20
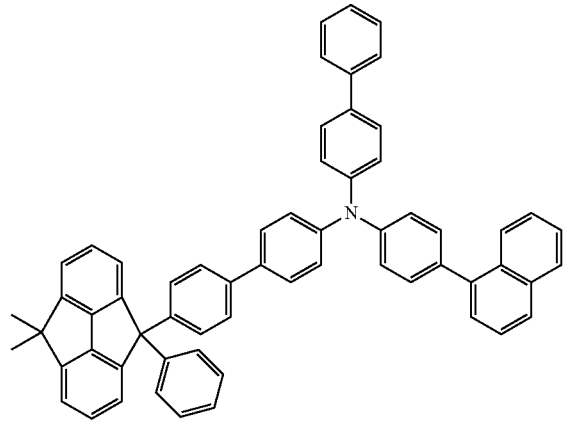
21
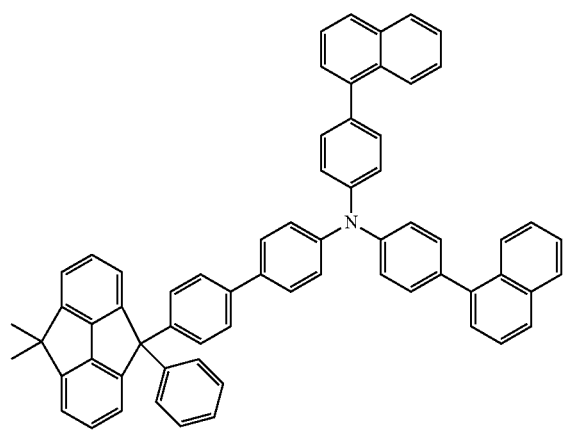
22
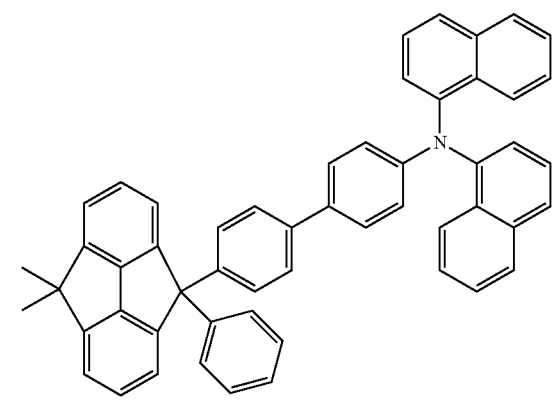
23
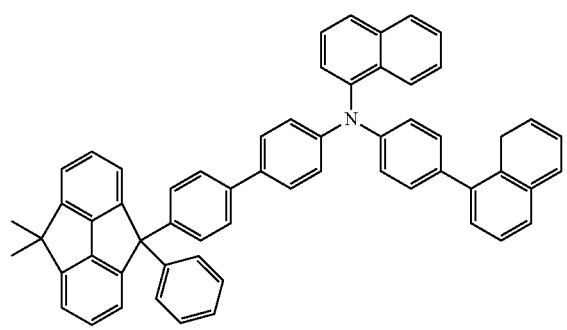

24
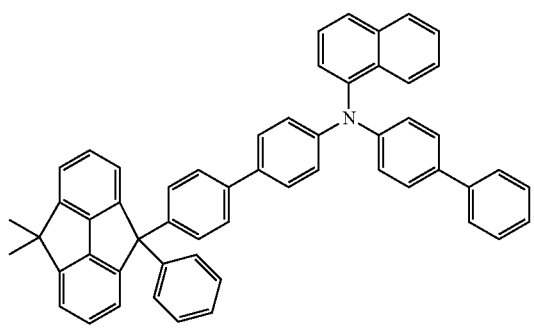
25
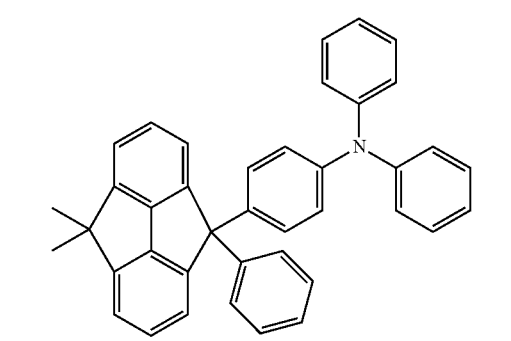
26
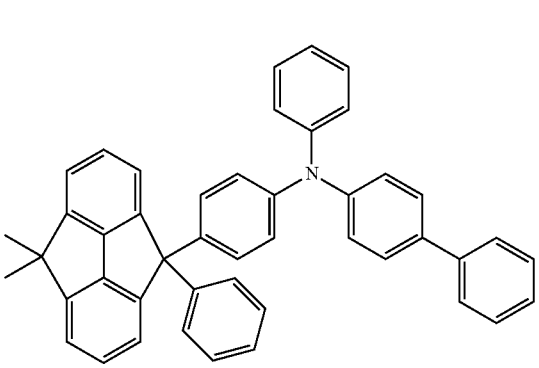
27
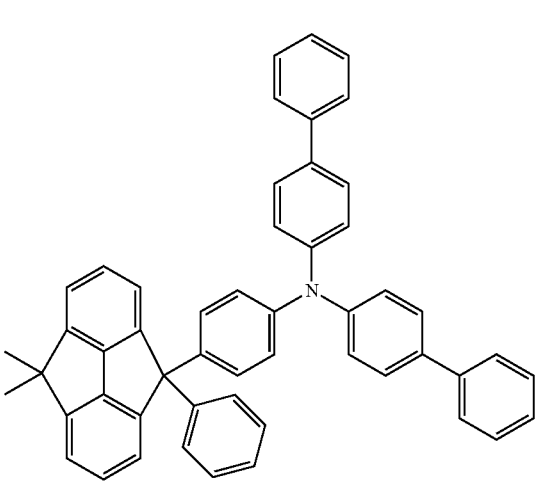
28
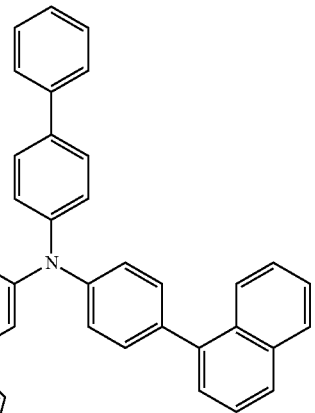
29
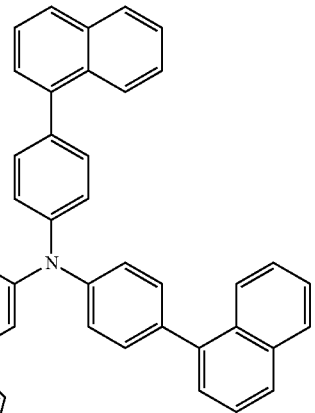
30
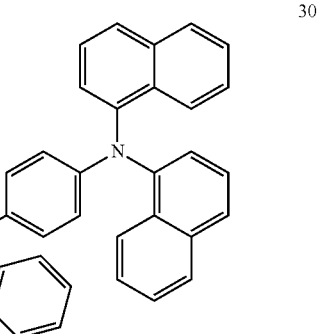
31

32
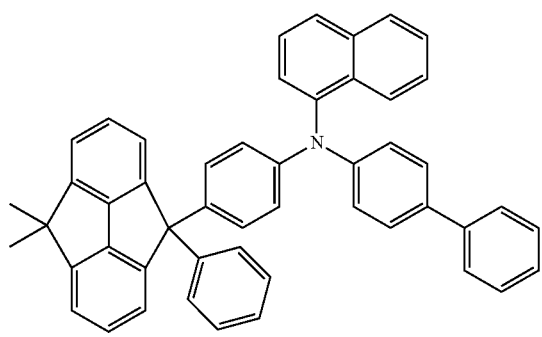
33
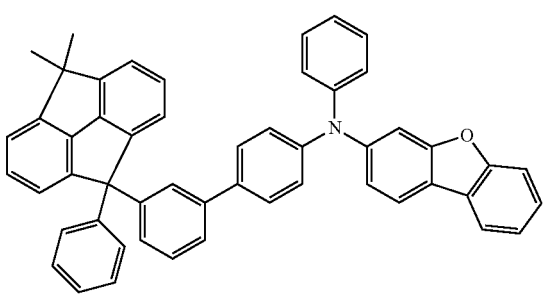
34
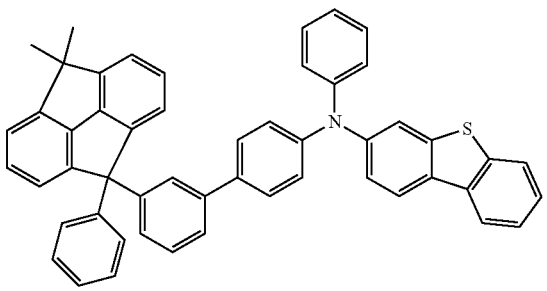
35
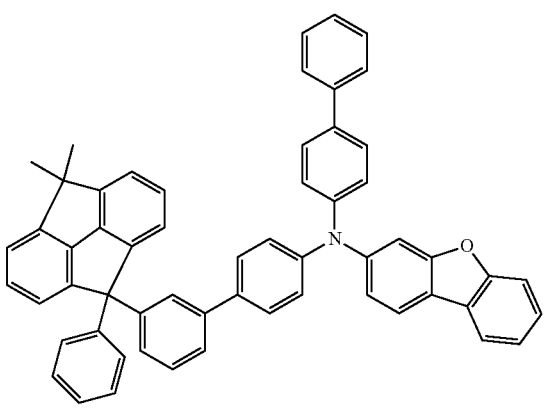
36
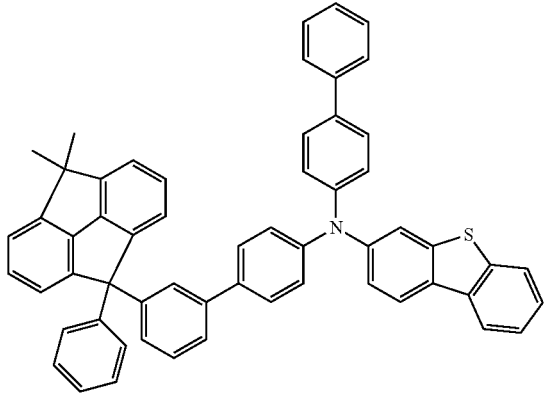
37
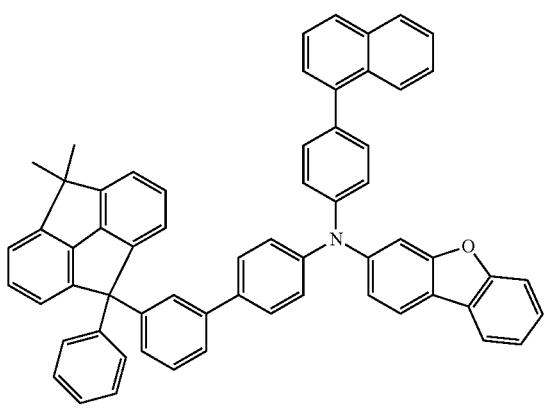
38
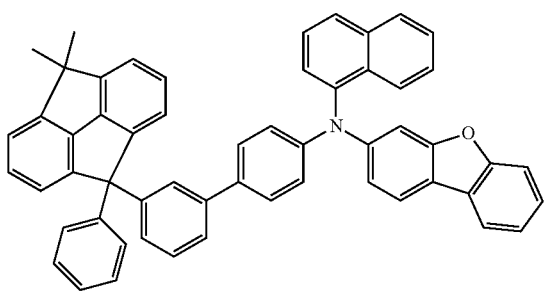
39
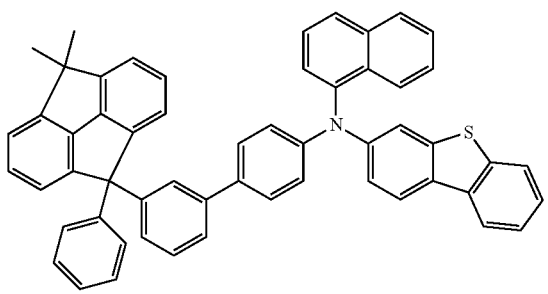

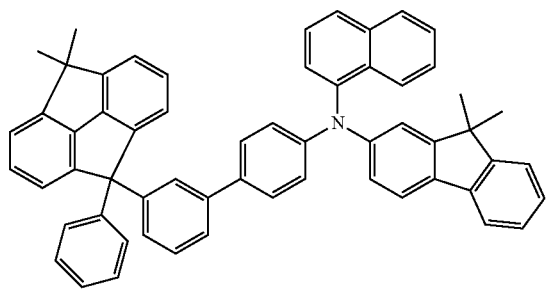
40
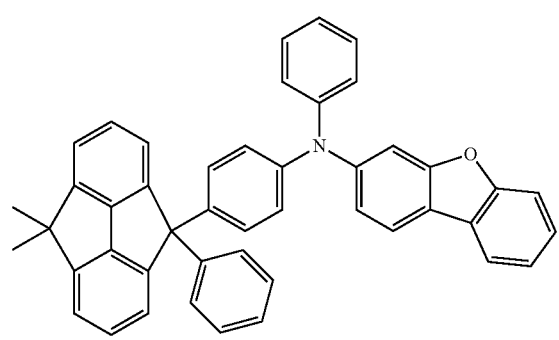
41
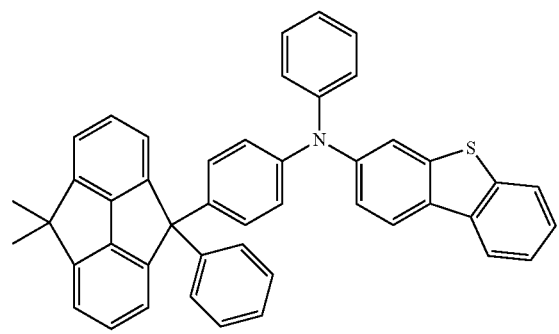
42
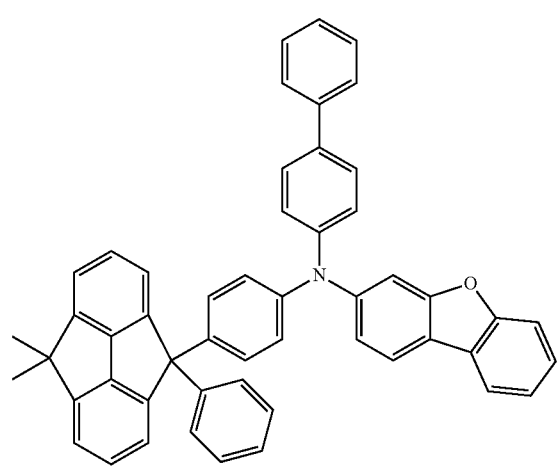
43
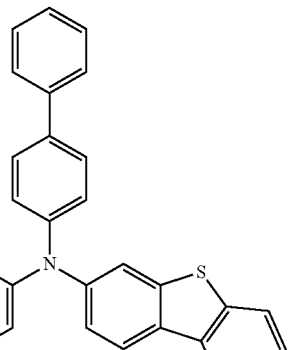
44
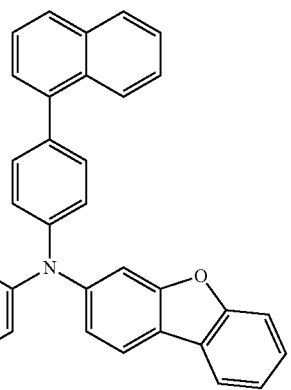
45
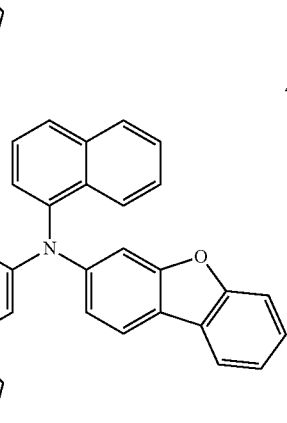
46
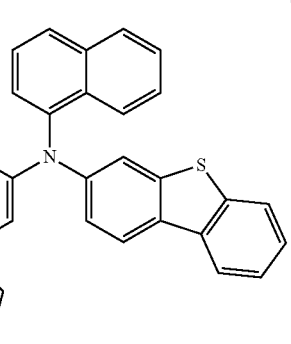
47

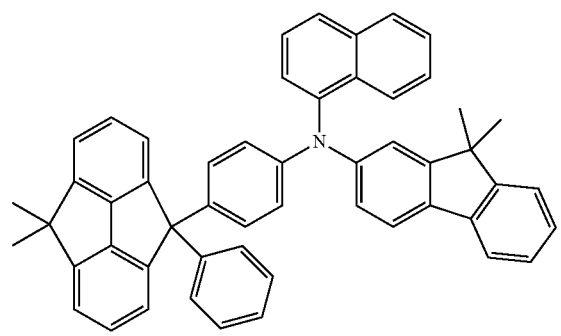
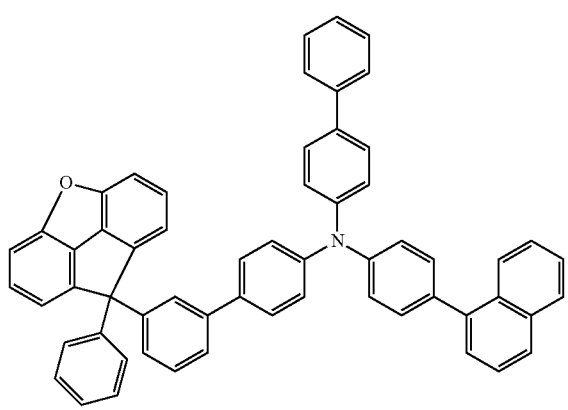

56
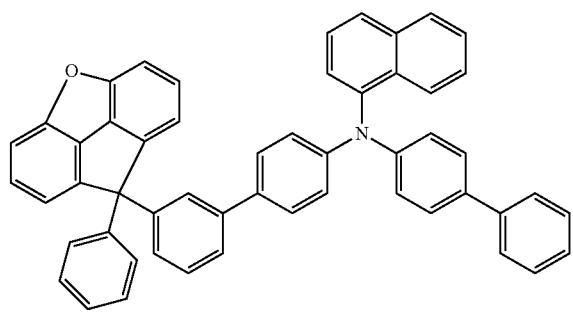
57
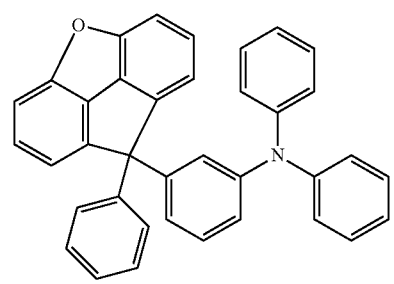
58
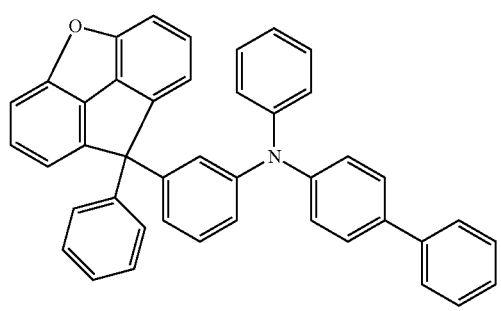
59
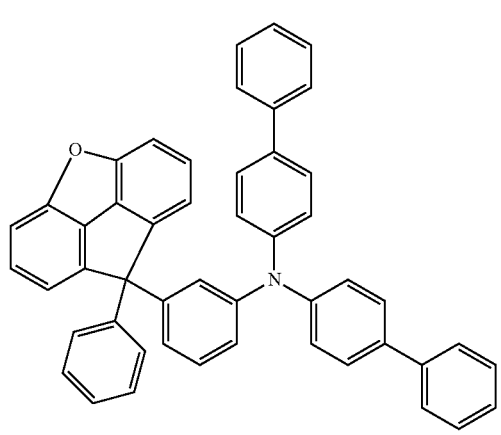
60
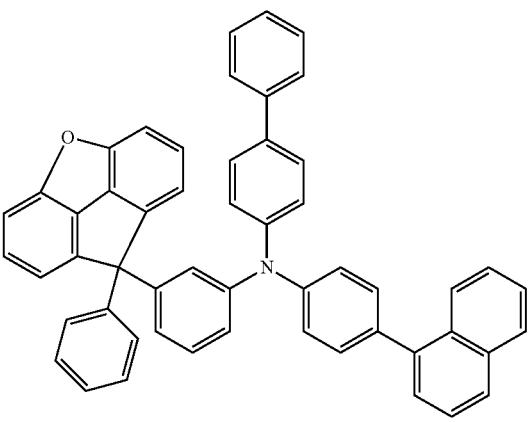
61
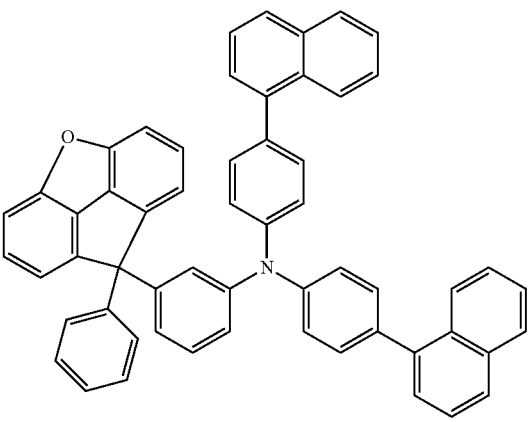
62
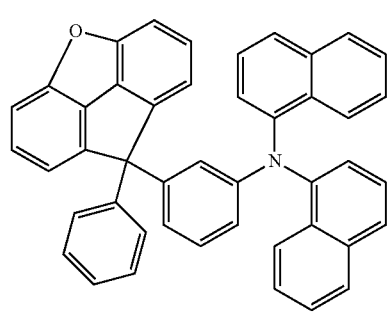
63
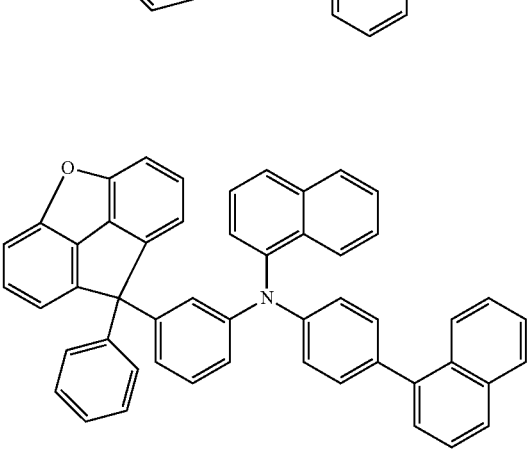

64
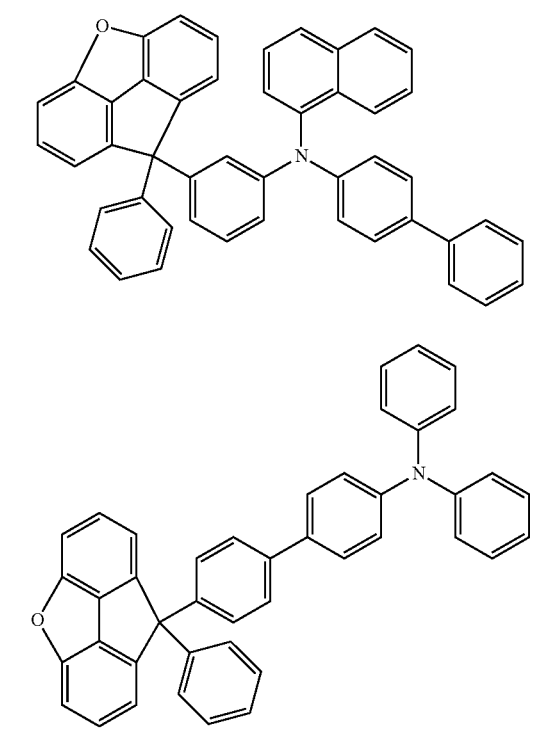
65
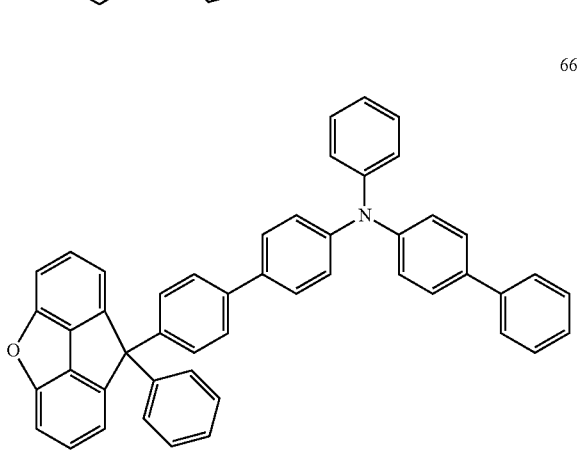
66
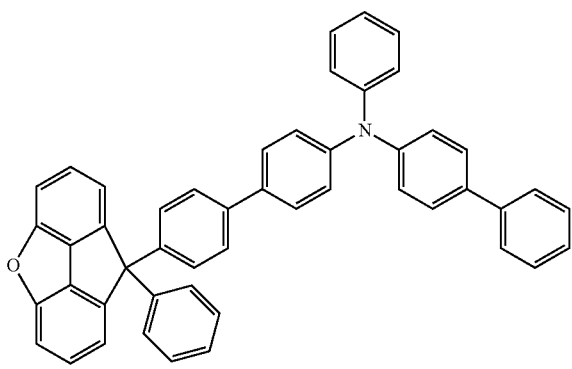
67
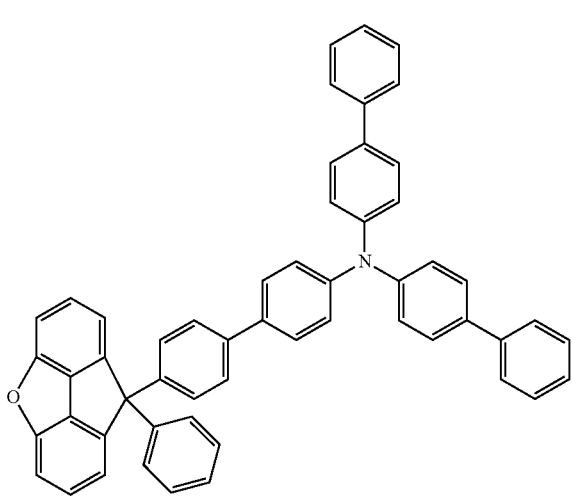
68
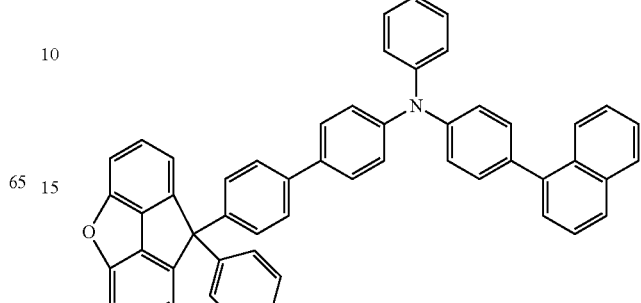
69
70

71
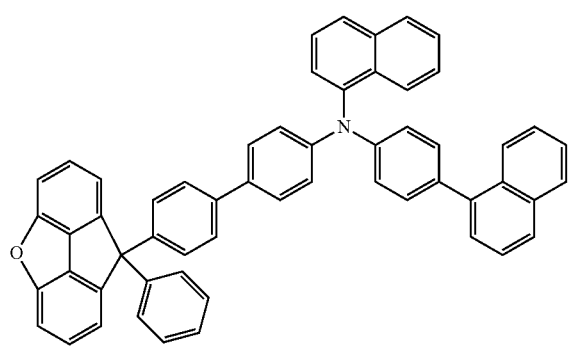
72
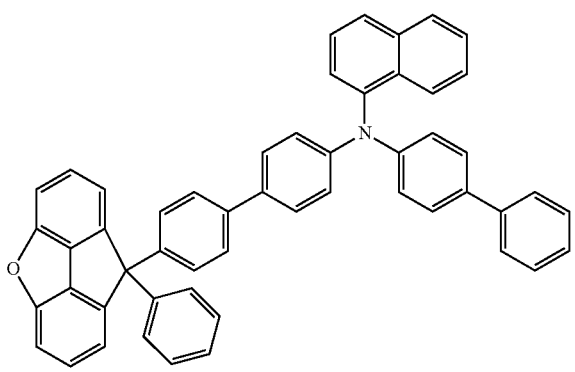
73
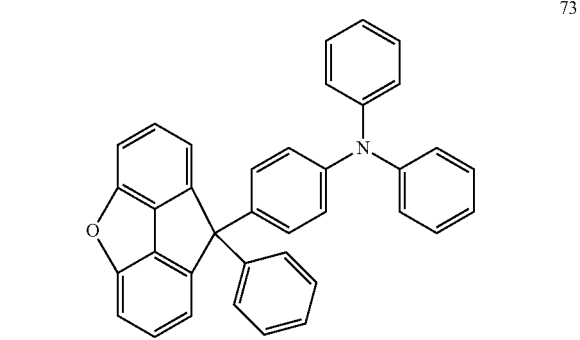
74
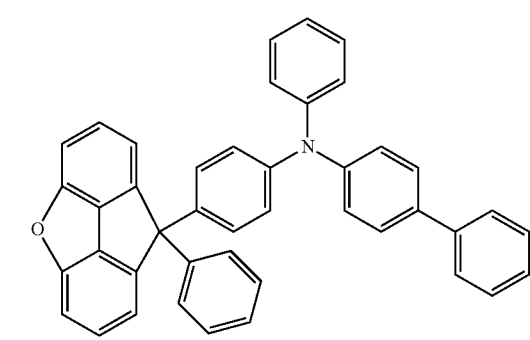
75
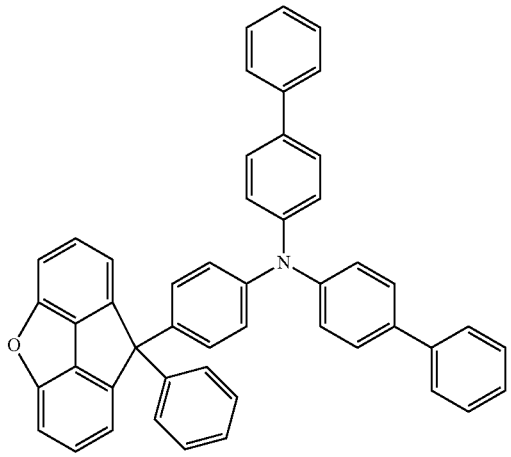
76
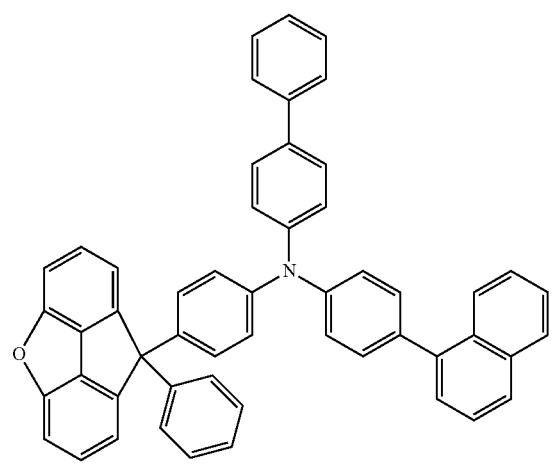
77
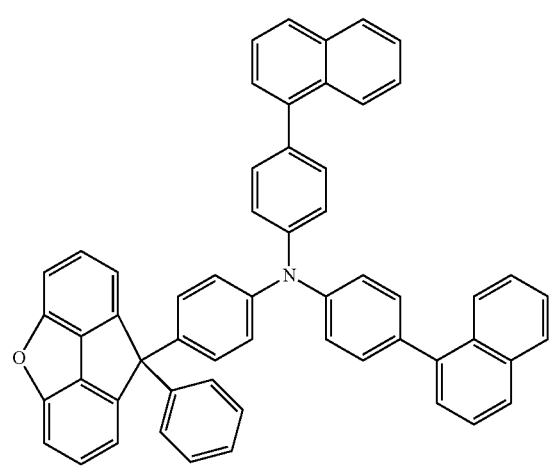

78
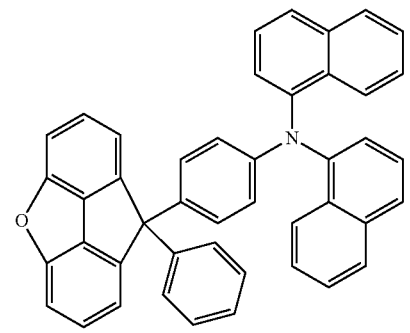
79
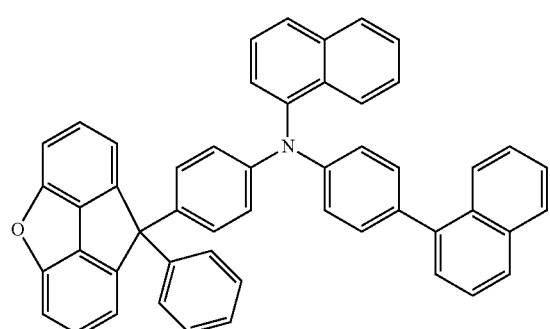
80
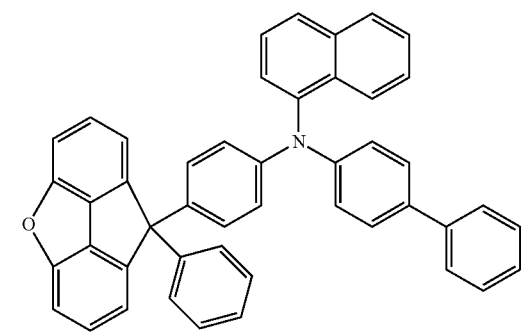
81

82
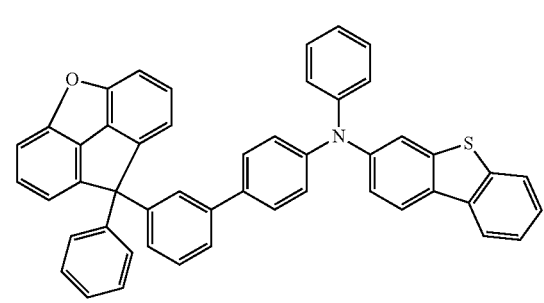
83
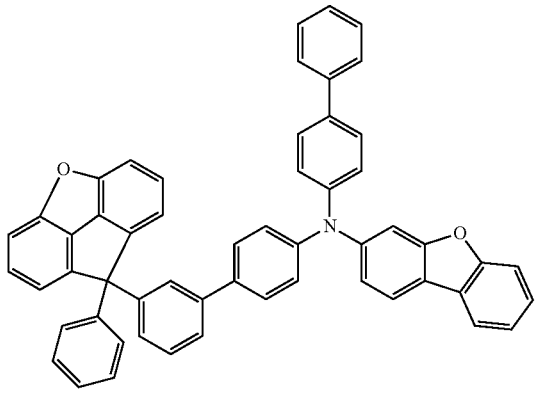
84
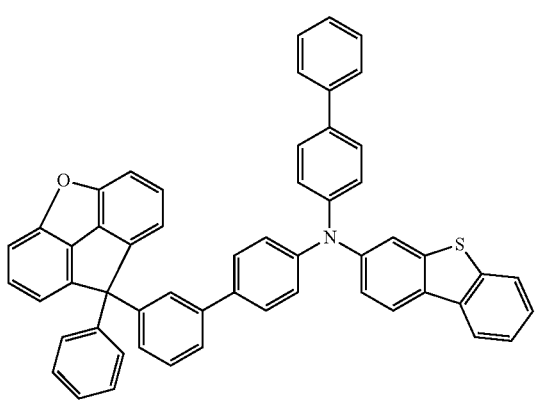
85
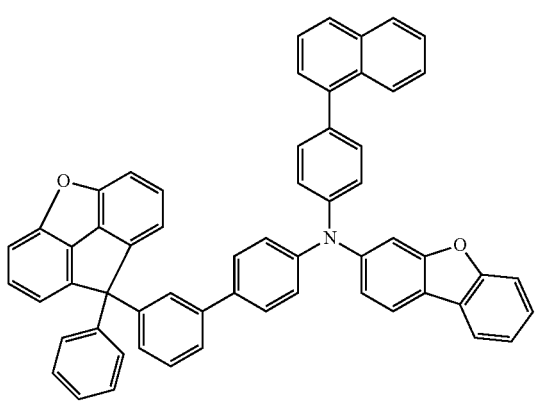
86
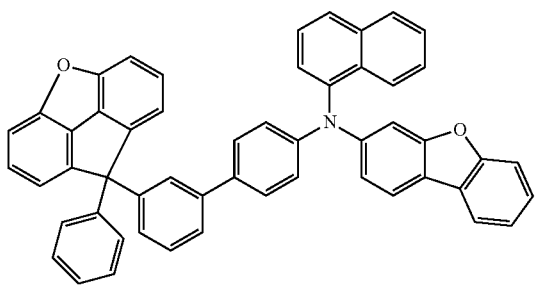

87
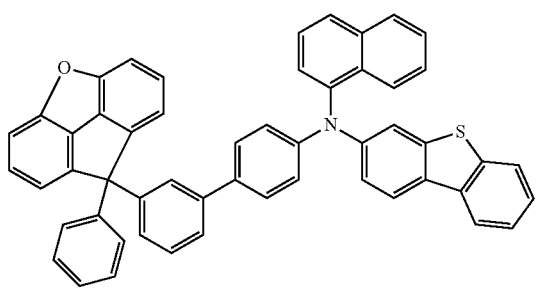
88
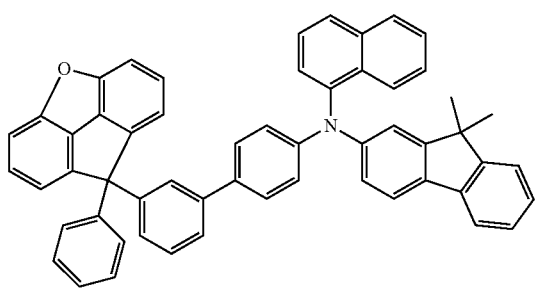
89
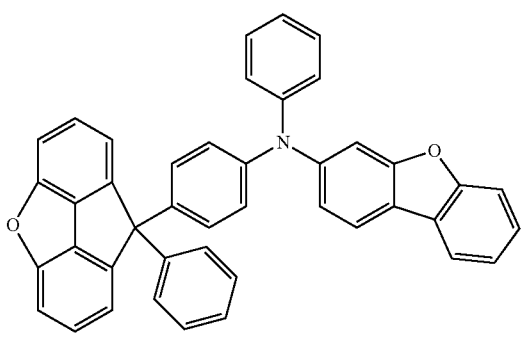
90
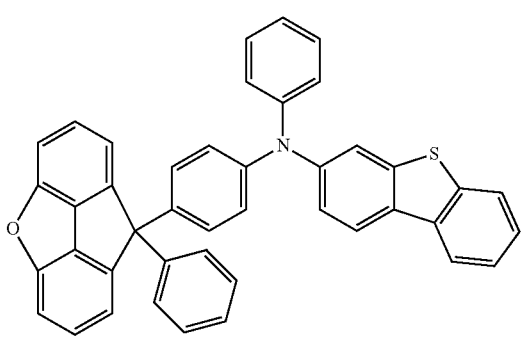
91
92
93
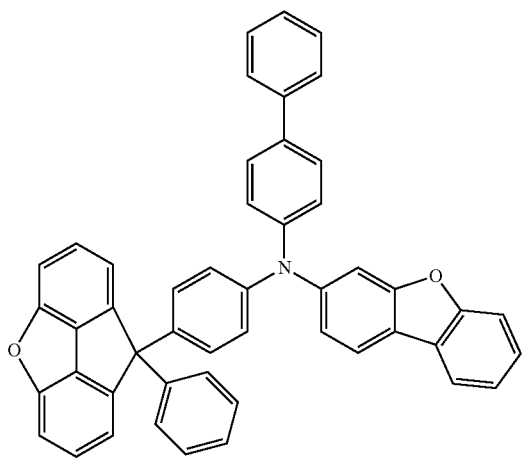

94
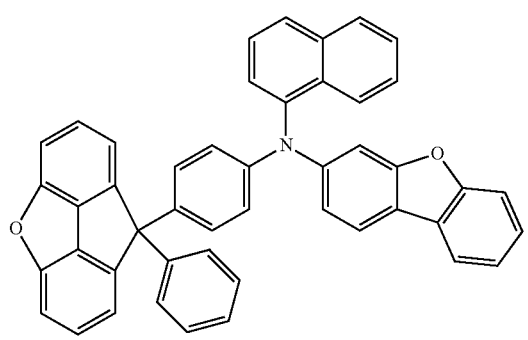
95
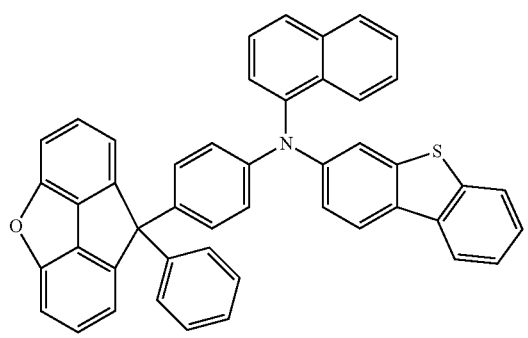
96
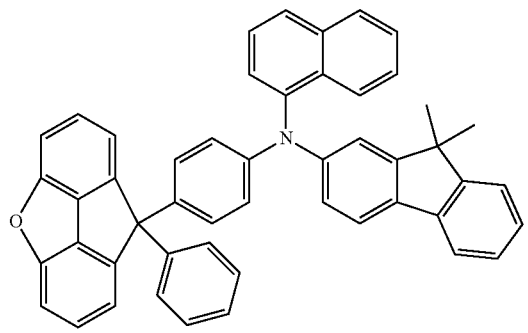
97
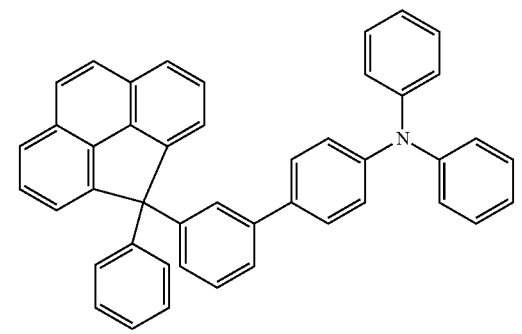
98
99
100
101
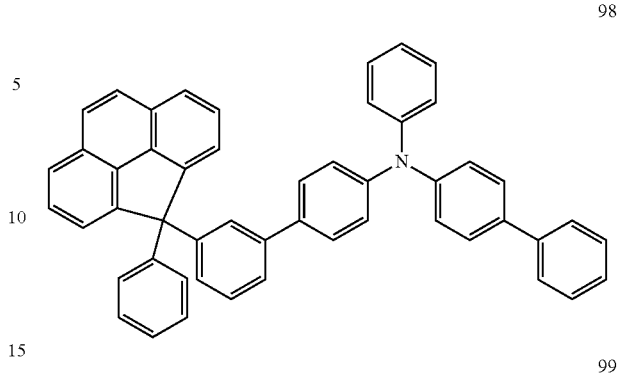

-continued
102
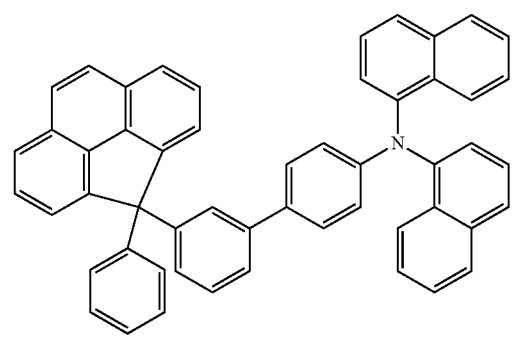
103
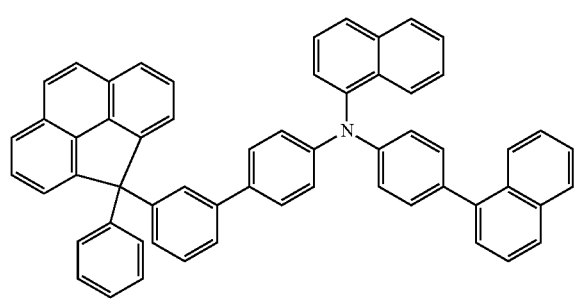
104
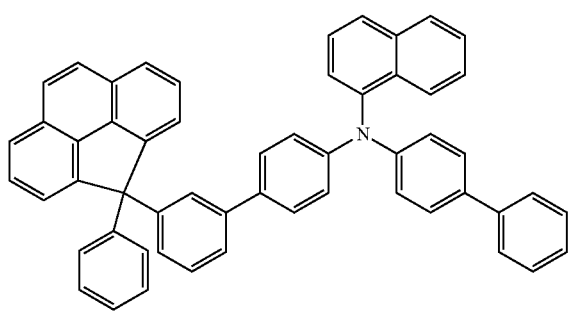
105
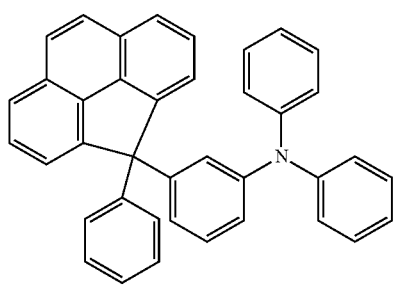
106
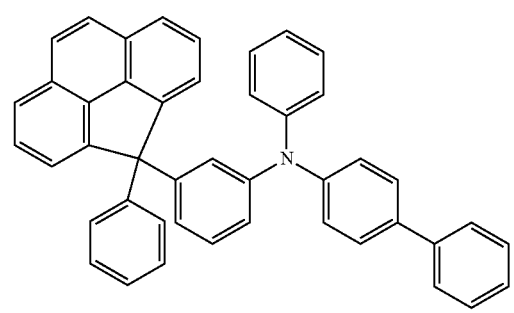
-continued
107
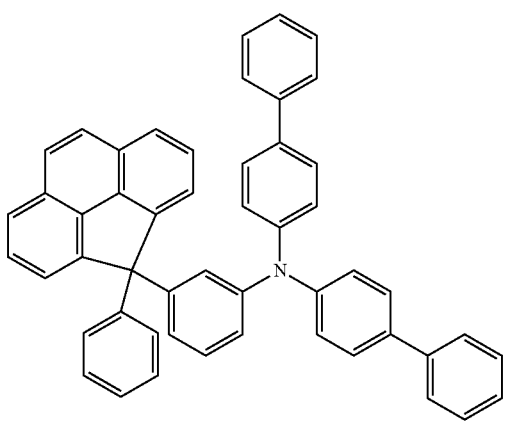
108
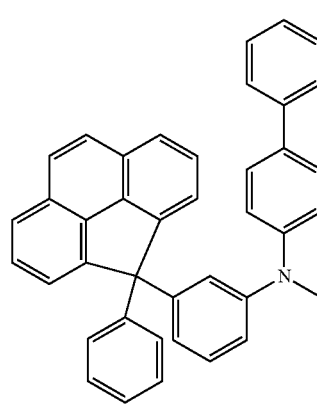
109
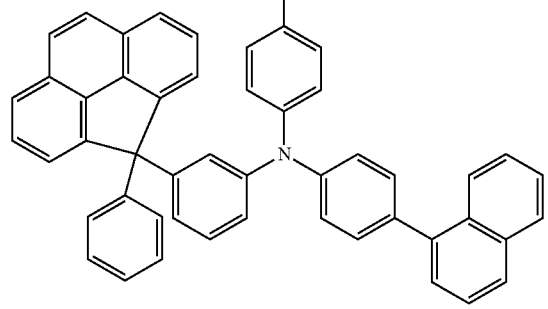
110
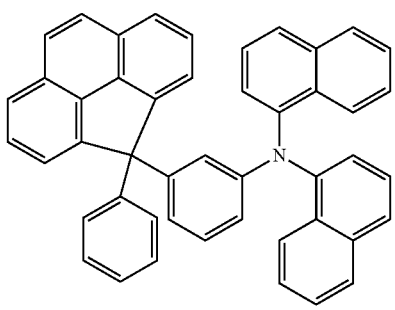
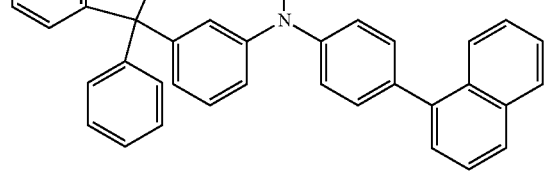

111
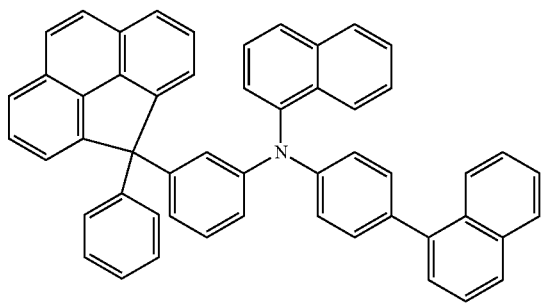
112
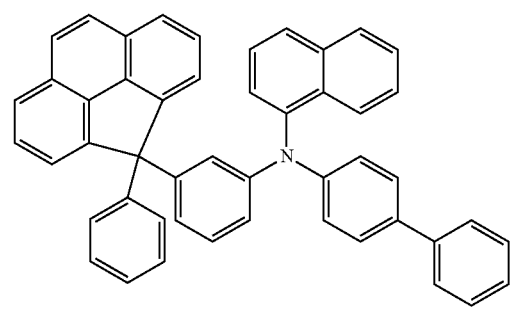
113
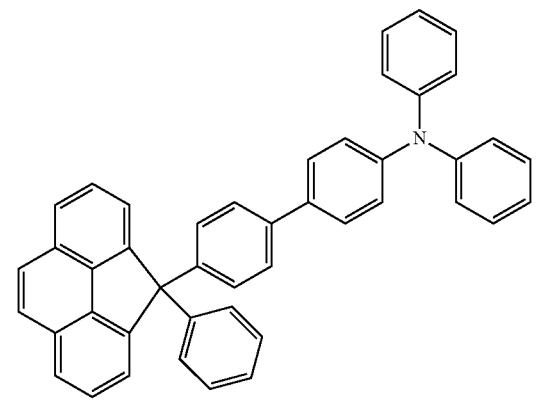
114
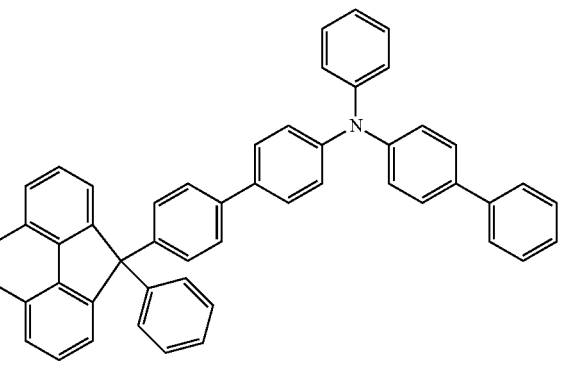
115
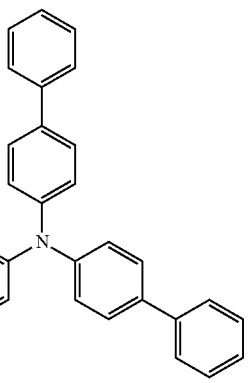
116
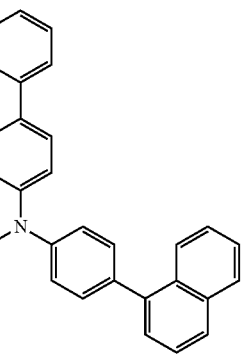
117
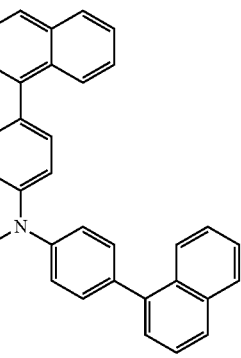

-continued
118
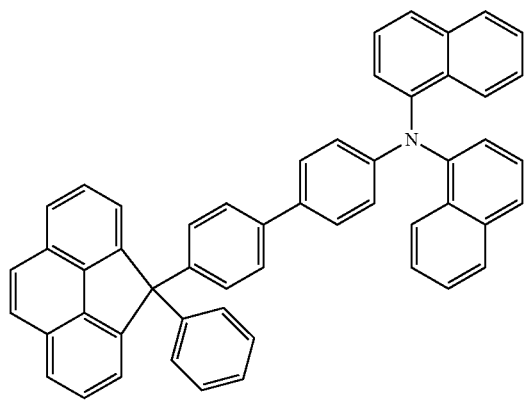
119
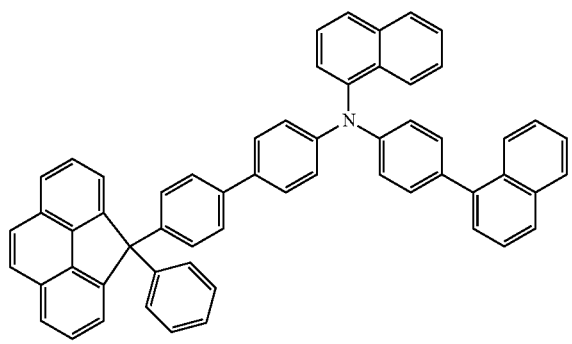
120
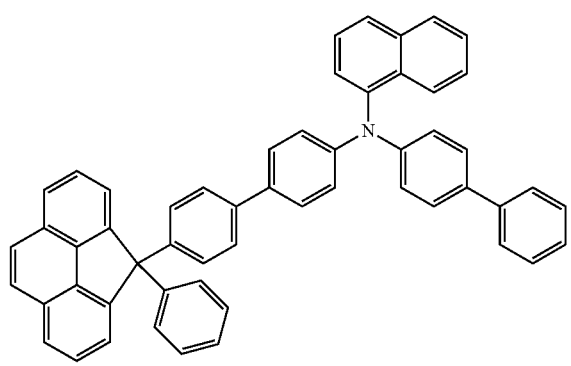
121
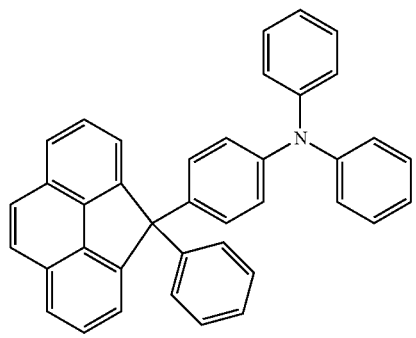
-continued
122
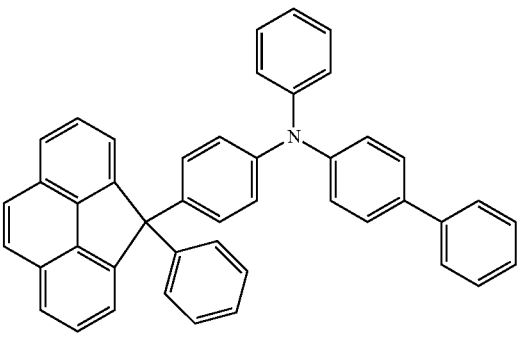
123
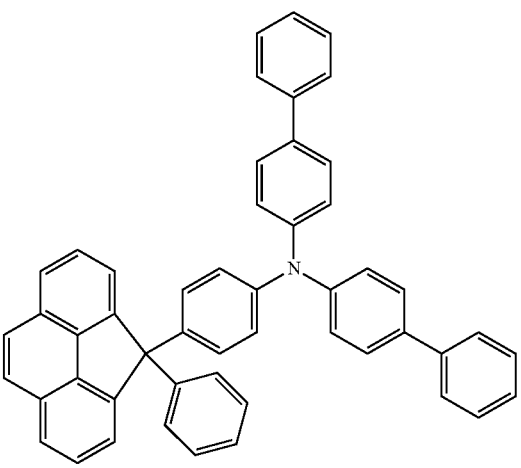
124
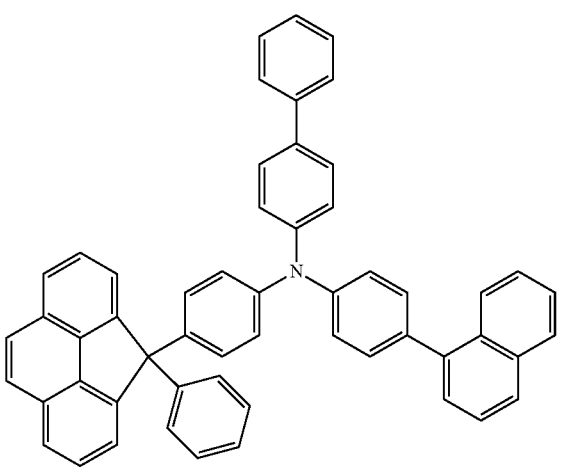

125
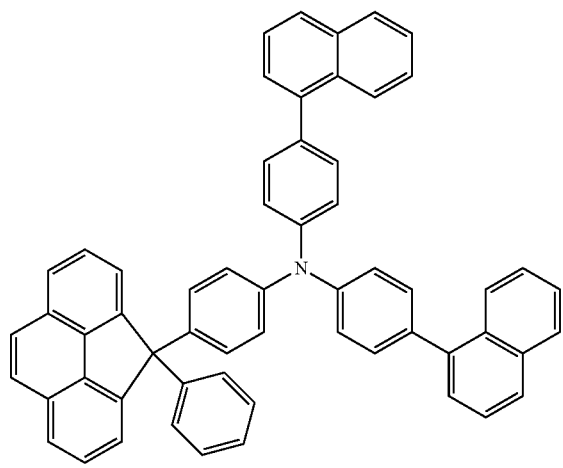
126
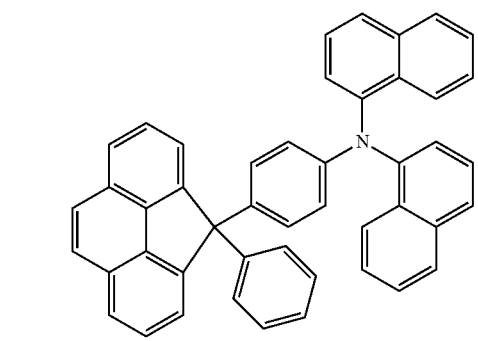
127
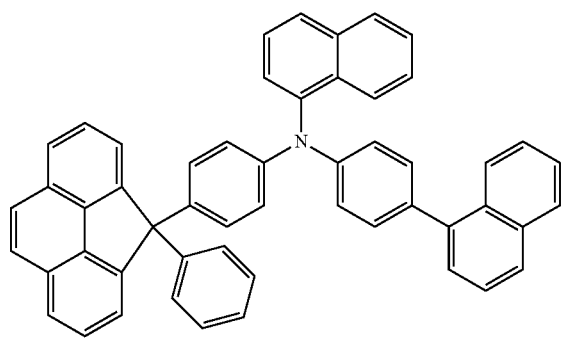
128
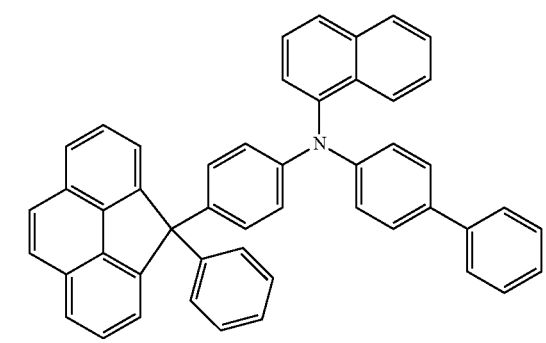
129
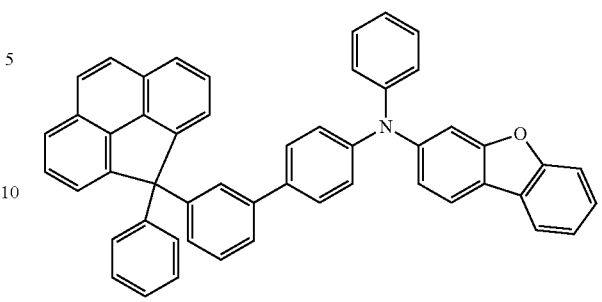
130
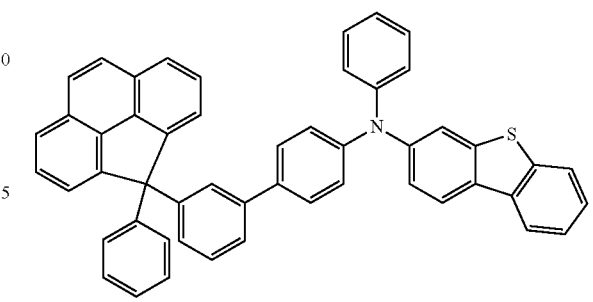
131
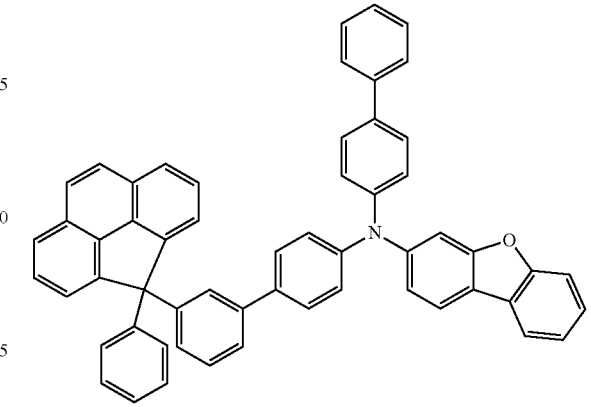
132
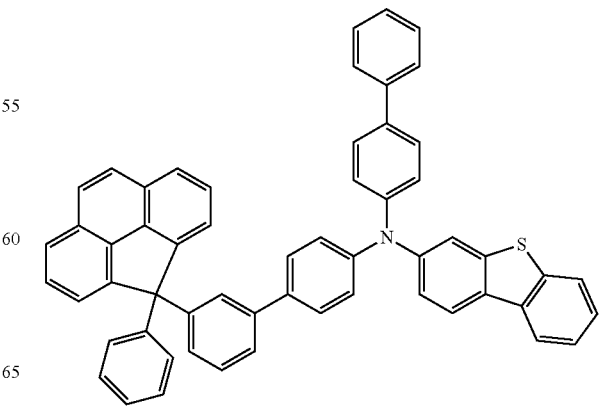

133
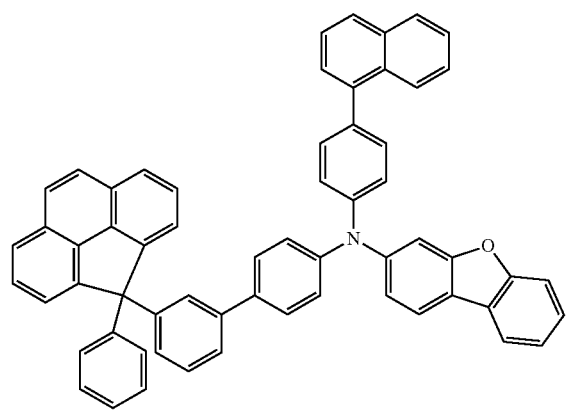
134
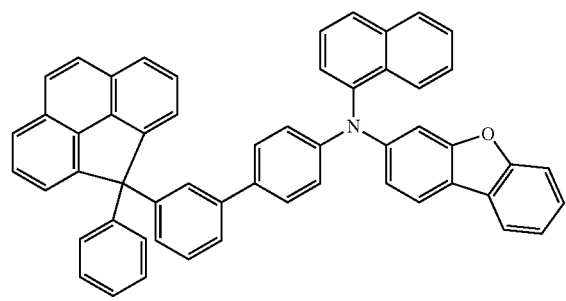
135
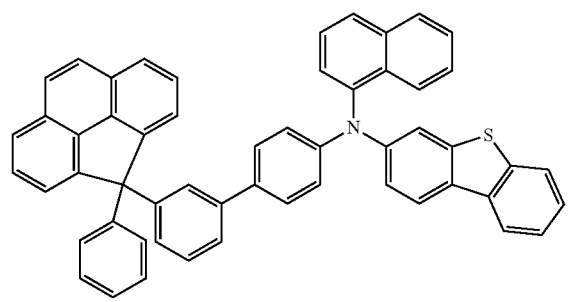
136
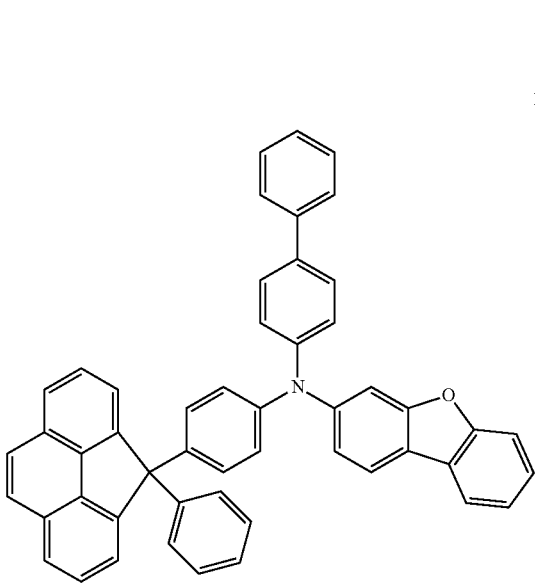
137
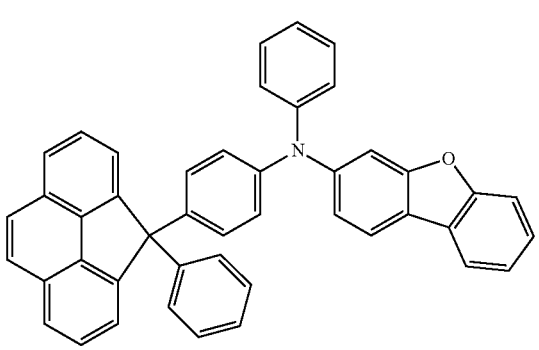
138
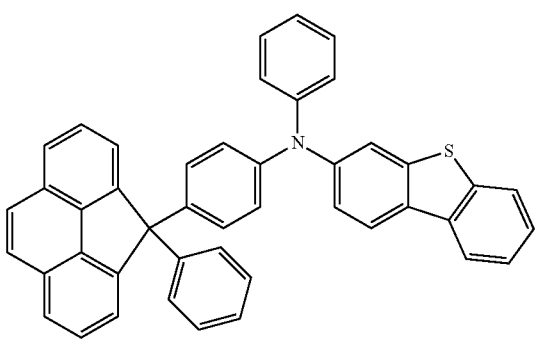
139
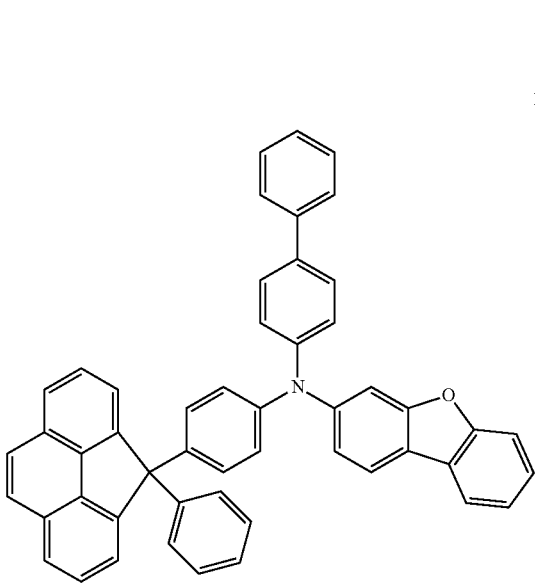

-continued
140
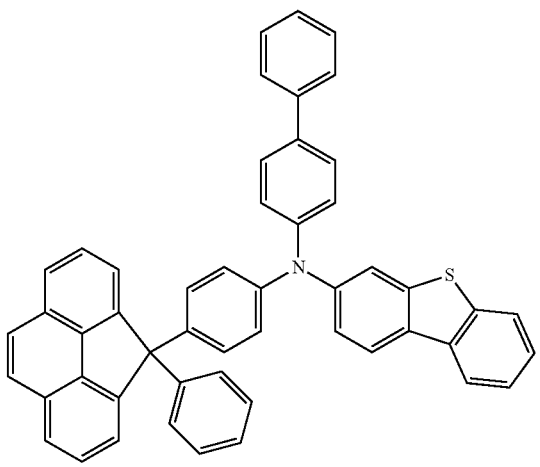
141
142
143
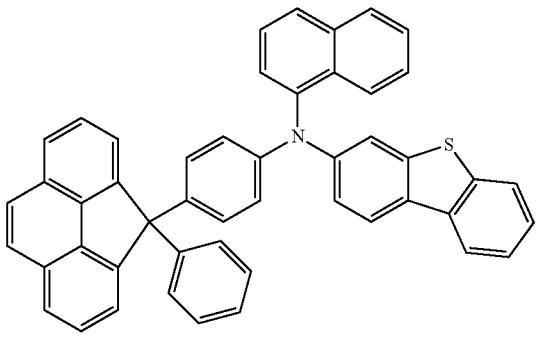
144
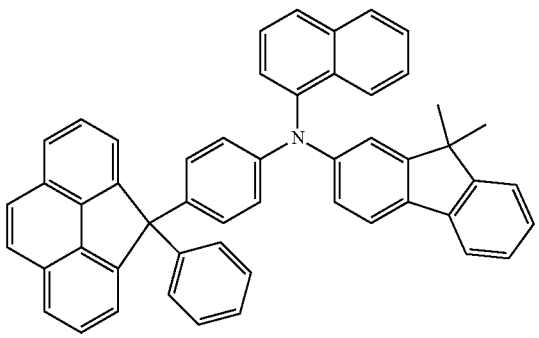
145
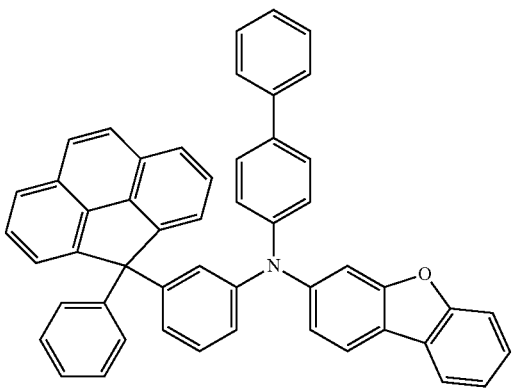
146
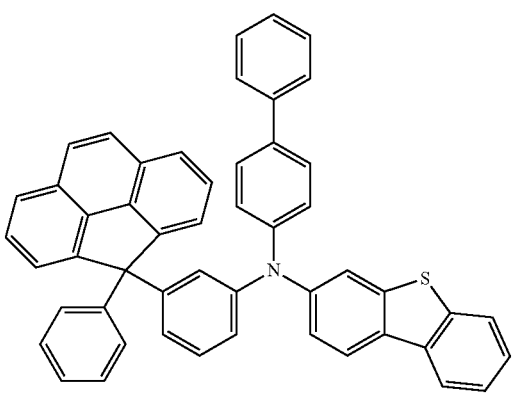

147

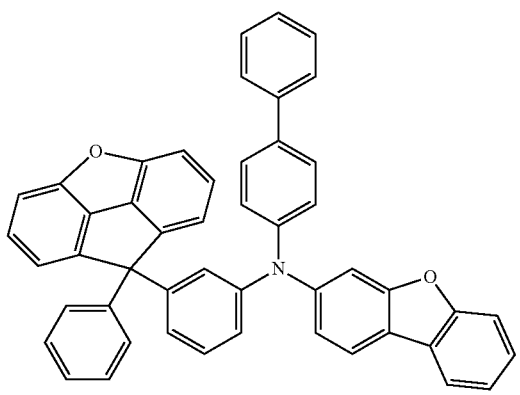

148

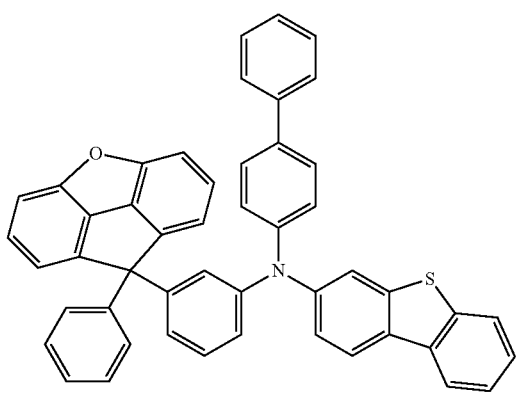

149

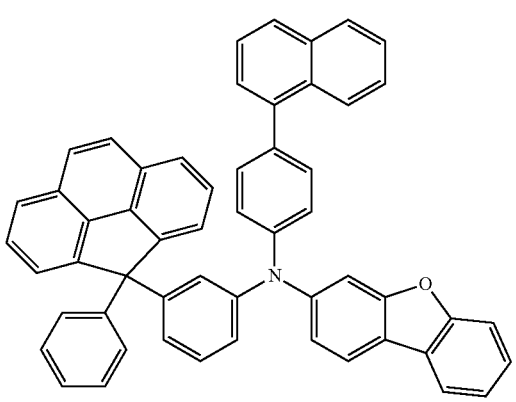

150

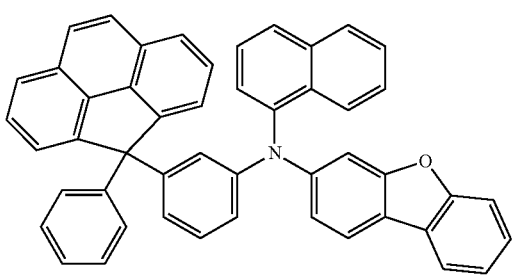

151

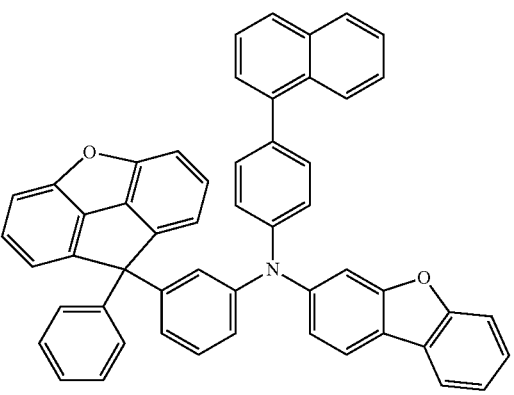

152

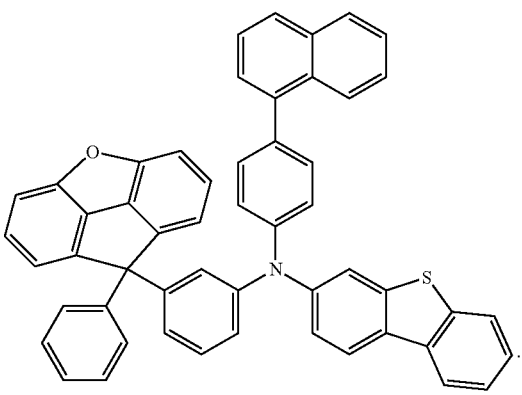

In one embodiment of the present disclosure, an organic light emitting device includes an anode, a hole transport region, an emission layer, an electron transport region, and a cathode. The hole transport region may be on the anode. The emission layer may be on the hole transport region. The electron transport region may be on the emission layer. The cathode may be on the electron transport region. The hole transport region may include an amine compound represented by Formula 1:

Formula 1

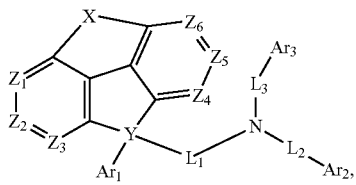

wherein X may be selected from the compounds represented by Formula 2:

Formula 2

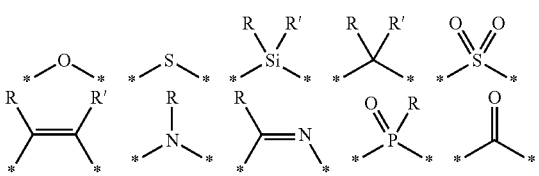

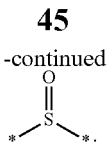

In Formulae 1 and 2,

Y may be C, Si, or Ge, $Z_1$ to $Z_6$ may each independently be CR or N, $Ar_1$ to $Ar_a$ may each independently be hydrogen, deuterium, a halogen atom, a substituted or unsubstituted aryl group having 6 to 30 carbon atoms for forming a ring, a substituted or unsubstituted heteroaryl group having 5 to 30 carbon atoms for forming a ring, an alkyl group having 1 to 20 carbon atoms, or a silyl group having 3 to 20 carbon atoms, $L_1$ to $L_3$ may each independently be a direct linkage, a substituted or unsubstituted arylene group having 6 to 30 carbon atoms for forming a ring, or a substituted or unsubstituted heteroarylene group having 5 to 30 carbon atoms for forming a ring, and R and R' may each independently be hydrogen, deuterium, a substituted or unsubstituted aryl group having 6 to 30 carbon atoms for forming a ring, a substituted or unsubstituted heteroaryl group having 5 to 30 carbon atoms for forming a ring, or an alkyl group having 1 to 20 carbon atoms.

In one embodiment, Formula 1 may be represented by Formula 3:

Formula 3

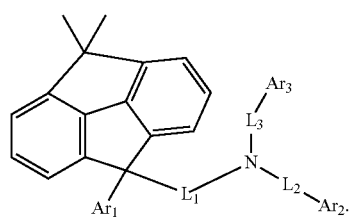

In one embodiment, Formula 1 may be represented by Formula 4:

Formula 4

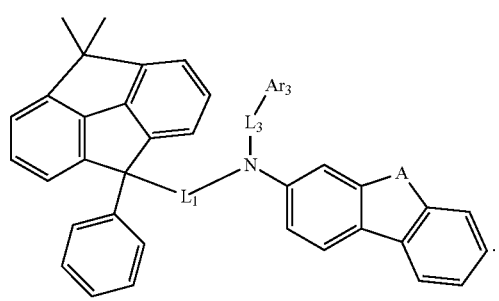

In Formula 4, A may be O, S, or $CR_2R_3$, and $R_2$ and $R_3$ may each independently be hydrogen, deuterium, an alkyl group having 1 to 20 carbon atoms, a substituted or unsubstituted aryl group having 6 to 30 carbon atoms for forming a ring, or a substituted or unsubstituted heteroaryl group having 5 to 30 carbon atoms for forming a ring.

In one embodiment, Formula 1 may be represented by Formula 5:

Formula 5

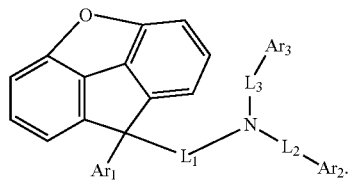

In one embodiment, Formula 1 may be represented by Formula 6:

Formula 6

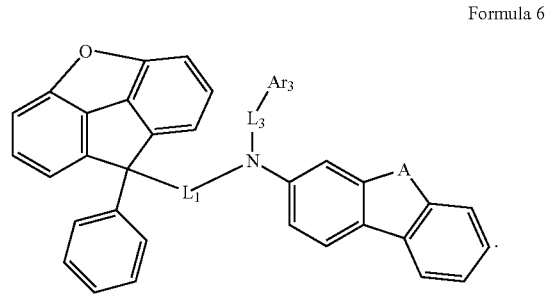

In Formula 6, A may be O, S, or $CR_2R_3$. $R_2$ and $R_3$ may be the same as defined above.

In one embodiment, Formula 1 may be represented by Formula 7:

Formula 7

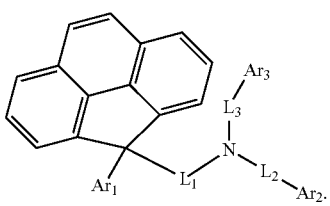

In one embodiment, Formula 1 may be represented by Formula 8:

Formula 8

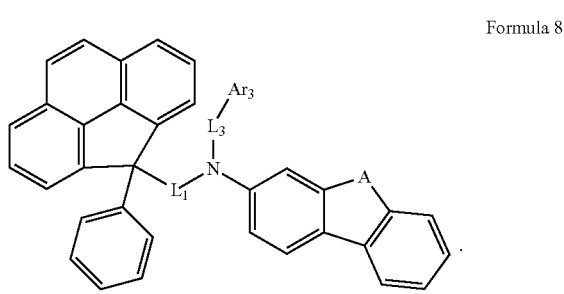

In Formula 8, A may be O, S, or $CR_2R_3$. $R_2$ and $R_3$ may be the same as defined above.

In Formulae 3 to 8, $L_1$ to $L_3$ and $Ar_1$ to $Ar_3$ may each independently be the same as described herein in connection with Formula 1.

In one embodiment, the hole transport region may include at least one selected from the compounds represented by Compound Group 1:

Compund Group 1
1
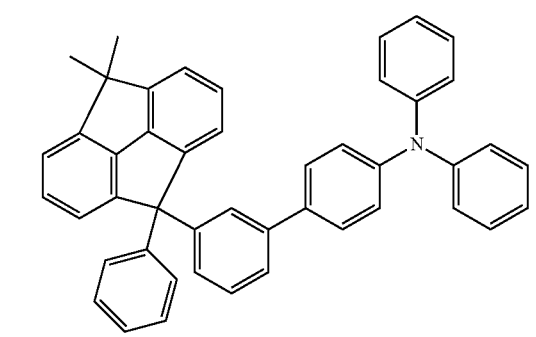
2
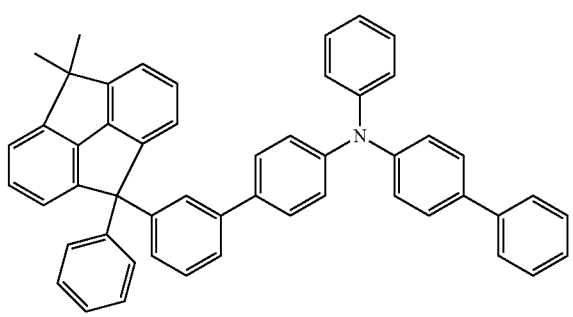
3
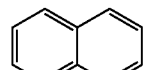
4
5
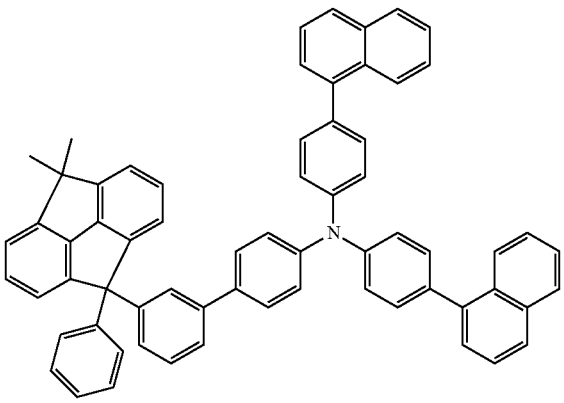
6
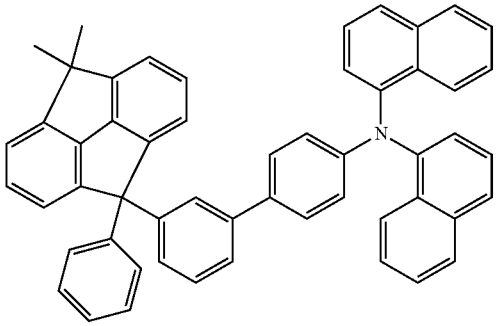
7
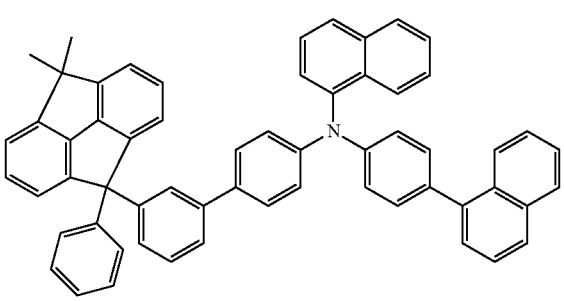
8
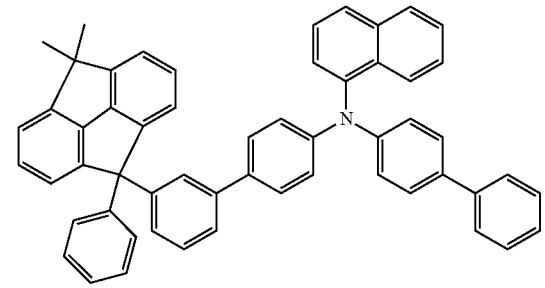

9
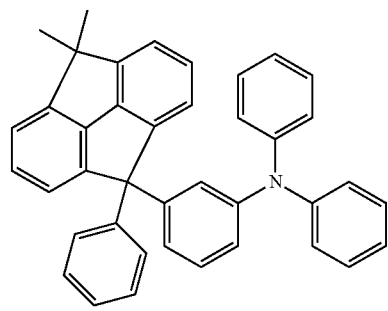
10
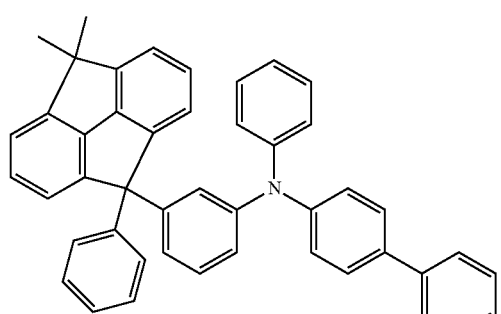
11
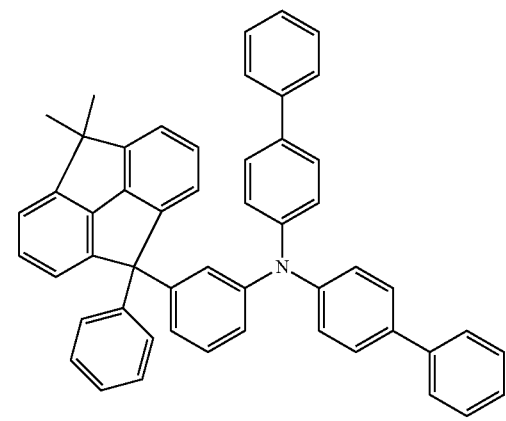
12
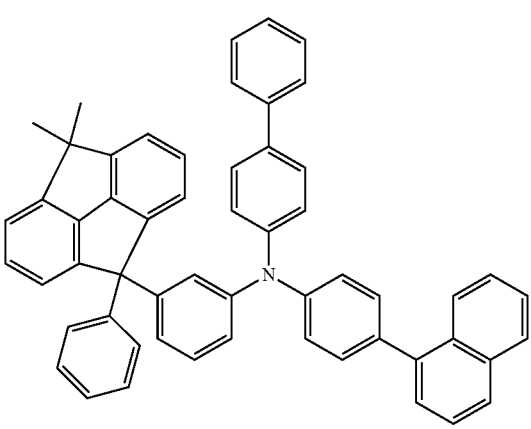
13
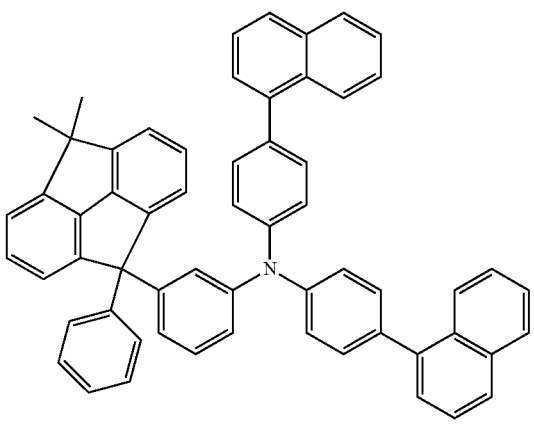
14
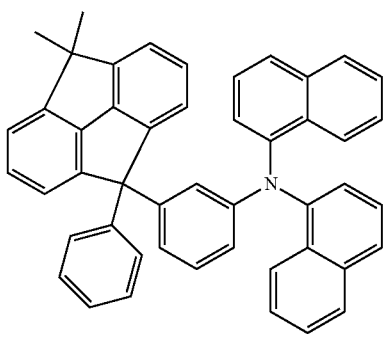
15
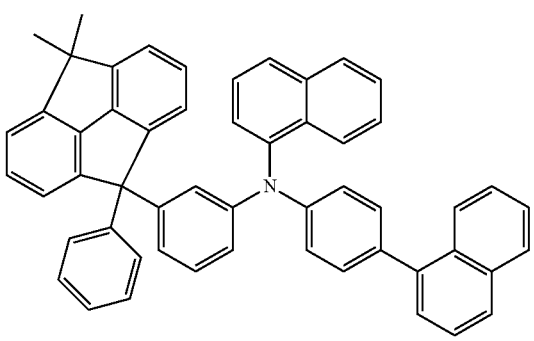
16
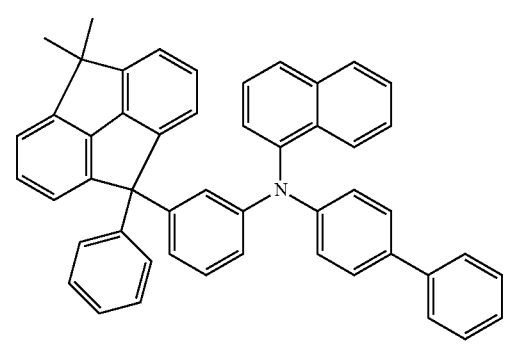

17

18

19

20

21

22

23

24
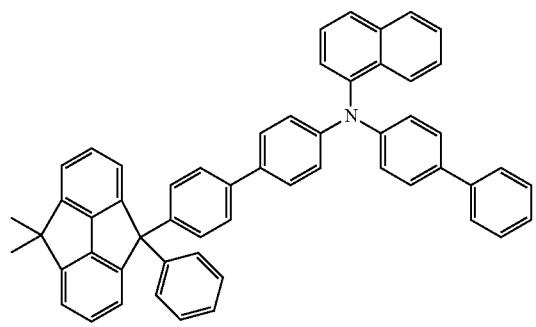
25
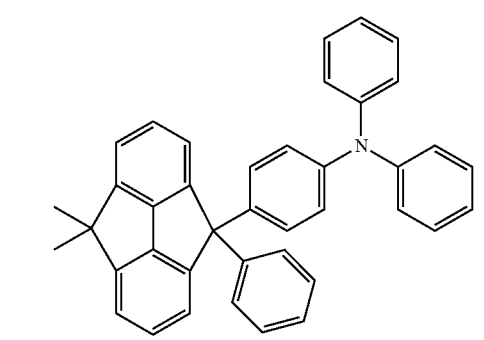
26
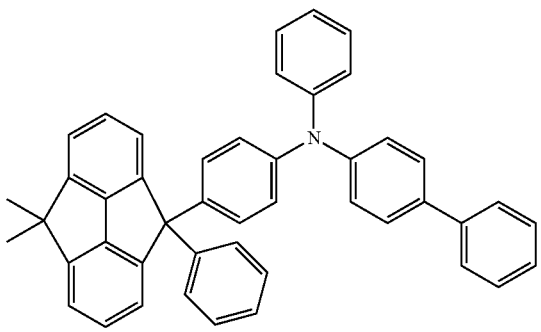
27
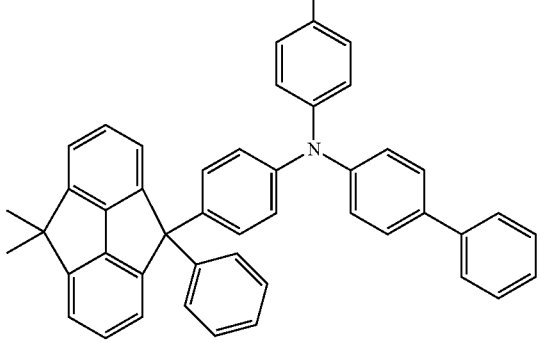
28
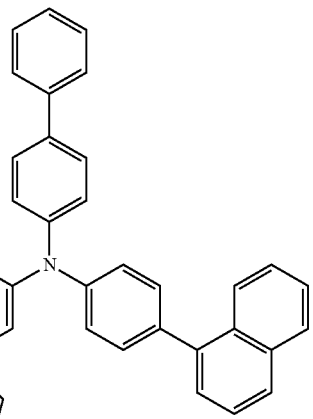
29
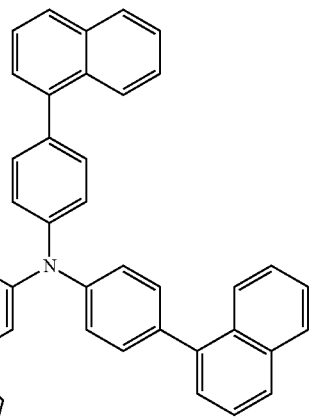
30
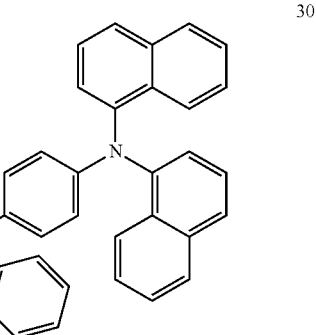
31

32
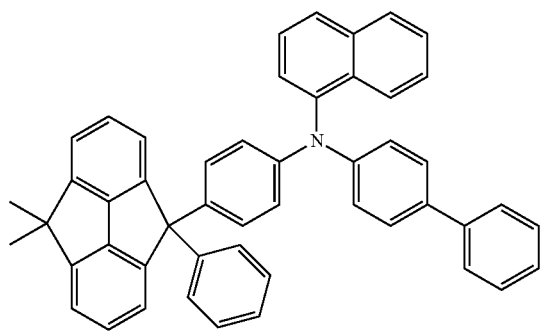
33
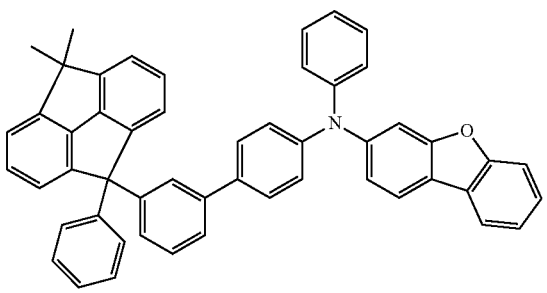
34
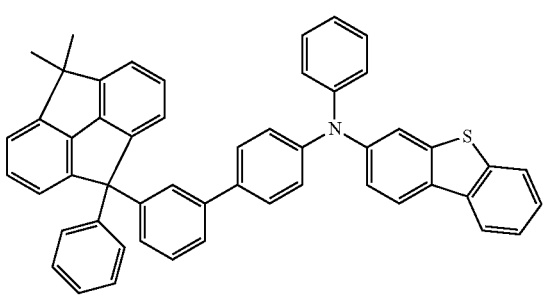
35
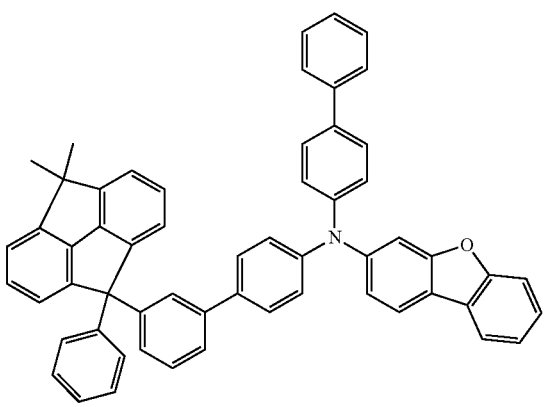
36
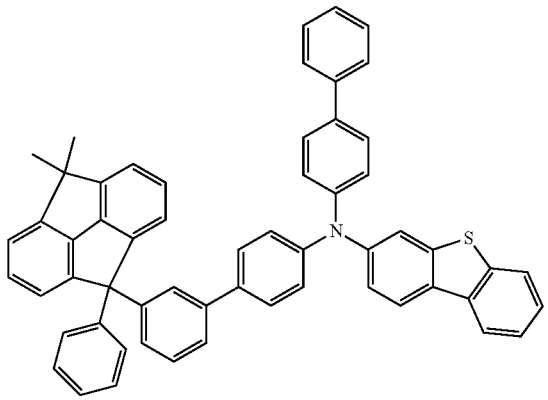
37
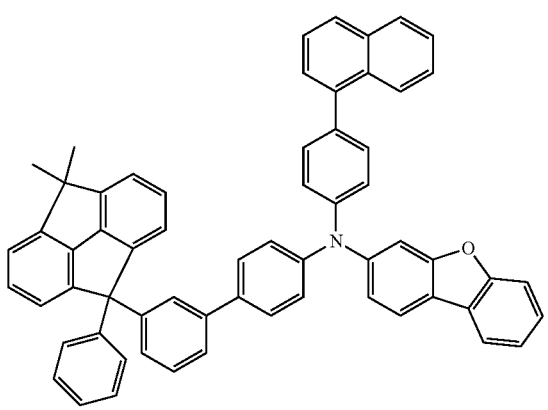
38
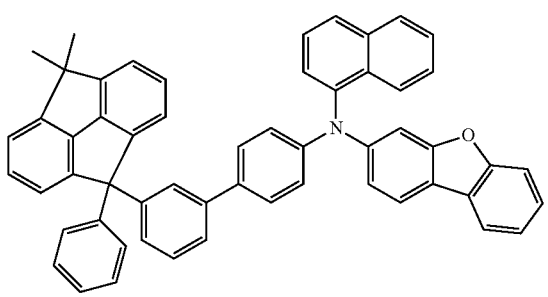
39
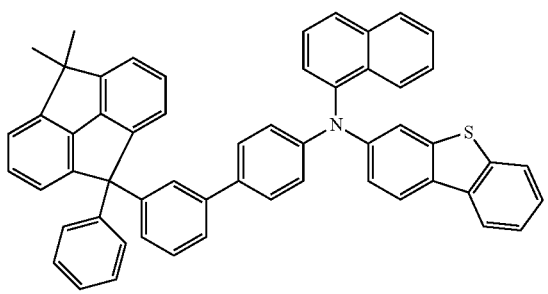

40
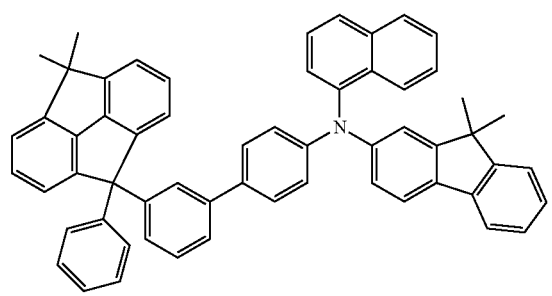
41
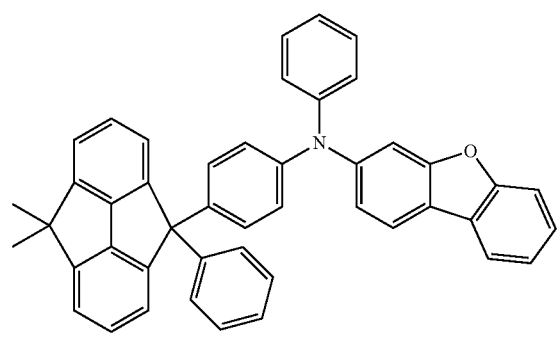
42
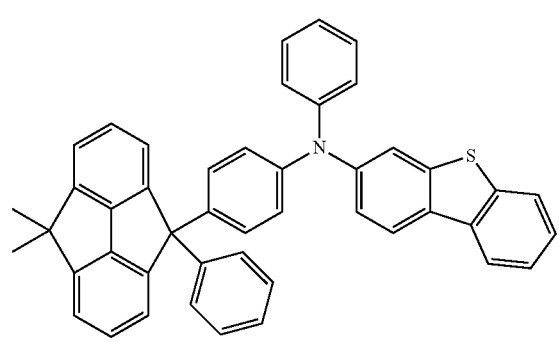
43
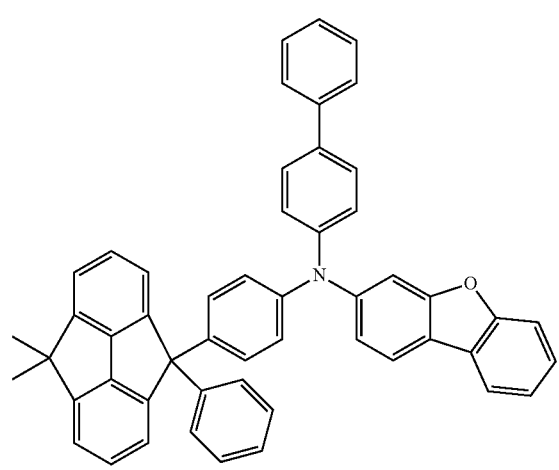
44
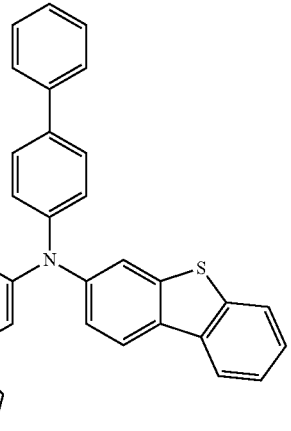
45
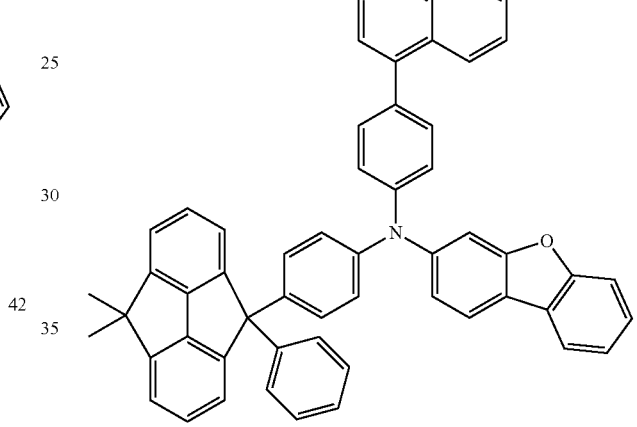
46
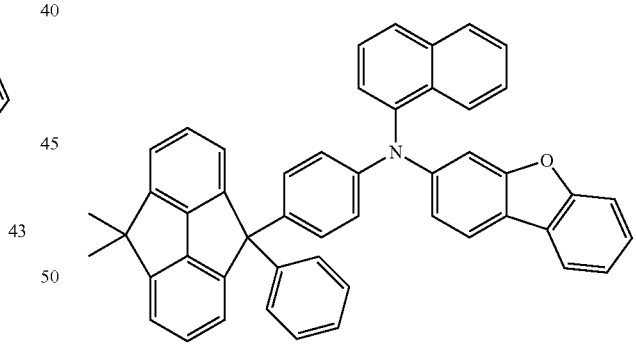
47
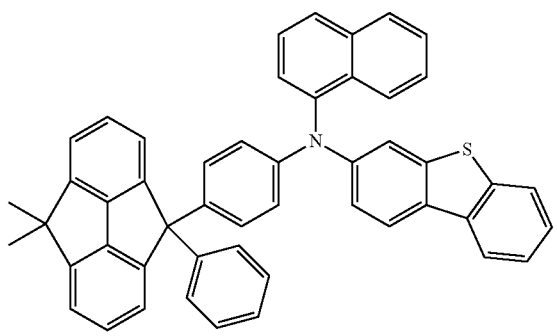

48
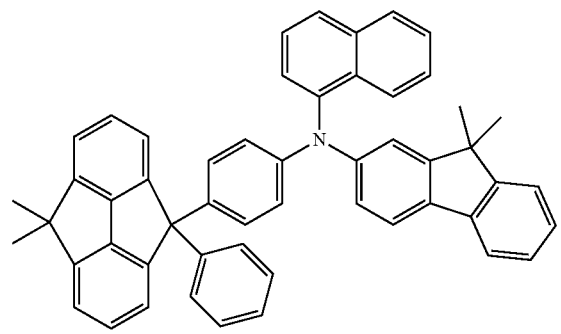
49
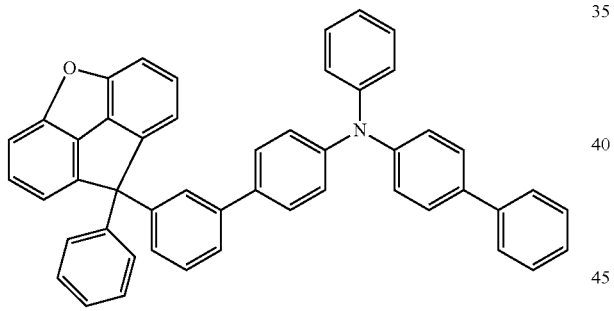
50
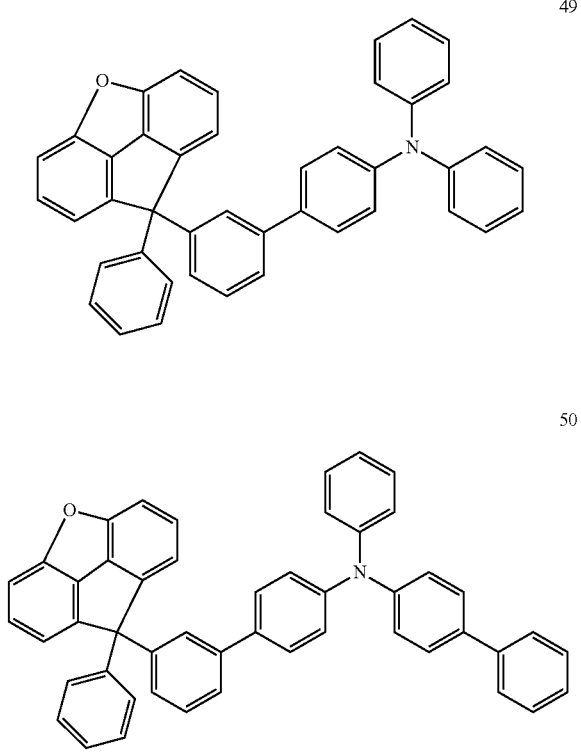
51
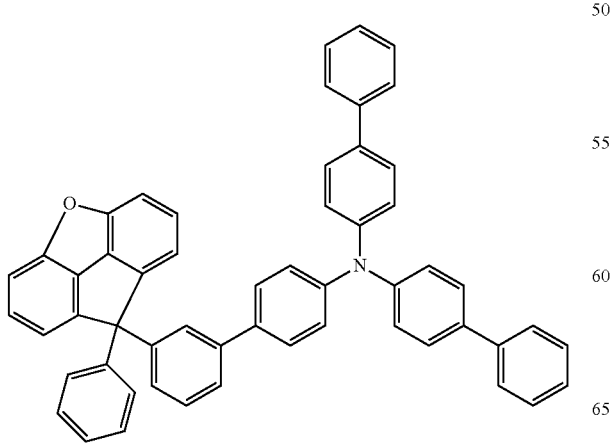
52
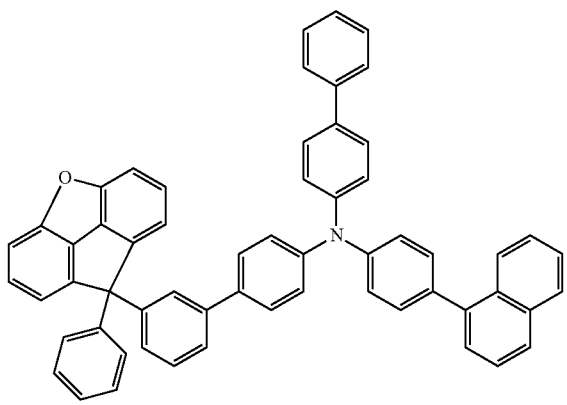
53
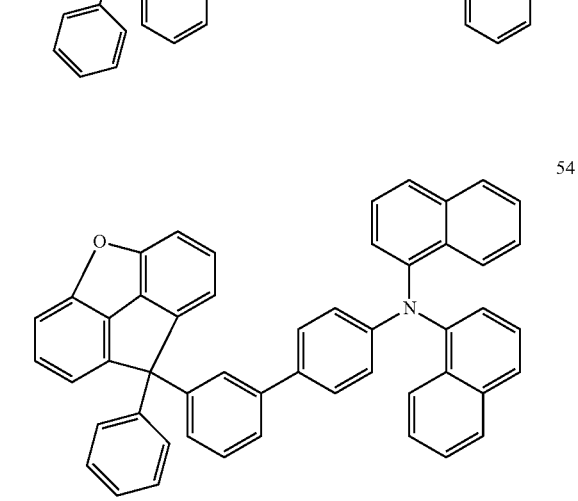
54
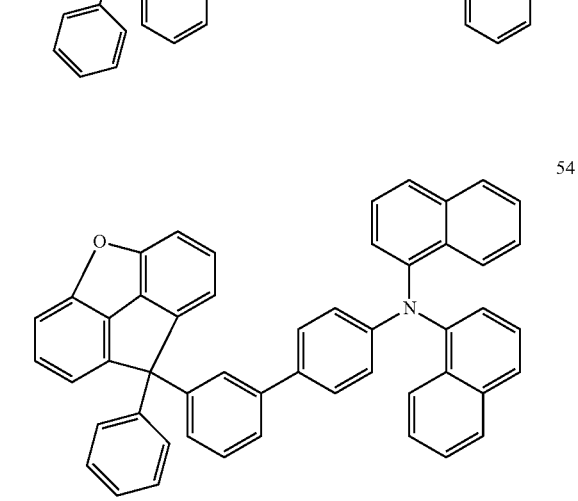
55
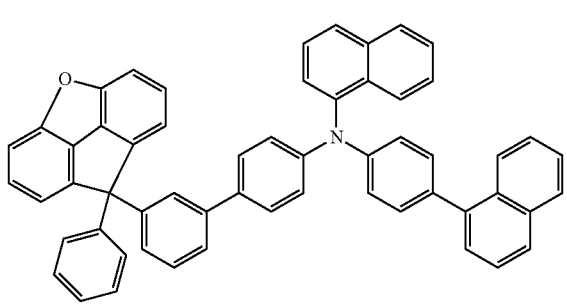

56 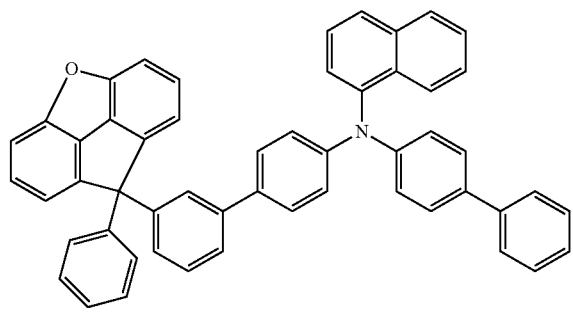
57 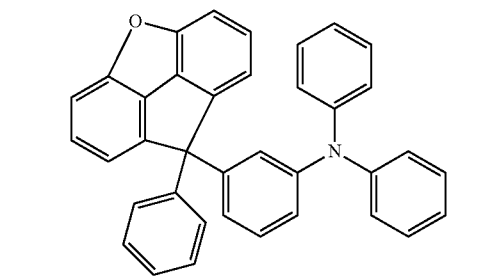
58 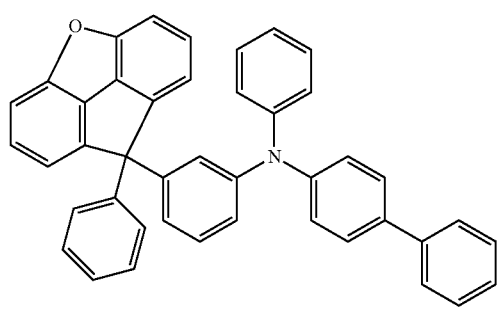
59 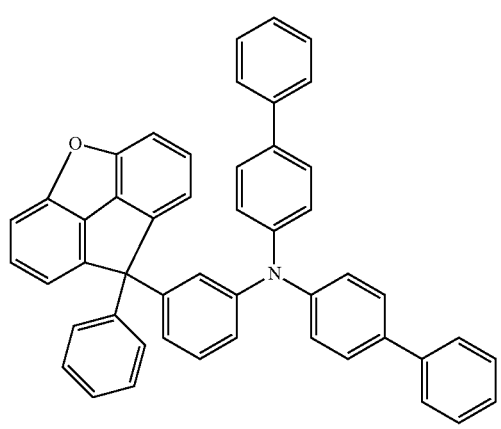
60 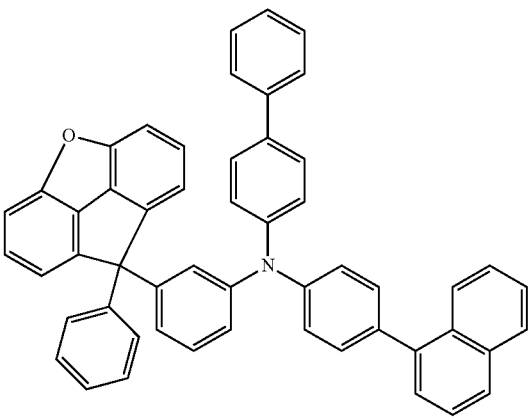
61 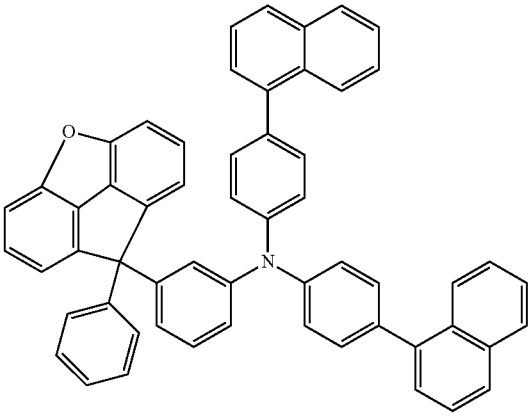
62
63 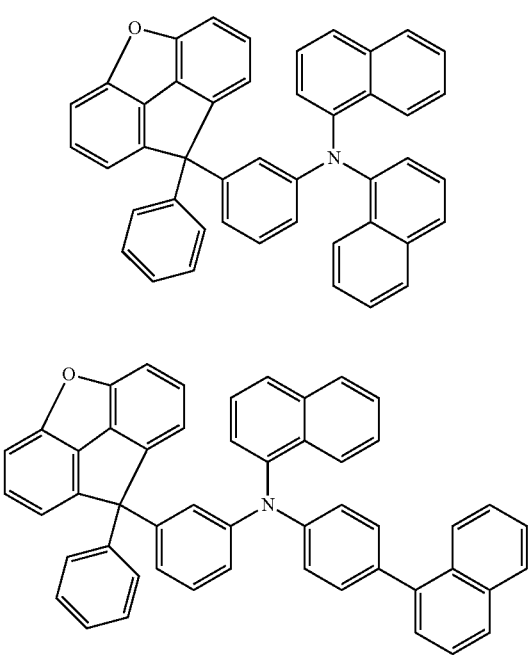

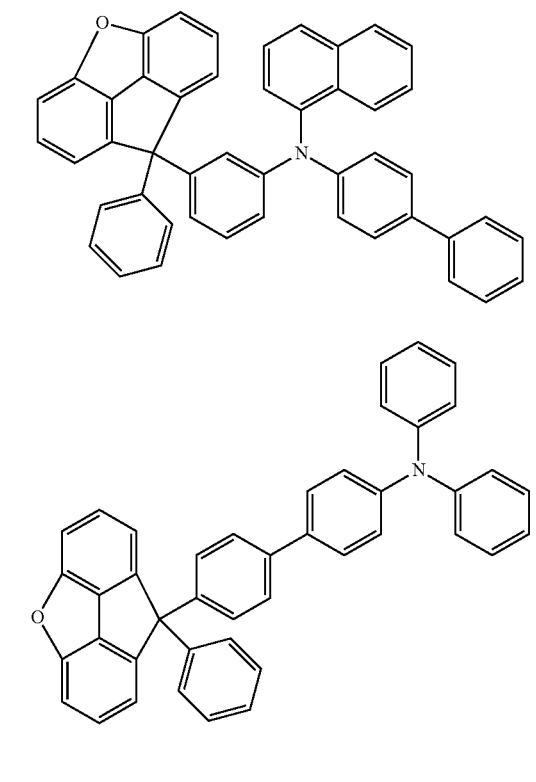
64
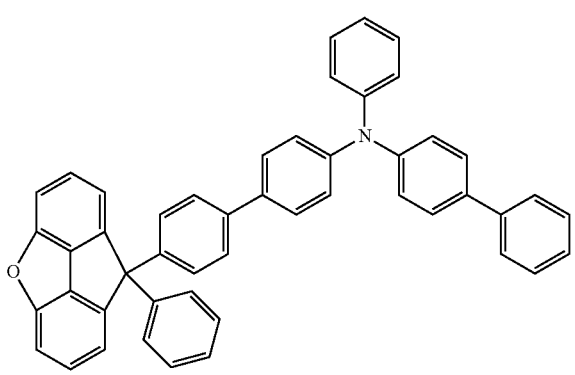
65
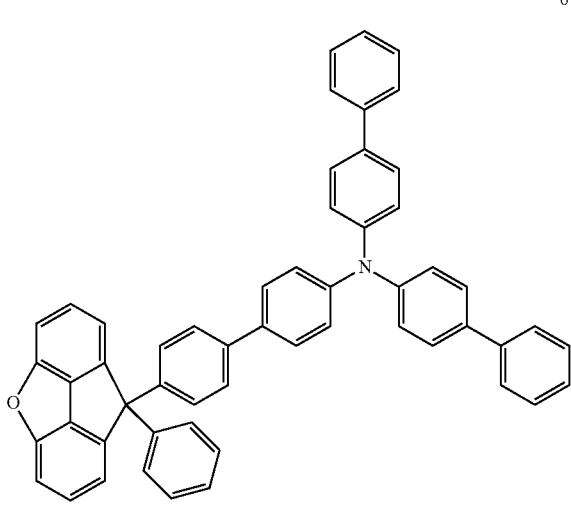
66
67
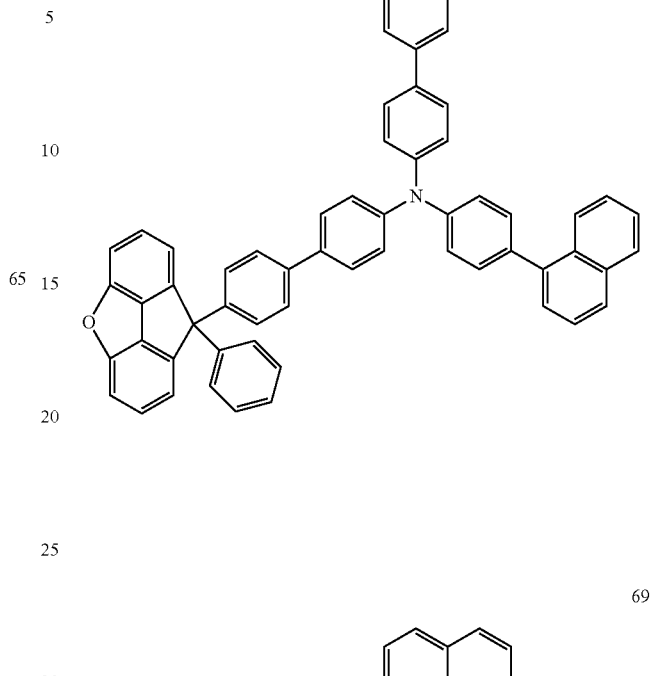
68
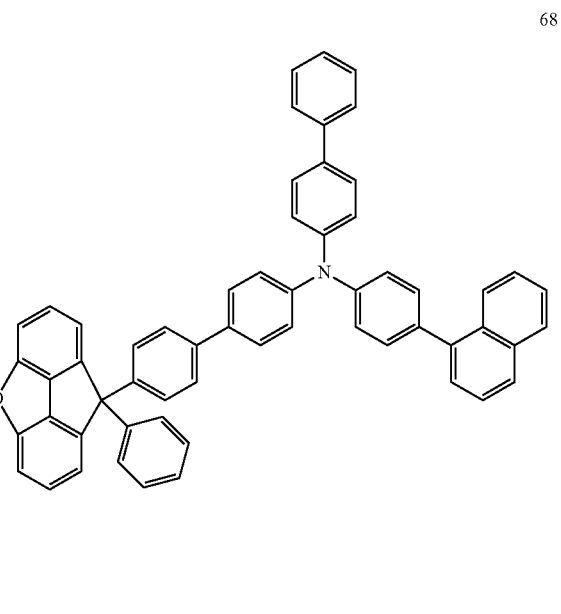
69
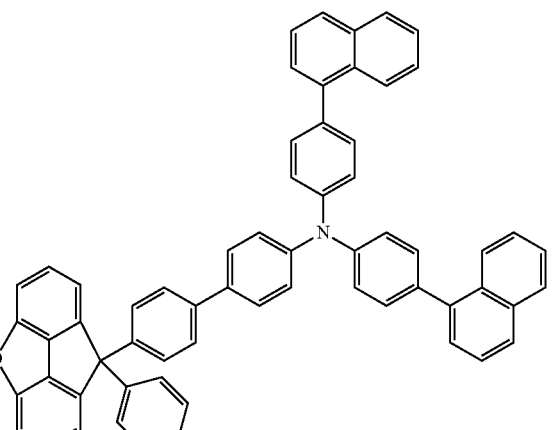
70
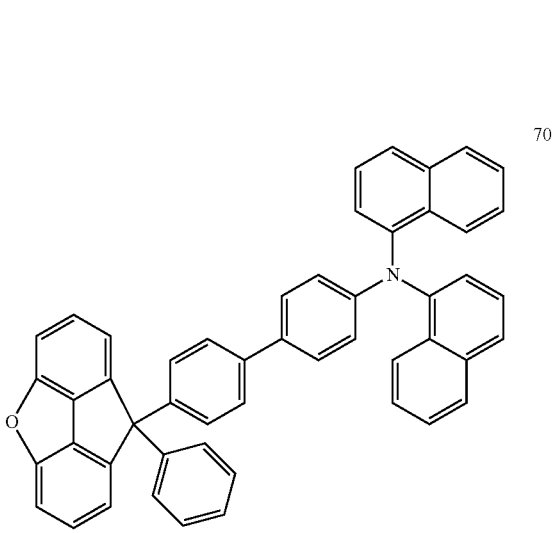

71
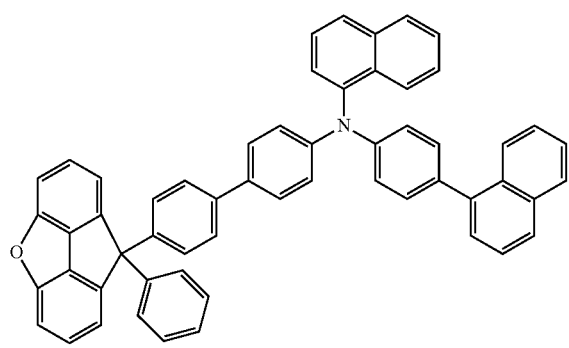
72
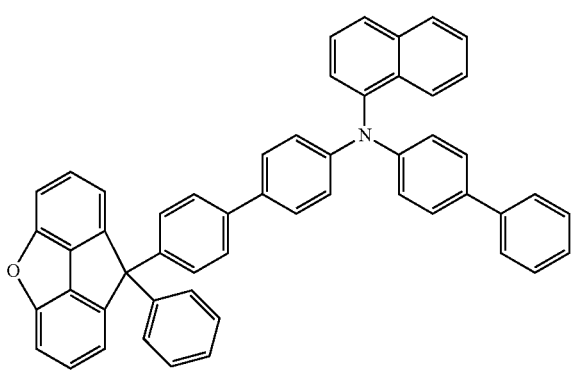
73
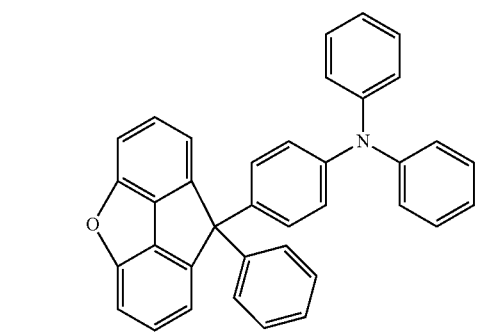
74
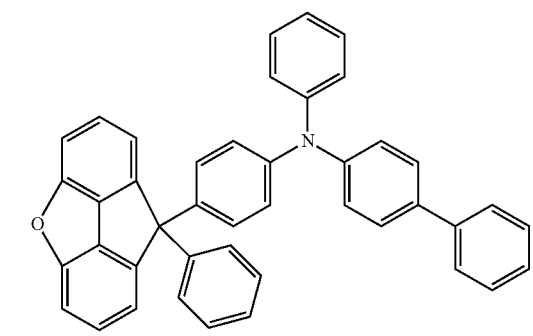
75
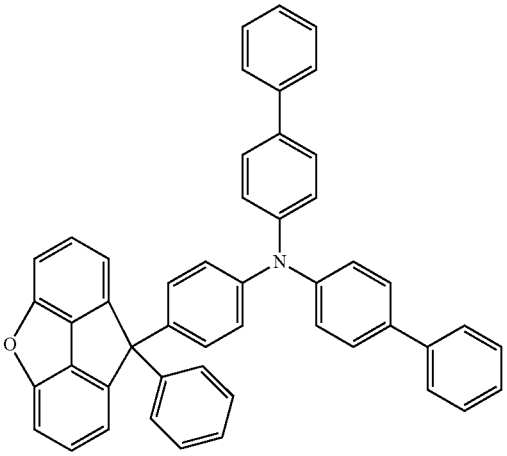
76
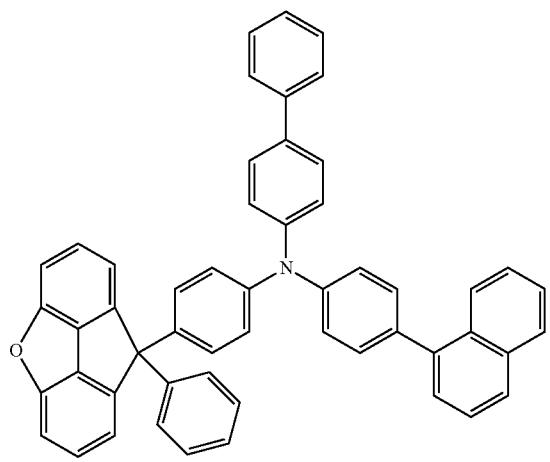
77
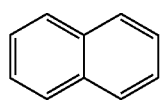
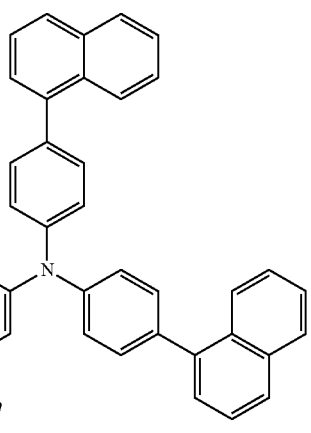

78
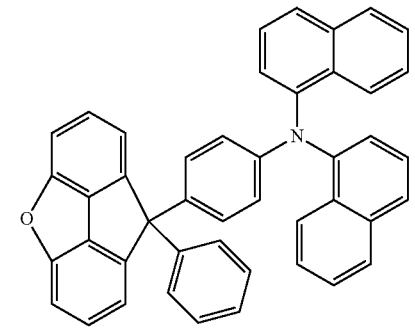
79
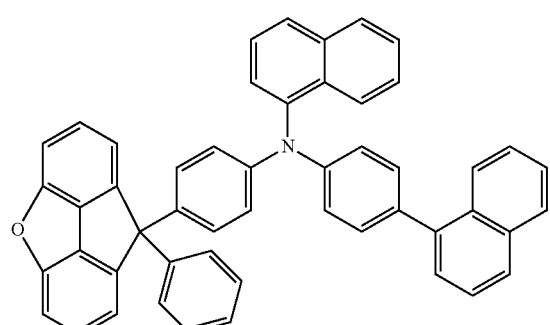
80
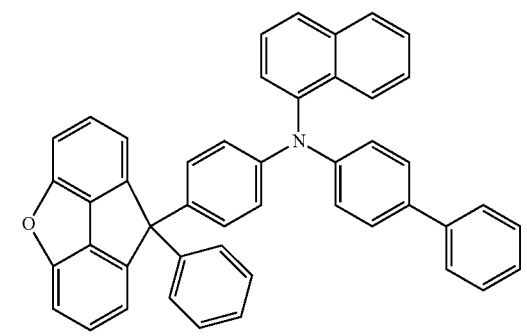
81
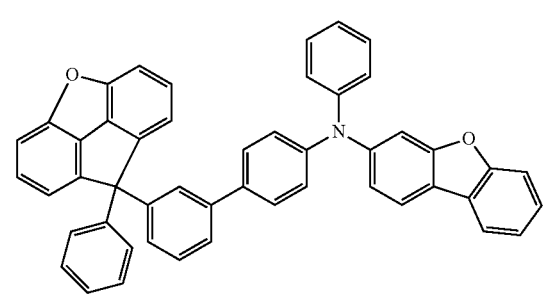
82
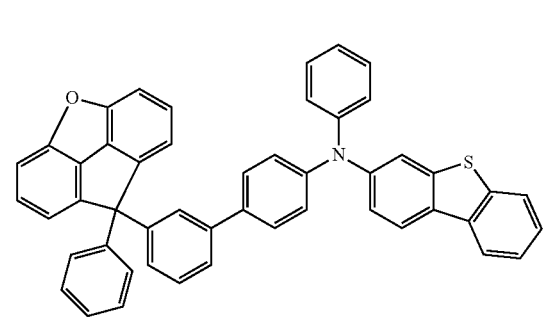
83
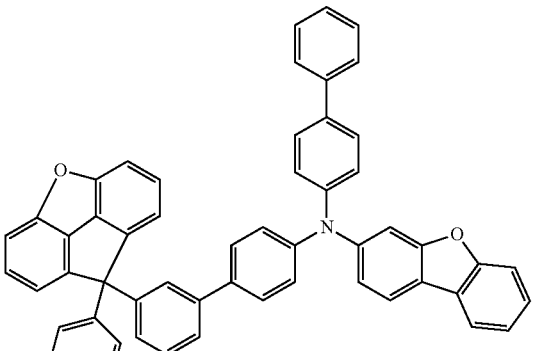
84
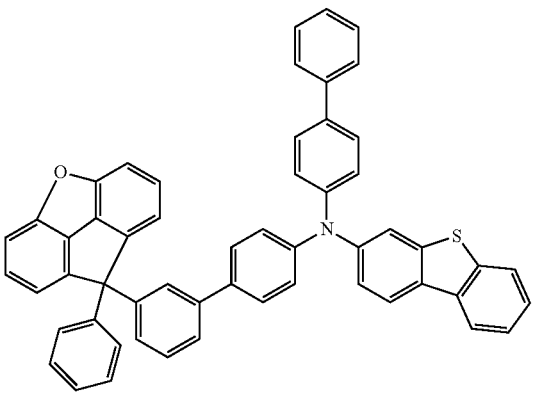
85
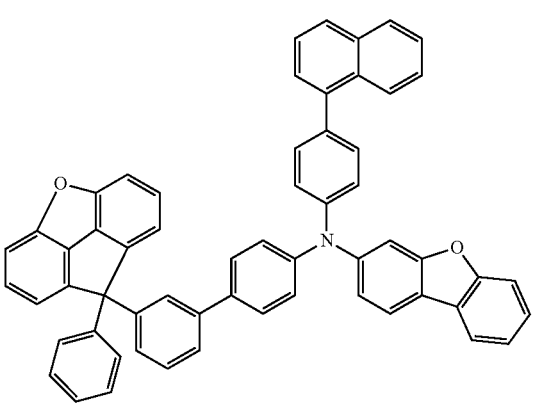
86
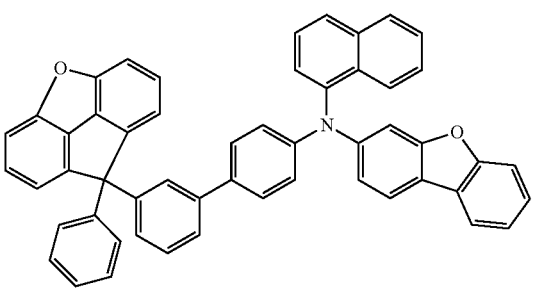

87
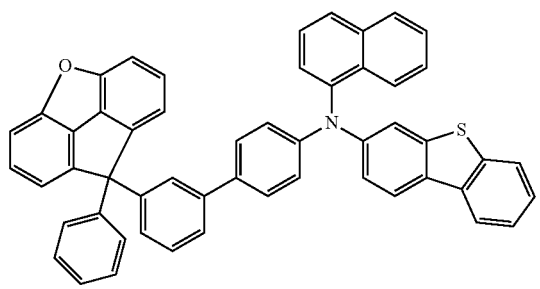
88
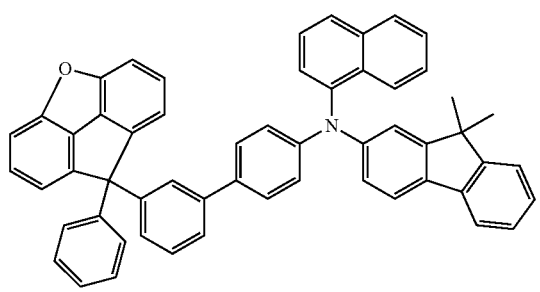
89
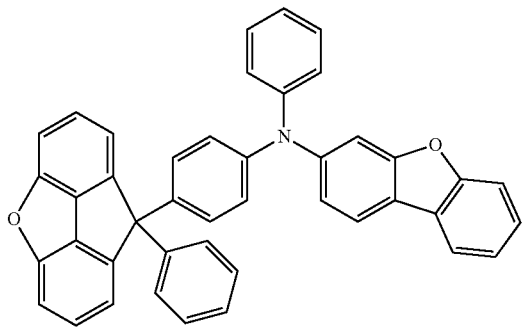
90
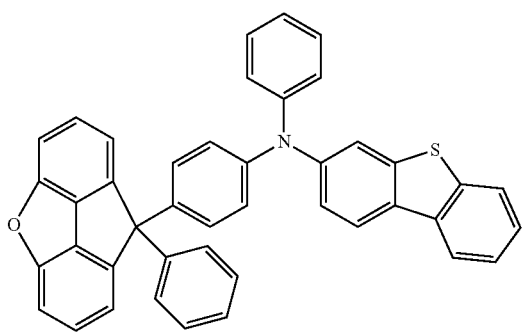
91
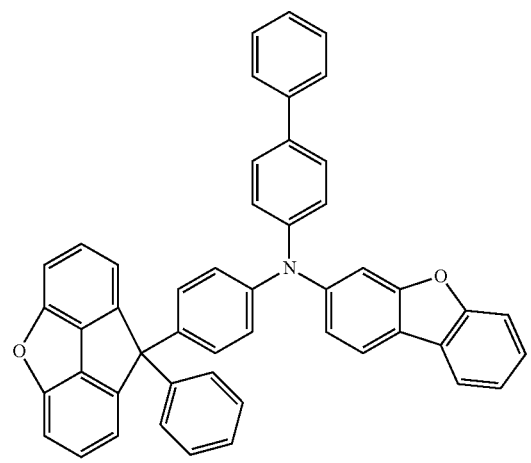
92
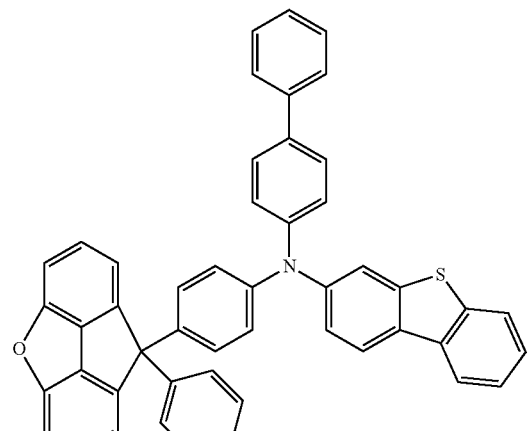
93
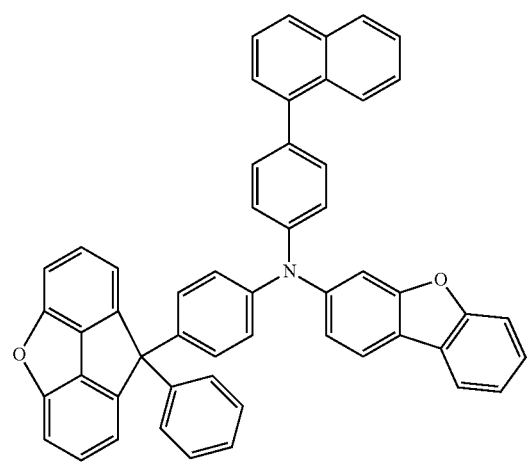

94
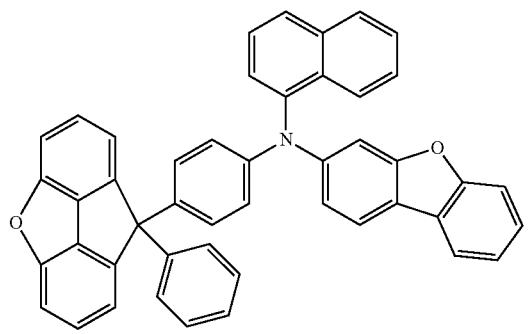
98
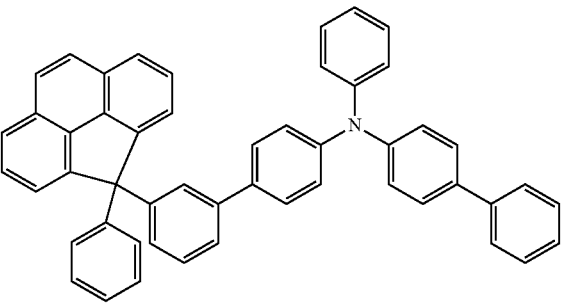
95
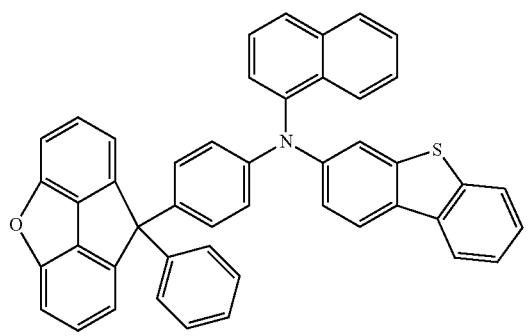
99
96
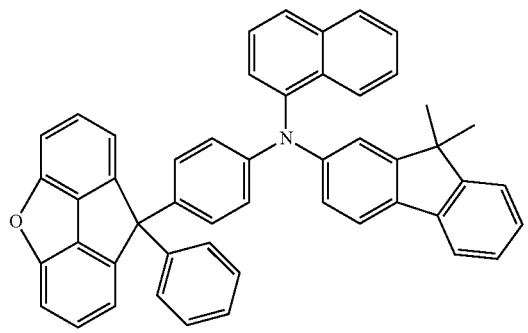
100
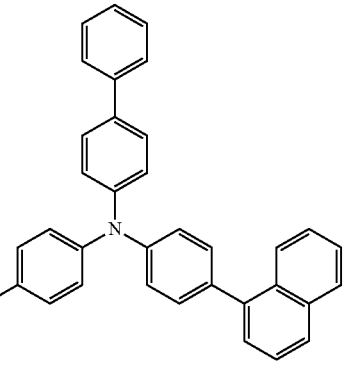
97
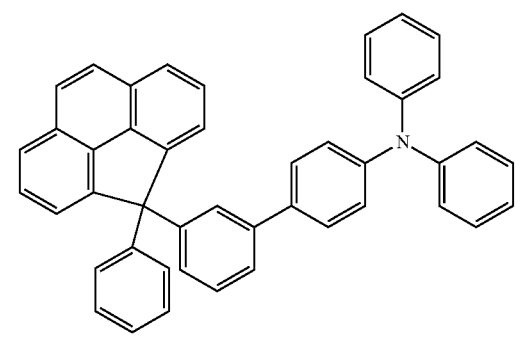
101
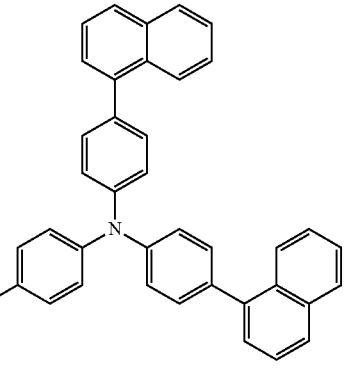

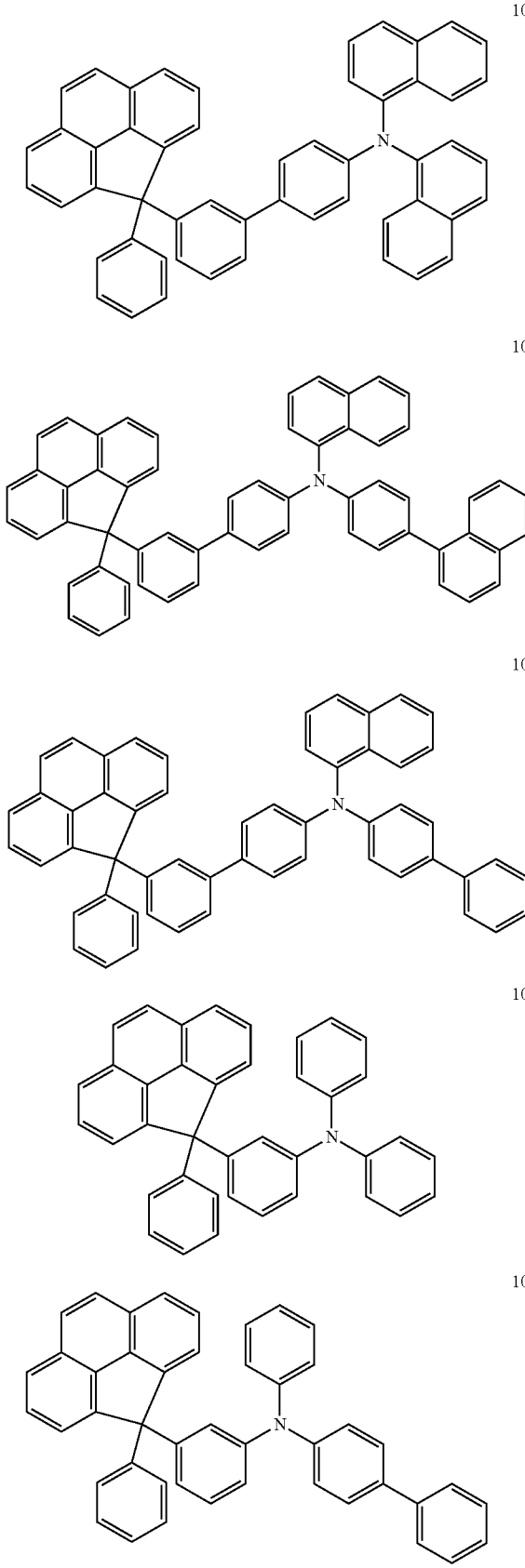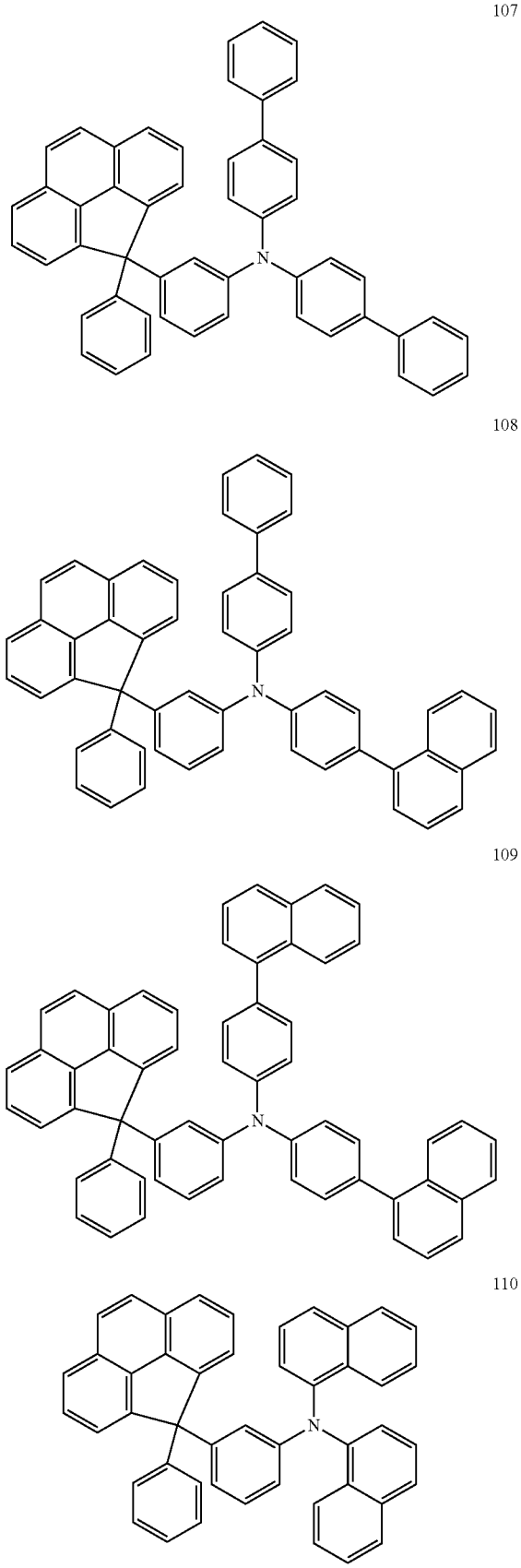

111
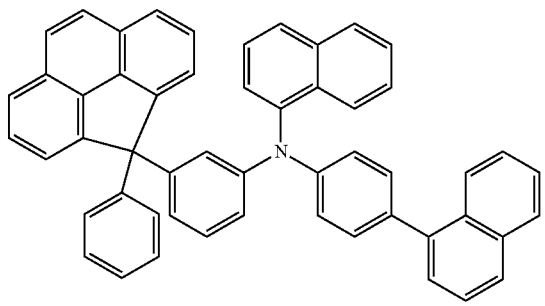
112
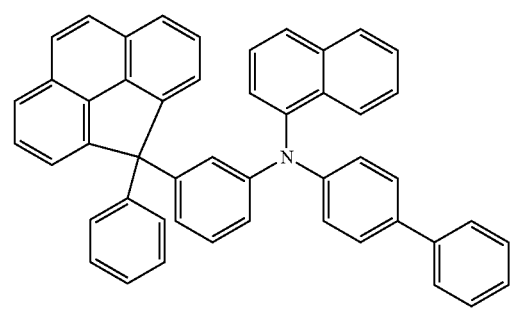
113
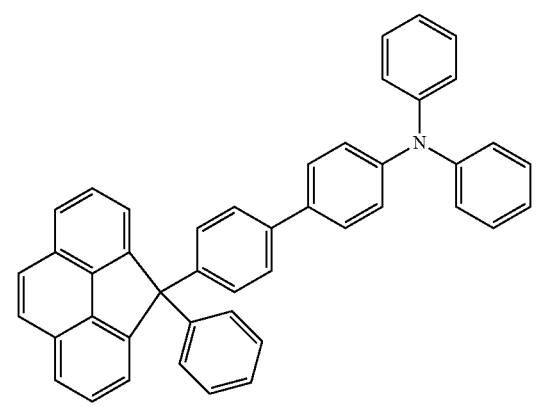
114
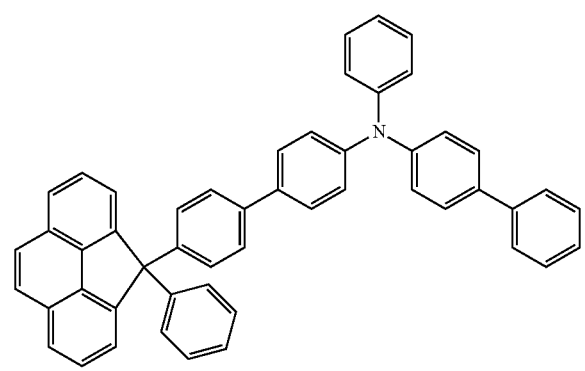
115
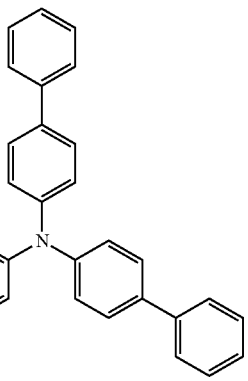
116
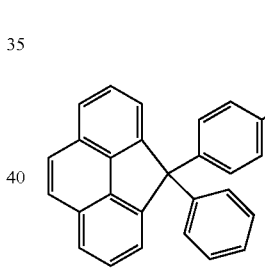
117
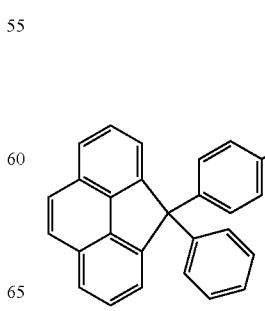

118
119
120
121
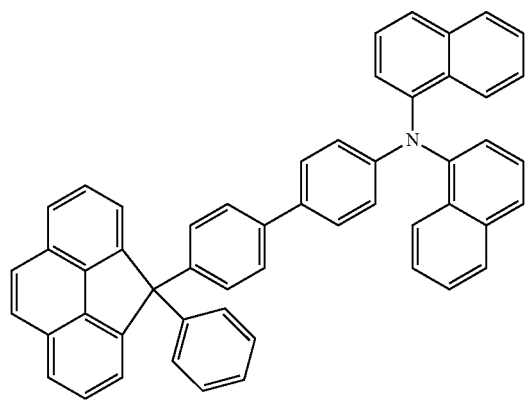
122
123
124
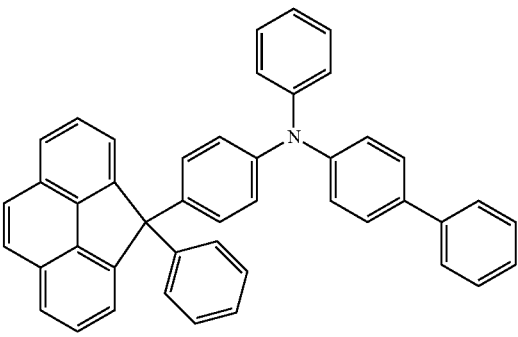
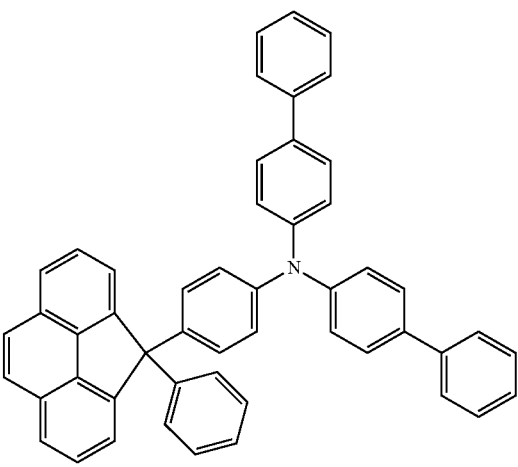
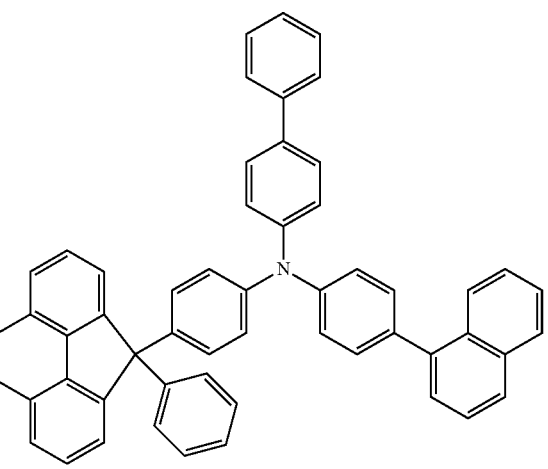

125
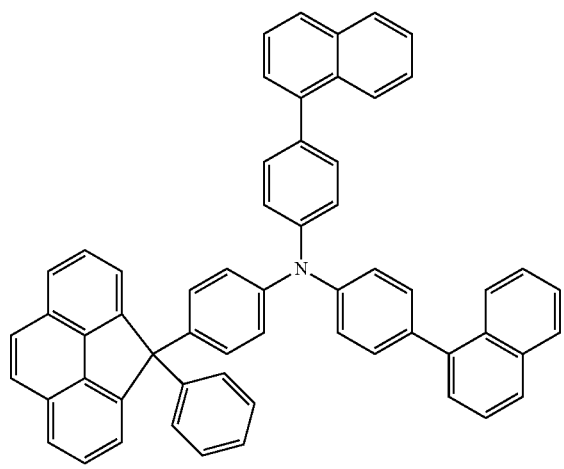
126
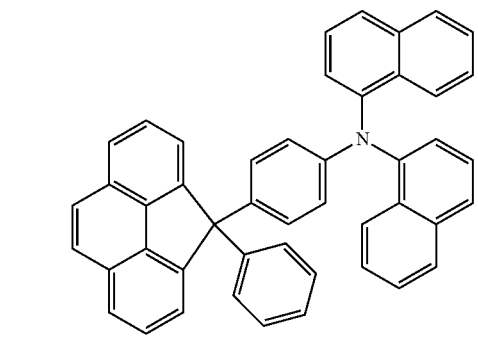
127
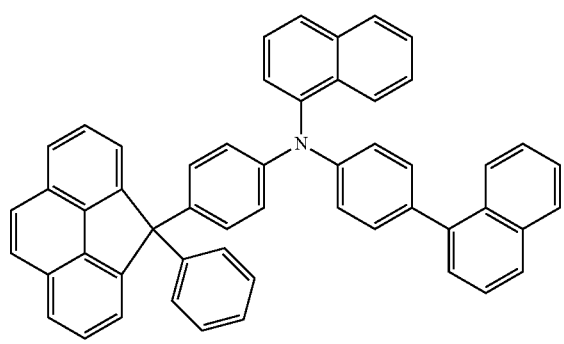
128
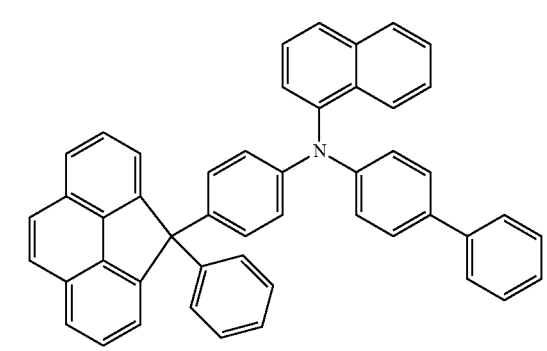
129
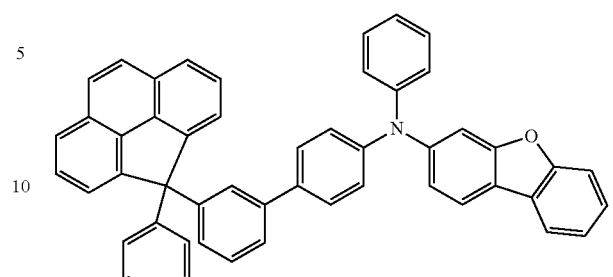
130
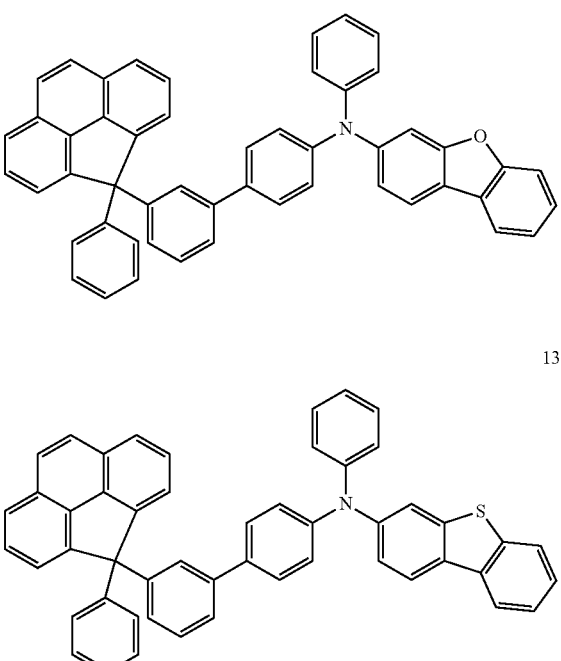
131
132
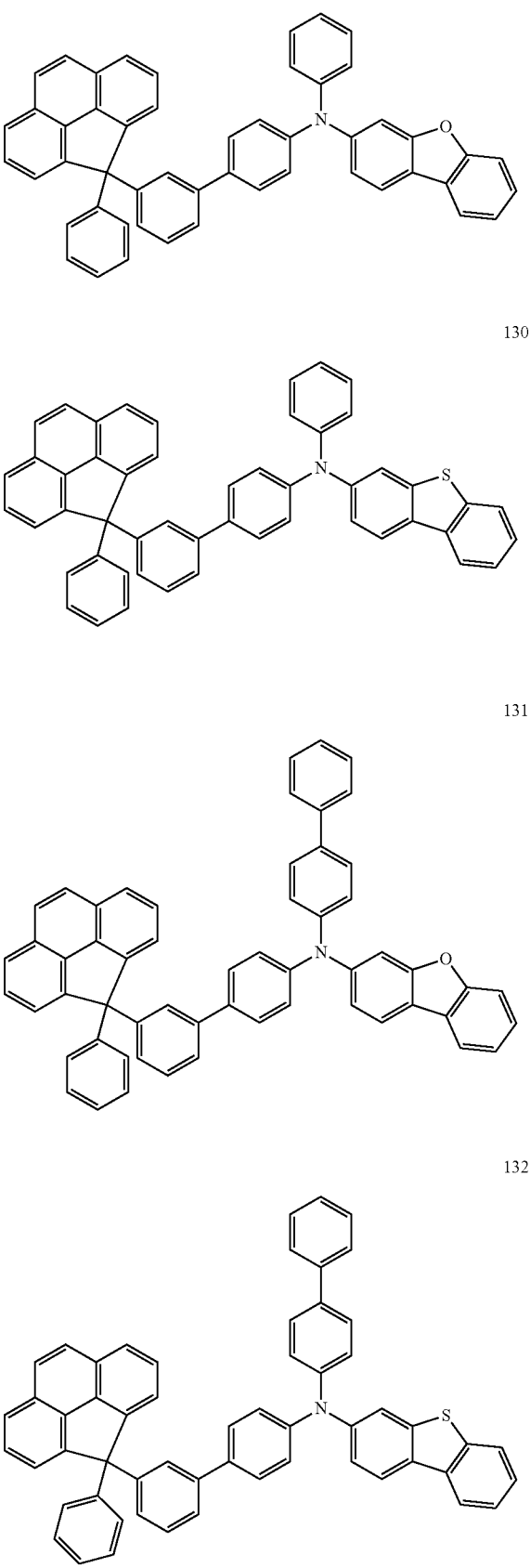

133
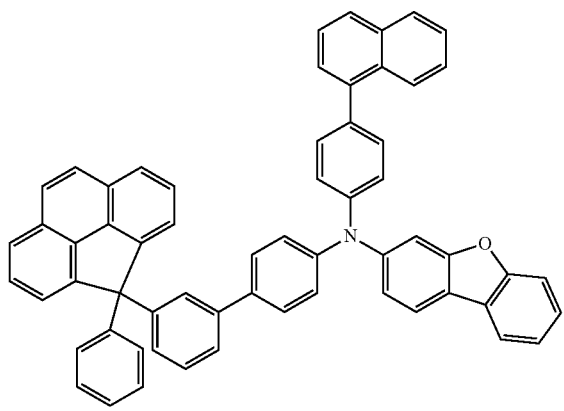
134
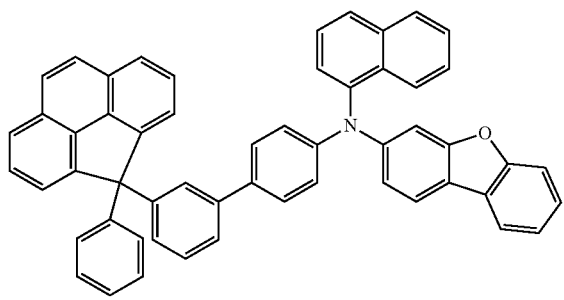
135
136
137
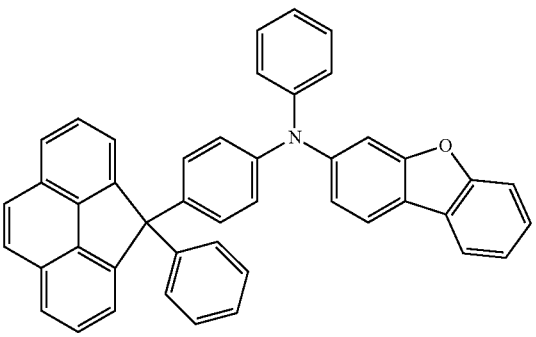
138
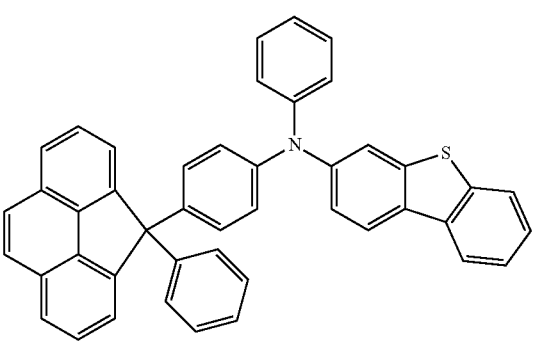
139
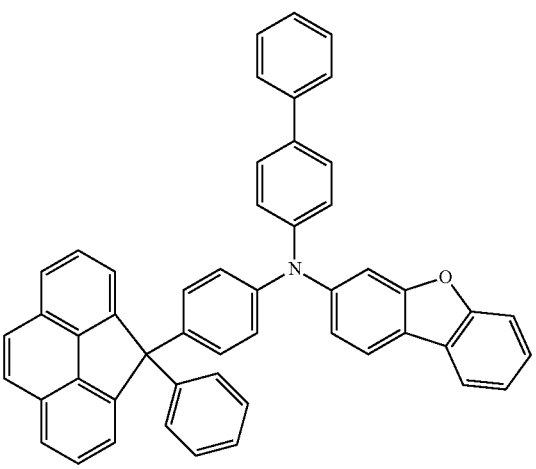

140
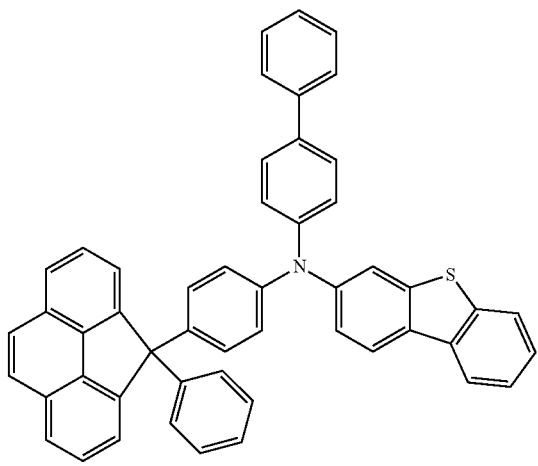
141
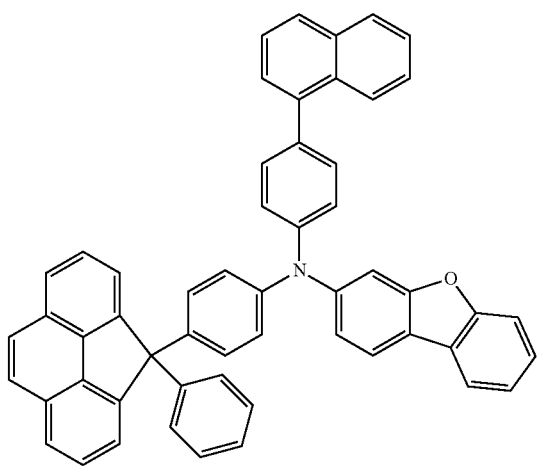
142
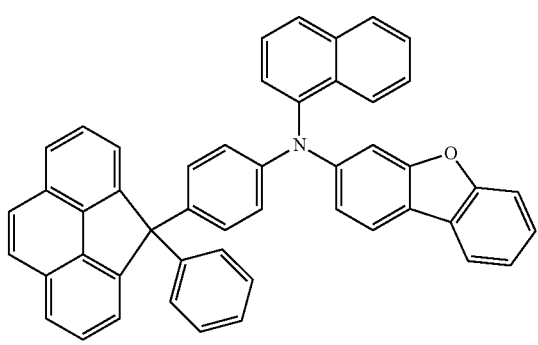
143
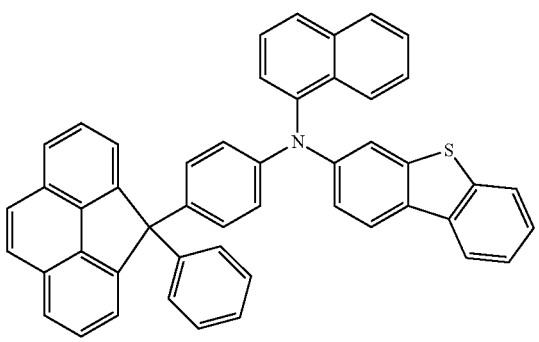
144
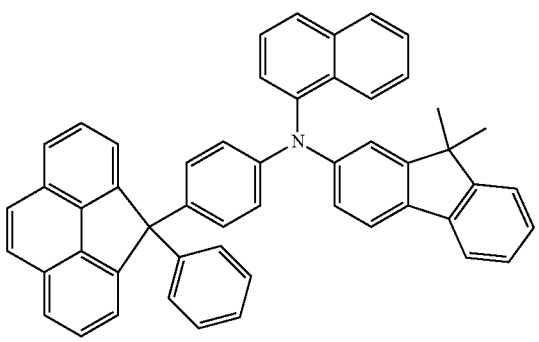
145
146
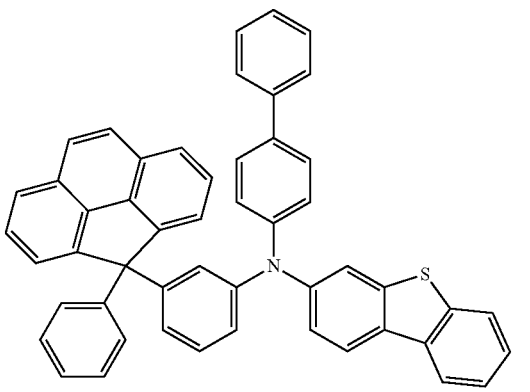

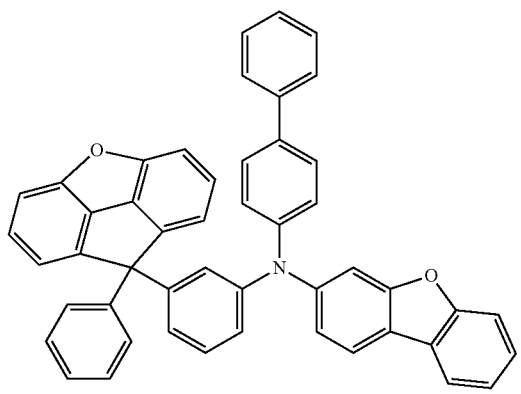

147

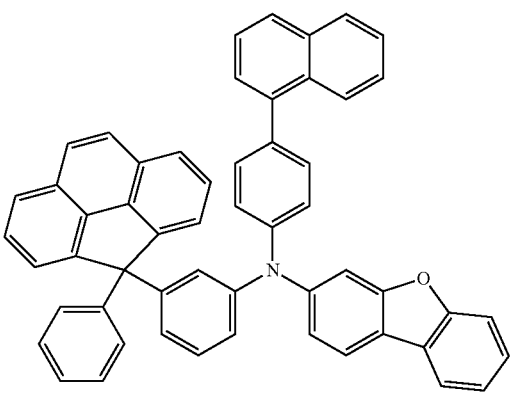

148

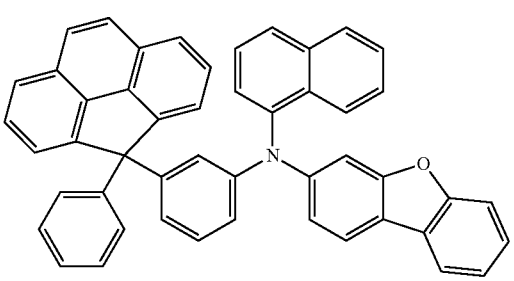

149

150

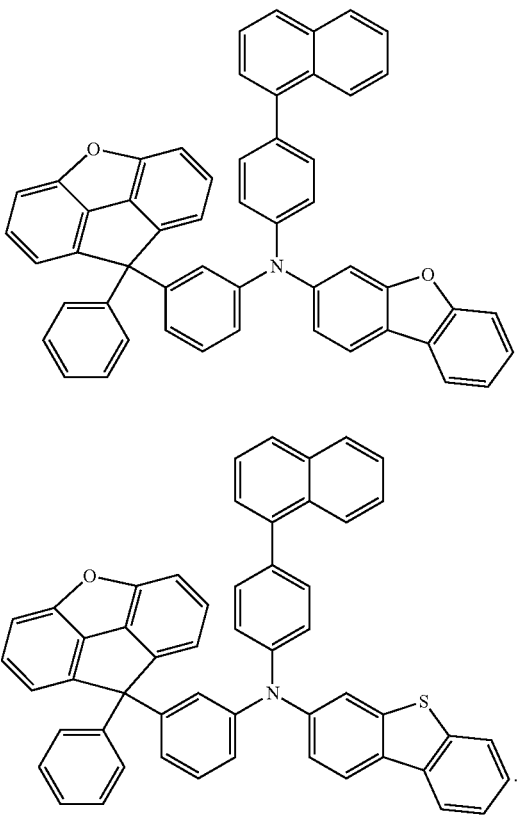

151

152

BRIEF DESCRIPTION OF THE DRAWINGS

The accompanying drawings are included to enable further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
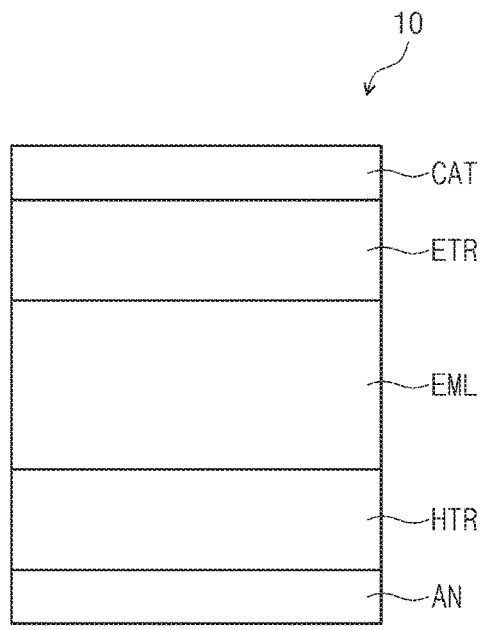
FIG. 1 is a cross-sectional schematic view illustrating the structure of an organic light emitting device according to an embodiment of the present disclosure.

The above objects, other objects, features, and advantages of the present disclosure will be described in more detail according to example embodiments with reference to the accompanying drawings. However, the present disclosure may, be embodied in different forms, and should not be construed as being limited to the example embodiments set forth herein. Rather, these embodiments are provided so that this disclosure will be thorough and complete, and will fully convey the scope of the present disclosure to those skilled in the art.

Like reference numerals refer to like elements throughout the specification, and duplicative descriptions thereof may not be provided. In the drawings, the sizes of thicknesses of layers, films, panels, regions, etc., may be enlarged for clarity. It will be understood that although the terms first, second, etc. may be used herein to describe one or more elements, these elements should not be limited by these terms. These terms are only used to distinguish one element from another element. For example, a first element could be equivalently termed a second element, and similarly, a second element could be equivalently termed a first element. As used herein, the singular forms are intended to include the plural forms as well, unless the context clearly indicates otherwise.

It will be further understood that the terms "comprises" and/or "comprising", when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being cony another part, it can be directly on the other part, or intervening layers may also be present. When a layer, a film, a region, a plate, etc. is referred to as being 'under' another part, it can be directly under the other part, or intervening layers may also be present.

Hereinafter, an amine compound according to an embodiment of the present disclosure will be explained in more detail.

An amine compound according to an embodiment of the present disclosure may be represented by Formula 1:

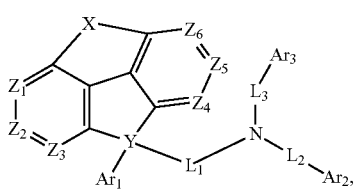

Formula 1 wherein X may be selected from the compounds in Formula 2:

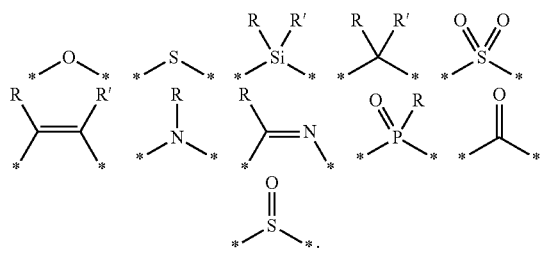

Formula 2

In Formulae 1 and 2,
Y may be C, Si, or Ge,
$Z_1$ to $Z_6$ may each independently be CR or N,
$Ar_1$ to $Ar_3$ may each independently be hydrogen, deuterium, a halogen atom, a substituted or unsubstituted aryl group having 6 to 30 carbon atoms for forming a ring, a substituted or unsubstituted heteroaryl group having 5 to 30 carbon atoms for forming a ring, an alkyl group having 1 to 20 carbon atoms, or a silyl group having 3 to 20 carbon atoms, $L_1$ to $L_3$ may each independently be a direct linkage, a substituted or unsubstituted arylene group having 6 to 30 carbon atoms for forming a ring, or a substituted or unsubstituted heteroarylene group having 5 to 30 carbon atoms for forming a ring, and R and R' may each independently be hydrogen, deuterium, a substituted or unsubstituted aryl group having 6 to 30 carbon atoms for forming a ring, a substituted or unsubstituted heteroaryl group having 5 to 30 carbon atoms for forming a ring, or an alkyl group having 1 to 20 carbon atoms.

Adjacent R and R' may combine (e.g., link or couple) with each other to form a ring.

In the description, the term "substituted or unsubstituted" may refer to: i) a substituted or unsubstituted group with at least one substituent selected from deuterium, a halogen group (e.g., halogen atom), a nitrile group, a nitro group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, and a heterocyclic group, or ii) a substituted or unsubstituted group with a substituent obtained by connecting at least two of the above-described substituents. For example, the substituent obtained by connecting at least two substituents may be a biphenyl group. The biphenyl group may be interpreted as an aryl group or may be interpreted as a substituent obtained by connecting two phenyl groups.

The aryl group may be a monocyclic aryl group or a polycyclic aryl group. The monocyclic aryl group may be, for example, a phenyl group, a biphenyl group, a terphenyl group, etc. The polycyclic aryl group may be a naphthyl group, an anthracenyl group, a phenanthryl group, a pyrenyl group, a perylenyl group, a chrysenyl group, a fluorenyl group, etc.

The fluorenyl group may be substituted, and two or more fluorenyl group substituents may combine to form a spiro structure. In the case where the fluorenyl group is substituted,

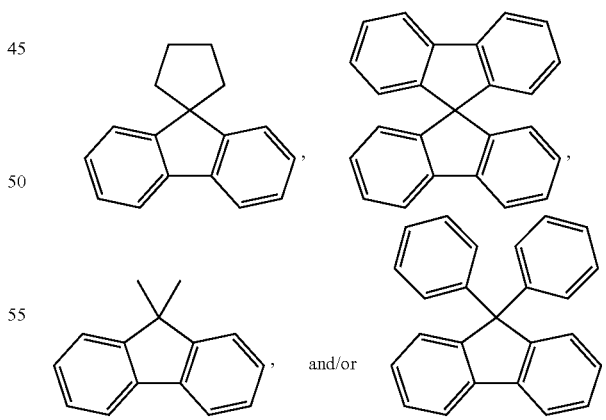

, , , and/or may be obtained. However embodiments of the present disclosure are not limited thereto.

The silyl group may be, for example, a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc.

The alkyl group may be, for example, methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimehtylbutyl, 2-ethylbutyl, heptyl, n-heptyl, 1-methylhexyl, cyclopentylmethyl, cyclohexylmethyl, octyl, n-octyl, tert-octyl, 1-methylhexyl, 2-ethylhexyl, 2-propylpentyl, n-nonyl, 2,2-dimethylheptyl, 1-ethyl-propyl, 1,1-dimethyl-propyl, isohexyl, 2-methylhexyl, 4-methylhexyl, 5-methylhexyl, etc., without limitation.

The formation of a ring via the combination (e.g., coupling) of adjacent groups may refer to that adjacent groups may combine (e.g., couple) to form a substituted or unsubstituted aliphatic hydrocarbon ring, a substituted or unsubstituted aromatic hydrocarbon ring, a substituted or unsubstituted aliphatic heterocyclic ring, or a substituted or unsubstituted aromatic heterocyclic ring.

In the description, the term "adjacent groups" may refer to substituents on atoms that are directly connected with each other, substituents that are positioned near each other in the three-dimensional structure, and/or two or more substituents substituted on a single atom. For example, two substituents at ortho positions in a benzene ring, and two substituents on the same carbon in an aliphatic ring may both be interpreted as being "adjacent groups".

$L_1$ may be a direct linkage, a substituted or unsubstituted divalent phenyl group, or a substituted or unsubstituted divalent biphenyl group. When $L_1$ is a substituted or unsubstituted divalent phenyl group, an amine group ring and Y may be combined (e.g., coupled) via positions 1 and 3 or positions 1 and 4 of the phenyl group.

$Ar_2$ may be a substituted or unsubstituted phenyl group, a substituted or unsubstituted naphthyl group, a substituted or unsubstituted dibenzofuranyl group, a substituted or unsubstituted dibenzothiophene group, or a substituted or unsubstituted fluorenyl group.

$Ar_3$ may be a substituted or unsubstituted phenyl group, a substituted or unsubstituted biphenyl group, or a substituted or unsubstituted naphthyl group.

Formula 1 may be represented by Formula 3:

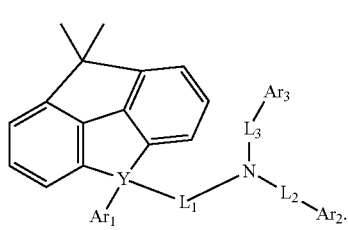

Formula 3

Formula 1 may be represented by Formula 9:

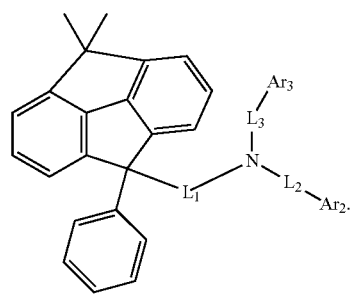

Formula 9

Formula 1 may be represented by Formula 4:

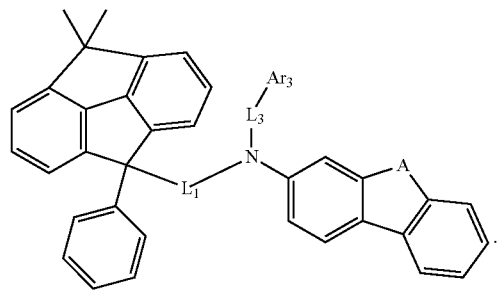

Formula 4

In Formula 4, A may be O, S, or $CR_2R_3$. $R_2$ and $R_3$ may each independently be hydrogen, deuterium, an alkyl group having 1 to 20 carbon atoms, a substituted or unsubstituted aryl group having 6 to 30 carbon atoms for forming a ring, or a substituted or unsubstituted heteroaryl group having 5 to 30 carbon atoms for forming a ring.

Formula 1 may be represented by Formula 5:

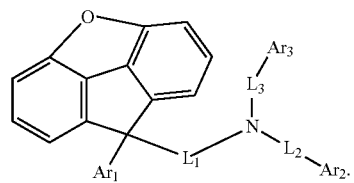

Formula 5

Formula 1 may be represented by Formula 10:

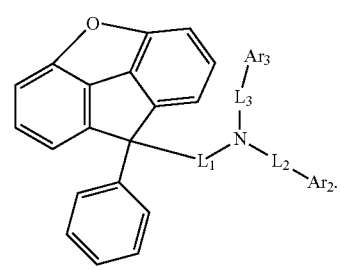

Formula 10

Formula 1 may be represented by Formula 6:

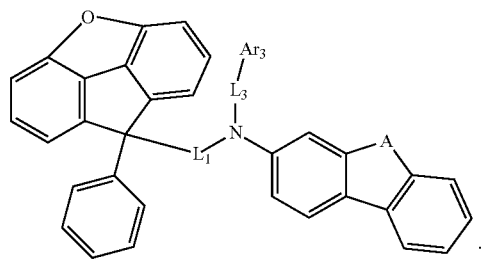

Formula 6

In Formula 6, A may be O, S, or $CR_2R_3$. $R_2$ and $R_3$ may be the same as defined above.

Formula 1 may be represented by Formula 7:

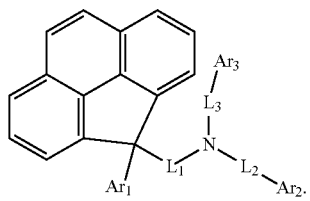

Formula 7

Formula 1 may be represented by Formula 11:

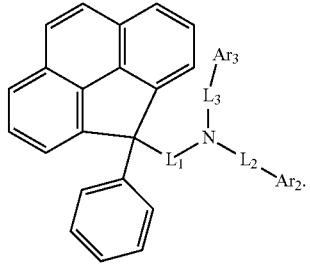

Formula 11

Formula 1 may be represented by Formula 8:

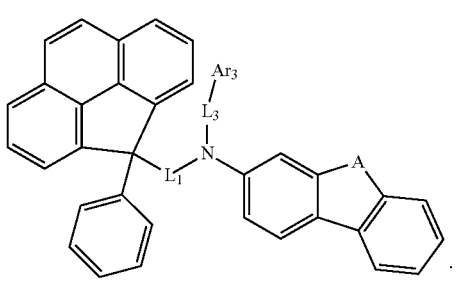

Formula 8

In Formula 8, A may be O, S, or $CR_2R_3$. $R_2$ and $R_3$ may be the same as defined above In Formulae 3 to 8, $L_1$ to $L_3$ and $Ar_1$ to $Ar_3$ may each independently be the same as described herein in connection with Formula 1.

Formula 1 may be selected from the compounds represented by Compound Group 1:

Compound Group 1

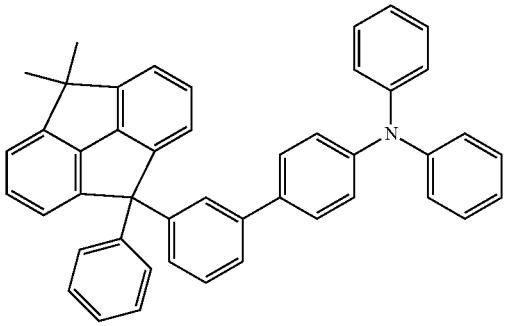

1

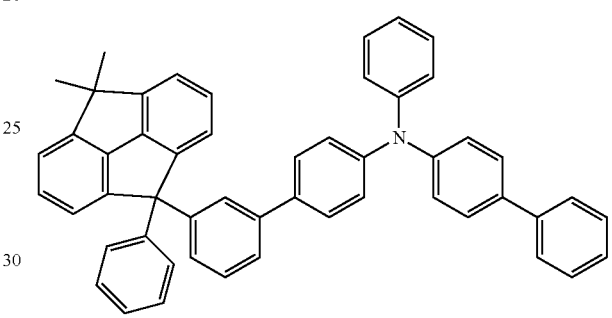

2

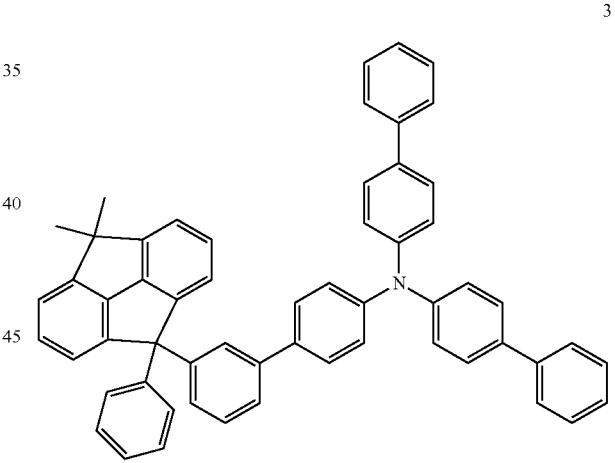

3

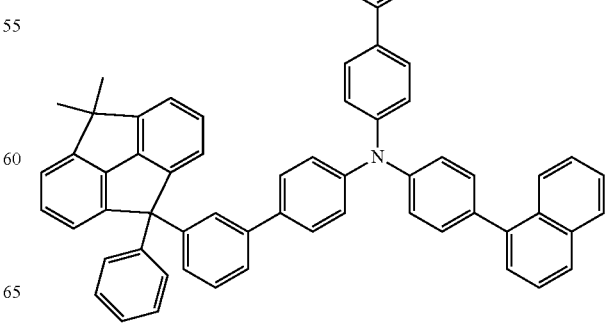

4

5
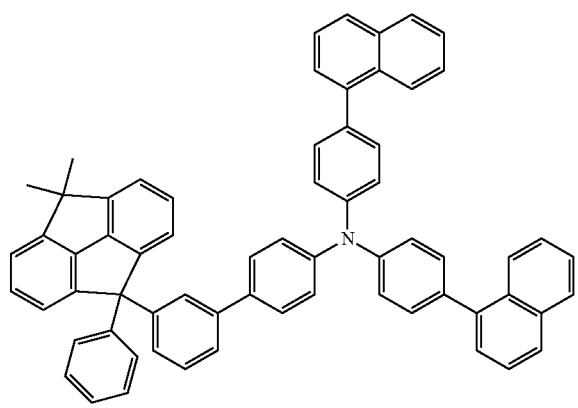
6
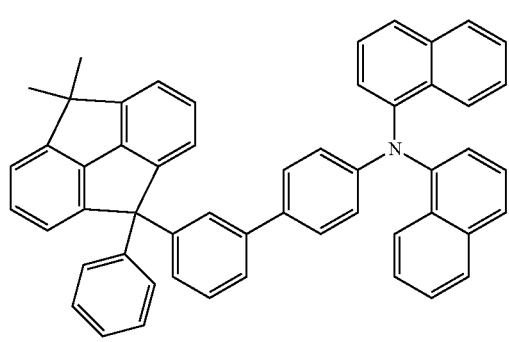
7
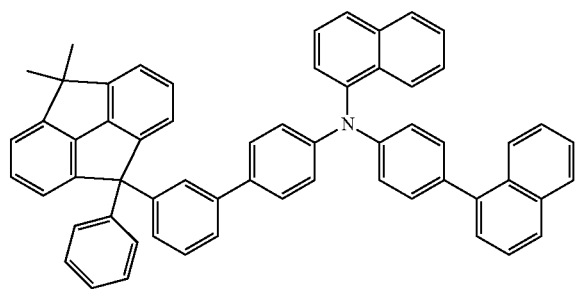
8
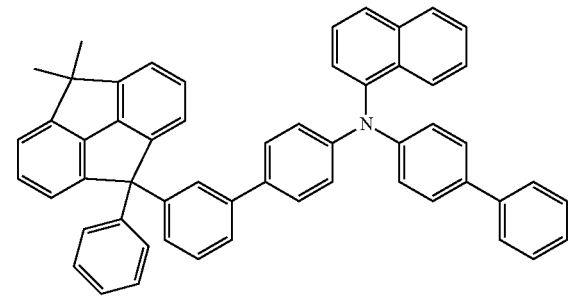
9
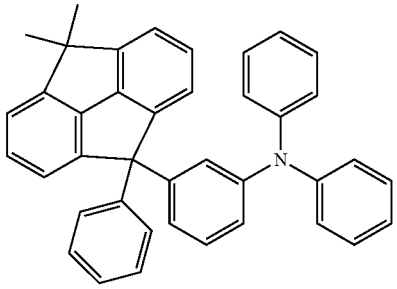
10
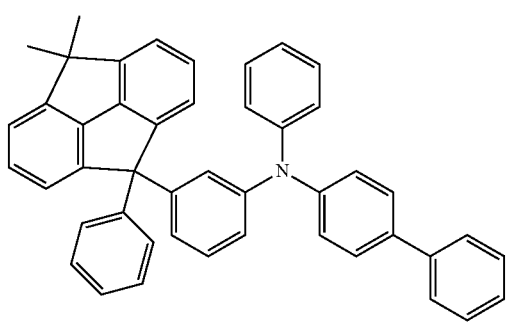
11
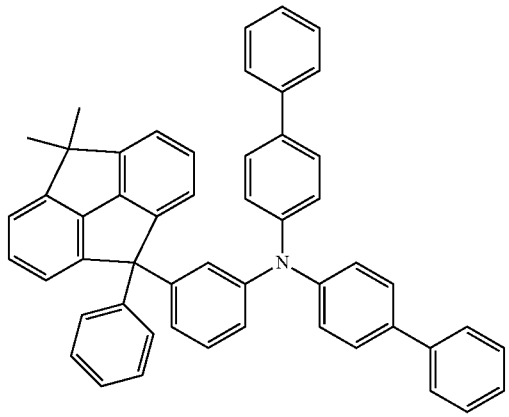
12
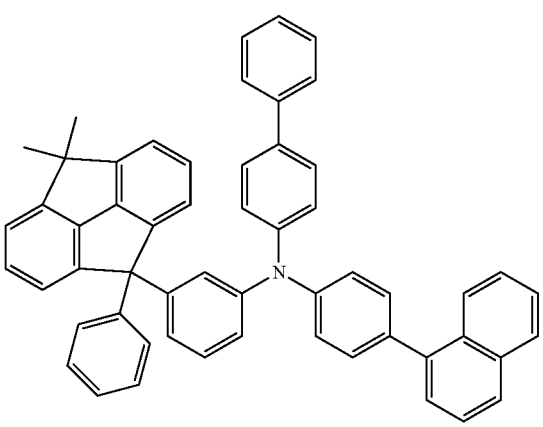

13
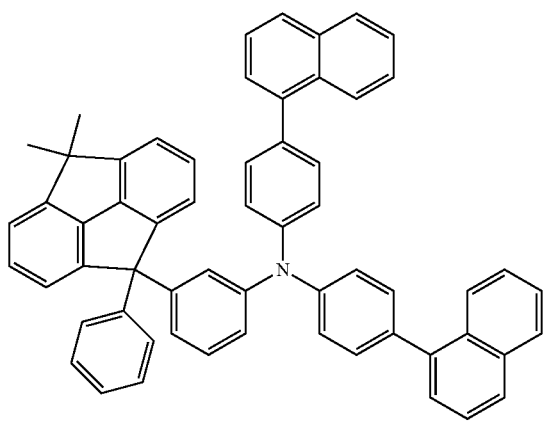
14
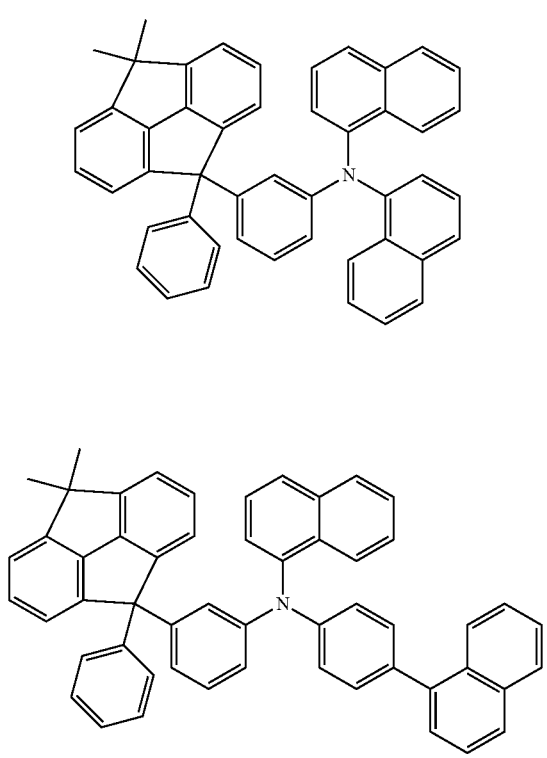
15
16
17
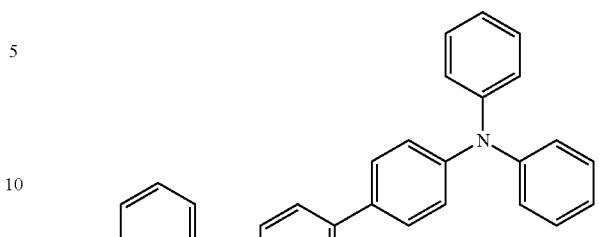
18
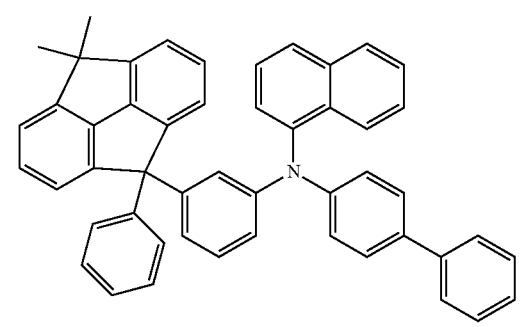
19
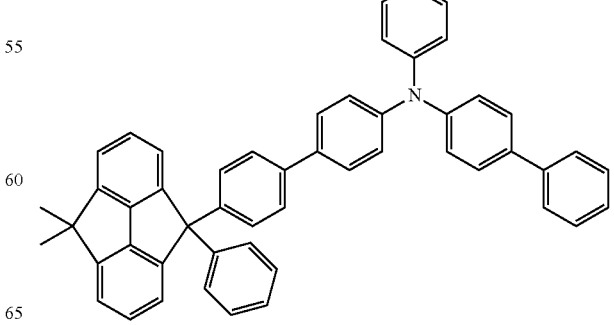

20
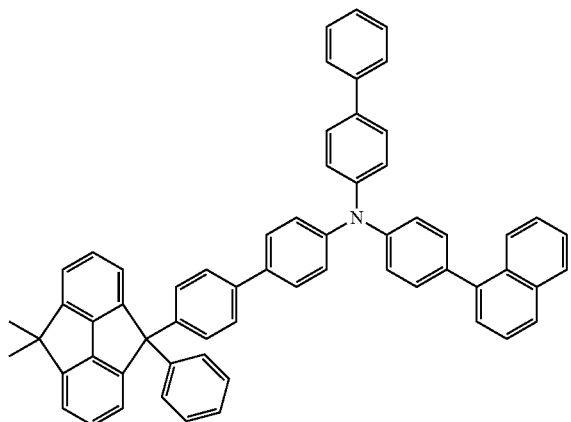
21
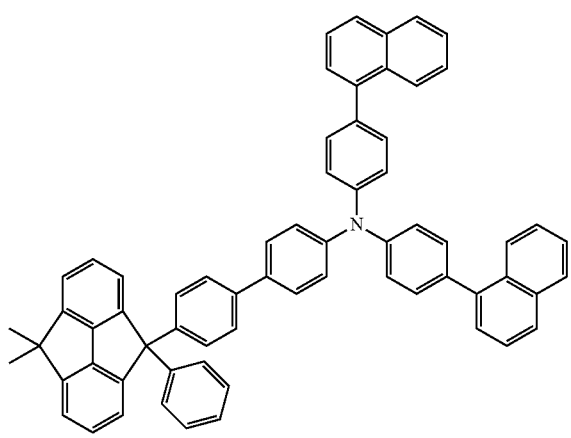
22
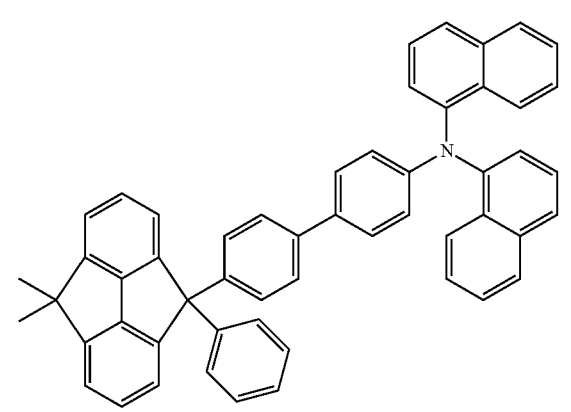
23
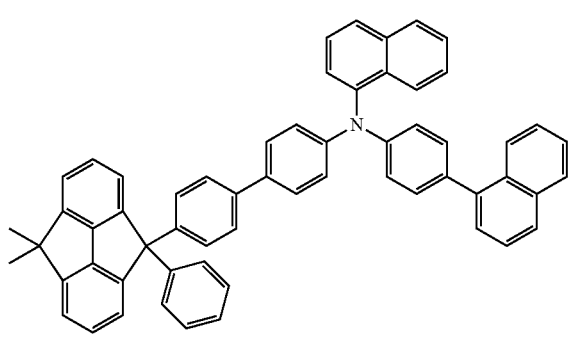
24
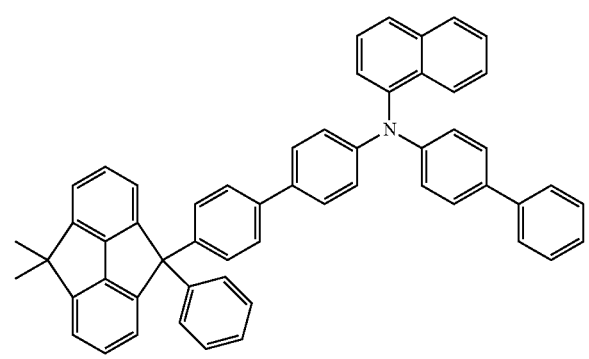
25
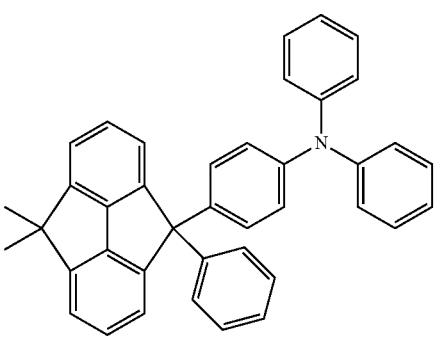
26
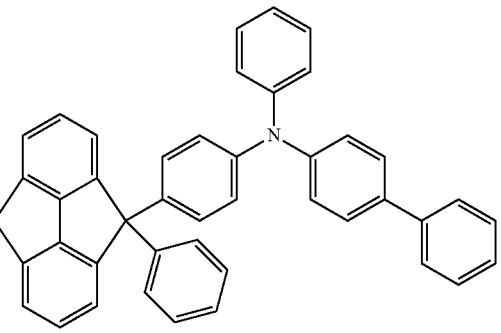
27
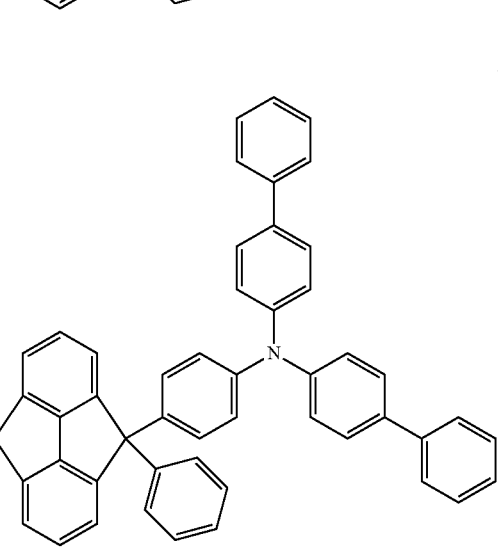

-continued
28
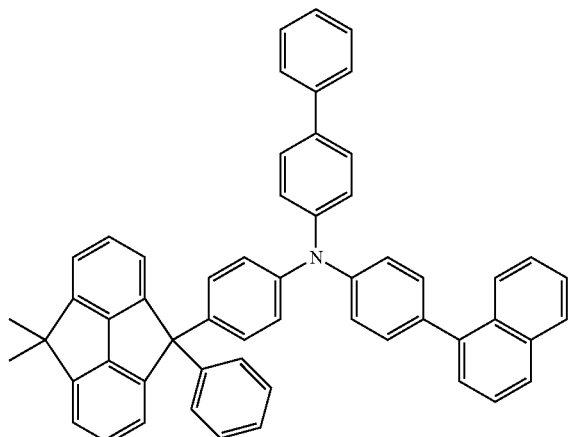
29
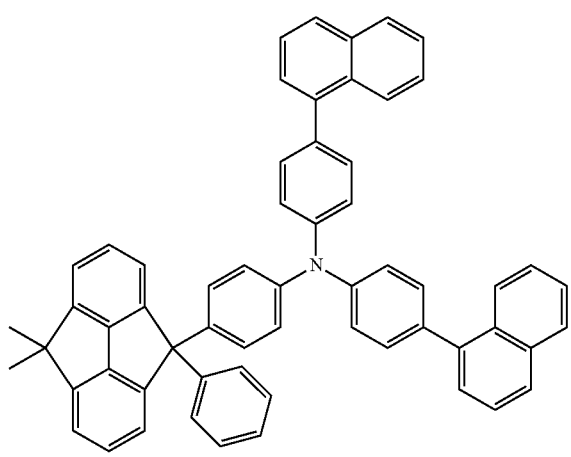
30
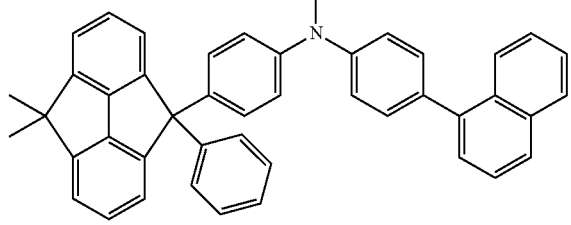
31
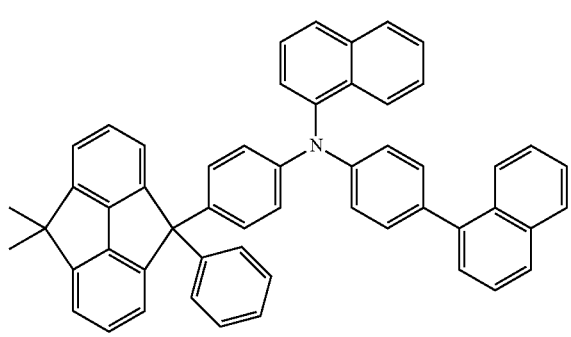
-continued
32
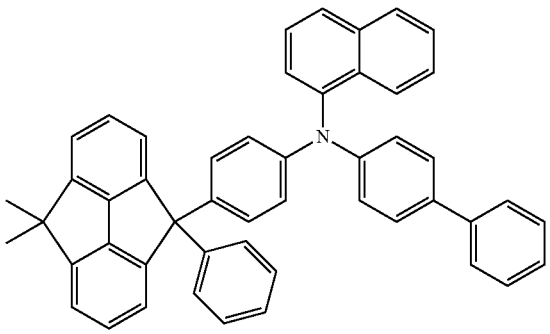
33
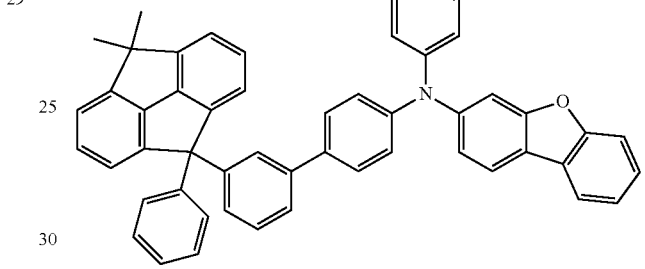
34
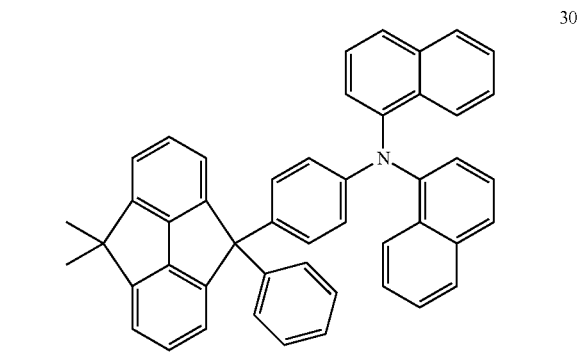
35
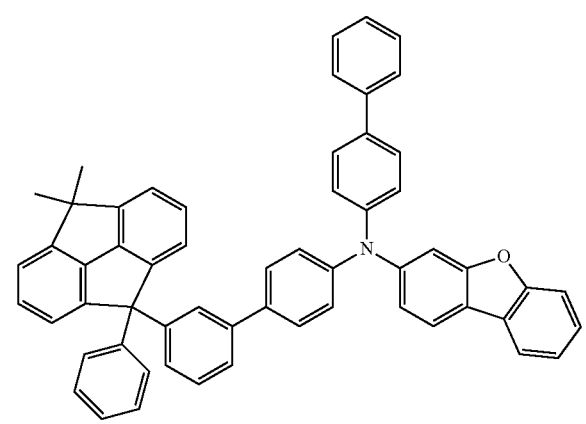

101
-continued
36
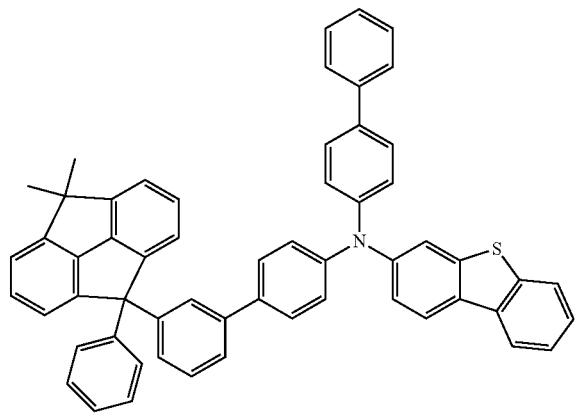
37
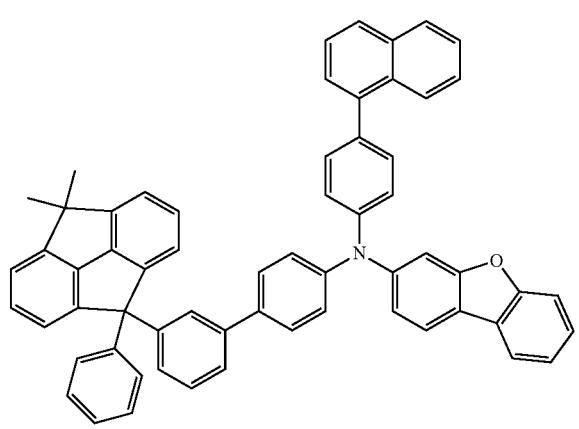
38
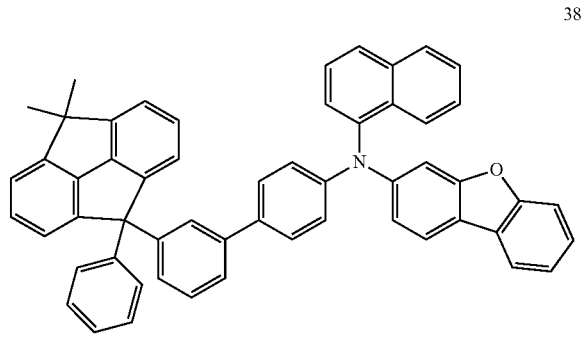
39
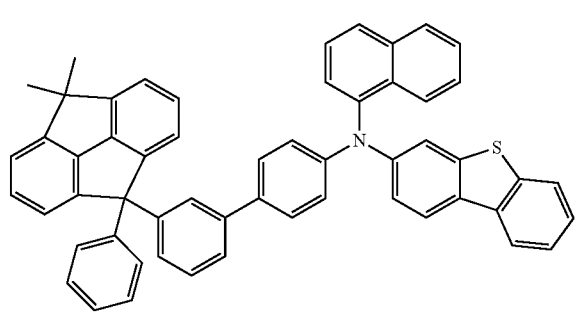
102
-continued
40
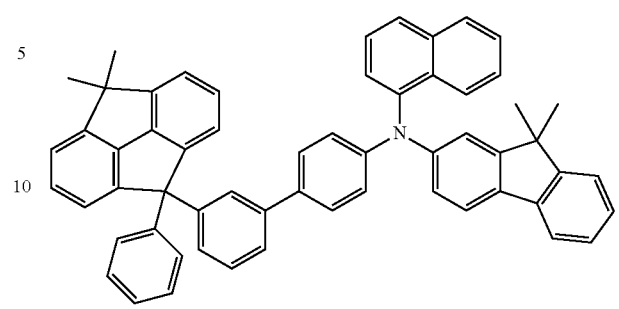
41
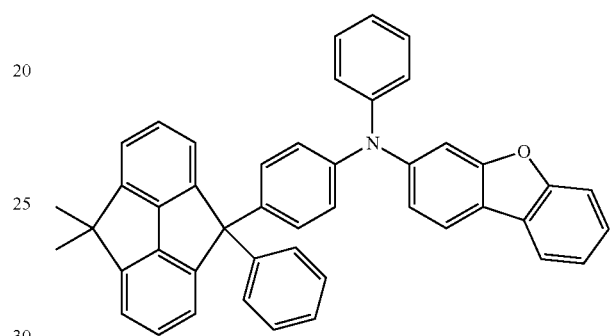
42
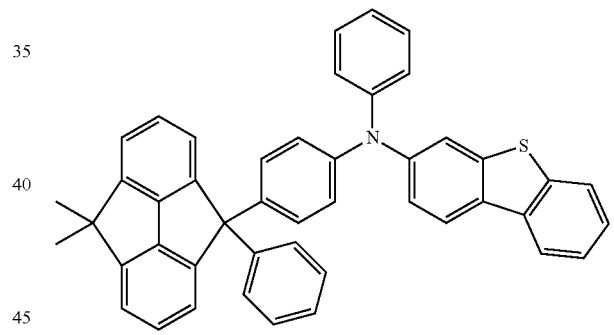
43
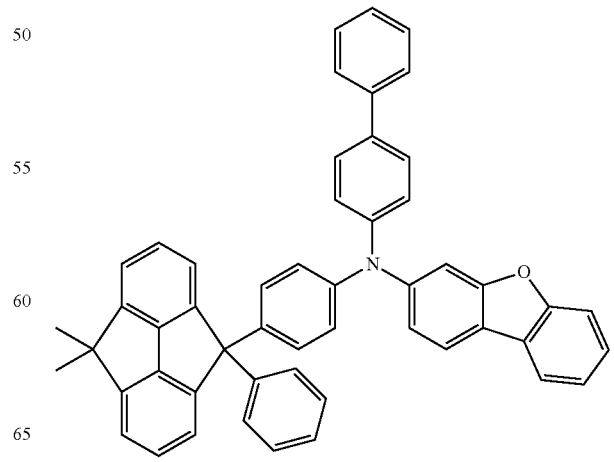

44
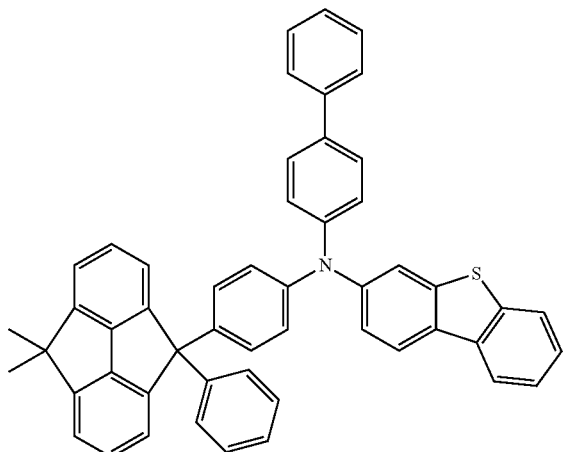
45
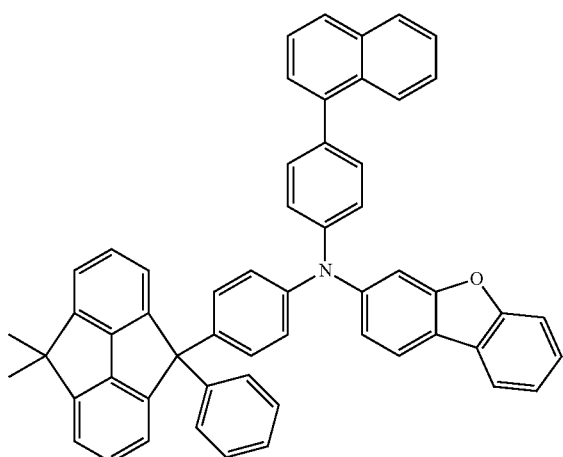
46
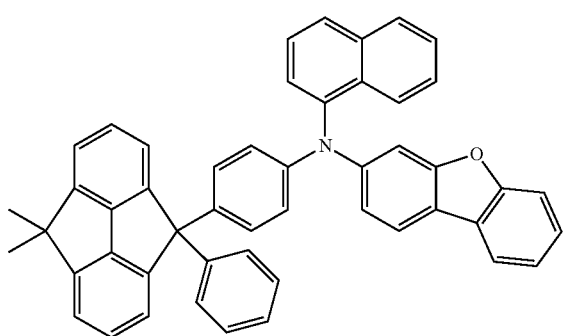
47
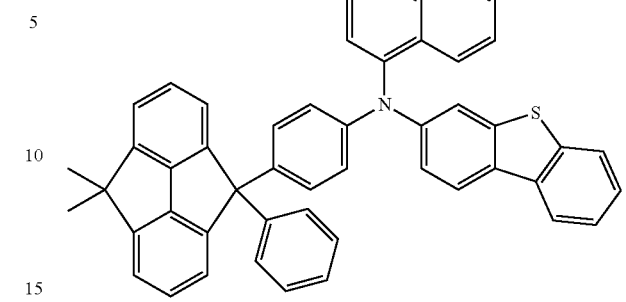
48
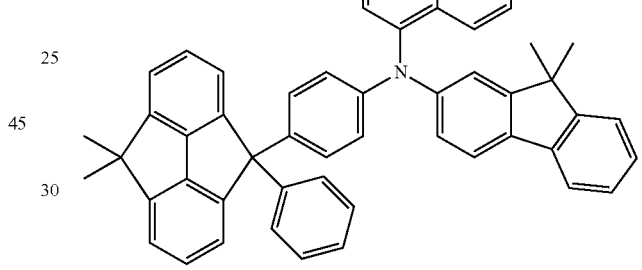
49
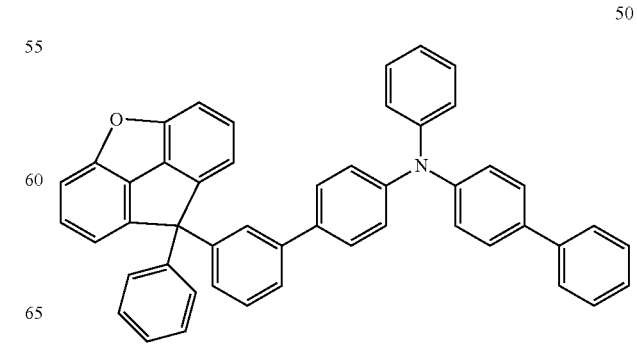
50

51
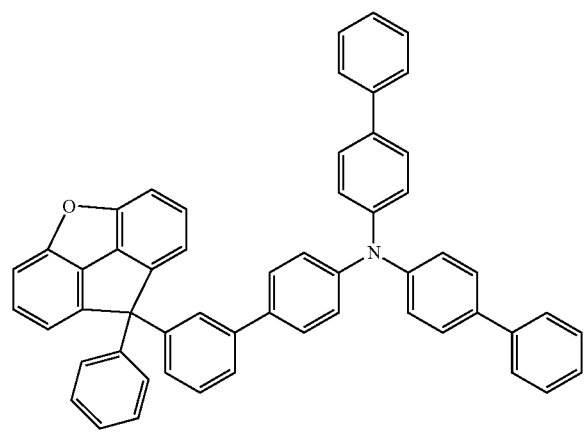
52
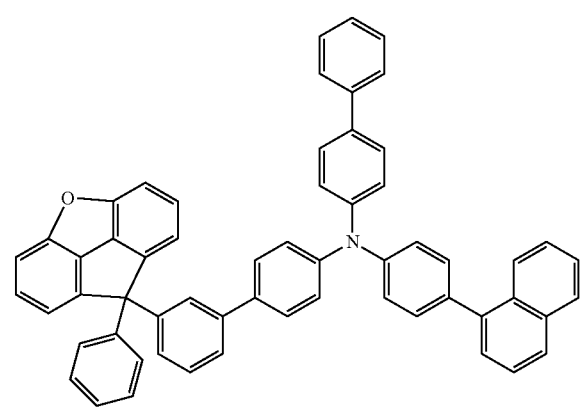
53
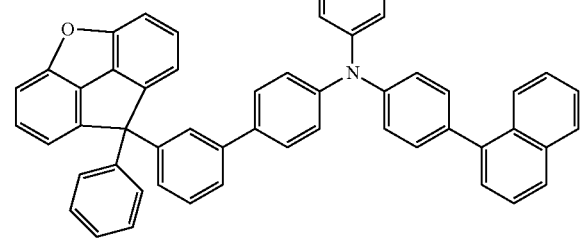
54
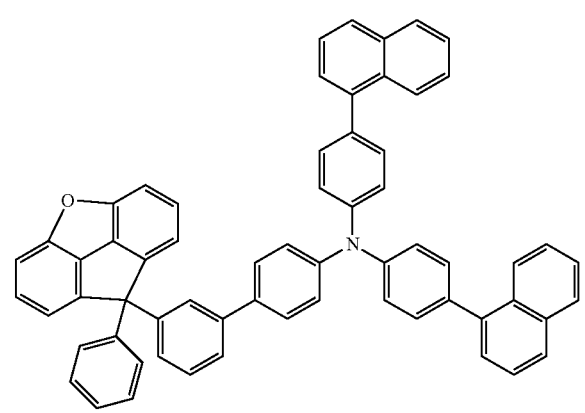
55
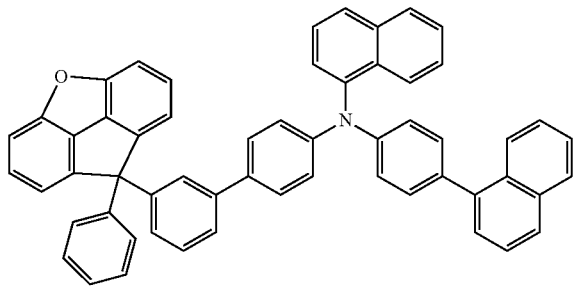
56
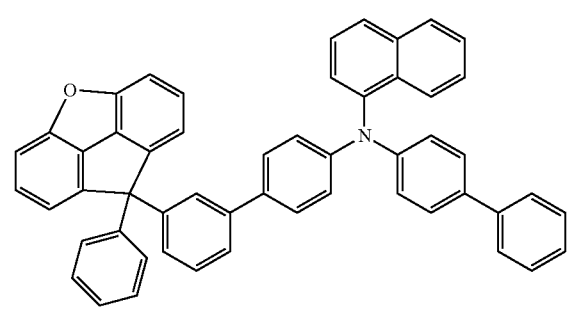
57
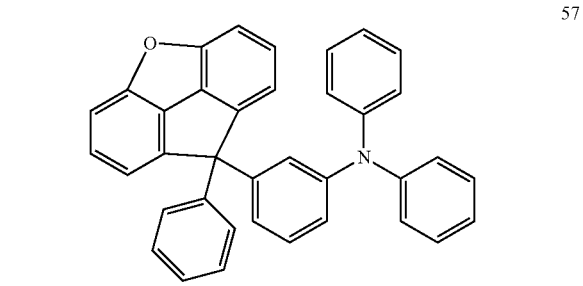
58
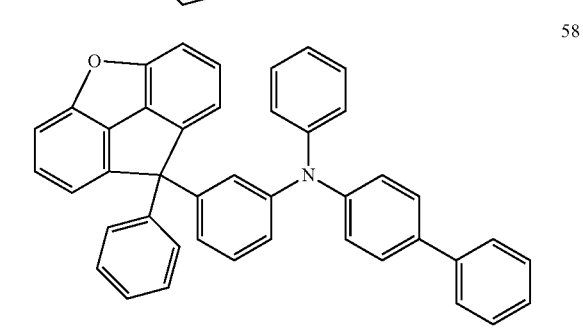
59
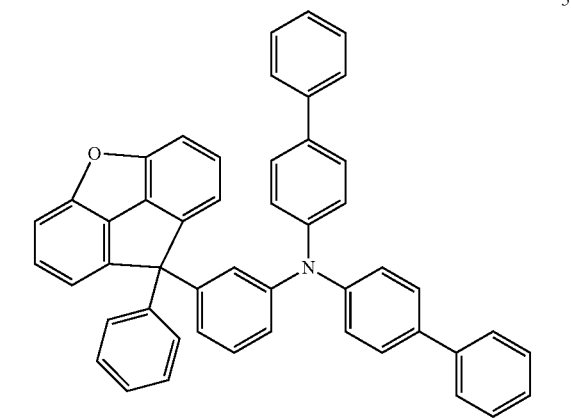

60
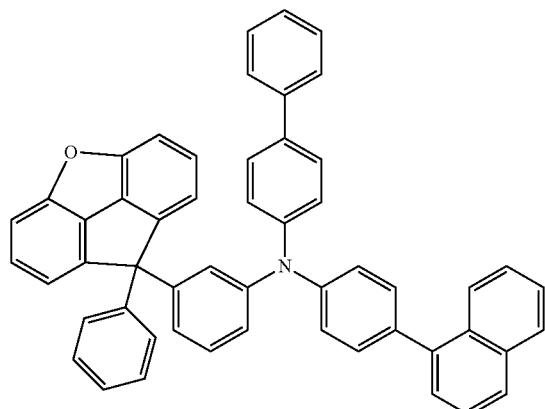
61
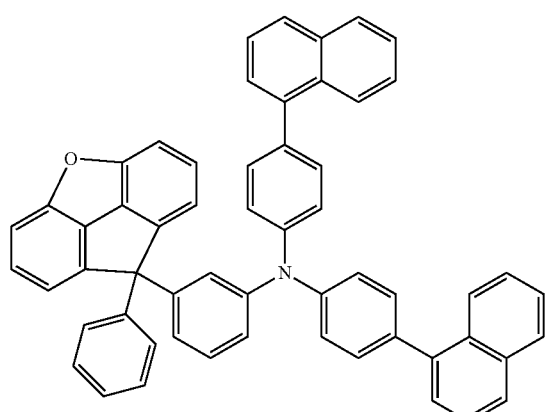
62
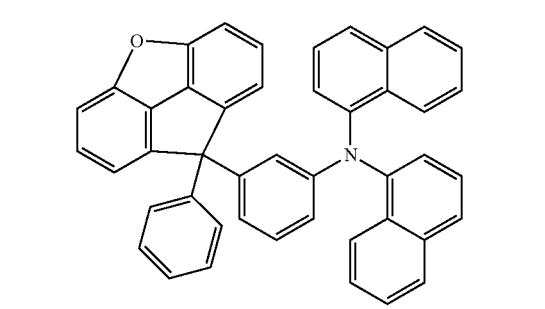
63
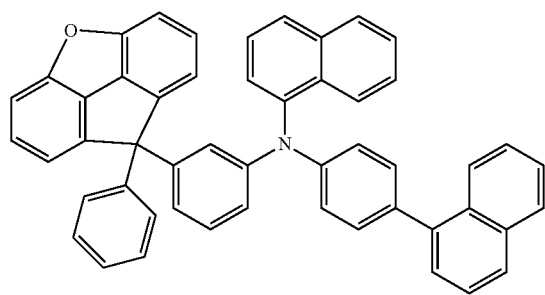
64
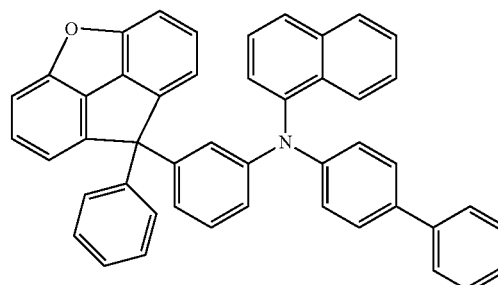
65
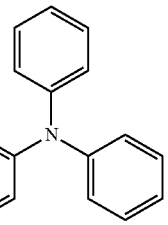
66
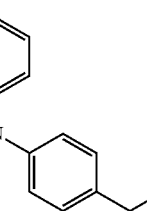
67
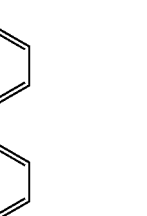
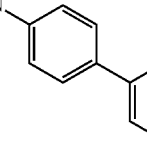

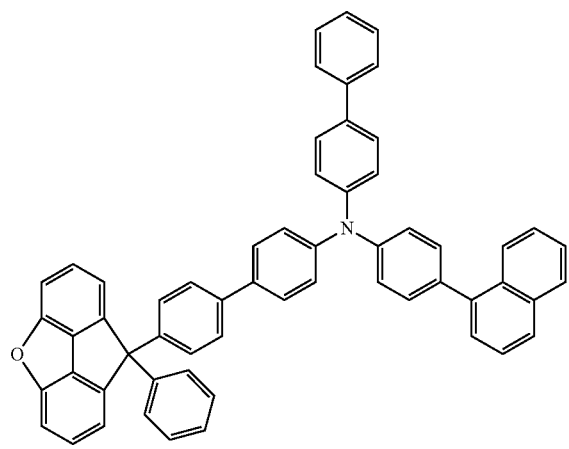
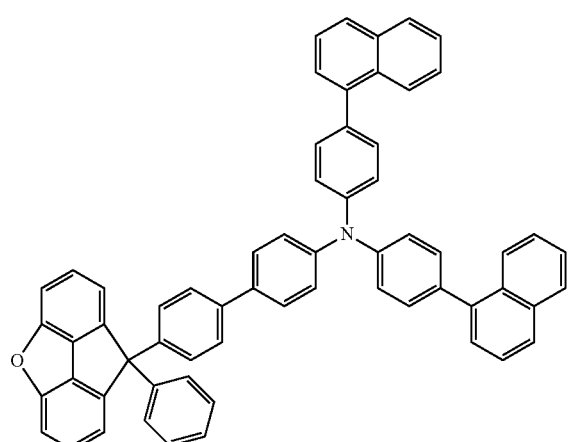
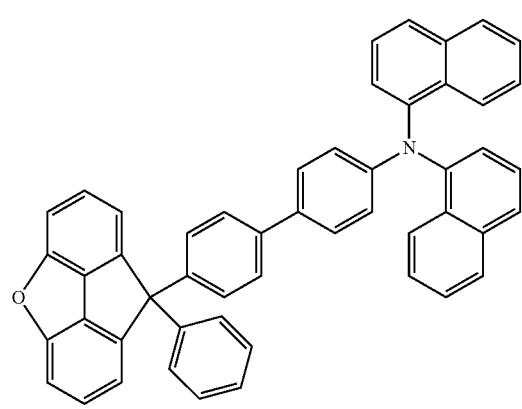
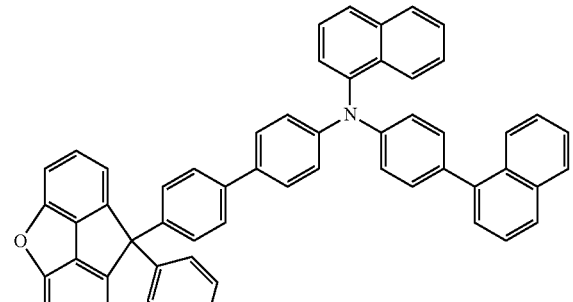
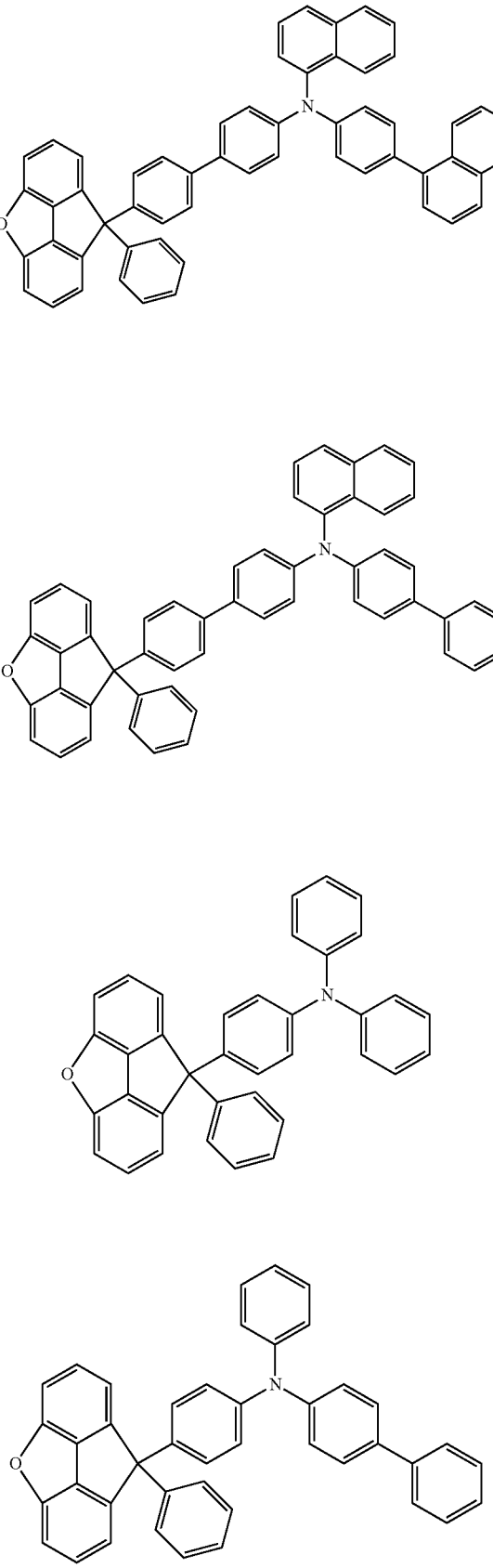

75 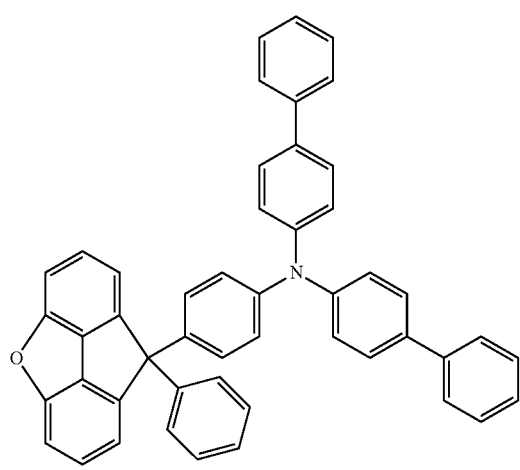
76 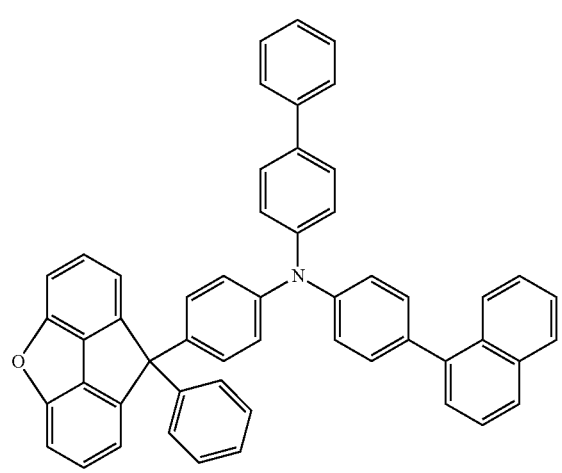
77 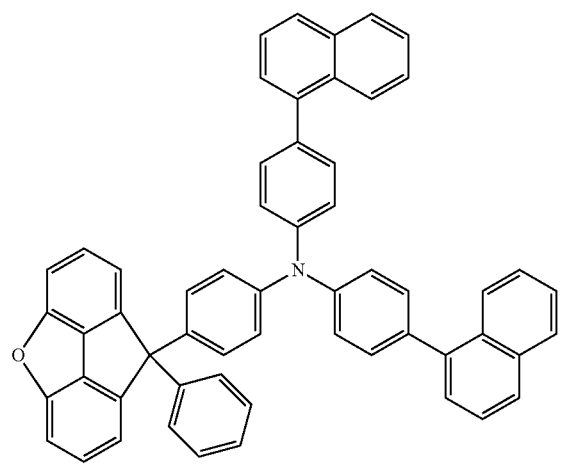
78 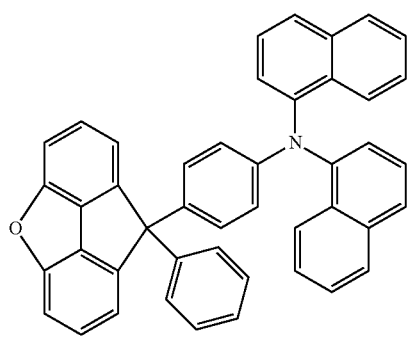
79 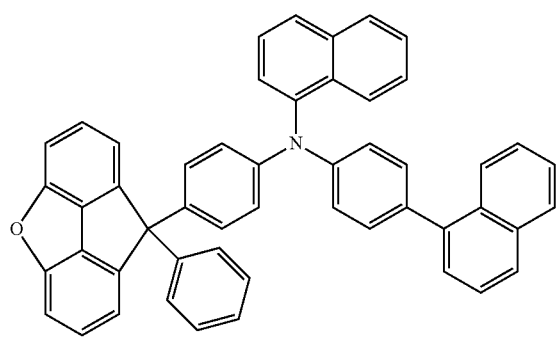
80 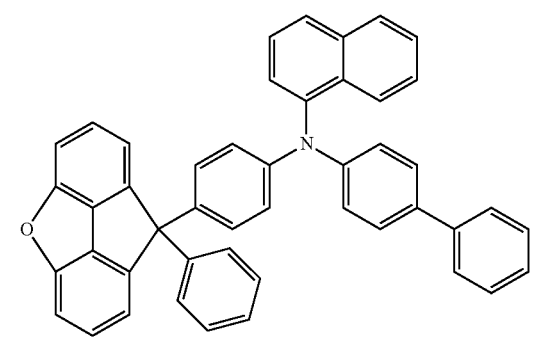
81 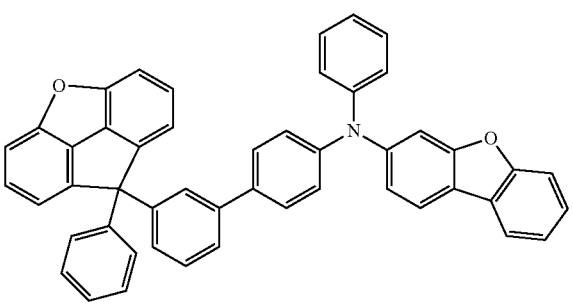

82
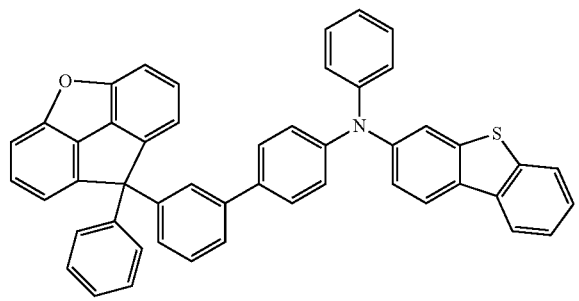
83
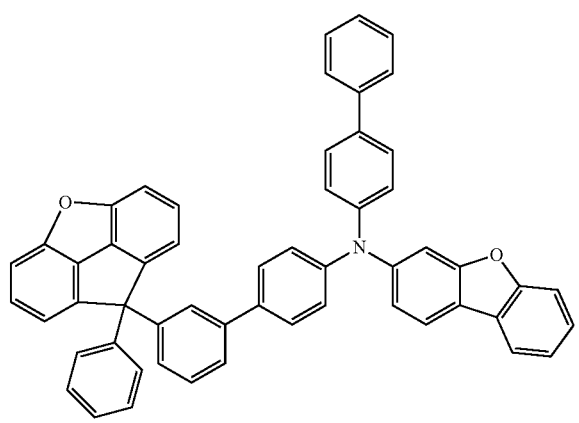
84
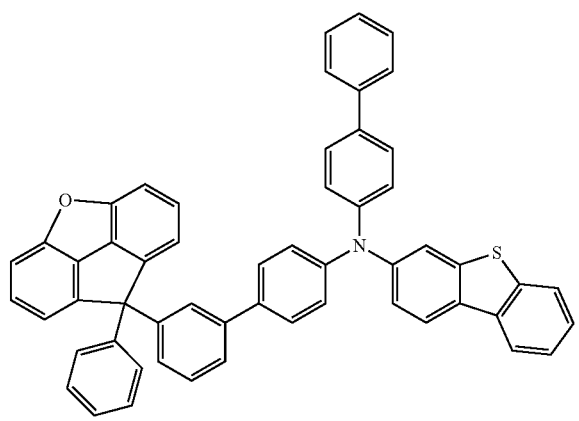
85
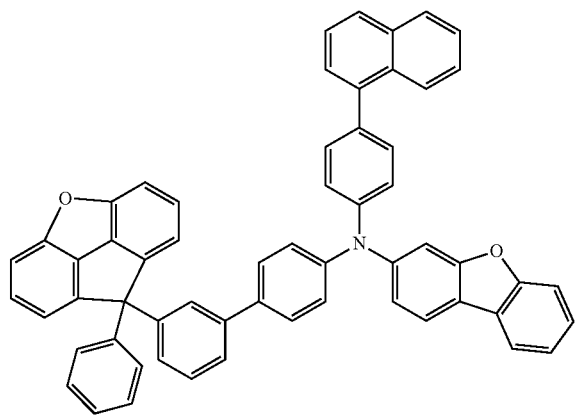
86
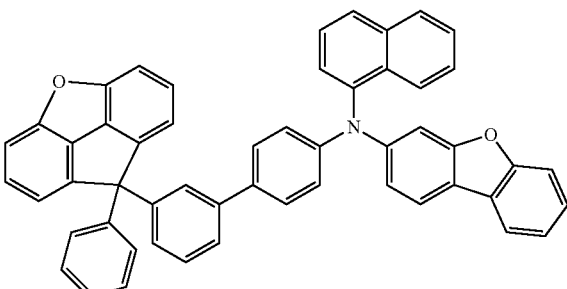
87
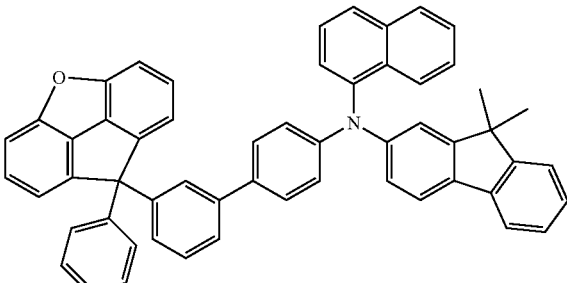
88
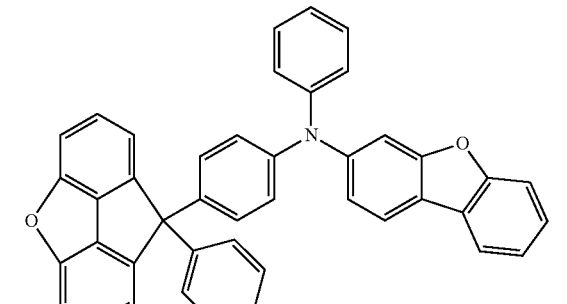
89

115
-continued
90
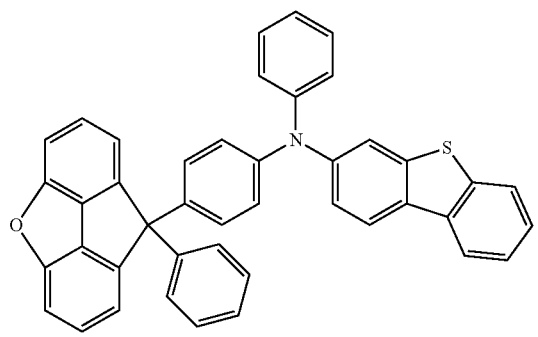
91
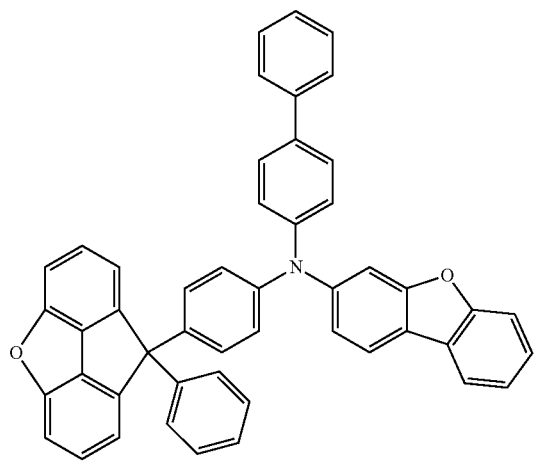
92
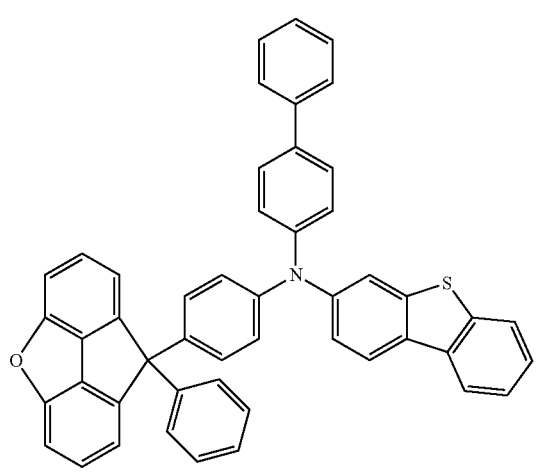
116
-continued
93
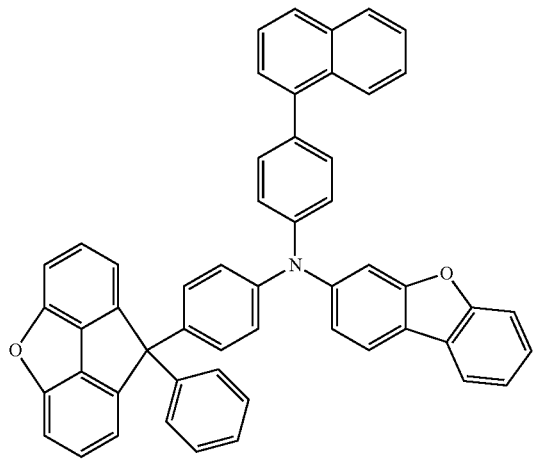
94
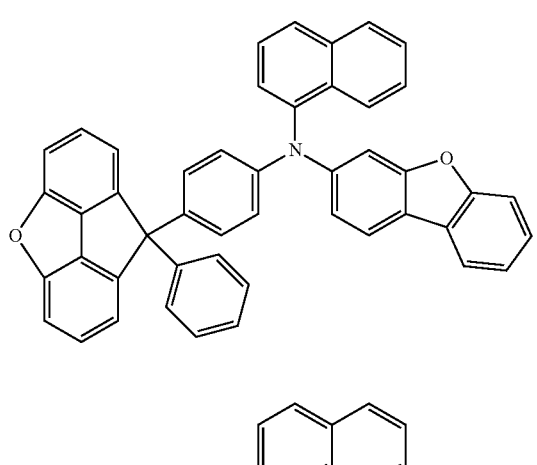
95
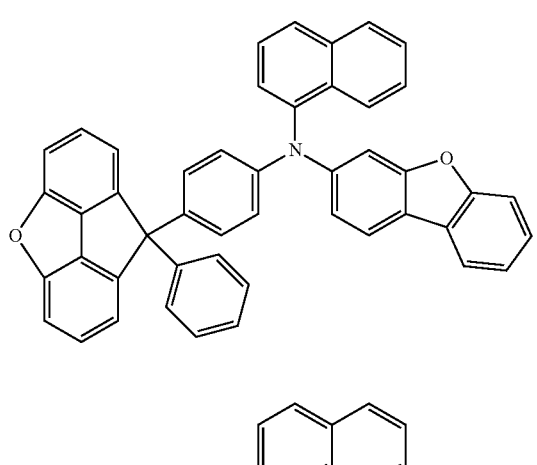
96
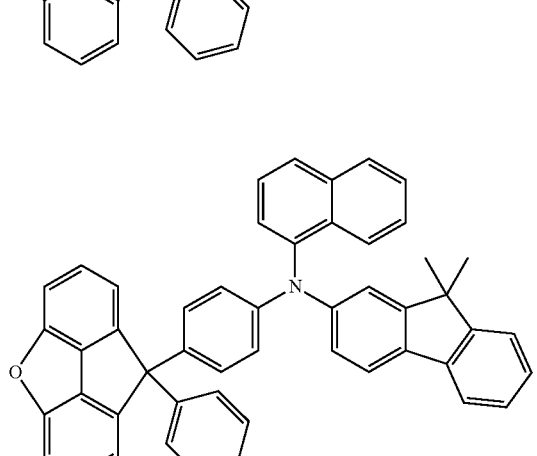

-continued
97
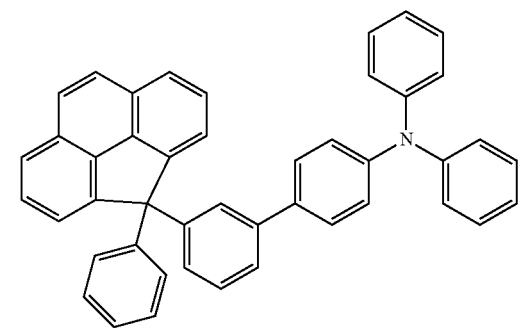
98
99
100
-continued
101
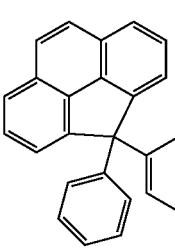
102
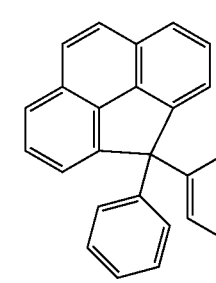
103
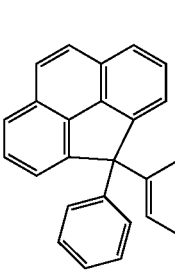
104
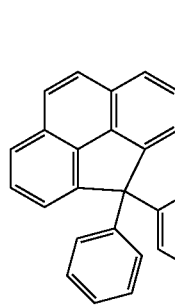
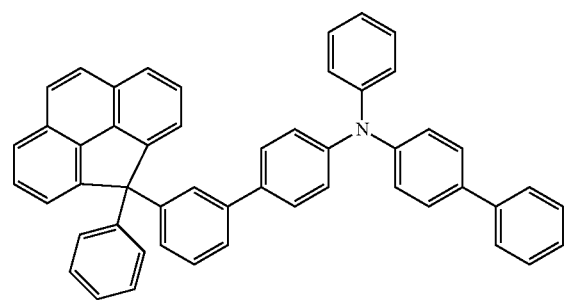
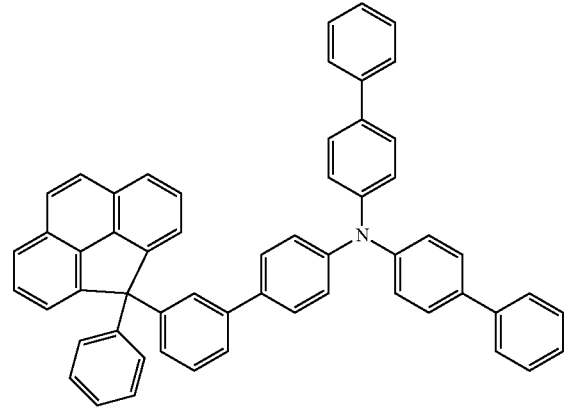

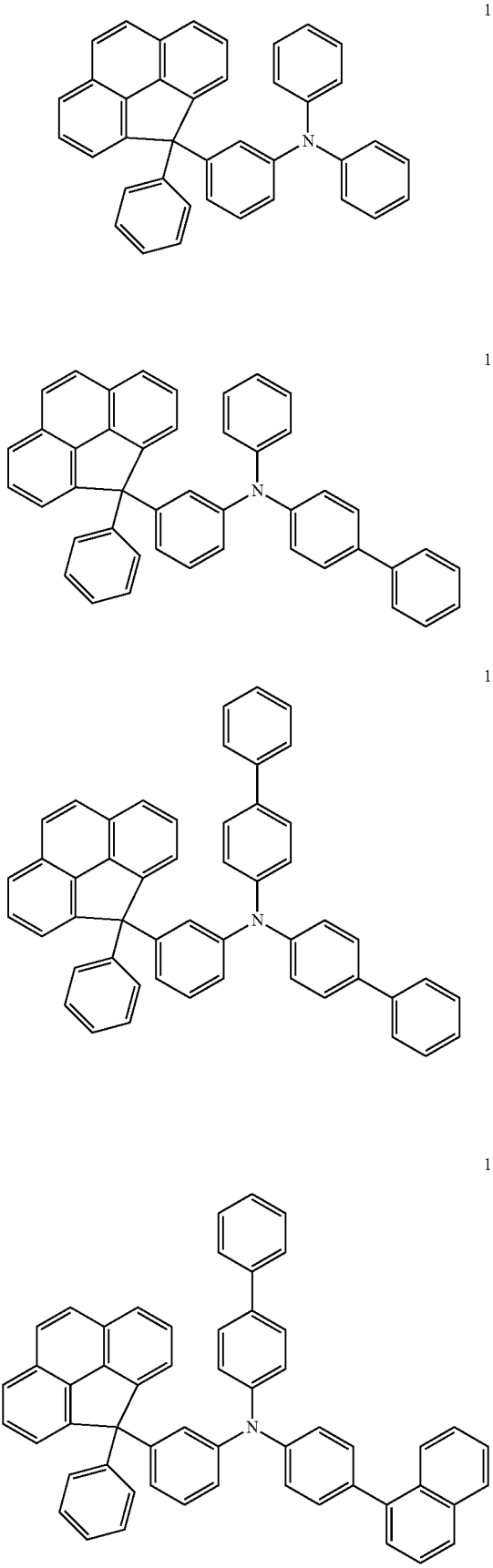

121
-continued
113
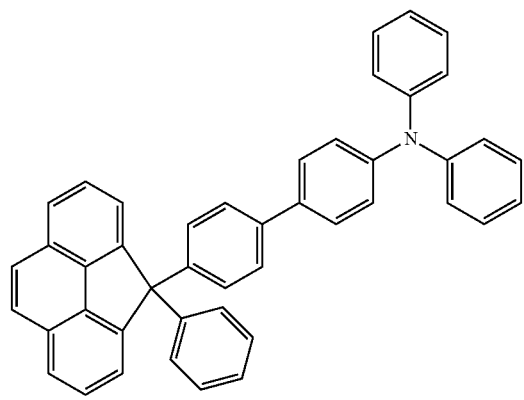
114
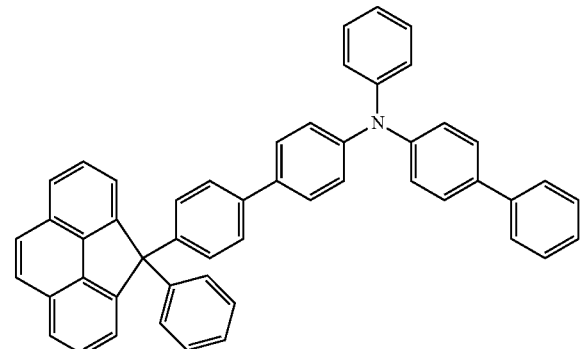
115
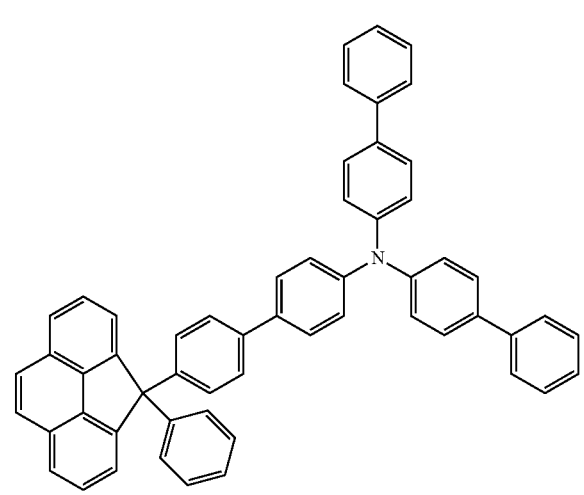
122
-continued
116
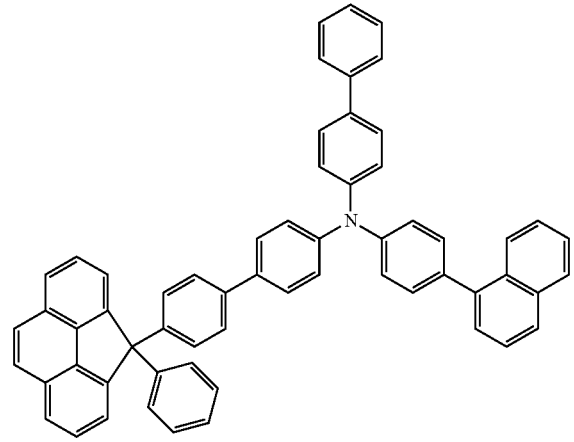
117
117
118
119

120
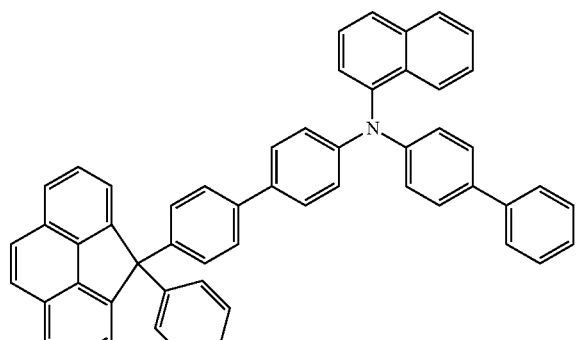
121
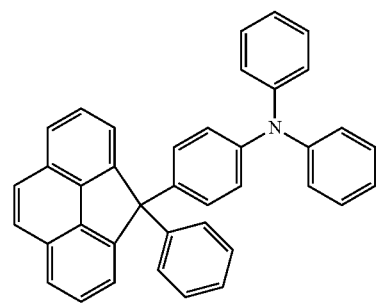
122
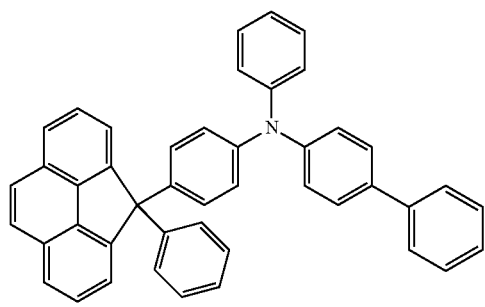
123
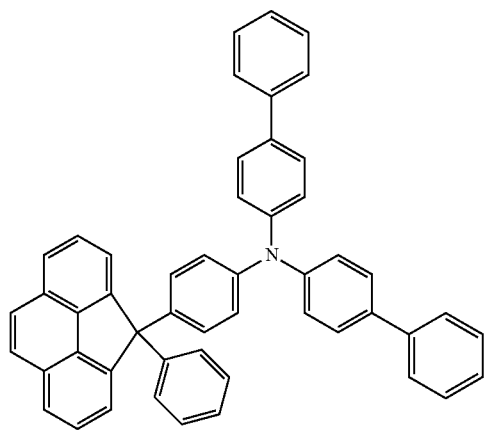
124
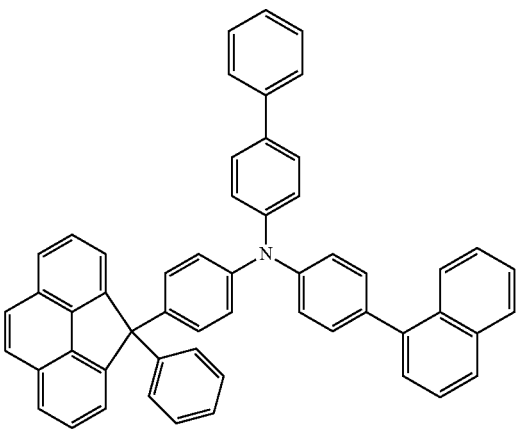
125
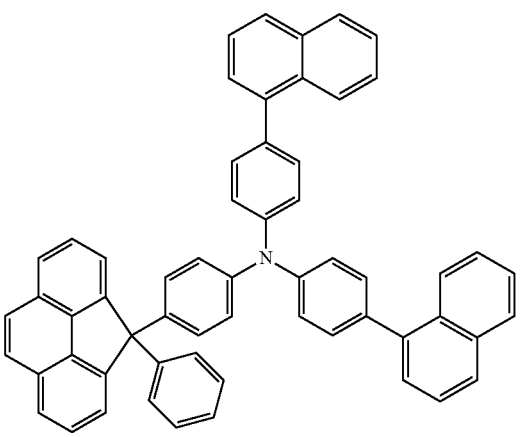
126
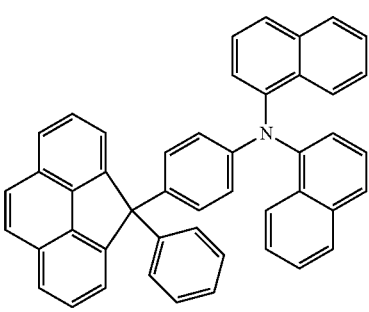
127
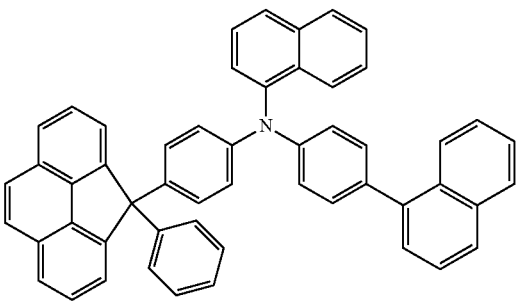

125
-continued
128
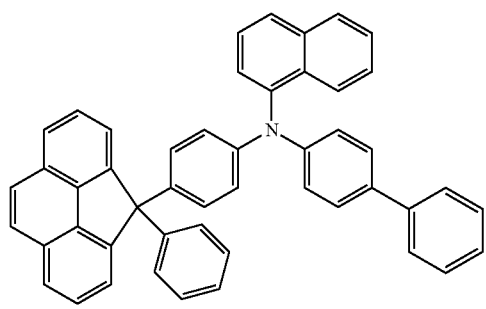
129
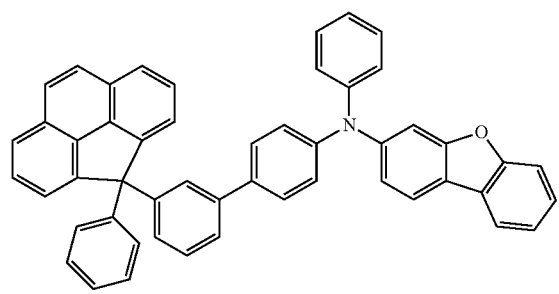
130
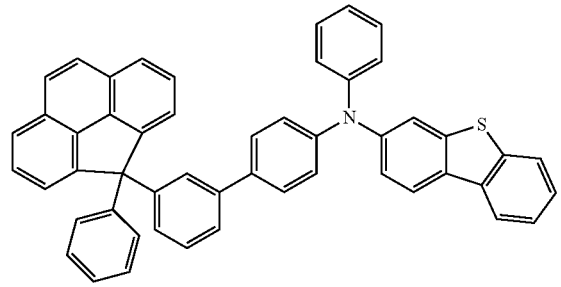
131
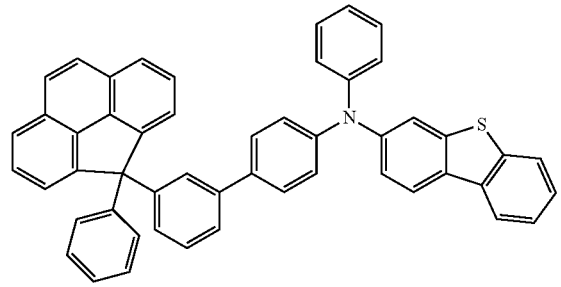
126
-continued
132
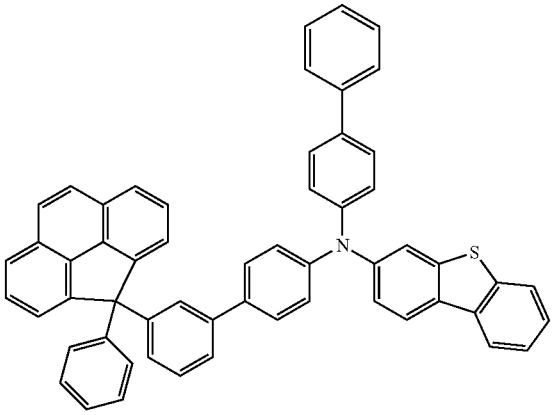
133
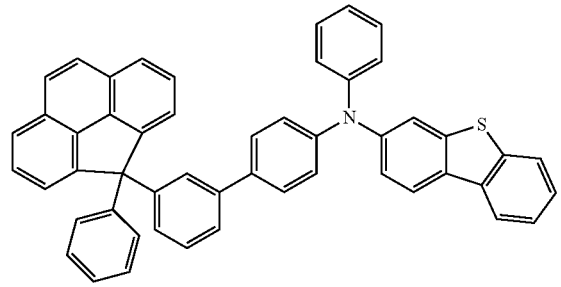
134
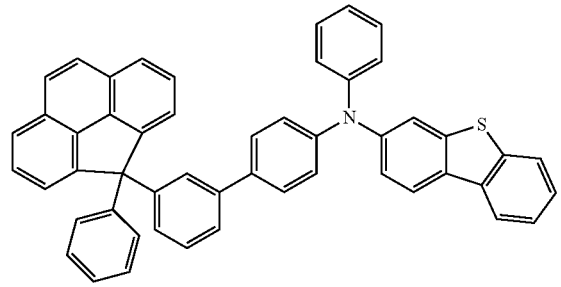
135
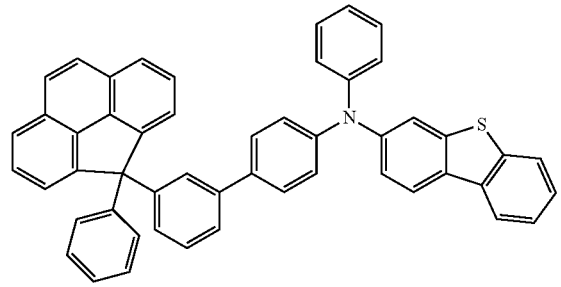

136
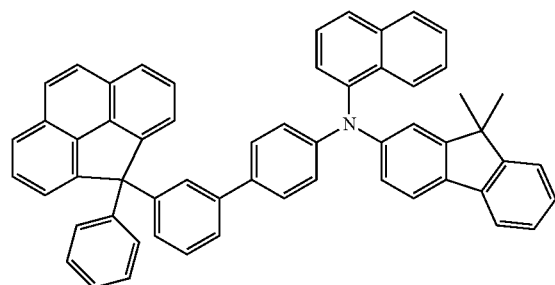
137
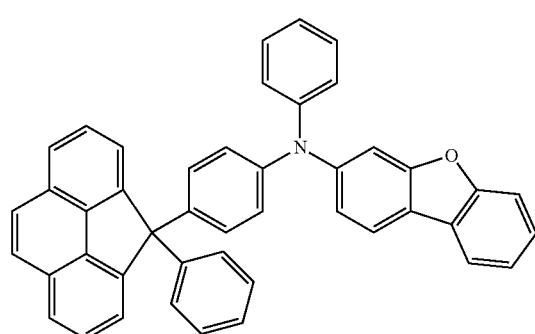
138
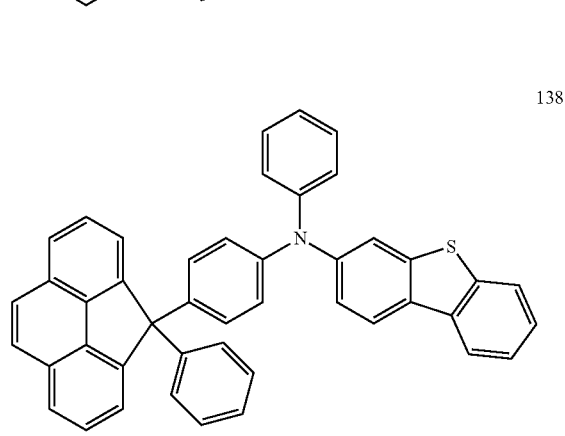
139
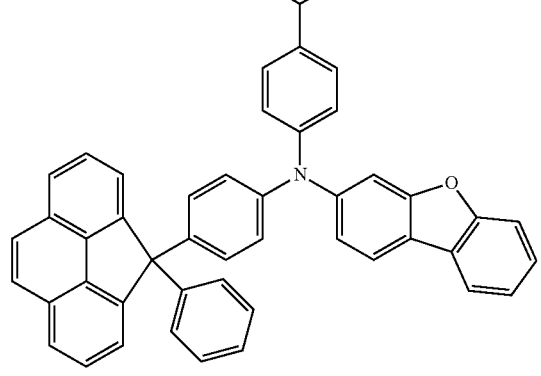
140
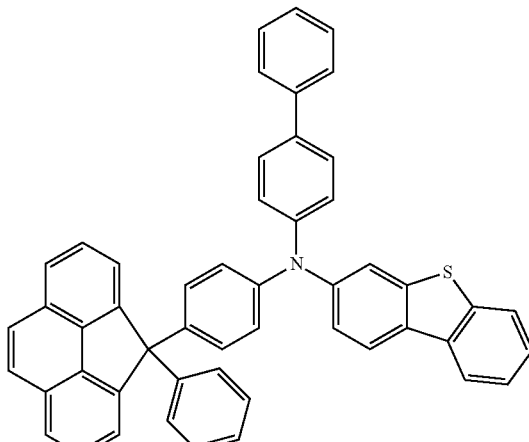
141
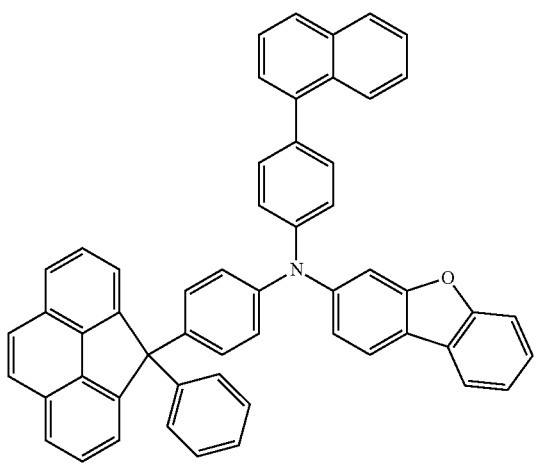
142
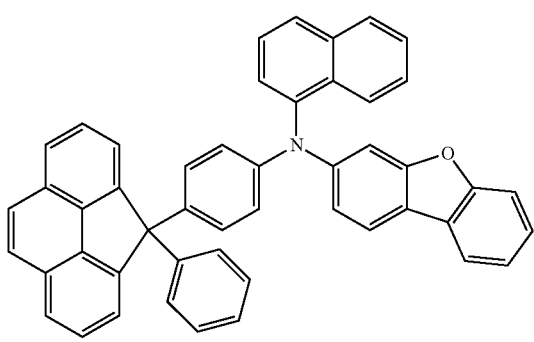
143
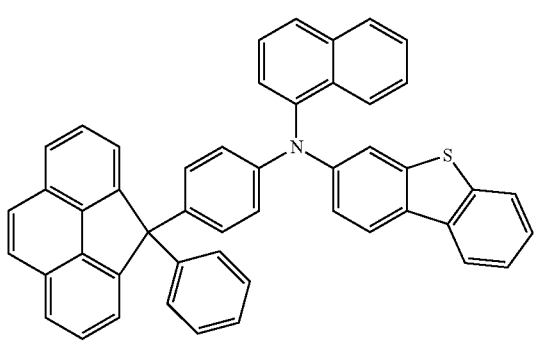

144
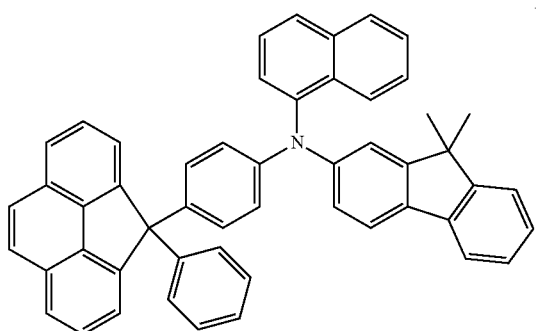
145
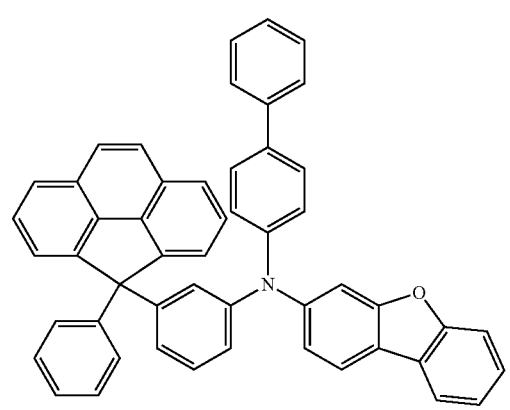
146
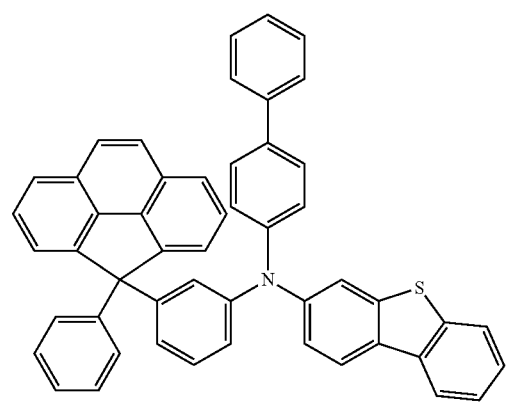
147
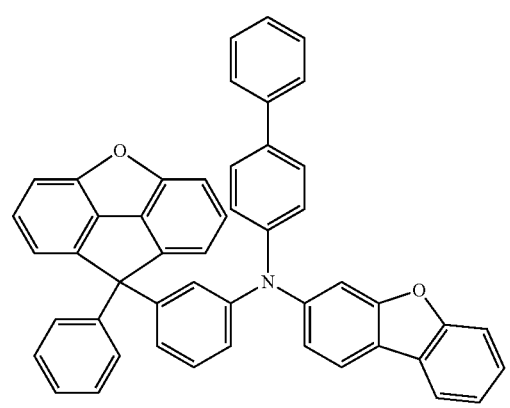
148
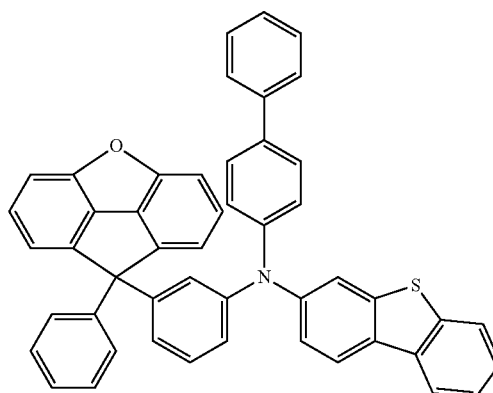
149
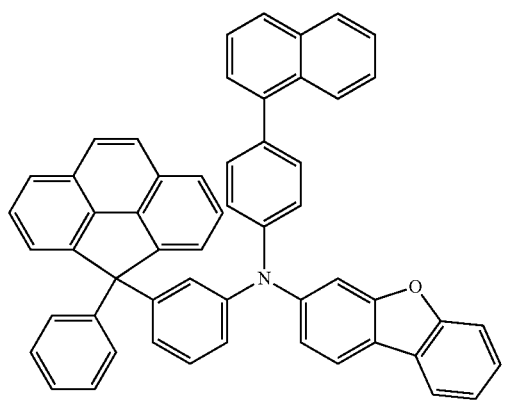
150
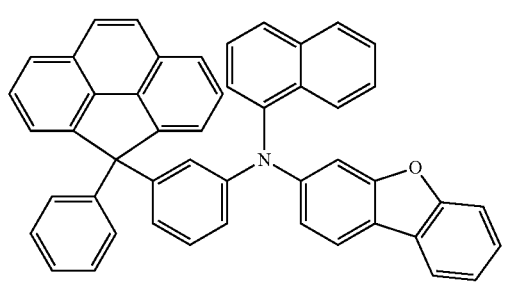
151
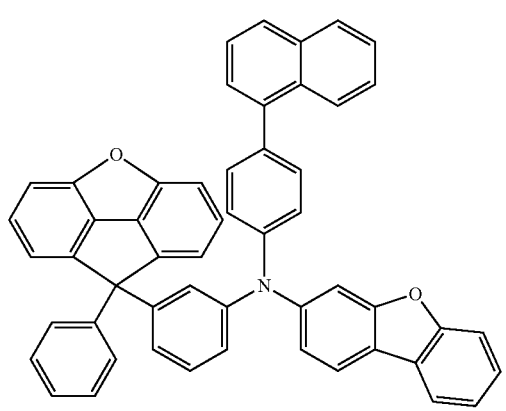

152

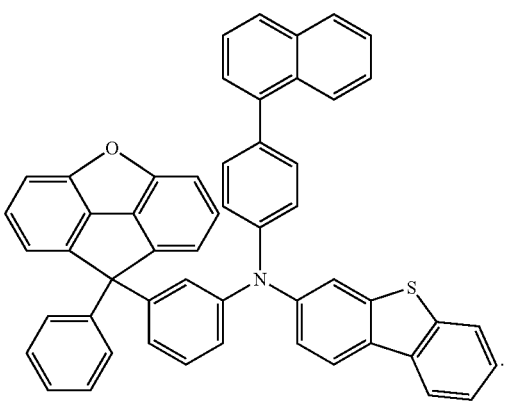

In the amine compound according to an embodiment of the present disclosure, an amine group contributing to long lifespan and a cyclic fluorenyl group contributing to high charge tolerance are combined. The stability of radicals may be improved due to conjugation around the amine group, thereby maintaining the properties of the amine group and further contributing to the high charge tolerance of an organic light emitting device.

Hereinafter, an organic light emitting device according to an embodiment of the present disclosure will be explained in more detail. The explanation will focus on different points of the amine compound according to an embodiment of the present disclosure as described above, and unexplained parts will follow.

Figure 2:
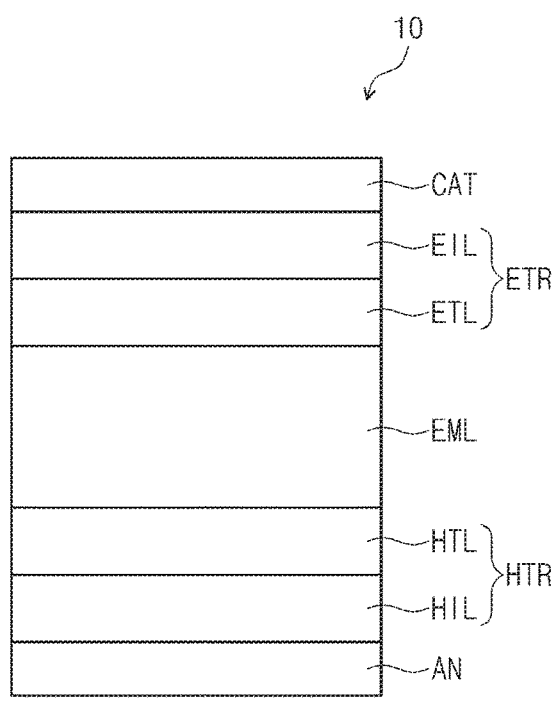
FIG. 2 is a cross-sectional schematic view illustrating the structure of an organic light emitting device according to an embodiment of the present disclosure.

FIG. 1 is a cross-sectional schematic view illustrating the structure of an organic light emitting device according to an embodiment of the present disclosure. FIG. 2 is a cross-sectional schematic view illustrating the structure of an organic light emitting device according to an embodiment of the present disclosure.

Referring to FIGS. 1 and 2, an organic light emitting device 10 according to an embodiment of the present disclosure includes an anode AN, a hole transport region HTR, an emission layer EML, an electron transport region ETR, and a cathode CAT.

The anode AN may have conductivity (e.g., be conductive). The anode AN may be a pixel electrode or an anode. The anode AN may be a transmissive electrode, a transflective electrode, or a reflective electrode. When the anode AN is a transmissive electrode, the anode AN may be formed using a transparent metal oxide (such as indium tin oxide (ITO), indium zinc oxide (IZO), zinc oxide (ZnO), and/or indium tin zinc oxide (ITZO)). When the anode AN is a transflective electrode or a reflective electrode, the anode AN may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), a compound thereof, or a mixture thereof (for example, a mixture of Ag and Mg). The anode AN may include a plurality of layers, including a reflective layer and/or a transflective layer formed using the above materials, and/or a transmissive layer formed using ITO, IZO, ZnO, or ITZO.

The hole transport region HTR may be provided on the anode AN. The hole transport region HTR may include at least one selected from a hole injection layer HIL, a hole transport layer HTL, a hole buffer layer, and an electron blocking layer. The thickness of the hole transport region HTR may be, for example, about 1,000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure (such as a hole injection layer HIL, and/or a hole transport layer HTL), or a single layer structure formed using a hole injection material and a hole transport material. In some embodiments, the hole transport region HTR may have a single layer structure formed using a plurality of different materials, or a laminated multi-layered structure laminated from (e.g., on or over) the anode AN, of hole injection layer HIL/hole transport layer HTL, hole injection layer HIL/hole transport layer HTL/buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed using one or more suitable methods (such as a vacuum deposition method, a spin coating method, a casting method, a Langmuir-Blodgett (LB) method, an inkjet printing method, a laser printing method, and/or a laser induced thermal imaging (LITI) method).

When the hole transport region HTR includes the hole injection layer HIL, the hole transport region HTR may include a phthalocyanine compound (such as copper phthalocyanine; N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), and/or polyaniline/poly(4-styrenesulfonate) (PANI/PSS), etc.), without limitation.

In the case where the hole transport region HTR includes the hole transport layer HTL, the hole transport region HTR may include an amine compound represented by Formula 1:

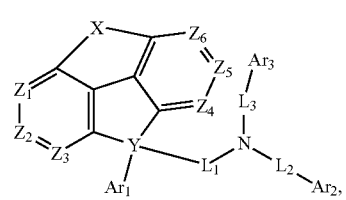

Formula 1 wherein X is selected from the compounds represented by Formula 2:

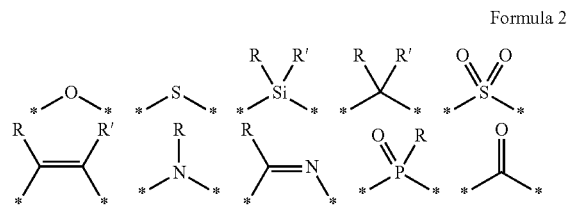

Formula 2

-continued

In Formulae 1 and 2,

Y may be C, Si, or Ge, $Z_1$ to $Z_6$ may each independently be CR or N, $Ar_1$ to $Ar_3$ may each independently be hydrogen, deuterium, a halogen atom, a substituted or unsubstituted aryl group having 6 to 30 carbon atoms for forming a ring, a substituted or unsubstituted heteroaryl group having 5 to 30 carbon atoms for forming a ring, an alkyl group having 1 to 20 carbon atoms, or a silyl group having 3 to 20 carbon atoms, $L_1$ to $L_3$ may each independently be a direct linkage, a substituted or unsubstituted arylene group having 6 to 30 carbon atoms for forming a ring, or a substituted or unsubstituted heteroarylene group having 5 to 30 carbon atoms for forming a ring, and R and R' may each independently be hydrogen, deuterium, a substituted or unsubstituted aryl group having 6 to 30 carbon atoms for forming a ring, a substituted or unsubstituted heteroaryl group having 5 to 30 carbon atoms for forming a ring, or an alkyl group having 1 to 20 carbon atoms.

Adjacent R and R' may combine (e.g., couple) with each other to form a ring.

$L_1$ may be a direct linkage, a substituted or unsubstituted divalent phenyl group, or a substituted or unsubstituted divalent biphenyl group. When $L_1$ is a substituted or unsubstituted divalent phenyl group, an amine group ring and Y may be combined (e.g., coupled) via positions 1 and 3 or positions 1 and 4 of the phenyl group.

$Ar_2$ may be a substituted or unsubstituted phenyl group, a substituted or unsubstituted naphthyl group, a substituted or unsubstituted dibenzofuranyl group, a substituted or unsubstituted dibenzothiophene group, or a substituted or unsubstituted fluorenyl group.

$Ar_3$ may be a substituted or unsubstituted phenyl group, a substituted or unsubstituted biphenyl group, or a substituted or unsubstituted naphthyl group.

Formula 1 may be represented by Formula 3:

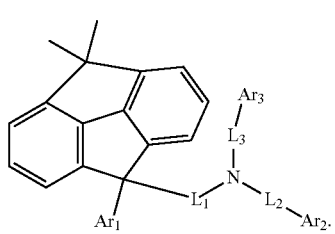

Formula 3

Formula 1 may be represented by Formula 9:

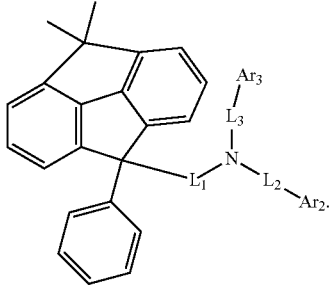

Formula 9

Formula 1 may be represented by Formula 4:

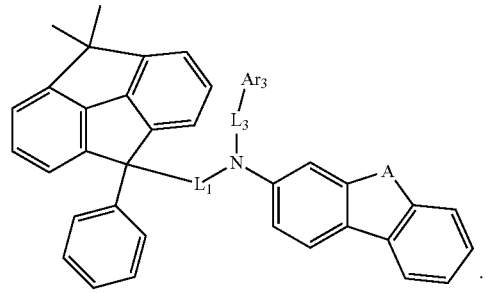

Formula 4

In Formula 4, A may be O, S, or $CR_2R_3$. $R_2$ and $R_3$ may each independently be hydrogen, deuterium, an alkyl group having 1 to 20 carbon atoms, a substituted or unsubstituted aryl group having 6 to 30 carbon atoms for forming a ring, or a substituted or unsubstituted heteroaryl group having 5 to 30 carbon atoms for forming a ring.

Formula 1 may be represented by Formula 5:

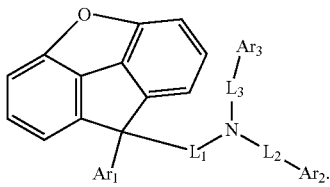

Formula 5

Formula 1 may be represented by Formula 10:

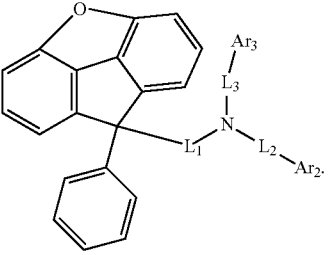

Formula 10

Formula 1 may be represented by Formula 6:

Formula 6

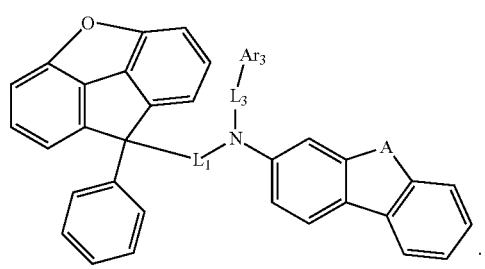

In Formula 6, A may be O, S, or $CR_2R_3$. $R_2$ and $R_3$ may be the same as defined above.

Formula 1 may be represented by Formula 7:

Formula 7

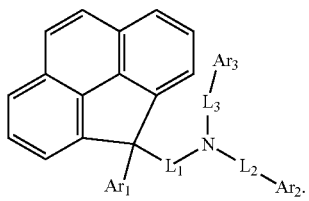

Formula 1 may be represented by Formula 11:

Formula 11

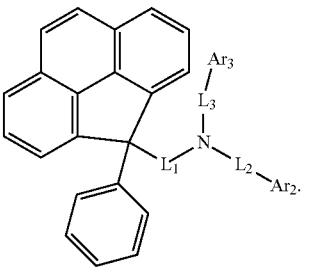

Formula 1 may be represented by Formula 8:

Formula 8

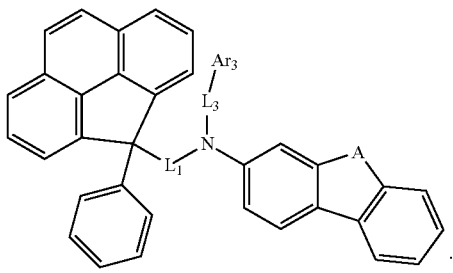

In Formula 8, A may be O, S, or $CR_2R_3$. $R_2$ and $R_3$ may be the same as defined above.

In Formulae 3 to 8, $L_1$ to $L_3$ and $Ar_1$ to $Ar_3$ may each independently be the same as described herein in connection with Formula 1.

The hole transport region HTR may include at least one selected from the compounds represented by Compound Group 1:

Compound Group 1

1

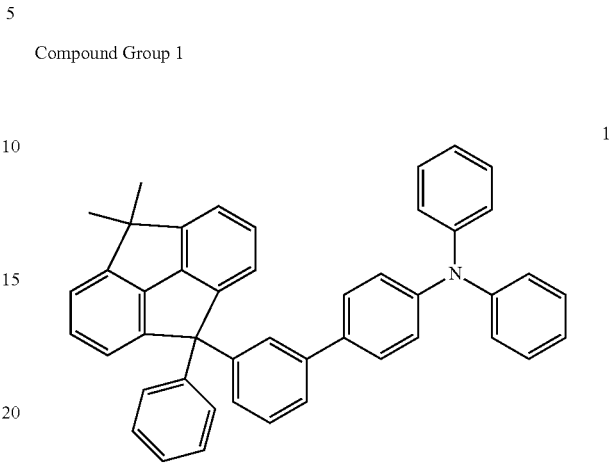

2

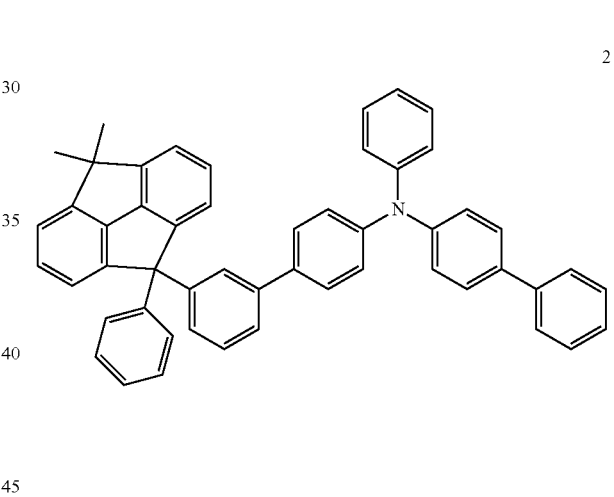

3

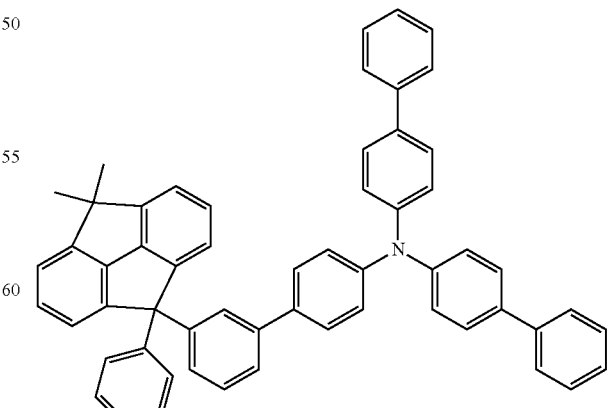

4
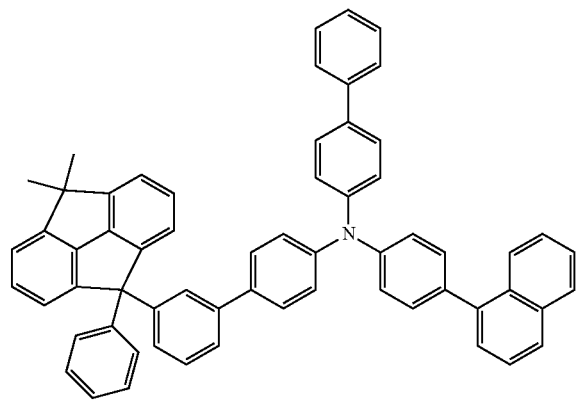
5
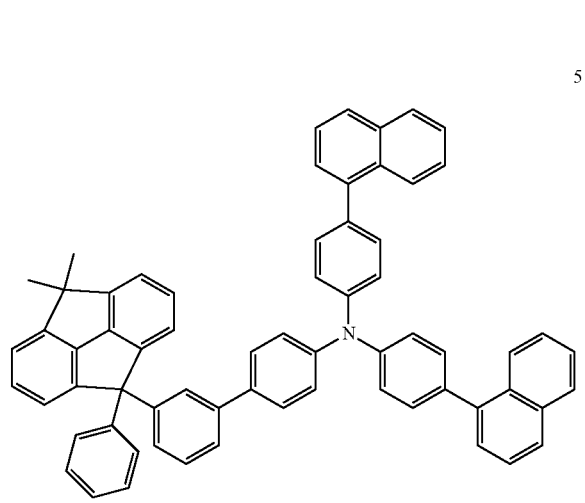
6
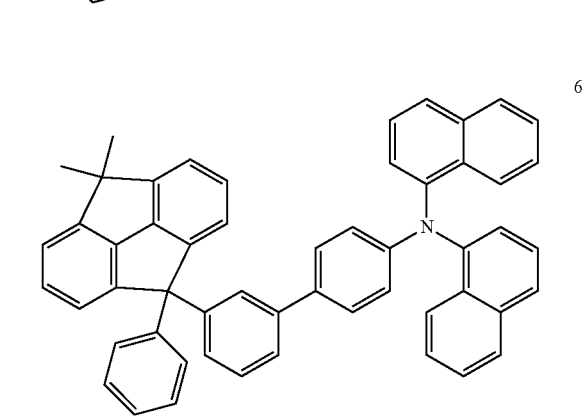
7
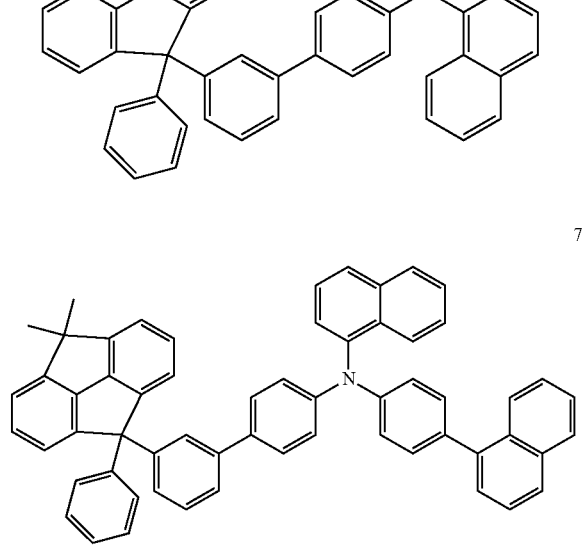
8
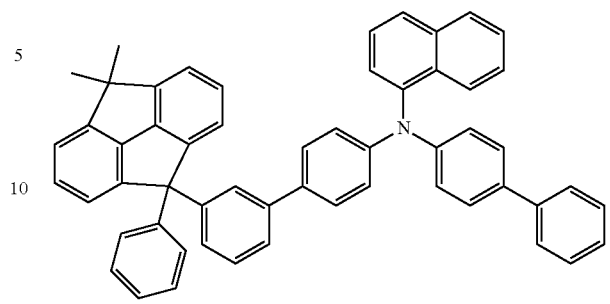
9
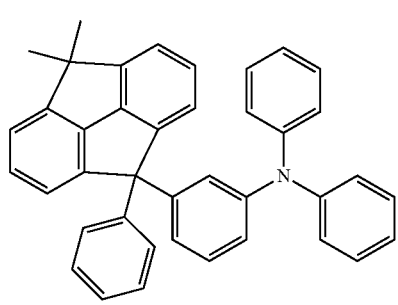
10
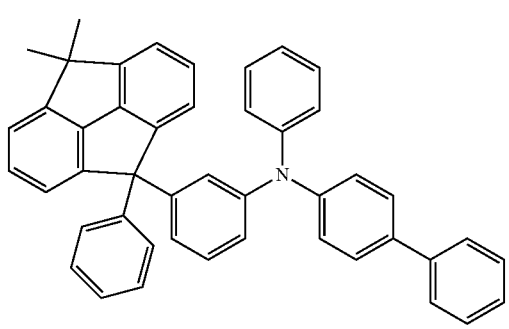
11
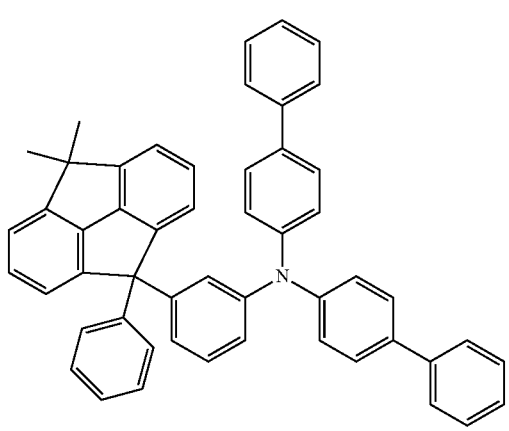

12
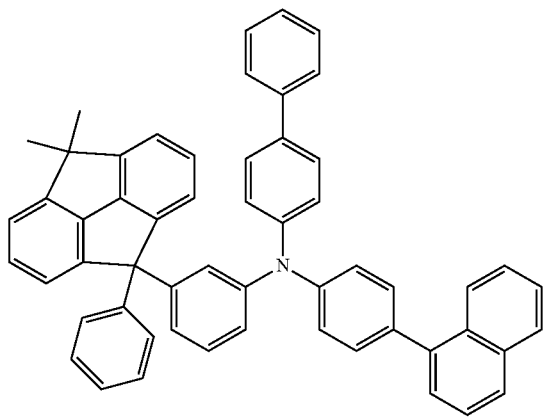
13
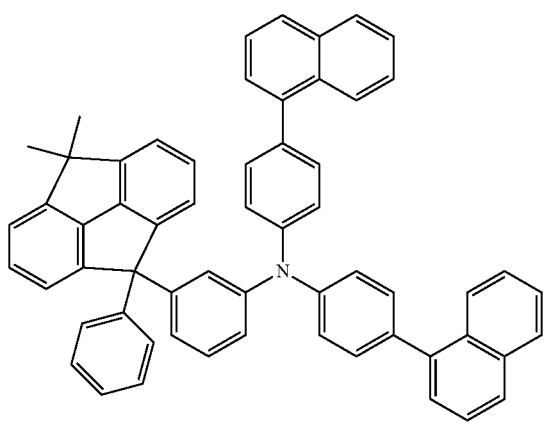
14
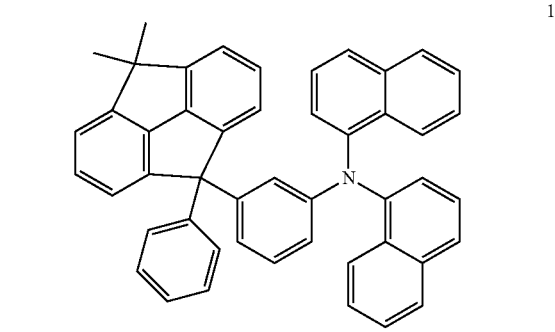
15
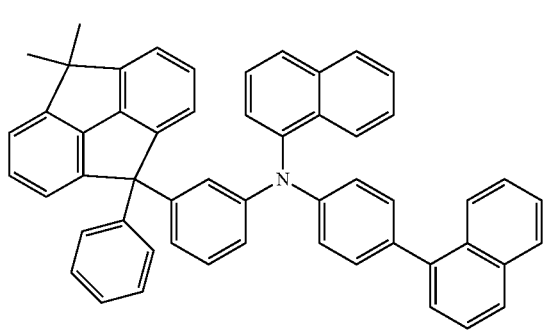
16
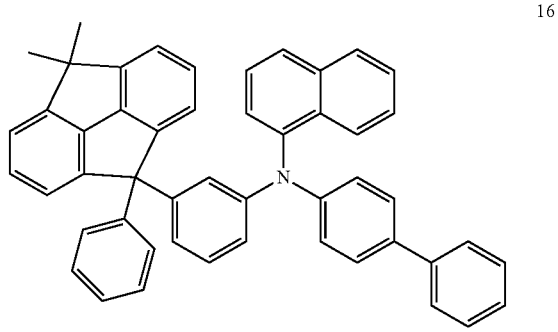
17
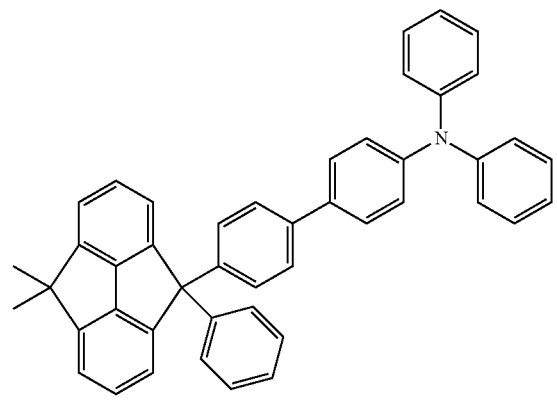
18
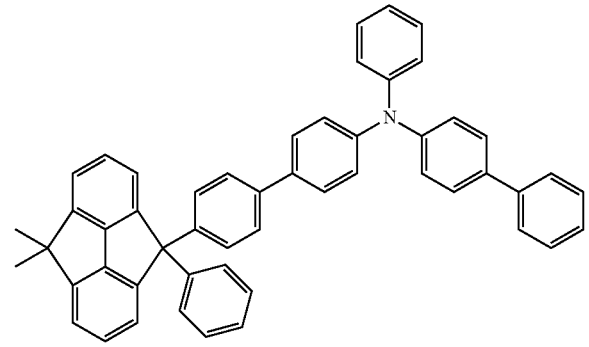
19
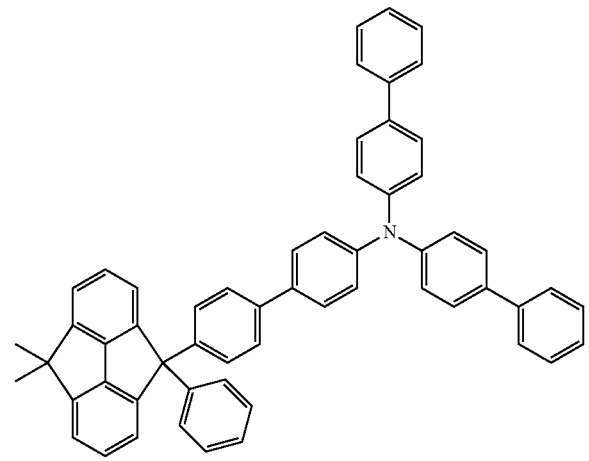

20
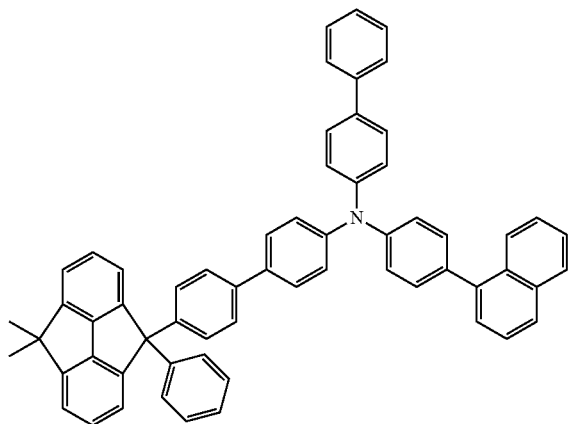
21
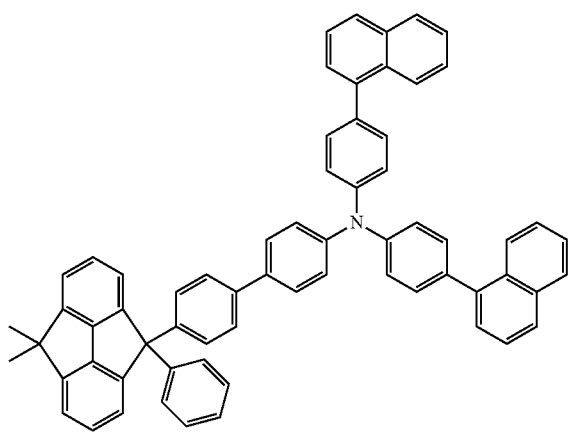
22
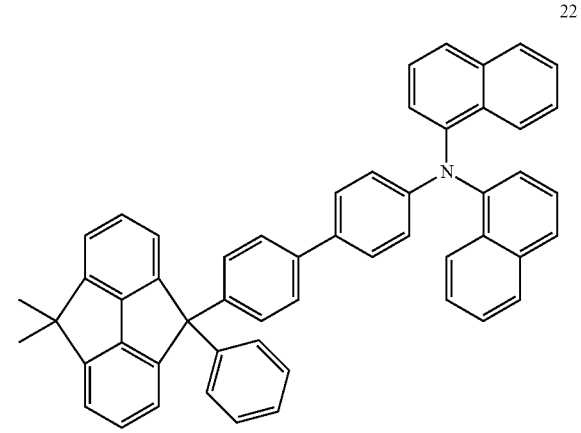
23
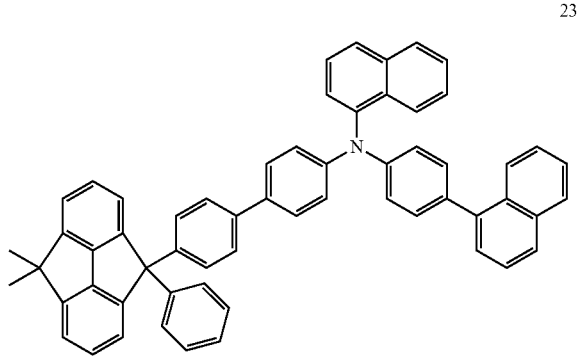
24
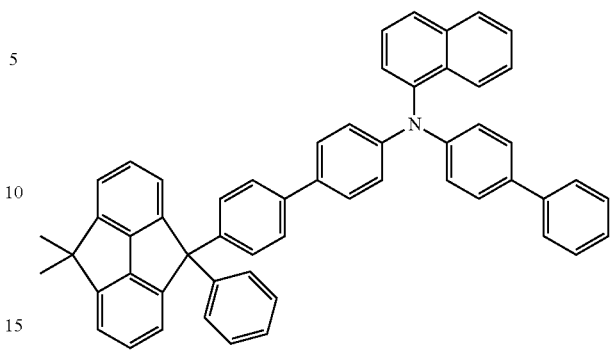
25
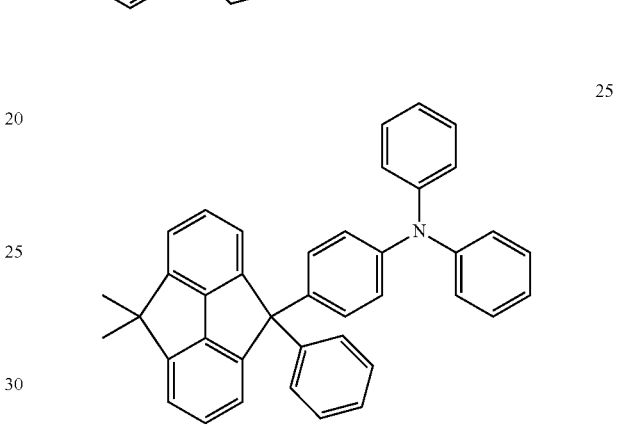
26
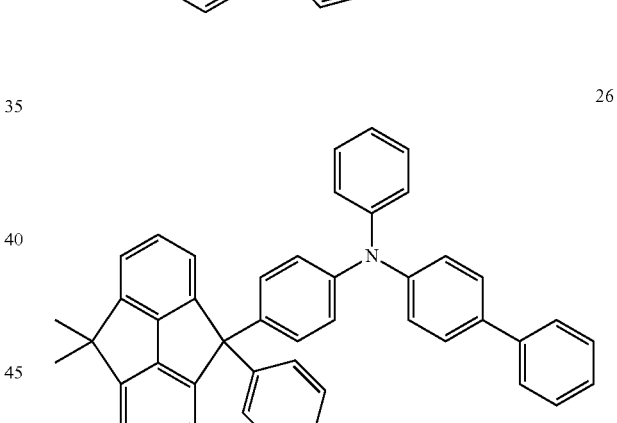
27
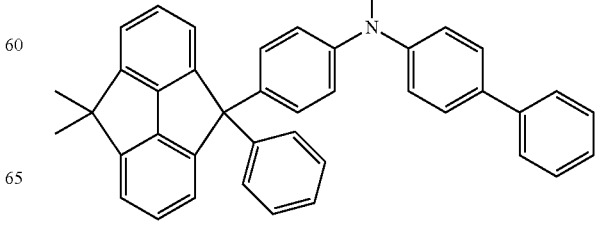

-continued
28
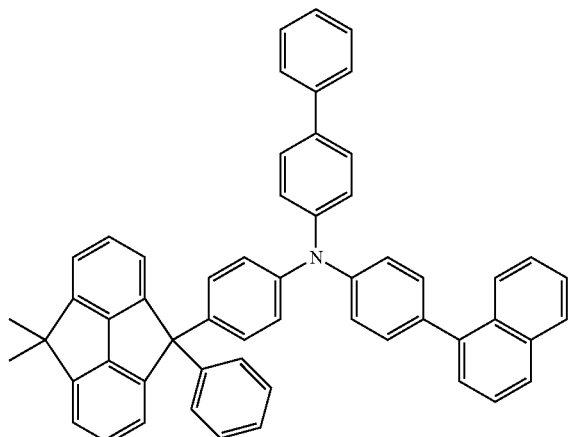
29
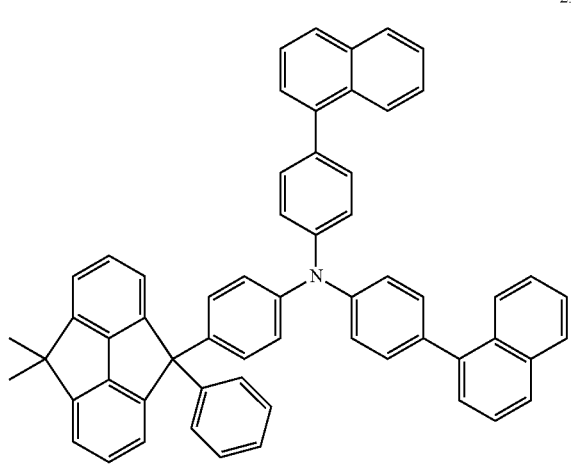
30
31
32
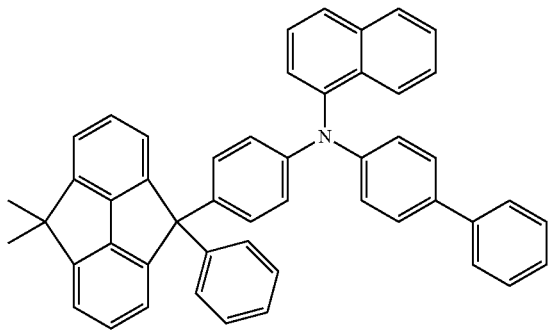
33
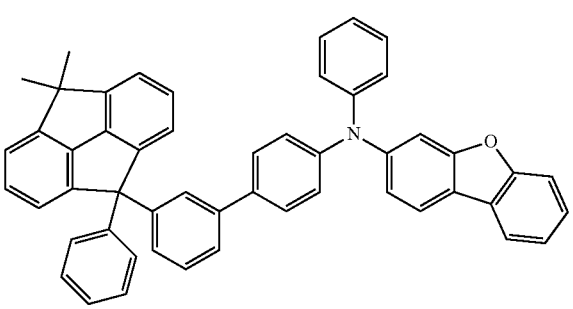
34
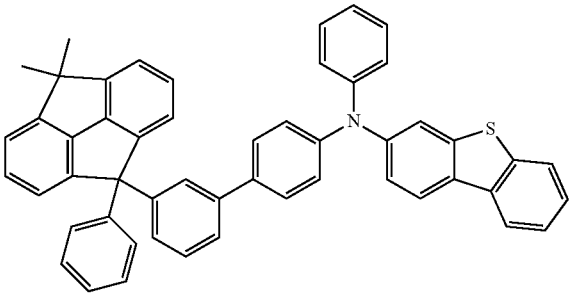
35
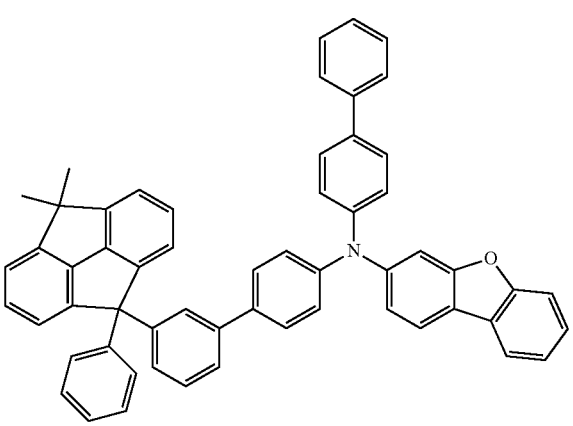

145 146
-continued -continued
36
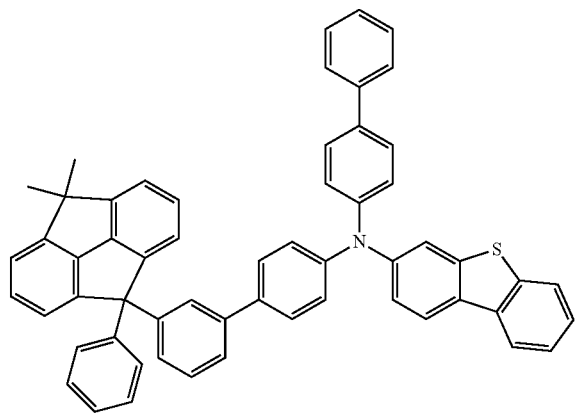
40
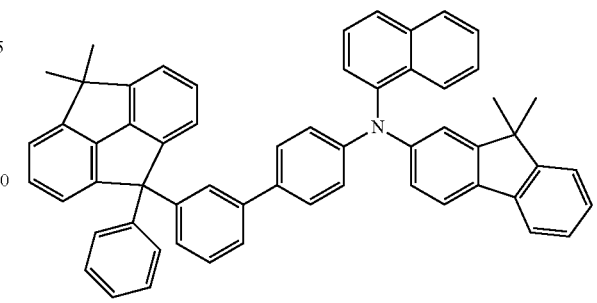
37
41
38
42
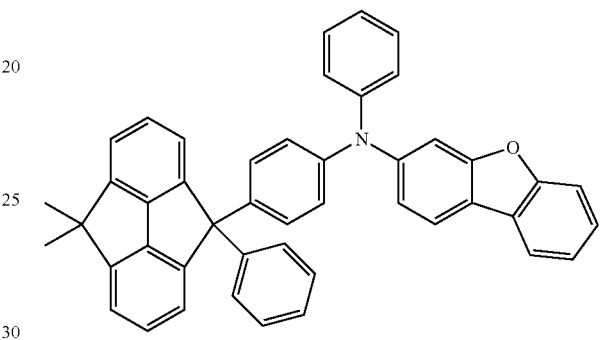
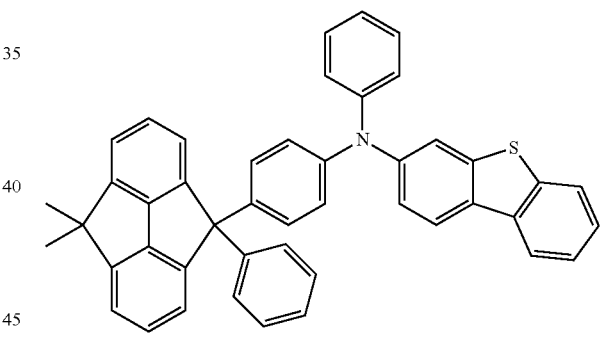
39
43
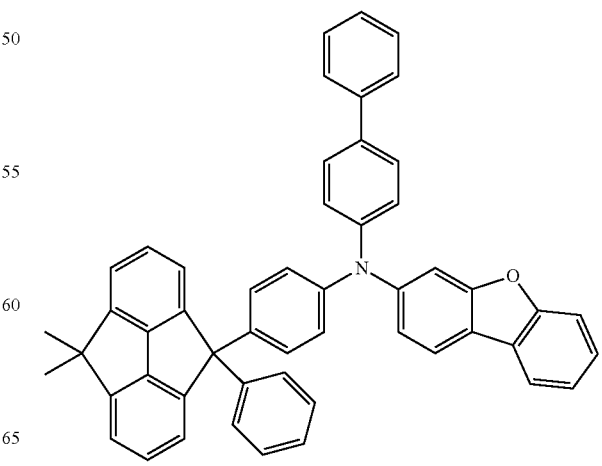

44
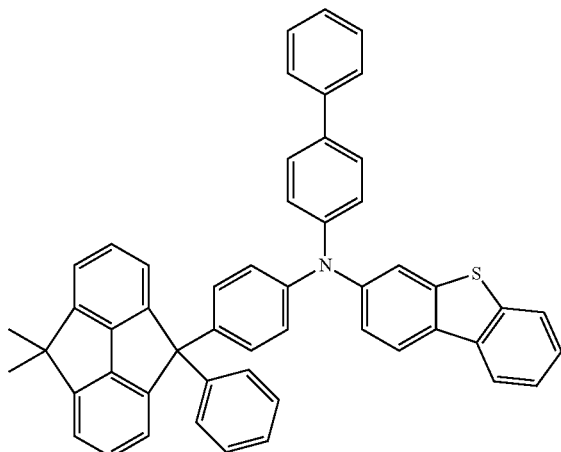
45
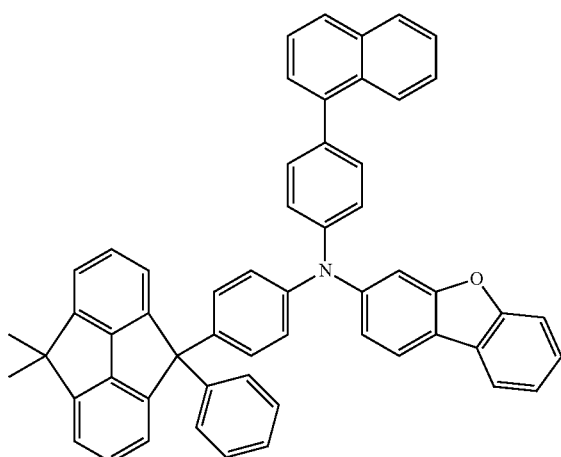
46
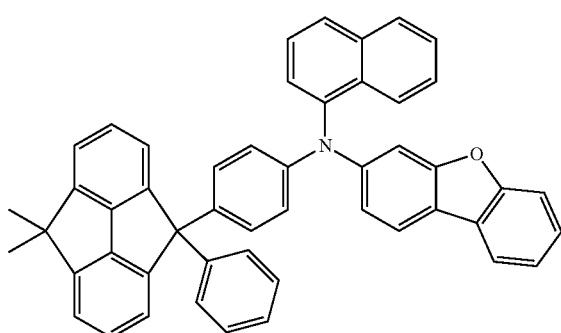
47
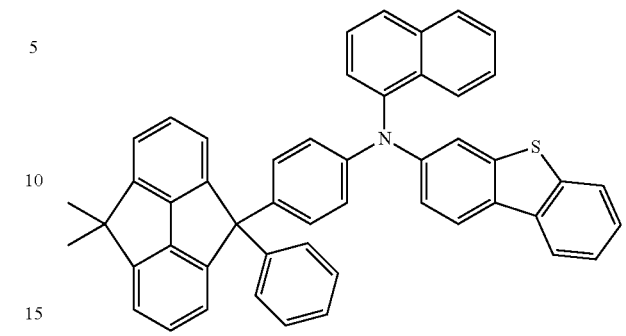
48
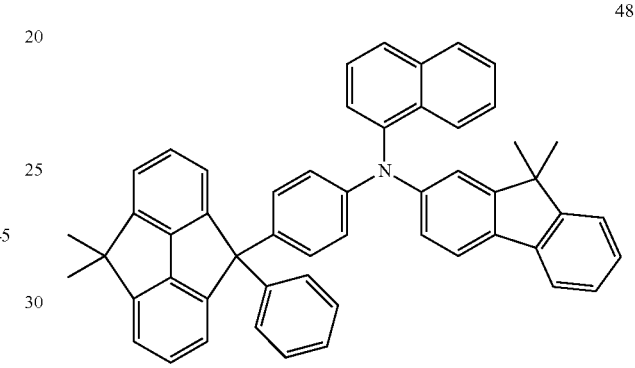
49
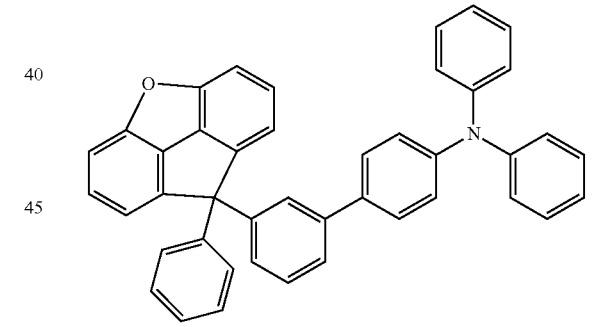
50
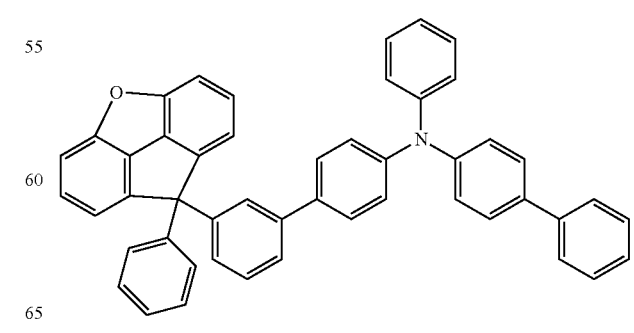

51
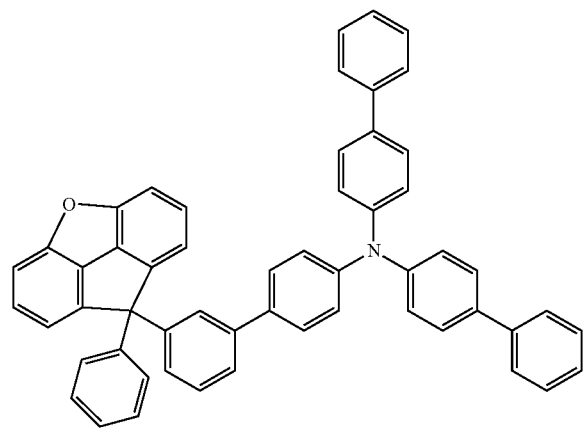
52
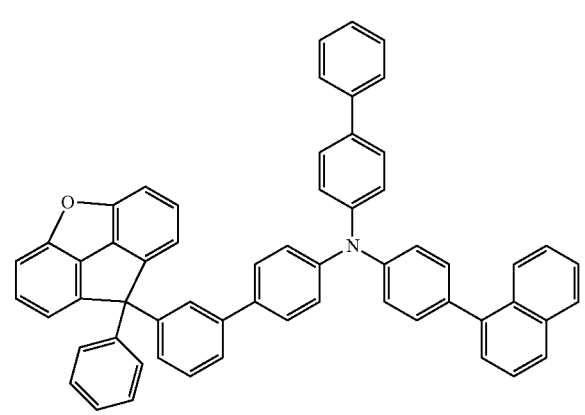
53
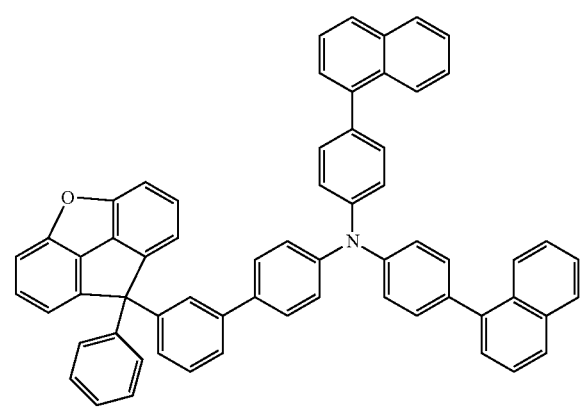
54
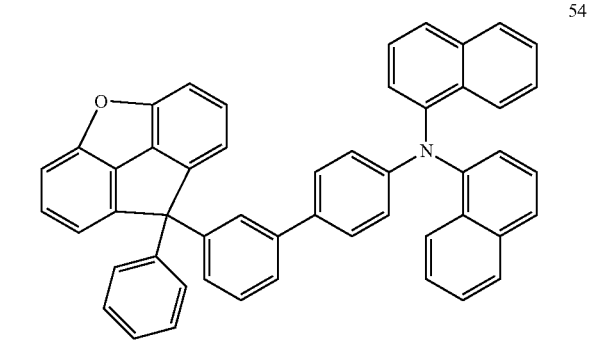
55
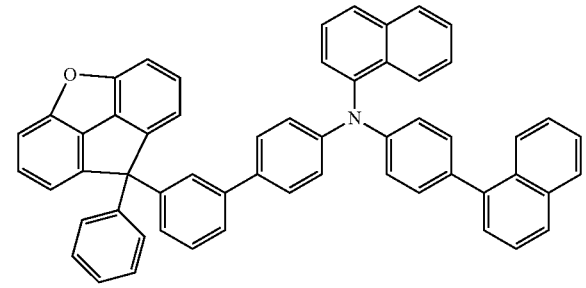
56
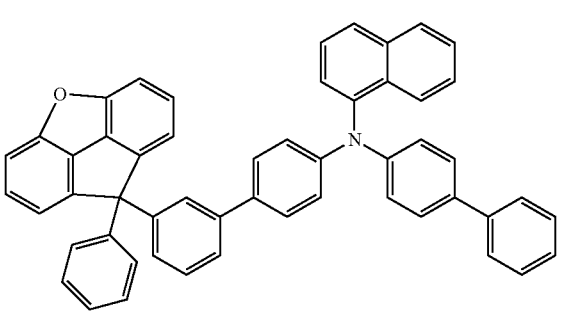
57
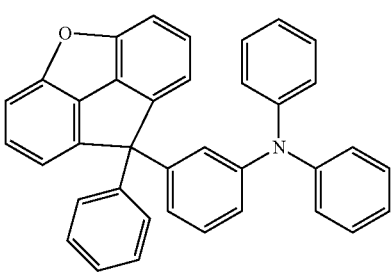
58
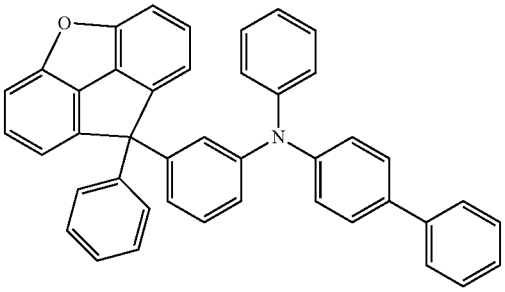
59
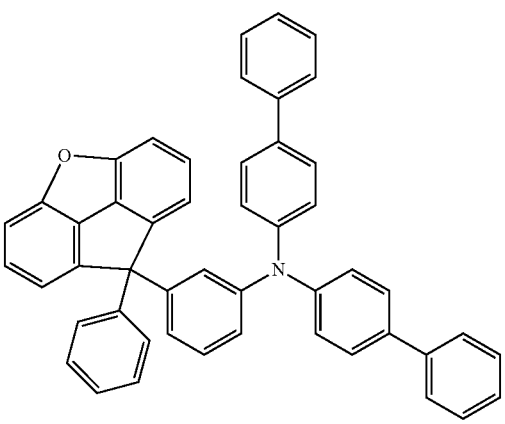

151
-continued
60
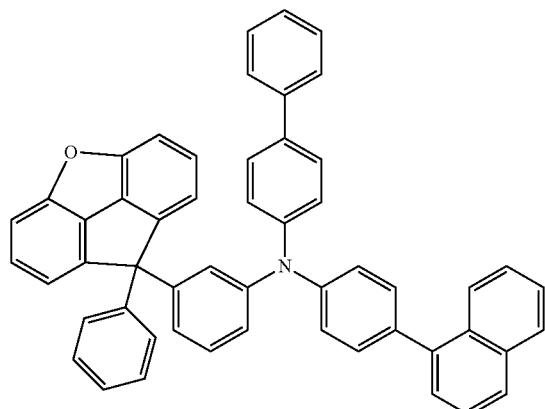
61
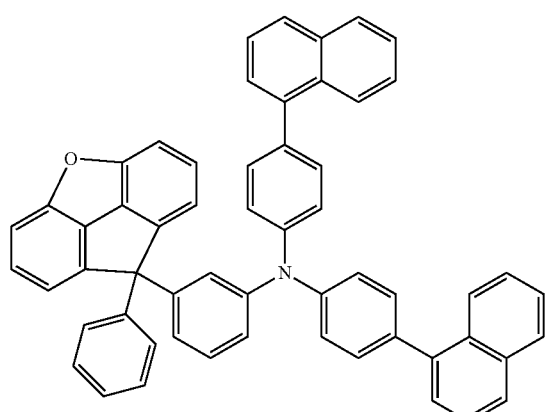
62
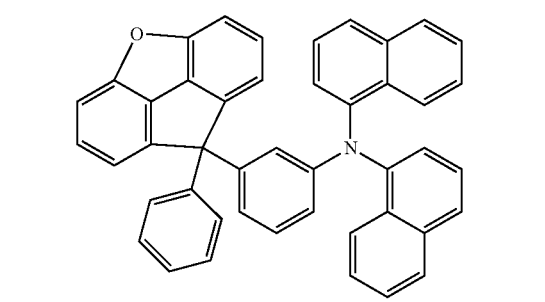
63
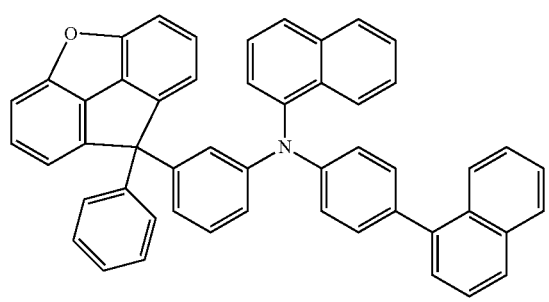
152
-continued
64
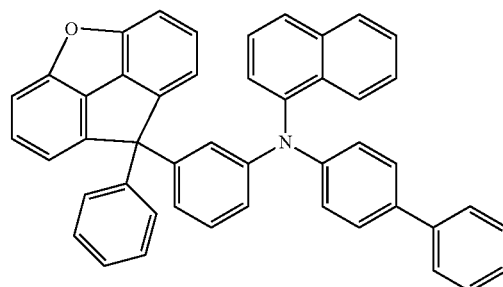
65
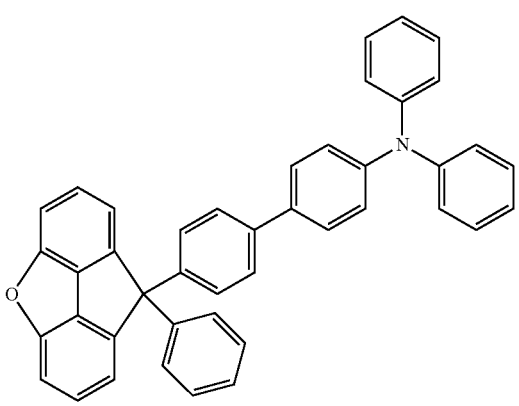
66
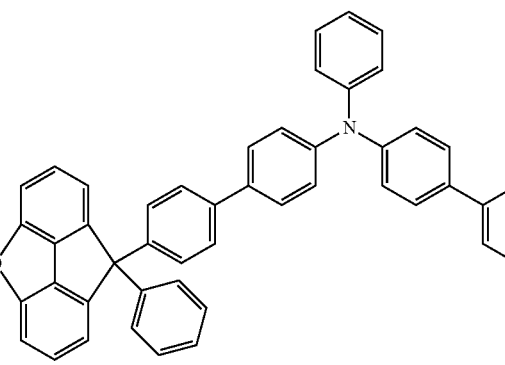
67
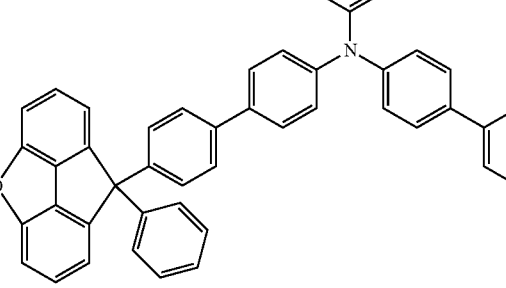

68
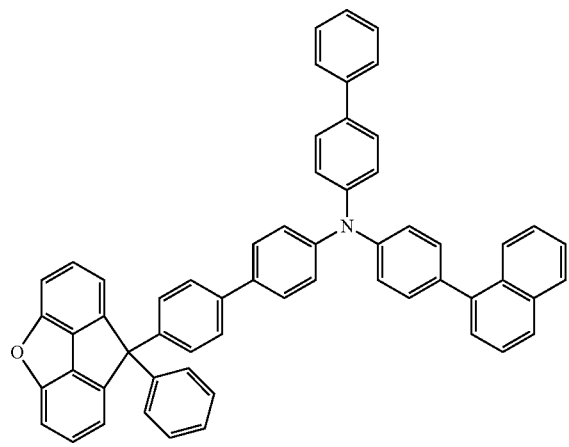
69
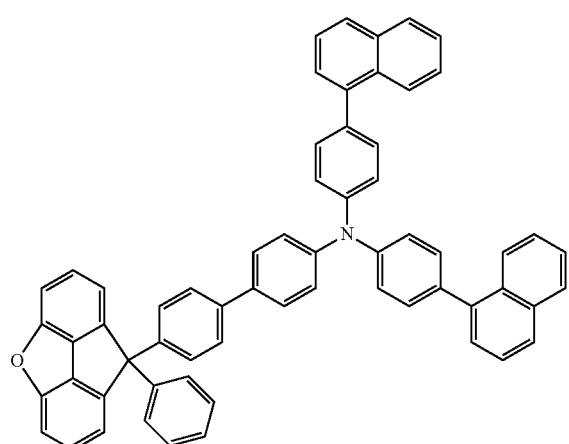
70
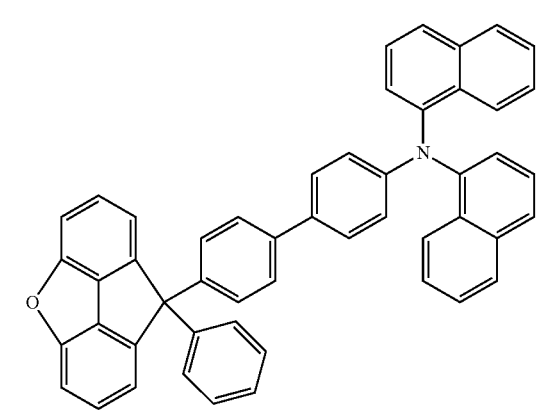
71
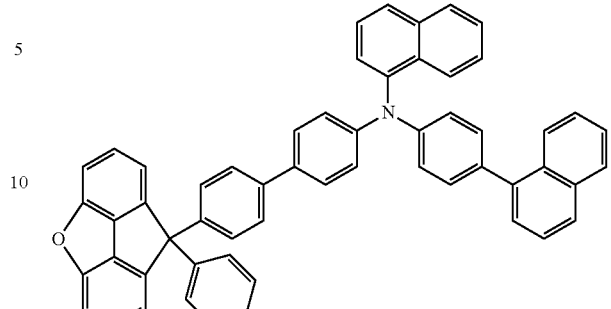
72
73
74
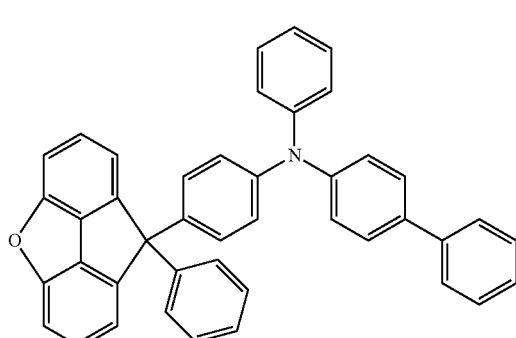

75
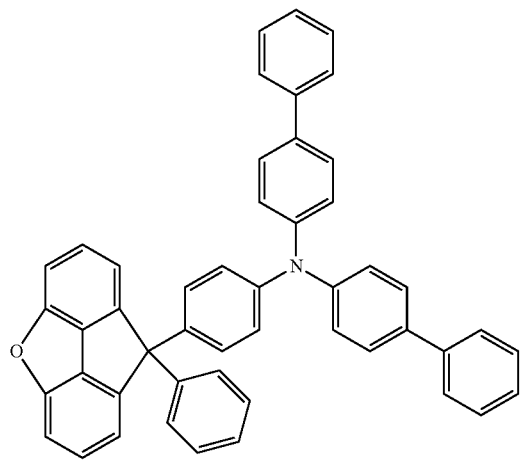
76
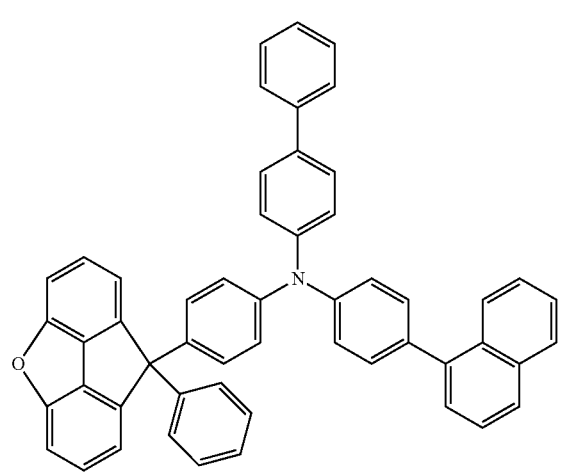
77
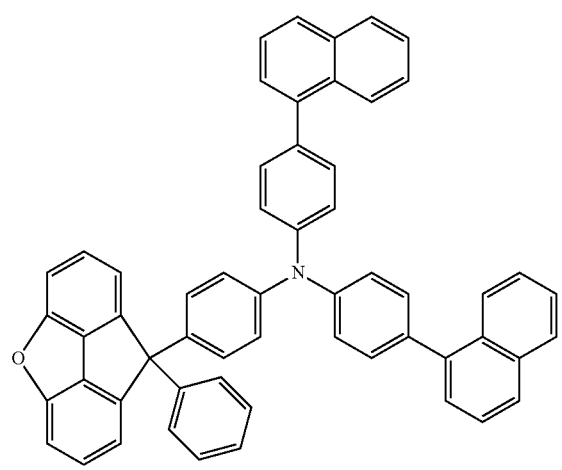
78
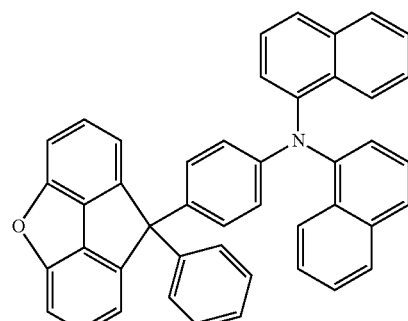
79
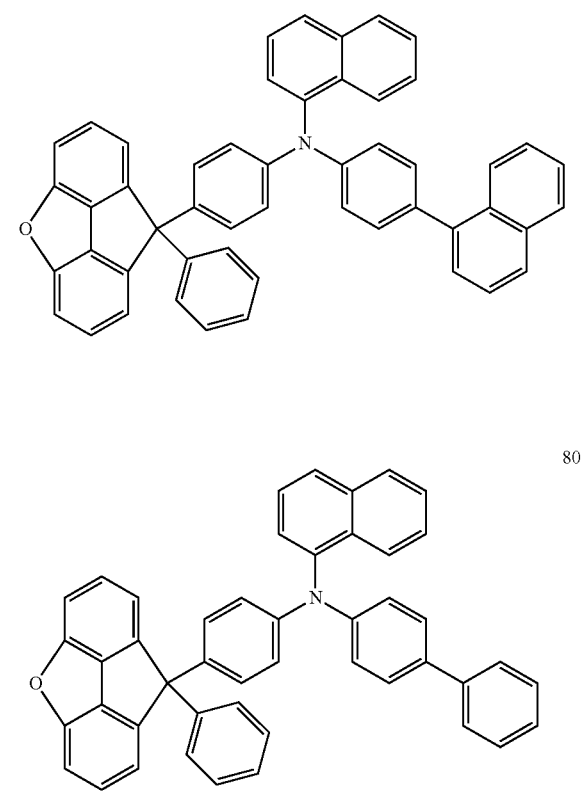
80
81
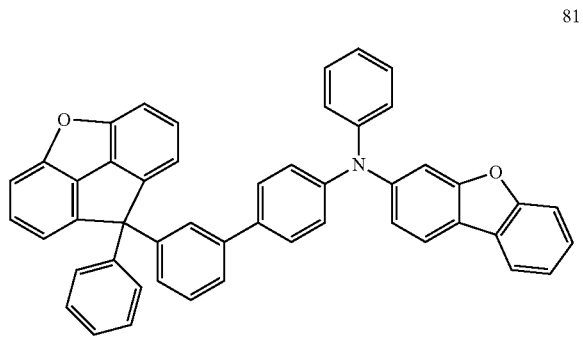

82
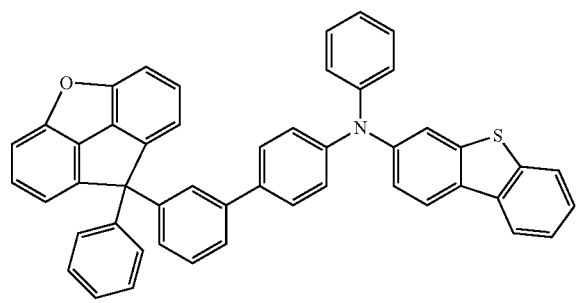
83
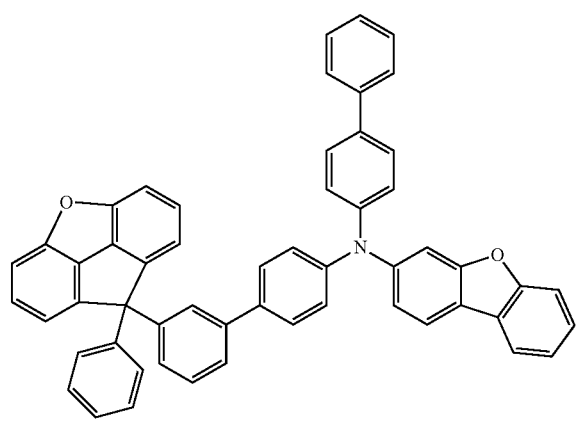
84
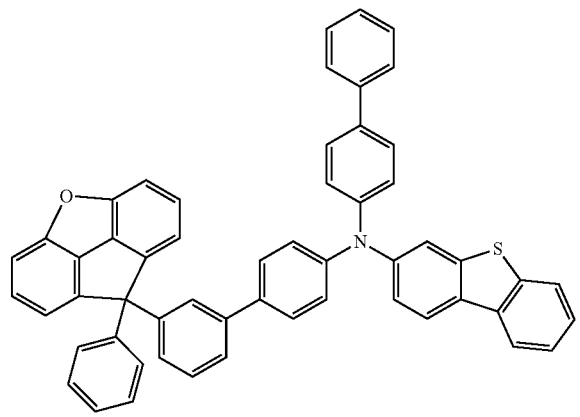
85
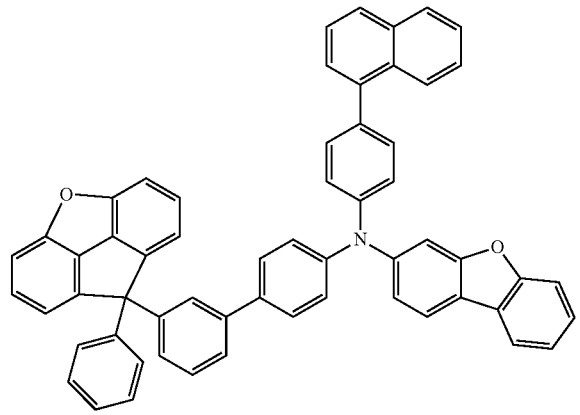
86
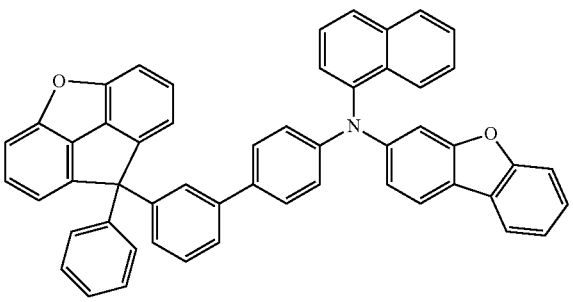
87
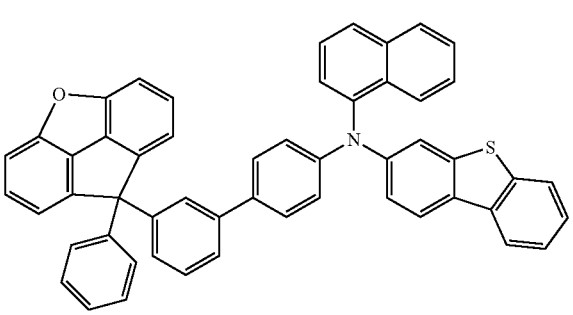
88
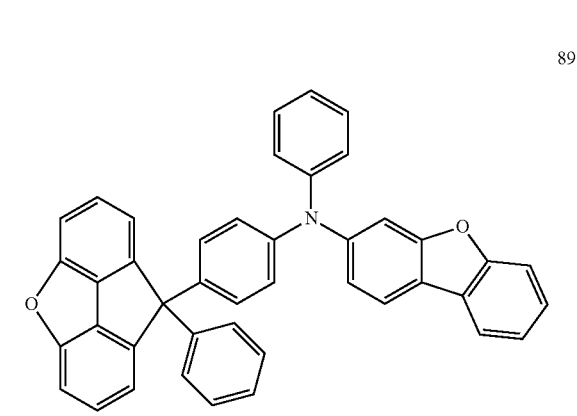
89

159
-continued
90
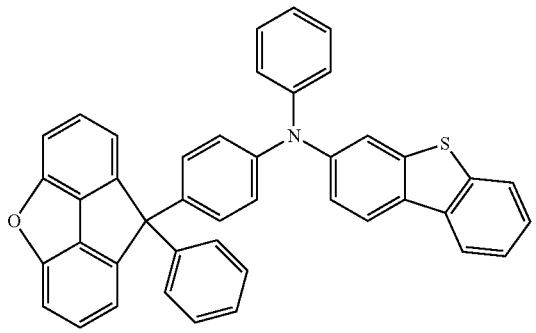
91
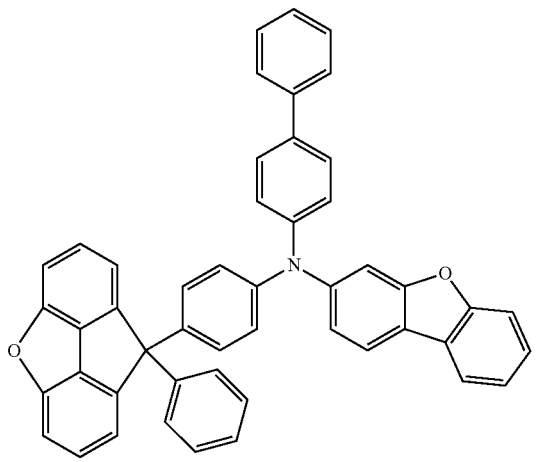
92
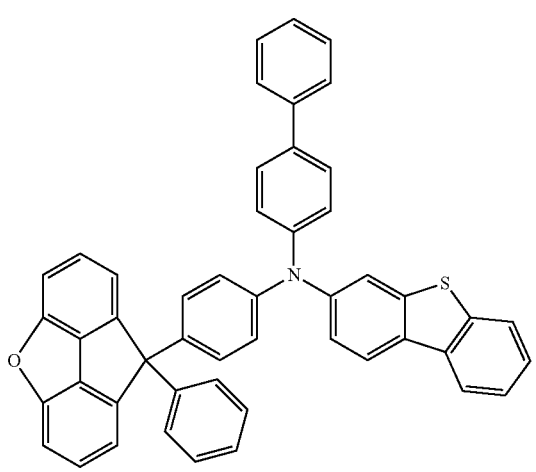
160
-continued
93
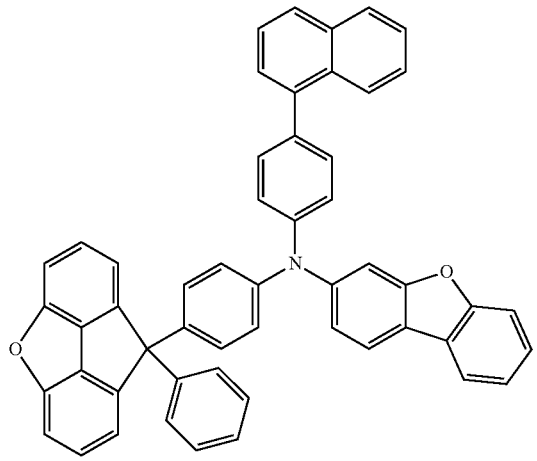
94
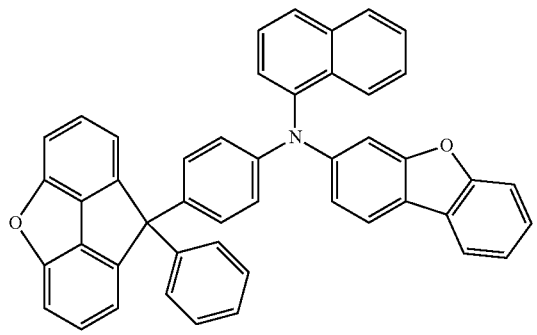
95
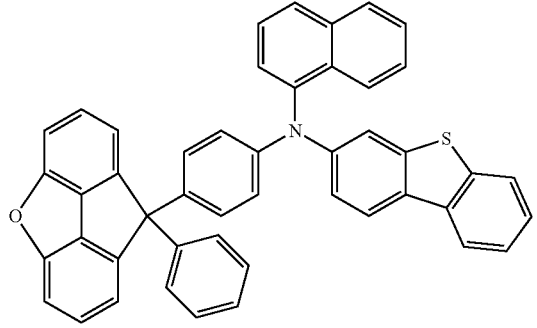
96
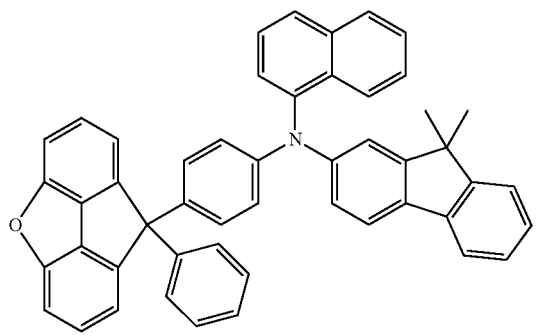

-continued
97
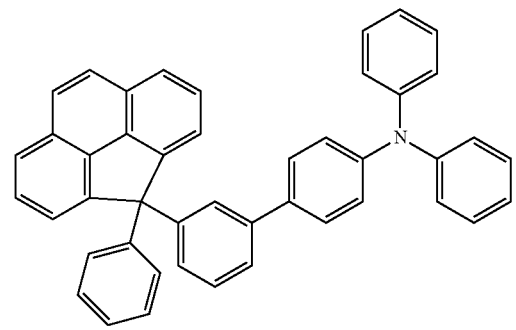
98
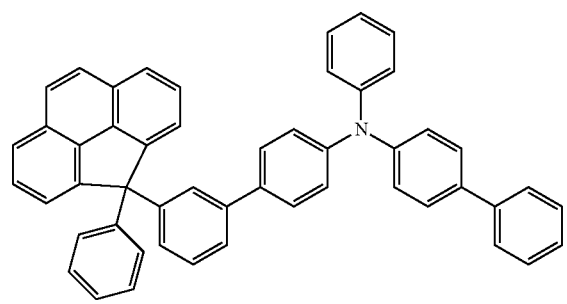
99
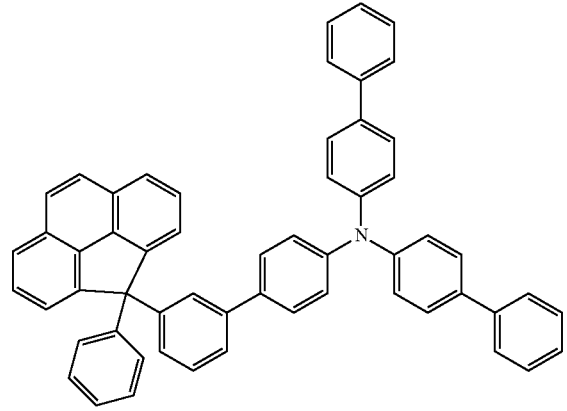
100
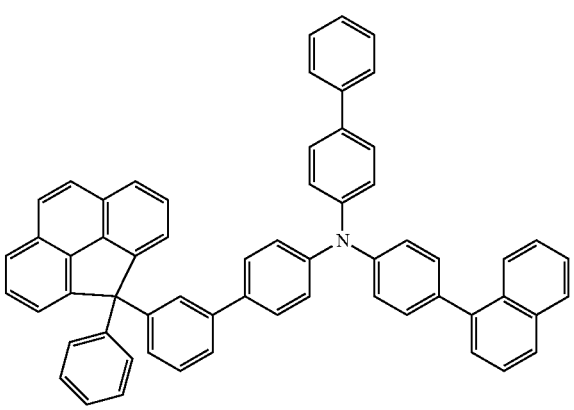
-continued
101
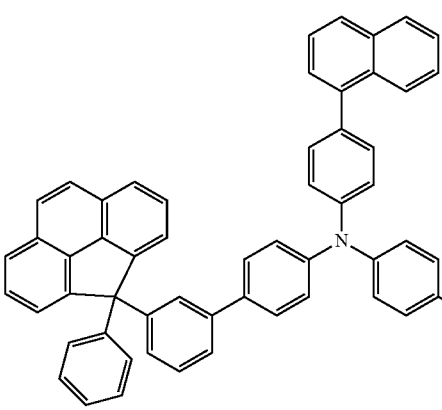
102
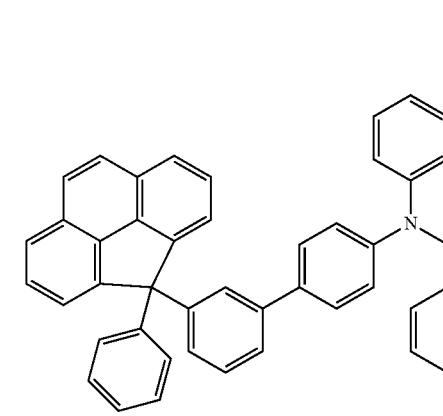
103
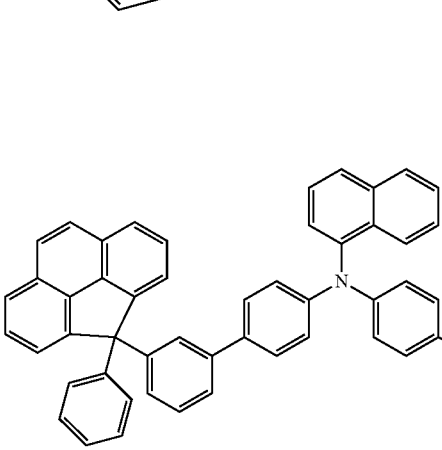
104
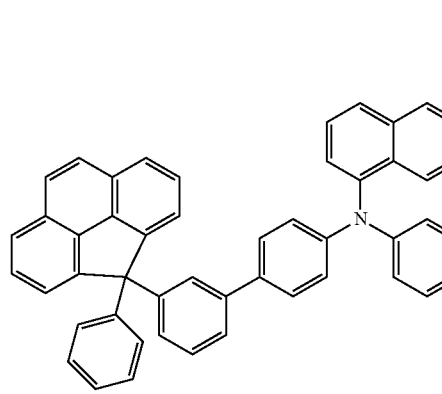

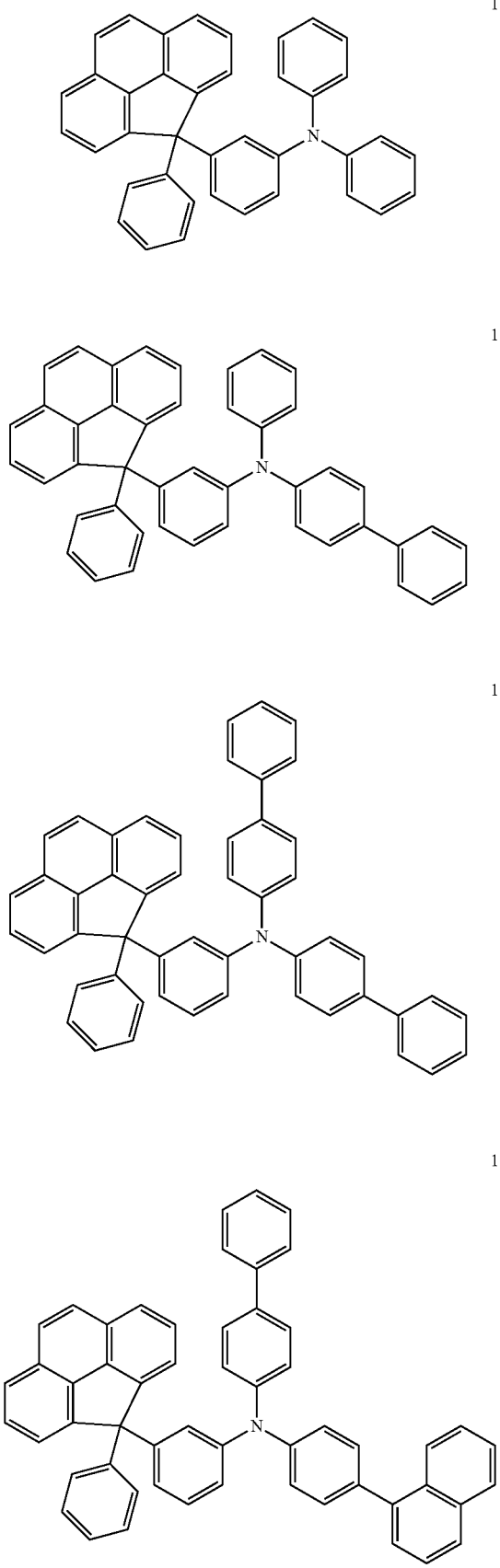
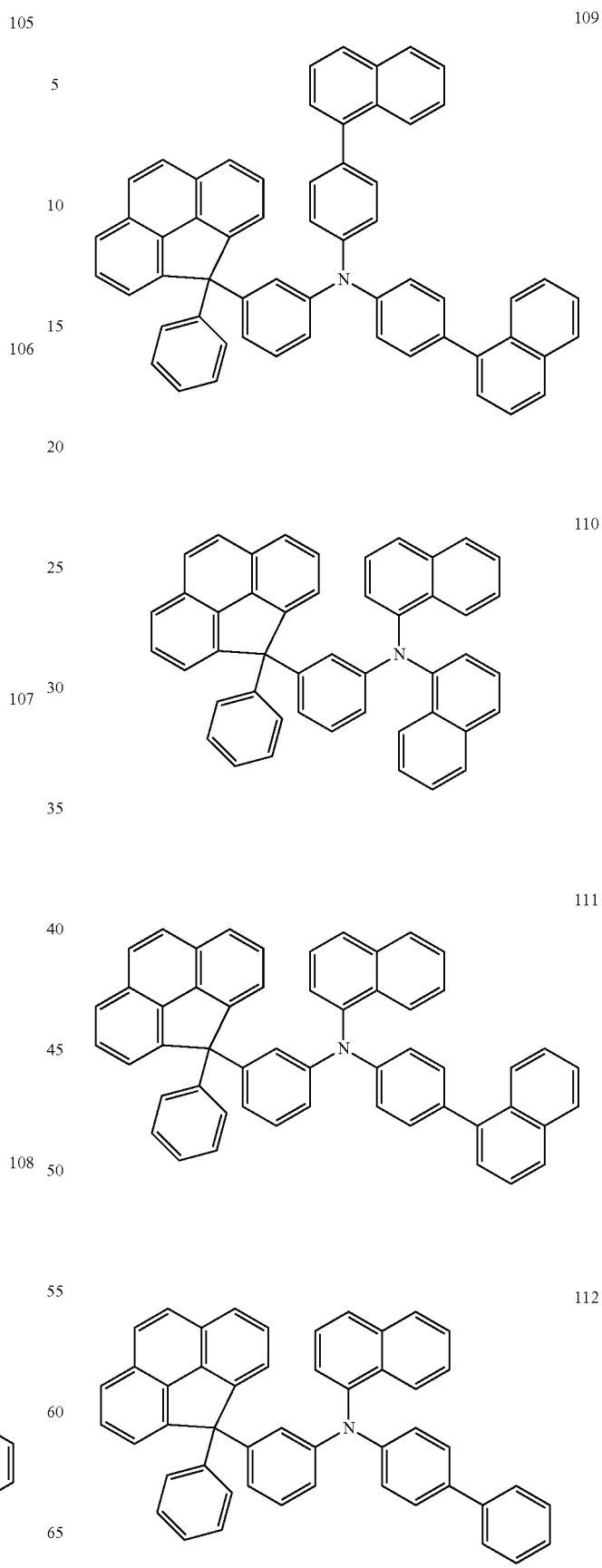

113
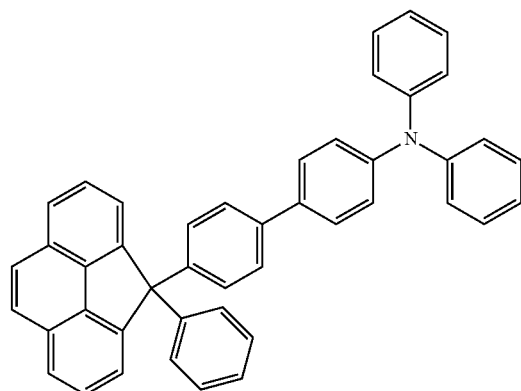
114
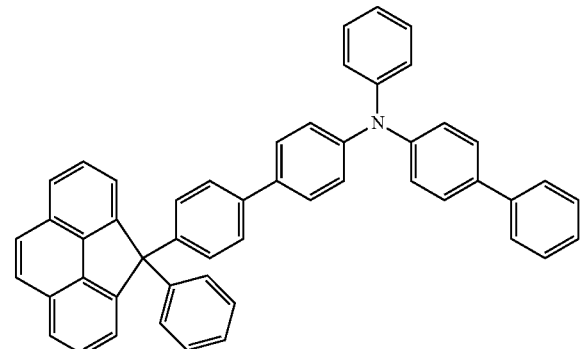
115
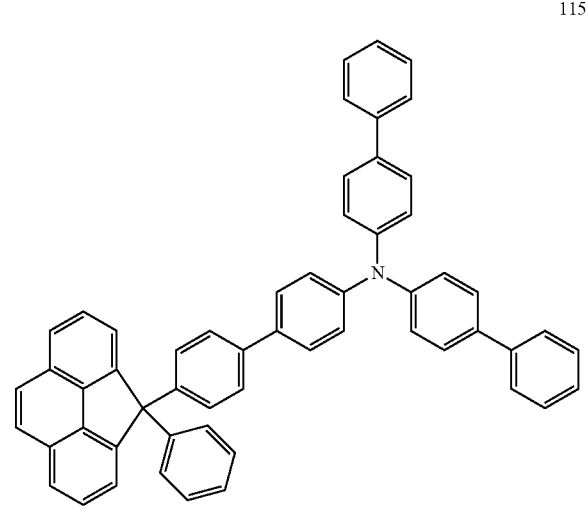
116
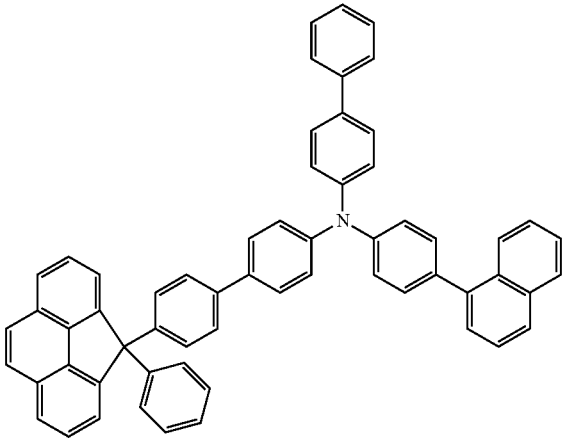
117
118
119
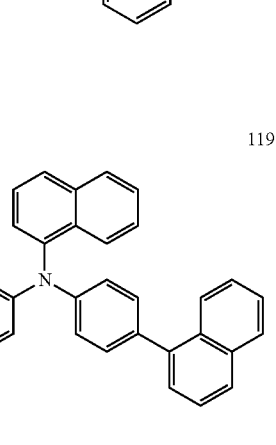

120
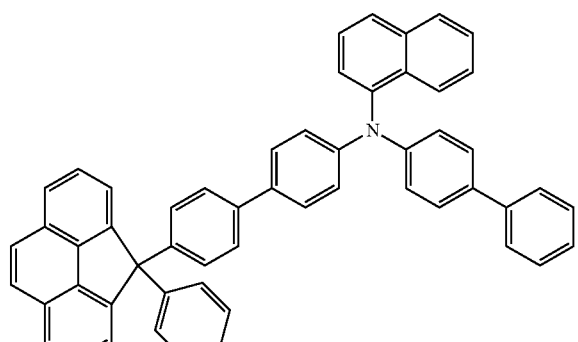
121
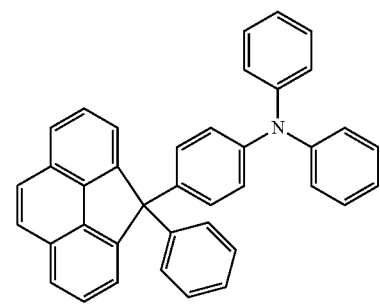
122
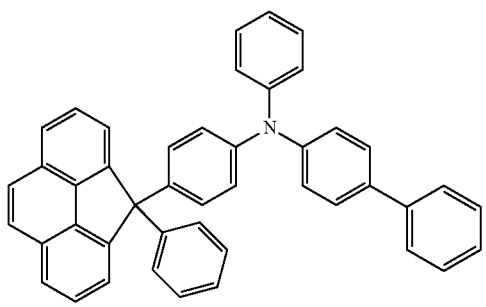
123
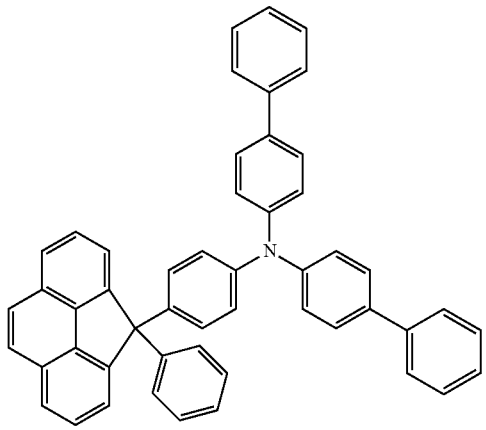
124
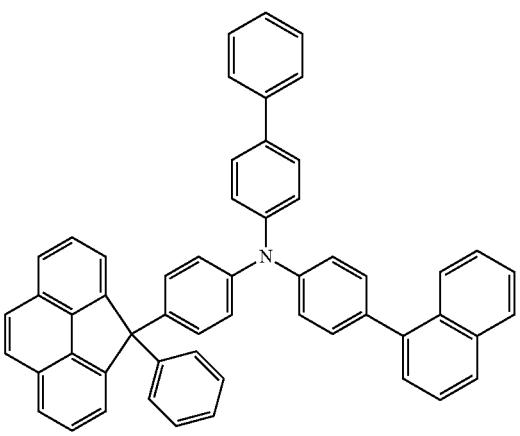
125
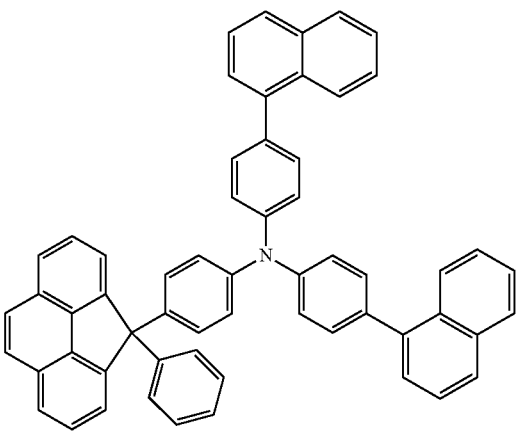
126
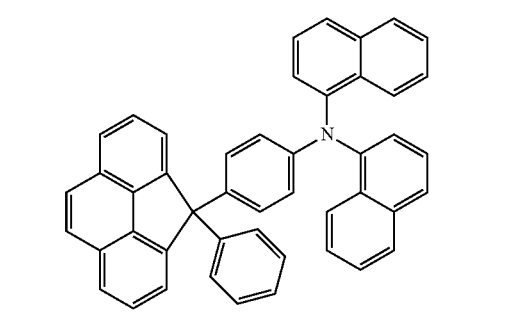
127
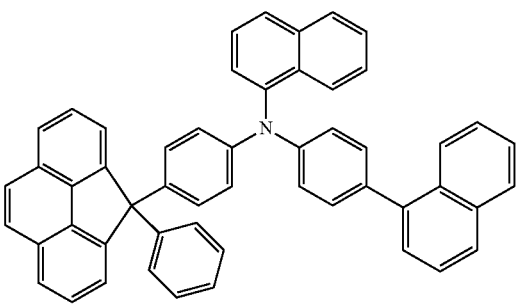

-continued
128
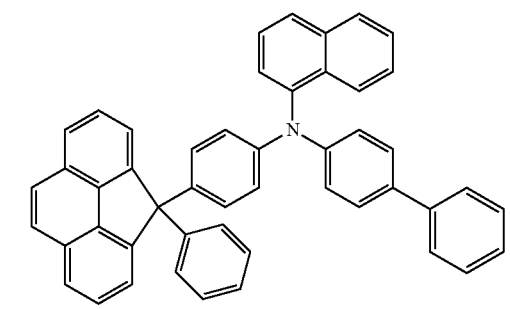
129
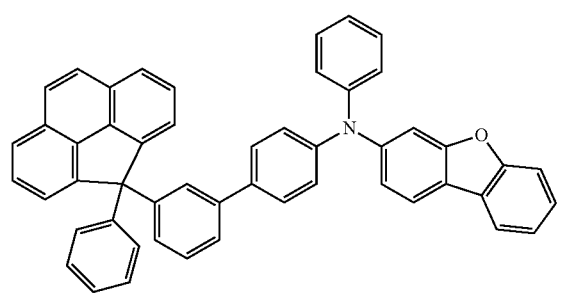
130
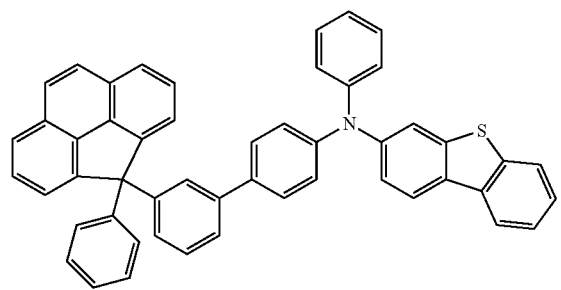
131
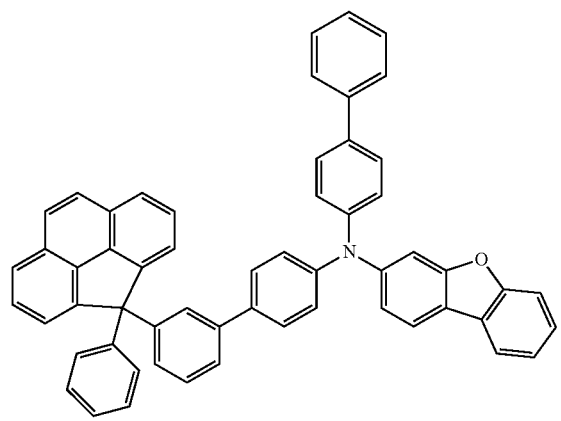
-continued
132
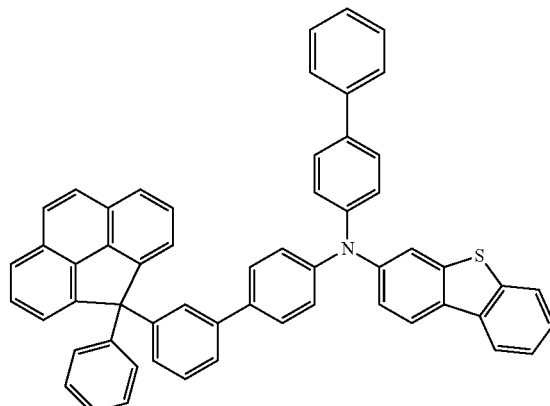
133
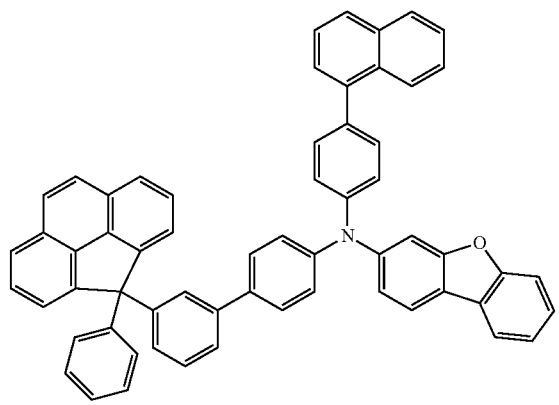
134
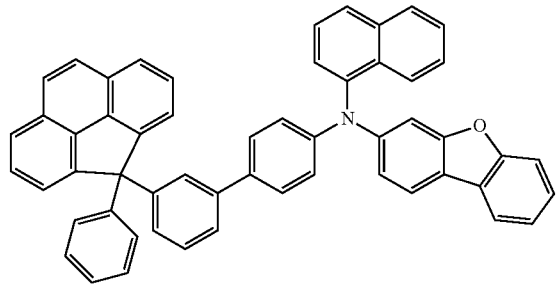
135
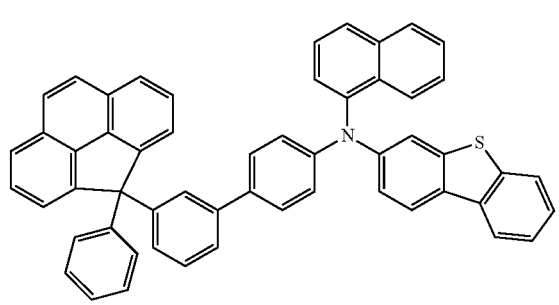

-continued
136
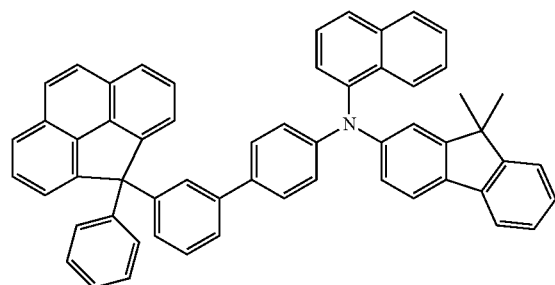
137
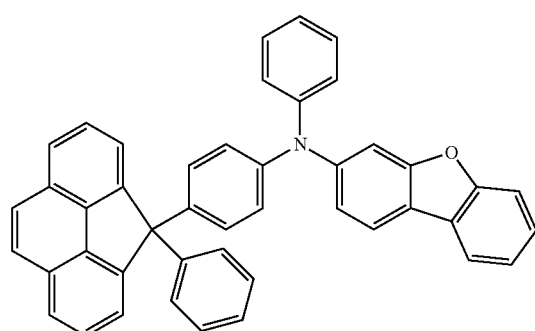
138
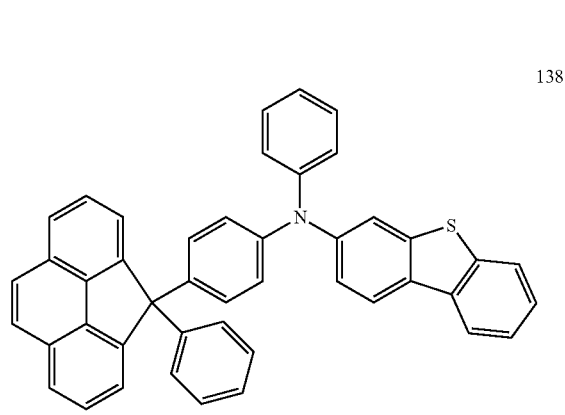
139
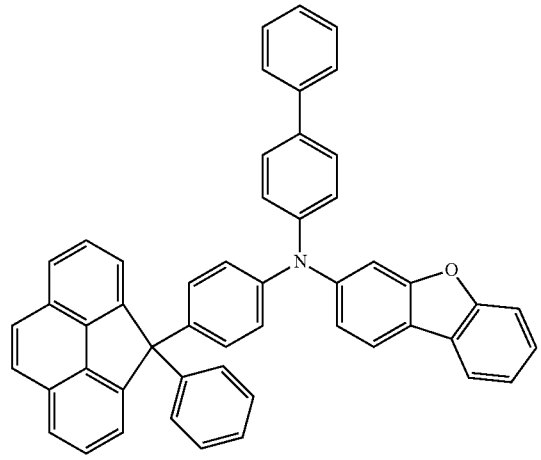
-continued
140
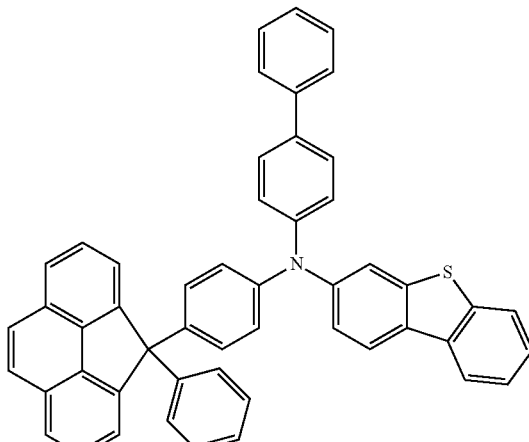
141
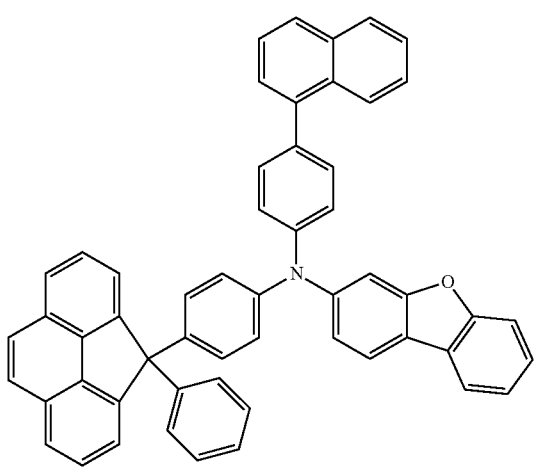
142
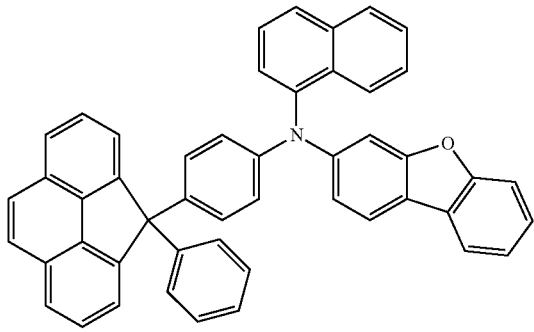
143
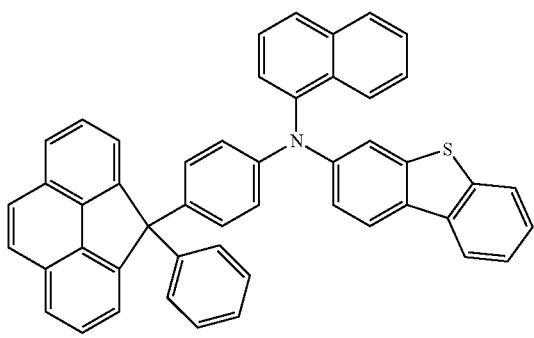

144
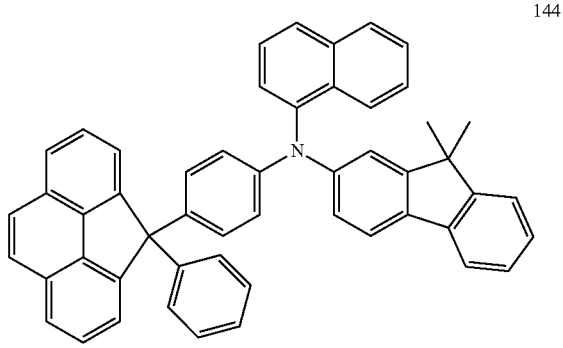
145
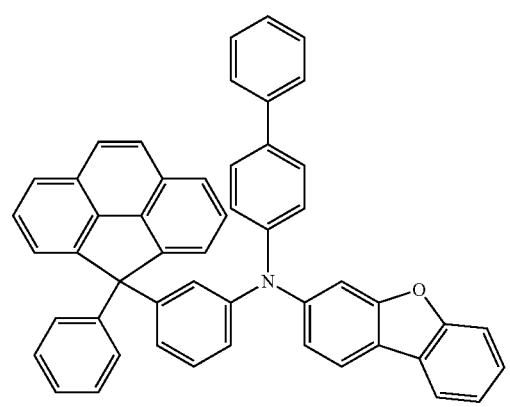
146
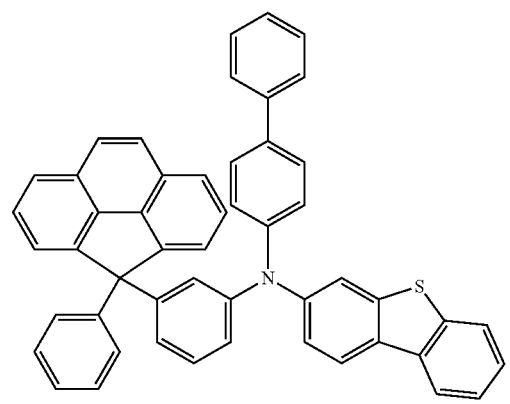
147
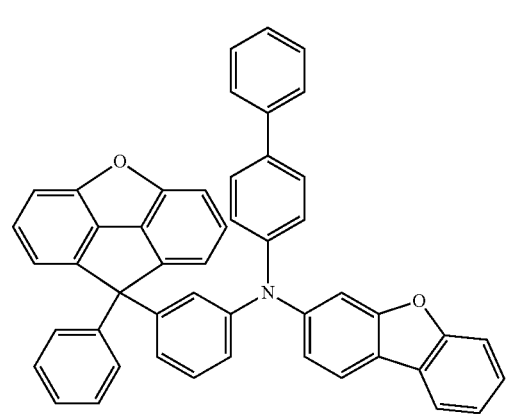
148
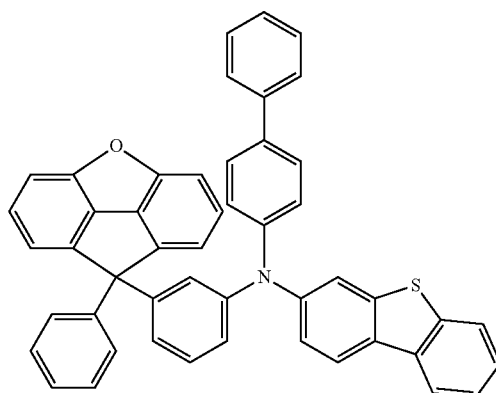
149
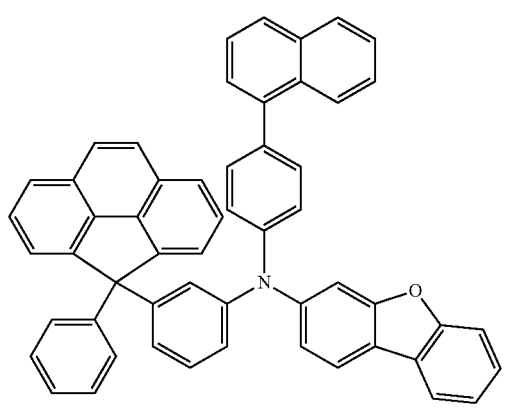
150
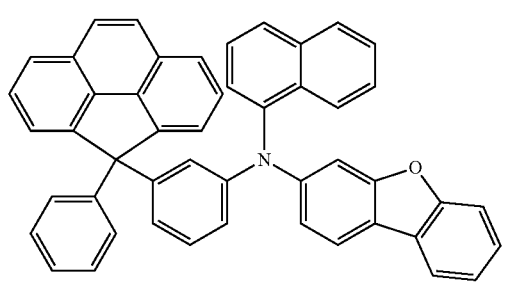
151
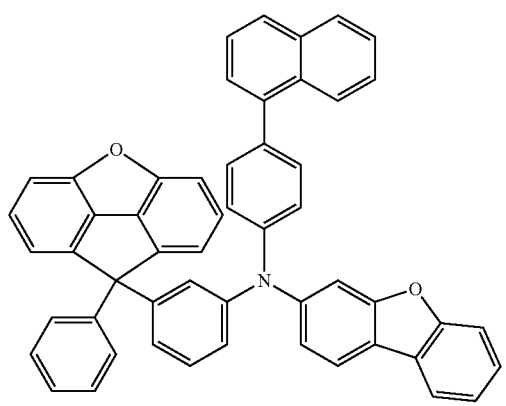

-continued

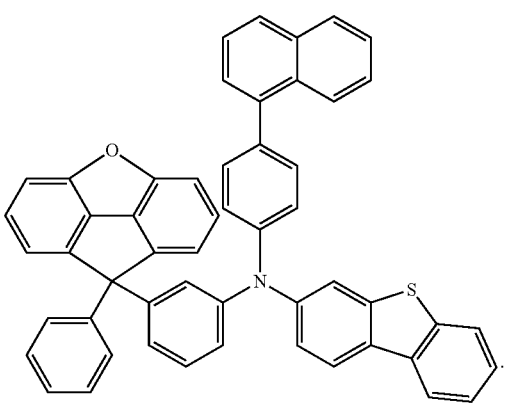

152

The thickness of the hole transport region HTR may be about 100 Å to about 10,000 Å, and in some embodiments, about 100 Å to about 1,000 Å. When the hole transport region HTR includes both (e.g., simultaneously includes) the hole injection layer HIL and the hole transport layer HTL, the thickness of the hole injection layer HIL may be about 100 Å to about 10,000 Å, and in some embodiments, about 100 Å to about 1,000 Å; the thickness of the hole transport layer HTL may be about 30 Å to about 1,000 Å. When the thicknesses of the hole transport region HTR, the hole injection layer HIL, and the hole transport layer HTL satisfy these ranges, satisfactory hole transport properties may be obtained without a substantial increase in driving voltage.

The hole transport region HTR may further include a charge generating material in addition to the above-described materials to improve conductivity. The charge generating material may be uniformly or non-uniformly dispersed in the hole transport region HTR. The charge generating material may be, for example, a p-dopant. The p-dopant may be selected from a quinone derivative, a metal oxide, and a cyano group-containing compound, without limitation. For example, non-limiting examples of the p-dopant may include a quinone derivative (such as tetracyanoquinodimethane (TCNQ) and/or 2,3,5,6-tetrafluoro-tetracyanoquinodimethane (F4-TCNQ)), and/or a metal oxide (such as tungsten oxide and/or molybdenum oxide), without limitation.

As described above, the hole transport region HTR may further include at least one selected from a hole buffer layer and an electron blocking layer in addition to the hole injection layer HIL and the hole transport layer HTL. The hole buffer layer may compensate for an optical resonance distance according to the wavelength of light emitted from the emission layer EML (e.g., be used to adjust the optical resonance distance to match the wavelength of light emitted from the emission layer) and increase the light emission efficiency. Materials included in the hole transport region HTR may also be included in the buffer layer. The electron blocking layer may prevent or reduce electron injection from the electron transport region ETR to the hole transport region HTR.

The emission layer EML may be on the hole transport region HTR. The thickness of the emission layer EML may be, for example, about 100 Å to about 300 Å. The emission layer EML may be a single layer formed using a single material, a single layer formed using a plurality of different materials, or a multilayer structure having a plurality of layers formed using a plurality of different materials.

The emission layer EML may emit red light, green light, blue light, white light, yellow light, or cyan light. The emission layer EML may include a fluorescent material and/or a phosphorescent material. In some embodiments, the emission layer EML may include a host and/or a dopant. The emission layer EML may have a thickness of, for example, about 10 nm to about 60 nm.

The emission layer may include a condensed polycyclic aromatic derivative as a host, which may be an anthracene derivative, a pyrene derivative, a fluoranthene derivative, a chrysene derivative, a benzoanthracene derivative, or a triphenylene derivative. The emission layer EML may include an anthracene derivative and/or a pyrene derivative.

The anthracene derivative may be represented by, for example, Formula 12:

Formula 12

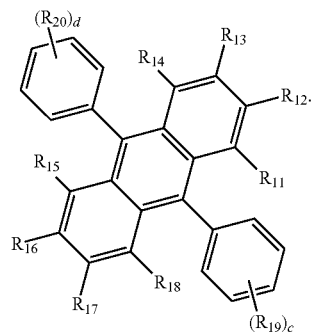

In Formula 12, $R_{11}$ to $R_{20}$ may each independently be an aryl group having 6 to 30 carbon atoms, a heteroaryl group having 1 to 30 carbon atoms, an alkyl group having 1 to 15 carbon atoms, a silyl group, a halogen atom, hydrogen, or deuterium. A plurality of adjacent $R_{11}$ to $R_{20}$ groups may combine to form a saturated or unsaturated ring. In some embodiments, c and d may each independently be an integer selected from 0 to 5.

Each substituted or unsubstituted heteroaryl group having 1 to 30 carbon atoms used as $R_{11}$ to $R_{20}$ may include a benzothiazolyl group, a thiophenyl group, a thienothiophenyl group, a thienothienothiophenyl group, a benzothiophenyl group, a benzofuryl group, a dibenzothiophenyl group, a dibenzofuryl group, an N-arylcarbazolyl group, an N-heteroarylcarbazolyl group, an N-alkylcarbazolyl group, a phenoxazyl group, a phenothiazyl group, a pyridyl group, a pyrimidyl group, a triazyl group, a quinolinyl group, a quinoxalyl group, etc., without limitation.

Each substituted or unsubstituted heteroaryl group having 1 to 30 carbon atoms used as $R_{11}$ to $R_{20}$ may include a benzothiazolyl group, a thiophenyl group, a thienothiophenyl group, a thienothienothiophenyl group, a benzothiophenyl group, a benzofuryl group, a dibenzothiophenyl group, a dibenzofuryl group, an N-arylcarbazolyl group, an N-heteroarylcarbazolyl group, an N-alkylcarbazolyl group, a phenoxazyl group, a phenothiazyl group, a pyridyl group, a pyrimidyl group, a triazyl group, a quinolinyl group, a quinoxalyl group, etc., without limitation. In some embodiments, each alkyl group having 1 to 15 carbon atoms used as $R_{11}$ to $R_{20}$ may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-am inoisobutyl group, a 1,2-diaminoethyl group, a 1,3-diaminoisopropyl group, a 2,3-diamino-t-butyl group, a 1,2,3-triaminopropyl group, a cyanom ethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, etc. A cyclopropyl group, a cyclobutyl group, a cyclopentyl group, a cyclohexyl group, a 4-methylcyclohexyl group, a 1-adamantyl group, a 2-adamantyl group, a 1-norbonyl group, a 2-norbonyl group, etc., may be included, without limitation.

The emission layer EML may include at least one selected from the compounds represented by Compound Group 2:

Compound Group 2 a-1
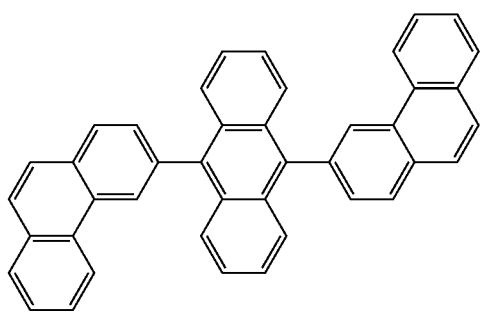

a-2
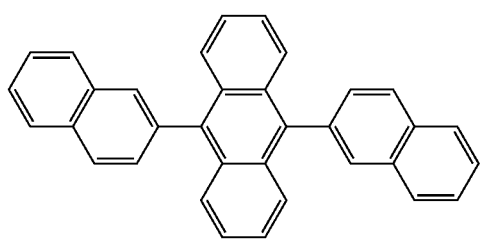

a-3
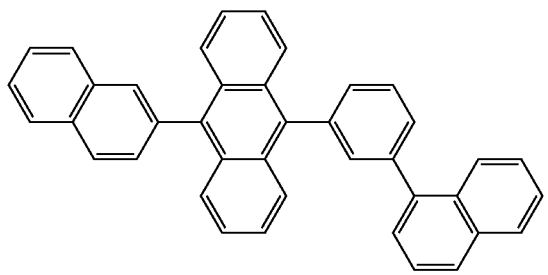

a-4
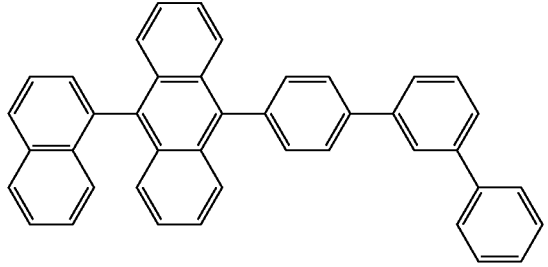

a-5
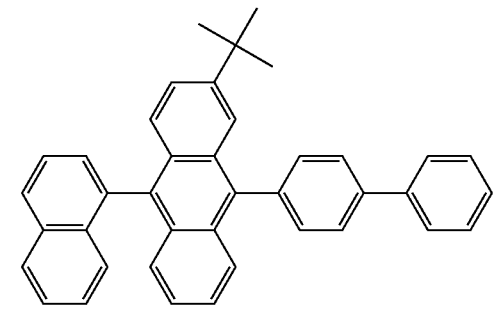

a-6
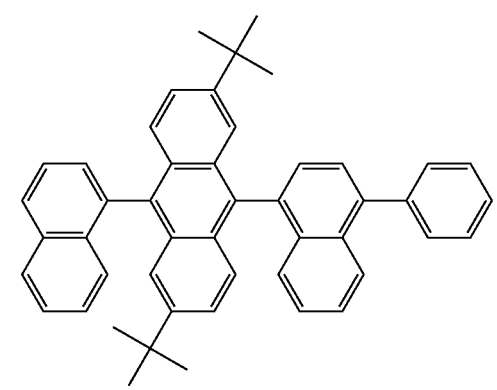

a-7
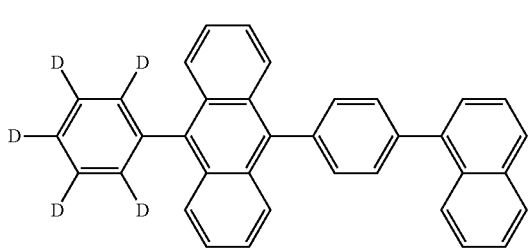

a-8
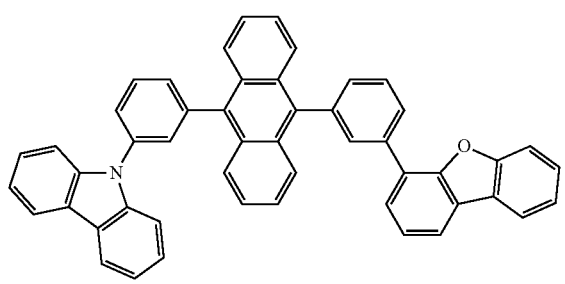

a-9
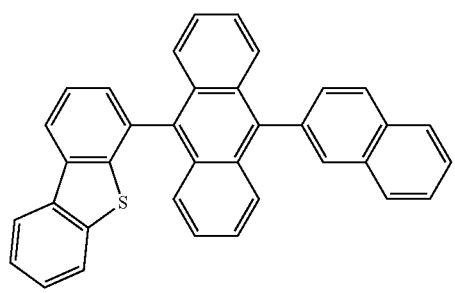

a-10
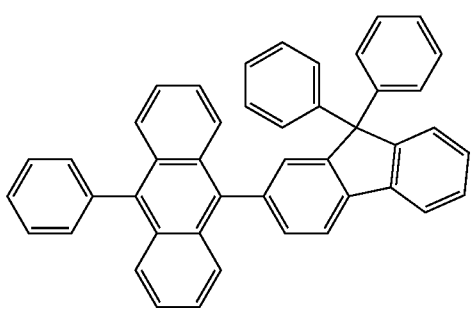

a-11
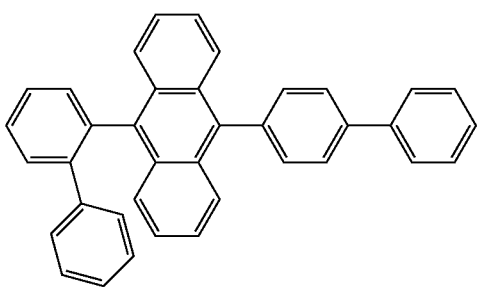

a-12
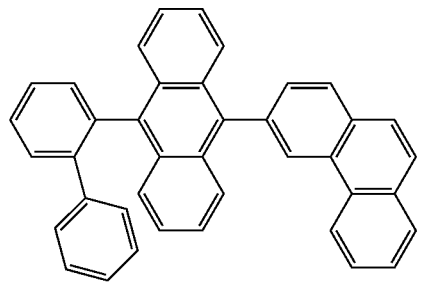

The emission layer may include a dopant, for example, a styryl derivative (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), and/or N-(4-((E)-2-(6-((E)-4-(diphenylamino)styryl)naphthalene-2-yl)vinyl)phenyl-N-phenylbenzenamine (N-BDAVBi)), perylene and derivatives thereof (for example, 2,5,8,11-tetra-t-butylperylene (TBPe)), and/or pyrene and derivatives thereof (for example, 1,1-dipyrene, 1,4-dipyrenylbenzene, 1,4-bis(N,N-diphenylamino)pyrene), etc., without limitation.

The electron transport region ETR may be on the emission layer EML. The electron transport region ETR may include at least one selected from an electron blocking layer, an electron transport layer ETL, and an electron injection layer EIL, without limitation.

The electron transport region ETR may have a single layer formed of a single material, a single layer formed of a plurality of materials, or a multilayer structure including a plurality of layers formed of a plurality of materials.

For example, the electron transport region ETR may have a single layer structure (such as the electron injection layer EIL and/or the electron transport layer ETL), or a single layer structure formed of an electron injection material and an electron transport material. In some embodiments, the electron transport region ETR may have a multi-layered laminated structure laminated from (e.g., on or over) the anode AN, of electron transport layer ETL/electron injection layer EIL, or hole blocking layer/electron transport layer ETL/electron injection layer EIL, without limitation. The thickness of the electron transport region ETR may be, for example, about 1,000 Å to about 1,500 Å.

The electron transport region ETR may be formed using one or more suitable methods (such as a vacuum deposition method, a spin coating method, a casting method, a Langmuir-Blodgett (LB) method, an inkjet printing method, a laser printing method, and/or a laser induced thermal imaging (LITI) method).

When the electron transport region ETR includes the electron transport layer ETL, the electron transport region ETR may include tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzimidazolyl-1-ylphenyl)-9,10-dinaphthylanthracene, 1,3,5-tri(1-phenyl-1H-benz[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), beryllium bis(benzoquinolin-10-olate (Bebq$_2$), 9,10-di(naphthalene-2-yl)anthracene (ADN), and/or a mixture thereof, without limitation. The thickness of the electron transport layer ETL may be about 100 Å to about 1,000 Å and in some embodiments, may be about 150 Å to about 500 Å. When the thickness of the electron transport layer ETL satisfies these ranges, satisfactory electron transport properties may be obtained without a substantial increase in driving voltage.

When the electron transport region ETR includes an electron injection layer EIL, the electron transport region ETR may include LiF, lithium quinolate (LiQ), Li$_2$O, BaO, NaCl, CsF, a lanthanide metal (such as ytterbium (Yb)), and/or a metal halide (such as RbCl and/or RbI), without limitation. The electron injection layer EIL may be formed using a mixture of a hole transport material and an insulating metal-organic salt (e.g., an organometallic complex). The metal-organic salt may have an energy band gap of about 4 eV or more. For example, the metal-organic salt may include, for example, a metal acetate, a metal benzoate, a metal acetoacetate, a metal acetylacetonate, and/or a metal stearate. The thickness of the electron injection layer EIL may be about 1 Å to about 100 Å, and in some embodiments, about 3 Å to about 90 Å. When the thickness of the electron injection layer EIL satisfies these ranges, satisfactory electron injection property may be obtained without inducing the substantial increase of a driving voltage.

The electron transport region ETR may include a hole blocking layer, as described above. The hole blocking layer may include, for example, 2,9-dimethyl-4,7-diphenyl-1,10-phenanthroline (BCP), and/or 4,7-diphenyl-1,10-phenanthroline (Bphen), without limitation.

The cathode CAT may be on the electron transport region ETR. The cathode CAT may be a common electrode or a cathode. The cathode CAT may be a transmissive electrode, a transflective electrode, or a reflective electrode. When the cathode CAT is a transmissive electrode, the cathode CAT may include a transparent metal oxide (for example, ITO, IZO, ZnO, ITZO, etc.).

When the cathode CAT is a transflective electrode or a reflective electrode, the cathode CAT may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The cathode CAT may have a multi-layered structure including a reflective layer and/or a transflective layer formed using the above-described materials and a transparent conductive layer formed using ITO, IZO, ZnO, ITZO, etc.

The cathode CAT may be connected with an auxiliary electrode. When the cathode CAT is connected with an auxiliary electrode, the resistance of the cathode CAT may decrease.

In the organic light emitting device 10, voltages may be applied to each of the anode AN and the cathode CAT, holes injected from the anode AN may move through the hole transport region HTR to the emission layer EML, and electrons injected from the cathode CAT may move through the electron transport region ETR to the emission layer EML. The electrons and the holes may recombine in the emission layer EML to generate excitons, and the excitons may emit light via transition (e.g., radiative decay) from an excited state to the ground state.

When the organic light emitting device 10 is a top emission type (e.g., top emission device), the anode AN may be a reflective electrode, and the cathode CAT may be a transmissive electrode or a transflective electrode. When the organic light emitting device 10 is a bottom emission type (e.g., bottom emission device), the anode AN may be a transmissive electrode or a transflective electrode, and the cathode CAT may be a reflective electrode.

An organic light emitting device according to an embodiment of the present disclosure may include an amine compound in a hole transport region, formed by combining an amine group contributing to long lifespan and a cyclic fluorenyl group contributing to high charge tolerance. The stability of radicals may be improved due to conjugation around the amine group, which may also maintain the properties of the amine group and contribute to high charge tolerance. Accordingly, an organic light emitting device according to an embodiment of the present disclosure may have long lifespan and high efficiency.

Hereinafter, methods of synthesizing the amine compound according to an embodiment of the present disclosure and a method of manufacturing an organic light emitting device according to an embodiment of the present disclosure will be explained in more detail by referring to example embodiments. The following embodiments are provided to assist understanding of the present disclosure, and the scope of the present disclosure is not limited thereto.

EXAMPLES

Synthetic Examples (Synthesis of Compound 61)
(Synthesis of Compound A)

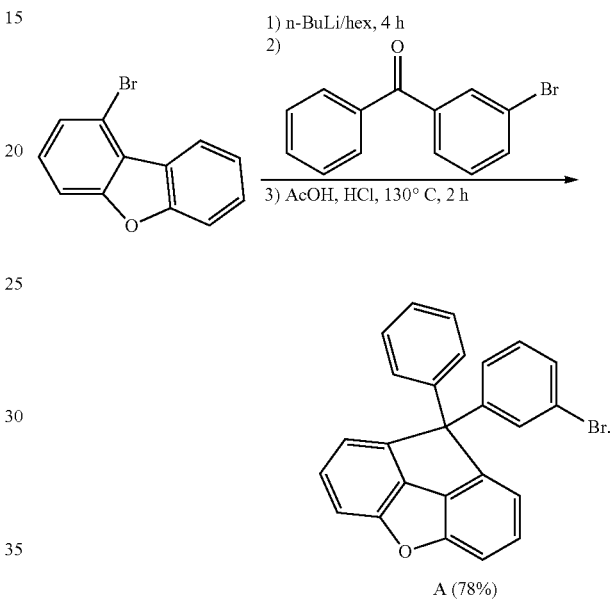

70 mL of an anhydrous THF solution of 10.6 g (42.9 mmol) of 1-bromodibenzofuran was added to a 500 mL, three-necked flask, and stirred at about −78° C. 27 mL (42.9 mmol) of a hexane solution of 1.58 M n-BuLi was added dropwise, followed by stirring for about 2.5 hours. 85 mL of an anhydrous THF solution of 9.30 g (35.6 mmol) of 3-bromobenzophenone was added dropwise, followed by stirring for about 2 hours and then stirring at room temperature for about 3 hours. After the reaction was complete, a 1 N aqueous hydrochloric acid solution was added thereto and stirred for about 1 hour. The resulting product was washed with water, and the organic phase was concentrated to obtain a material having a candy-like consistency. The material having a candy-like consistency, 50 mL of glacial acetic acid, and 2.4 mL of hydrochloric acid were added to a 500 mL eggplant (e.g., pear-shaped) flask, followed by heating and stirring under a nitrogen atmosphere at about 130° C. for about 2 hours. The reaction mixture was added dropwise to 350 mL of water in a flask stored over ice, thus precipitating white crystals. The solid thus produced was filtered, washed with methanol, and dried. 13.3 g of a white powder was obtained as the target material at a yield of 78%.

The molecular weight of the product was measured using fast atom bombardment-mass spectrometry (FAB-MS) to be 411, consistent with Compound A.

Synthesis of Compound 61

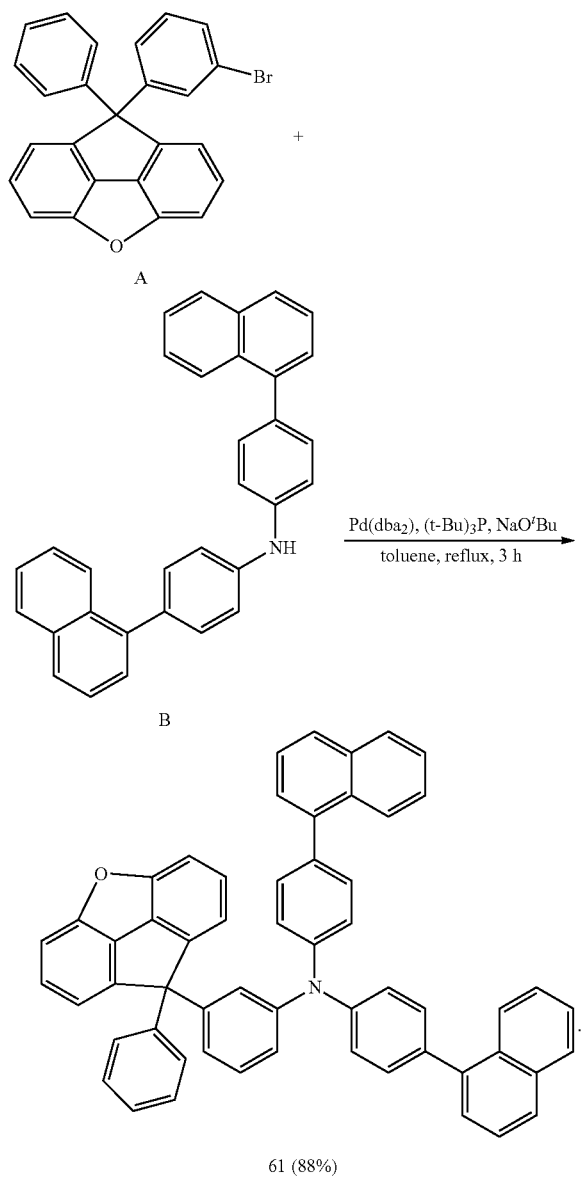

Under an argon atmosphere, 4.10 g of Compound A, 4.42 g of Compound B, 0.563 g of Pd(dba)$_2$, 0.23 g of (t-Bu)$_3$P, and 4.13 g of sodium tert-butoxide were added to a 200 mL, three-necked flask, followed by refluxing while stirring in 140 mL of toluene for about 3 hours. The reaction was allowed to cool to room temperature, water was added, an organic layer was separated, and solvents were removed via vacuum distillation. The crude product thus obtained was separated by silica gel column chromatography (using toluene and hexane) to produce 6.62 g (Yield 88%) of Compound 61 as a white solid.

The molecular weight of the product was measured using FAB-MS to be 752, consistent with Compound 61.

The chemical shift values (δ) of Compound 61 were measured by $^1$H-NMR (CDCl$_3$) to be 8.56 (d, 2H, J=7.60 Hz), 8.05-8.02 (m, 1H), 7.87-7.84 (m, 4H), 7.80 (s, 1H), 7.70-7.50 (m, 11H), 7.40-7.27 (m, 10H), 7.16-7.11 (m, 3H), 7.08-7.03 (m, 6H).

Synthesis of Compound 109
(Synthesis of Compound C)

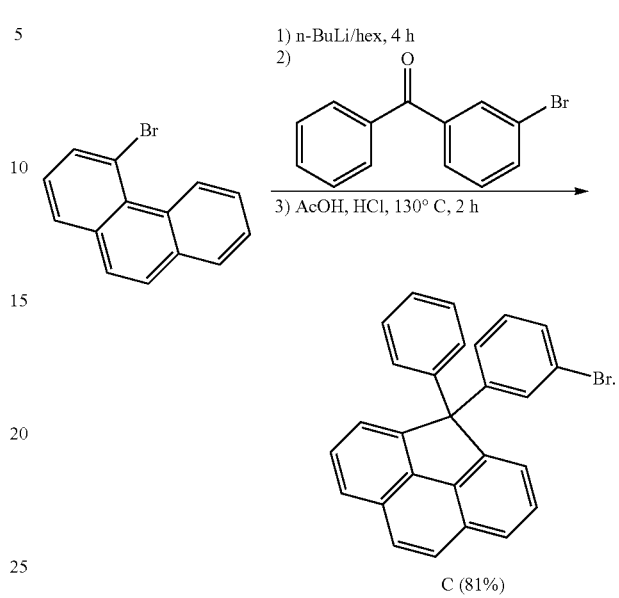

70 mL of an anhydrous THF solution of 11.0 g (42.9 mmol) of 4-bromophenanthrene was added to a 500 mL, three-necked flask, and stirred at about −78° C. 27 mL (42.9 mmol) of a hexane solution of 1.58 M n-BuLi was added dropwise, followed by stirring for about 2.5 hours. 85 mL of an anhydrous THF solution of 9.30 g (35.6 mmol) of 3-bromobenzophenone was added dropwise, followed by stirring for about 2 hours and stirring at room temperature for about 3 hours. After the reaction was complete, a 1 N aqueous hydrochloric acid solution was added thereto and stirred for about 1 hour. The resulting product was washed with water, and the resulting organic phase was concentrated to produce a white solid having a candy-like consistency. The material having a candy-like consistency, 50 mL of glacial acetic acid, and 2.4 mL of hydrochloric acid were added to a 500 mL eggplant (e.g., pear-shaped) flask, followed by heating and stirring under a nitrogen atmosphere at about 130° C. for about 2 hours. The reaction mixture was added dropwise to 350 mL of water in a flask stored over ice, thus precipitating white crystals. The resulting solid was filtered, washed with methanol, and dried. 13.8 g of a white powder was obtained as the target material at a yield of 81%.

The molecular weight of the product was measured using FAB-MS to be 421, consistent with Compound C.

(Synthesis of Compound 109)

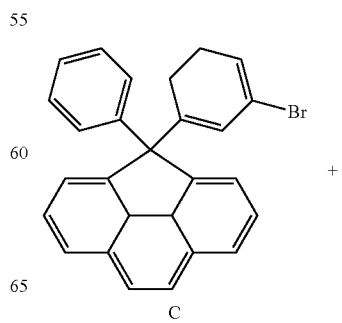

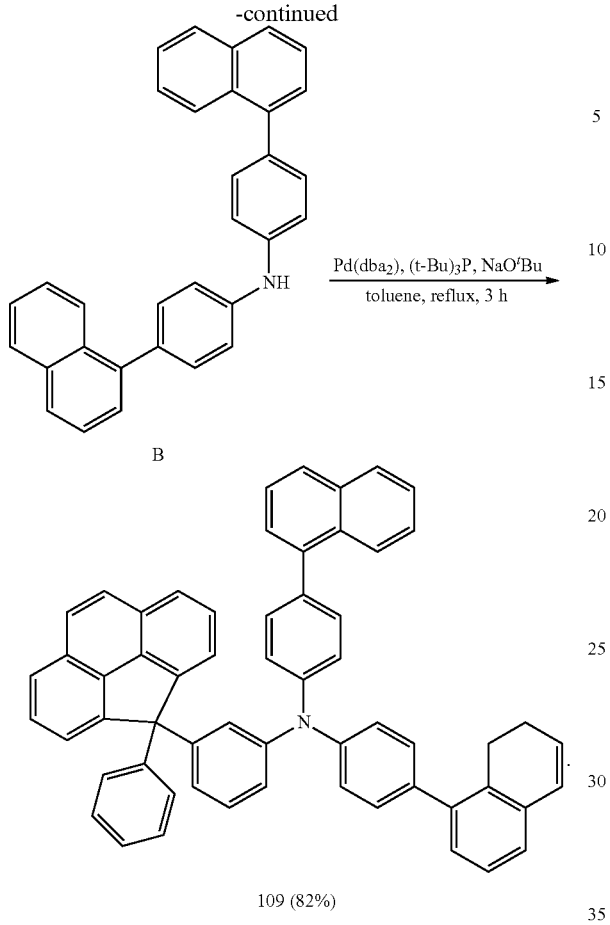

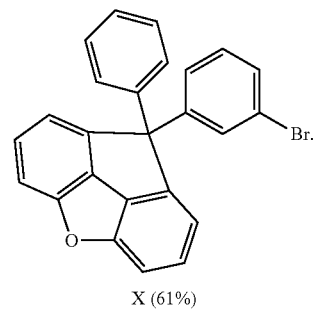

X (61%)

Under an argon atmosphere, 4.23 g of Compound C, 5.00 g of Compound B, 0.563 g of Pd(dba)$_2$, 0.23 g of (t-Bu)$_3$P, and 4.13 g of sodium tert-butoxide were added to a 200 mL, three-necked flask, followed by refluxing while stirring in 140 mL of toluene for about 3 hours. The reaction was allowed to cool to room temperature, water was added, an organic layer was separated, and solvents were removed via vacuum distillation. The crude product thus obtained was separated by silica gel column chromatography (using toluene and hexane) to produce 6.24 g (Yield 82%) of Compound 109 as a white solid.

The molecular weight of the product was measured using FAB-MS to be 761, consistent with Compound 109.

The chemical shift values (δ) of Compound 109 were measured by $^1$H-NMR (CDCl$_3$) to be 8.57 (d, 2H, J=7.70 Hz), 8.35 (d, 1H, J=7.80 Hz), 8.04-8.02 (m, 2H), 7.88-7.84 (m, 4H), 7.80 (s, 1H), 7.60-7.50 (m, 11H), 7.36-7.27 (m, 10H), 7.16-7.11 (m, 3H), 7.08-7.05 (m, 6H).

(Synthesis of Compound X)

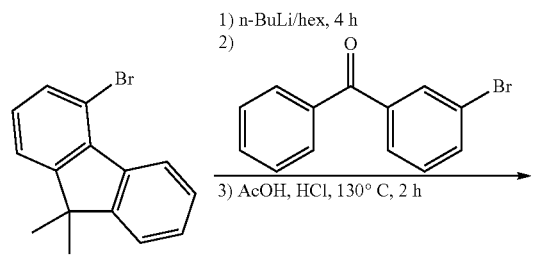

70 mL of an anhydrous THF solution of 9.40 g (42.9 mmol) of 4-bromo-9,9-dimethylfluorene was added to a 500 mL, three-necked flask and stirred at about −78° C. 27 mL (42.9 mmol) of a hexane solution of 1.58 M n-BuLi was added dropwise, followed by stirring for about 2.5 hours. 85 mL of an anhydrous THF solution of 9.30 g (35.6 mmol) of 3-bromobenzophenone was added thereto dropwise, followed by stirring for about 2 hours and then stirring at room temperature for about 3 hours. After the reaction was complete, a 1 N aqueous hydrochloric acid solution was added thereto and stirred for about 1 hour. The resulting product was washed with water, and the resulting organic phase was concentrated to obtain a white solid having a candy-like consistency. The material having a candy-like consistency, 50 mL of glacial acetic acid, and 2.4 mL of hydrochloric acid were added to a 500 mL eggplant (e.g., pear shaped) flask, followed by heating and stirring under a nitrogen atmosphere at about 130° C. for about 2 hours. The reaction mixture was added dropwise to 350 mL of water in a flask stored over ice, thus precipitating white crystals. The solid thus produced was filtered, washed with methanol, and dried. 9.50 g of a white powder was obtained as the target material at a yield of 61%.

The molecular weight of the product was measured using FAB-MS to be 437, consistent with Compound X.

(Synthesis of Compound 13)

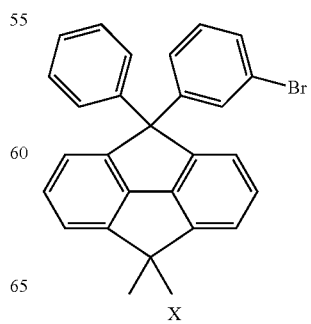

187

-continued

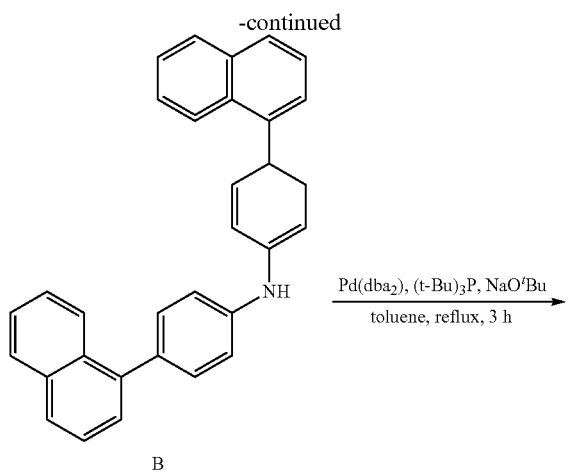

188

(Synthesis of Compound 145)

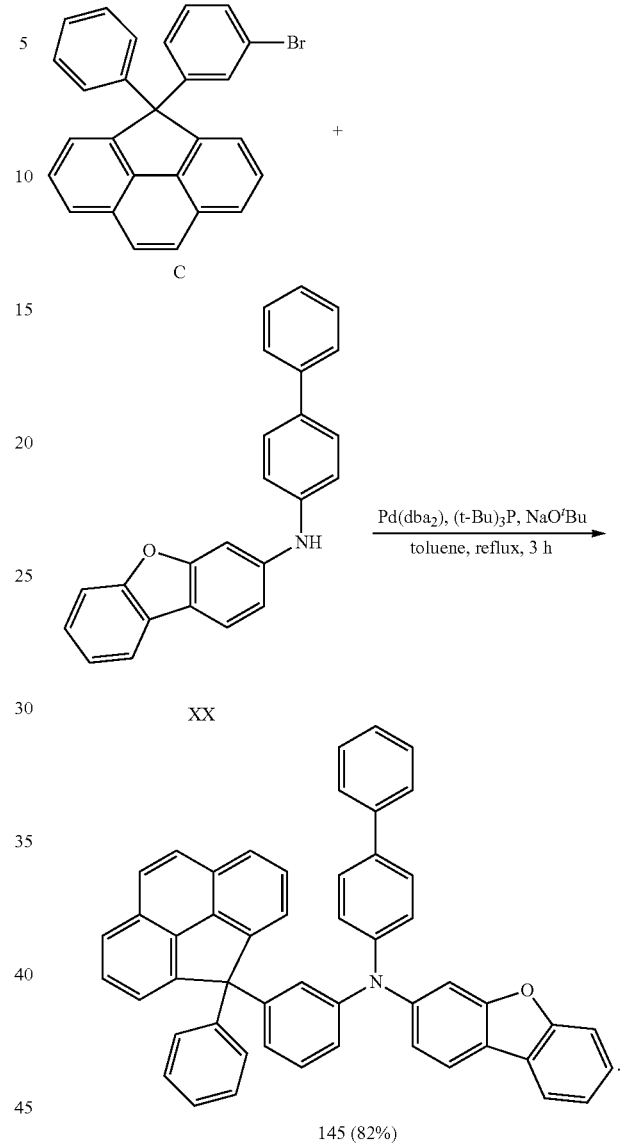

Under an argon atmosphere, 3.70 g of Compound X, 4.42 g of Compound B, 0.563 g of Pd(dba)$_2$, 0.23 g of (t-Bu)$_3$P, and 4.13 g of sodium tert-butoxide were added to a 200 mL, three-necked flask, followed by refluxing while stirring in 140 mL of toluene for about 3 hours. The reaction was allowed to cool to room temperature, water was added, an organic layer was separated, and solvents were removed via vacuum distillation. The crude product thus obtained was separated by silica gel column chromatography (using toluene and hexane) to produce 6.62 g (Yield 88%) of Compound 13 as a white solid.

The molecular weight of the product was measured using FAB-MS to be 778, consistent with Compound 13.

The chemical shift values (δ) of Compound 13 were measured by $^1$H-NMR (CDCl$_3$) to be 8.36 (d, 2H, J=7.60 Hz), 8.15-8.12 (m, 1H), 7.99-7.84 (m, 4H), 7.80 (s, 1H), 7.70-7.50 (m, 10H), 7.40-7.27 (m, 11H), 7.19-7.11 (m, 3H), 7.06-7.03 (m, 6H).

Under an argon atmosphere, 4.21 g of Compound C, 3.35 g of Compound XX, 0.563 g of Pd(dba)$_2$, 0.23 g of (t-Bu)$_3$P, and 4.13 g of sodium tert-butoxide were added to a 200 mL, three-necked flask, followed by refluxing while stirring in 140 mL of toluene for about 3 hours. The reaction was allowed to cool to room temperature, water was added, an organic layer was separated, and solvents were removed via vacuum distillation. The crude product thus obtained was separated by silica gel column chromatography (using toluene and hexane) to produce 6.38 g (Yield 82%) of Compound 145 as a white solid.

The molecular weight of the product was measured using FAB-MS to be 676, consistent with Compound 145.

The chemical shift values (δ) of Compound 145 were measured by $^1$H-NMR (CDCl$_3$) to be 8.57 (d, 2H, J=7.70 Hz), 8.21 (d, 1H, J=7.80 Hz), 8.04-8.02 (m, 2H), 7.98-7.94 (m, 4H), 7.80 (s, 1H), 7.64-7.58 (m, 5H), 7.44-7.29 (m, 10H), 7.16-7.11 (m, 3H), 7.08-7.05 (m, 6H).

(Synthesis of Compound 147)

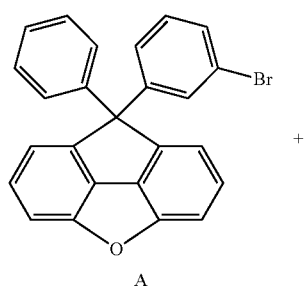

A

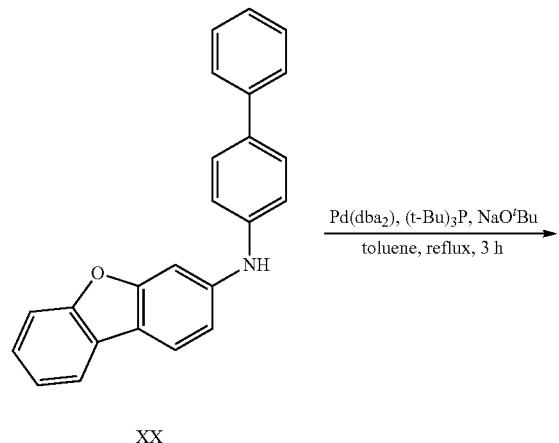

XX

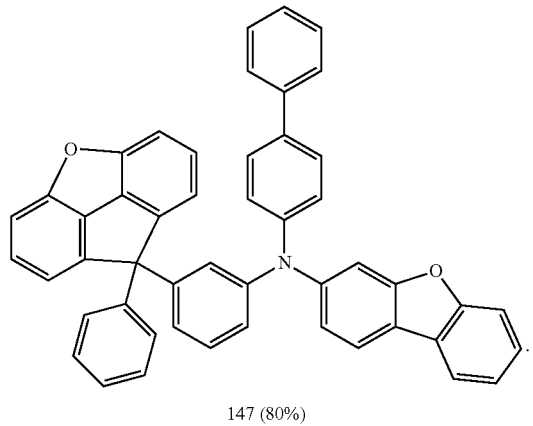

147 (80%)

Under an argon atmosphere, 4.11 g of Compound A, 3.35 g of Compound XX, 0.563 g of Pd(dba)$_2$, 0.23 g of (t-Bu)$_3$P, and 4.13 g of sodium tert-butoxide were added to a 200 mL, three-necked flask, followed by refluxing while stirring in 140 mL of toluene for about 3 hours. The reaction was allowed to cool to room temperature, water was added, an organic layer was separated, and solvents were removed via vacuum distillation. The crude product thus obtained was separated by silica gel column chromatography (using toluene and hexane) to produce 6.22 g (Yield 88%) of Compound 147 as a white solid.

The molecular weight of the product was measured using FAB-MS to be 666, consistent with Compound 147.

The chemical shift values (δ) of Compound 147 were measured by $^1$H-NMR (CDCl$_3$) to be 8.57 (d, 2H, J=7.70 Hz), 8.04 (s, 1H), 7.98-7.94 (m, 4H), 7.80 (s, 1H), 7.64-7.58 (m, 5H), 7.49-7.29 (m, 10H), 7.16-7.11 (m, 3H), 7.08-7.02 (m, 6H).

Manufacture of Organic Light Emitting Device

An anode 204 was formed using ITO to a thickness of about 150 nm, a hole injection layer was formed using 2-TNATA to a thickness of about 60 nm, a hole transport layer was formed to a thickness of about 30 nm, an emission layer was formed using ADN doped with 3% TBP to a thickness of about 25 nm, an electron transport layer was formed using Alq3 to a thickness of about 25 nm, an electron injection layer was formed using LiF to a thickness of about 1 nm, and a cathode was formed using Al to a thickness of about 100 nm.

The compounds used for forming the hole transport layers in each of Examples 1 to 8 and Comparative Examples 1 to 5 are shown in Table 2.

The driving voltage and half-life of each of the organic light emitting devices thus manufactured were evaluated. The voltage represents the value at 10 mA/cm$^2$, and the half-life represents the time required for the luminance to decrease to half of the initial luminance of 1,000 cd/m$^2$. The evaluation results are shown in Table 1.

TABLE 1

| Device manufacturing example | Hole transport layer | Voltage (V) | Half Life LT50 (h) |
|---|---|---|---|
| Example 1 | Example Compound 1 | 10 | 1,900 |
| Example 2 | Example Compound 55 | 10 | 1,900 |
| Example 3 | Example Compound 60 | 10 | 1,950 |
| Example 4 | Example Compound 61 | 10 | 1,950 |
| Example 5 | Example Compound 145 | 10 | 1,900 |
| Example 6 | Example Compound 147 | 10 | 1,900 |
| Example 7 | Example Compound 108 | 10 | 2,000 |
| Example 8 | Example Compound 109 | 10 | 2,000 |
| Comparative Example 1 | Comparative Compound A-1 | 10 | 1,500 |
| Comparative Example 2 | Comparative Compound A-2 | 10 | 1,550 |
| Comparative Example 3 | Comparative Compound A-3 | 10 | 1,300 |
| Comparative Example 4 | Comparative Compound A-4 | 10 | 1,400 |
| Comparative Example 5 | Comparative Compound A-5 | 10 | 1,550 |

TABLE 2
Example Compound 1
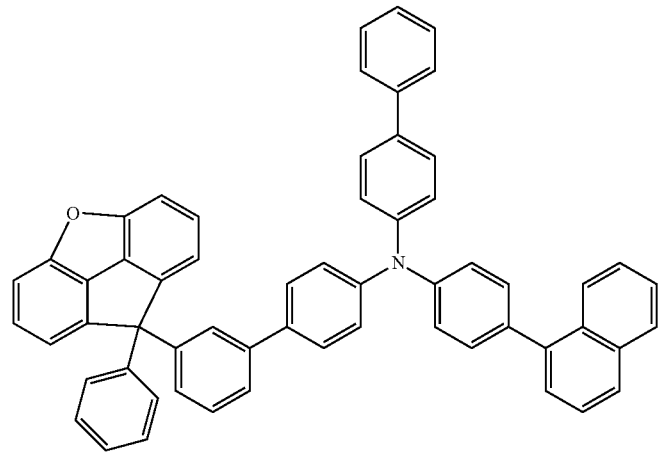 [SMILES: c1ccc(-c2ccc(N(c3ccc(-c4cccc(C5(c6ccccc6)c6cccc7oc8cccc5c8c67)c4)cc3)c3ccc(-c4cccc5ccccc45)cc3)cc2)cc1]
Example Compound 55
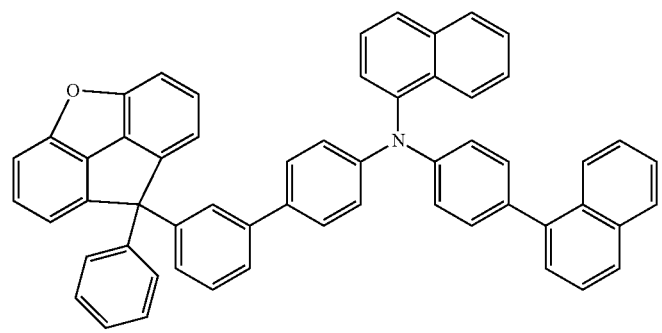 [SMILES: c1ccc(C2(c3cccc(-c4ccc(N(c5ccc(-c6cccc7ccccc67)cc5)c5cccc6ccccc56)cc4)c3)c3cccc4oc5cccc2c5c34)cc1]
Example Compound 60
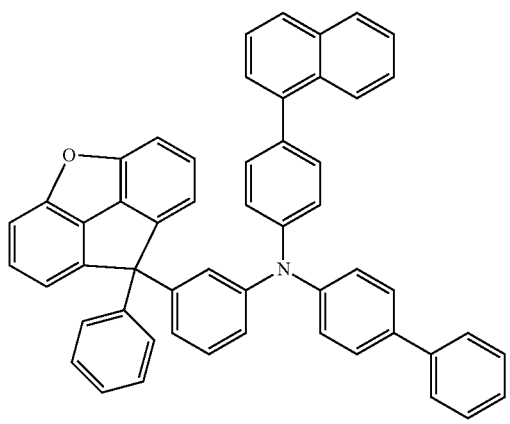 [SMILES: c1ccc(-c2ccc(N(c3ccc(-c4cccc5ccccc45)cc3)c3cccc(C4(c5ccccc5)c5cccc6oc7cccc4c7c56)c3)cc2)cc1]
Example Compound 61
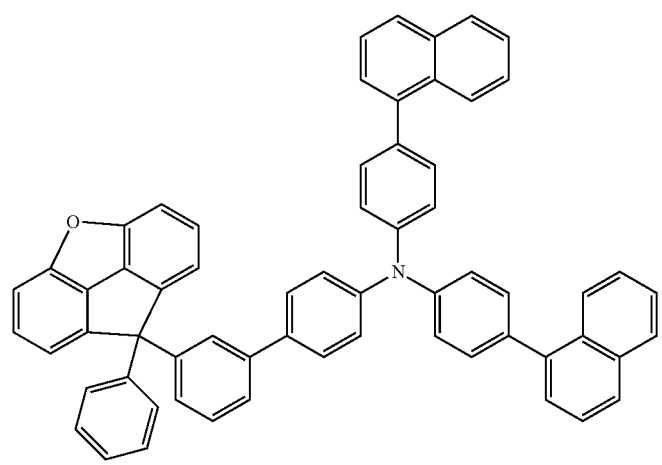 [SMILES: c1ccc(C2(c3cccc(-c4ccc(N(c5ccc(-c6cccc7ccccc67)cc5)c5ccc(-c6cccc7ccccc67)cc5)cc4)c3)c3cccc4oc5cccc2c5c34)cc1]

TABLE 2-continued
Example Compound 145
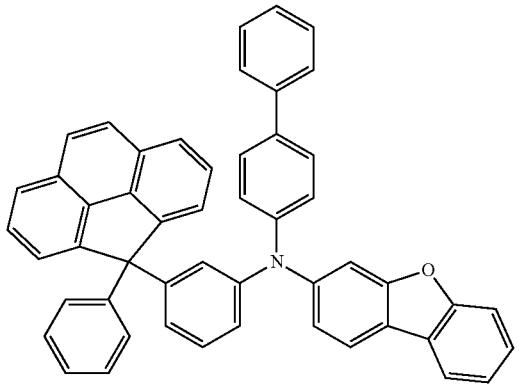 [SMILES: c1ccc(-c2ccc(N(c3cccc(C4(c5ccccc5)c5cccc6ccc7cccc4c7c56)c3)c3ccc4c(c3)oc3ccccc34)cc2)cc1]
Example Compound 147
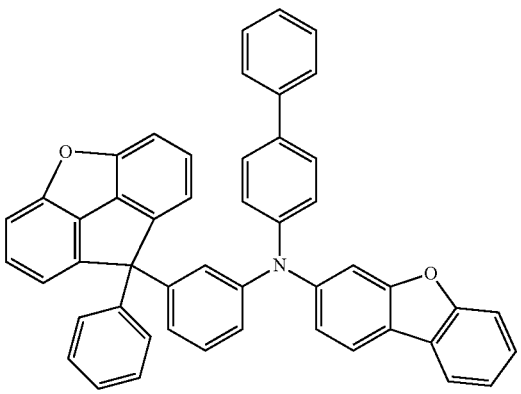 [SMILES: c1ccc(-c2ccc(N(c3cccc(C4(c5ccccc5)c5cccc6oc7cccc4c7c56)c3)c3ccc4c(c3)oc3ccccc34)cc2)cc1]
Example Compound 108
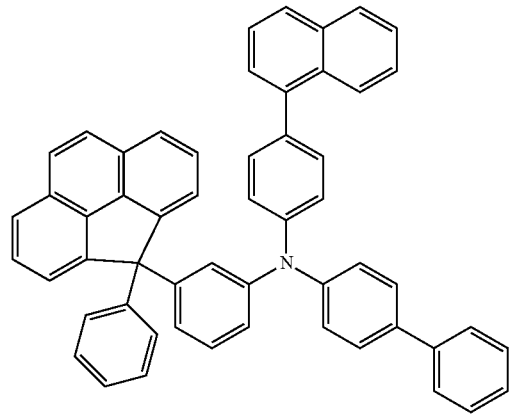 [SMILES: c1ccc(-c2ccc(N(c3ccc(-c4cccc5ccccc45)cc3)c3cccc(C4(c5ccccc5)c5cccc6ccc7cccc4c7c56)c3)cc2)cc1]
Example Compound 109
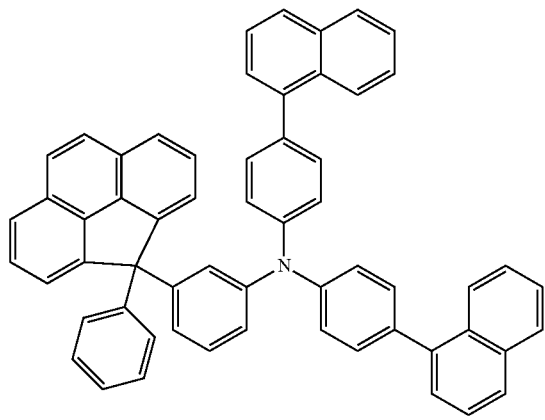 [SMILES: c1ccc(C2(c3cccc(N(c4ccc(-c5cccc6ccccc56)cc4)c4ccc(-c5cccc6ccccc56)cc4)c3)c3cccc4ccc5cccc2c5c34)cc1]

TABLE 2-continued
Comparative Compound A-1
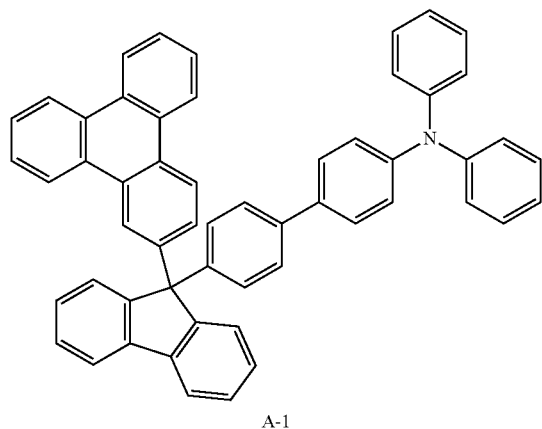
A-1
Comparative Compound A-2
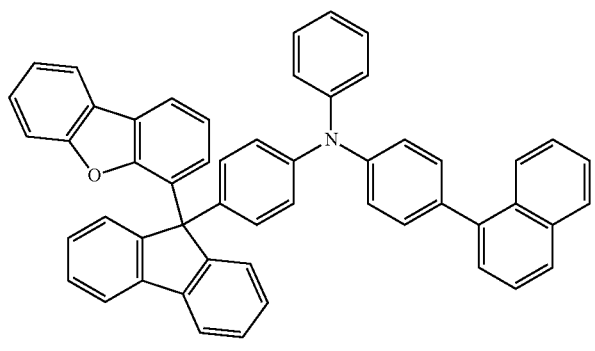
A-2
Comparative Compound A-3
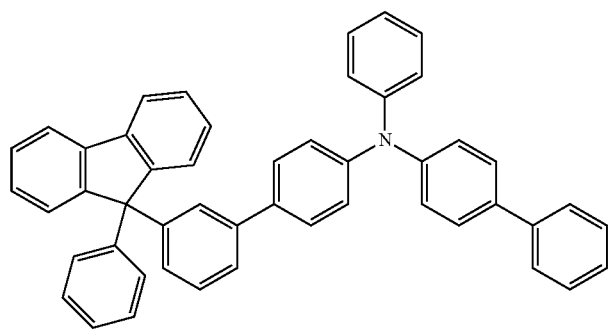
A-3
Comparative Compound A-4
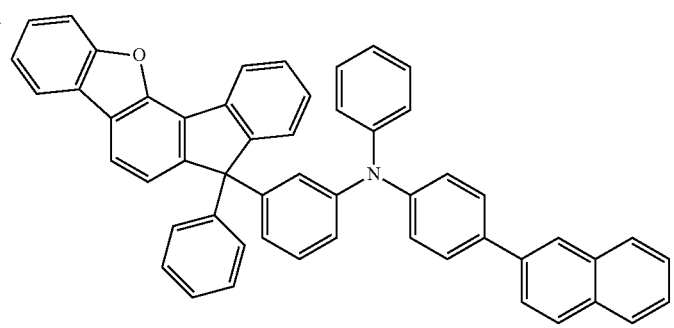
A-4

TABLE 2-continued

Comparative Compound A-5

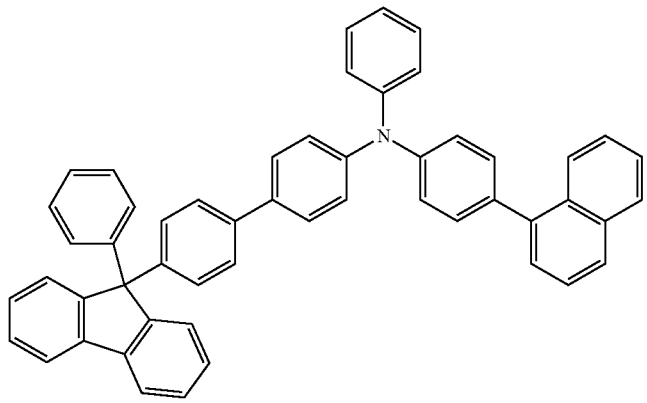

A-5

Referring to Table 1, the organic light emitting devices of Examples 1 to 8 each had longer lifespans than the organic light emitting devices of Comparative Examples A-1 to A-5. In Comparative Examples A-1 and A-2, the combined volume of the fluorene group and its substituent is large, and the steric hindrance of this group is large. The stability of the compound may have been accordingly deteriorated, and the life and efficiency of the organic light emitting device was decreased. In Comparative Examples 3 and 5, only a fluorene group and an amine group are combined, and the charge tolerance may have been comparatively low. Therefore, the lifespan and efficiency of each were decreased. In Comparative Example 4, the volume of the heteroaryl group fused with the fluorene group has large steric hindrance, which may decrease the stability of the compound, and the life and efficiency of the organic light emitting device was decreased.

The organic light emitting device including the amine compound according to an embodiment of the present disclosure may achieve long lifespan and high efficiency.

As used herein, expressions such as "at least one of", "one of", and "selected from", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more example embodiments of the present disclosure have been described with reference to the drawings, it is to be understood that the present disclosure should not be limited to these example embodiments, and that various changes and modifications can be made by one of ordinary skill in the art within the spirit and scope of the present disclosure as defined by the following claims and equivalents thereof.

What is claimed is:

1. A monoamine compound represented by Formula 1, 4, 7, or 8:

Formula 1

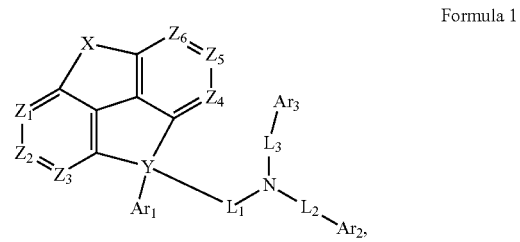

Formula 4

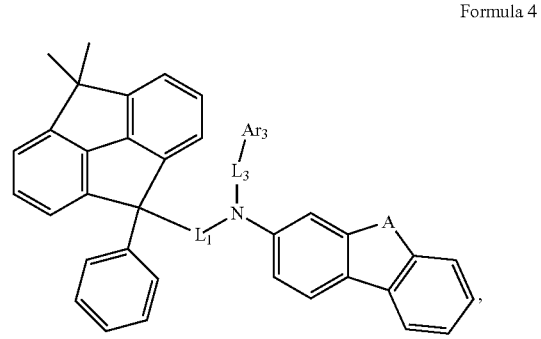

-continued

Formula 7

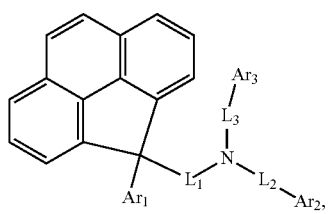

Formula 8

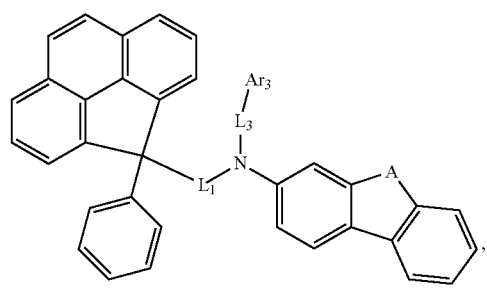

wherein, in Formula 1,
X is selected from the compounds in Formula 2:

Formula 2

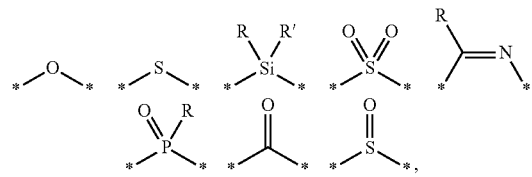

Y is C, Si, or Ge,
$Z_1$ to $Z_6$ are each independently CR or N,
$Ar_1$ to $Ar_3$ are each independently hydrogen, deuterium, a halogen atom, a substituted or unsubstituted aryl group having 6 to 30 carbon atoms for forming a ring, a substituted or unsubstituted heteroaryl group having 5 to 30 carbon atoms for forming a ring, an alkyl group having 1 to 20 carbon atoms, or a silyl group having 3 to 20 carbon atoms,
$L_1$ is a divalent phenyl group,
$L_2$ and $L_3$ are each independently a direct linkage, a substituted or unsubstituted arylene group having 6 to 30 carbon atoms for forming a ring, or a substituted or unsubstituted heteroarylene group having 5 to 30 carbon atoms for forming a ring, and
R and R' are each independently hydrogen, deuterium, a substituted or unsubstituted aryl group having 6 to 30 carbon atoms for forming a ring, a substituted or unsubstituted heteroaryl group having 5 to 30 carbon atoms for forming a ring, or an alkyl group having 1 to 20 carbon atoms;
wherein, in Formula 4,
A is O, S or $CR_2R_3$,
$R_2$ and $R_3$ are each independently hydrogen, deuterium, an alkyl group having 1 to 20 carbon atoms, a substituted or unsubstituted aryl group having 6 to 30 carbon atoms for forming a ring, or a substituted or unsubstituted heteroaryl group having 5 to 30 carbon atoms for forming a ring, and $L_1$, $L_3$, and $Ar_3$ are each independently the same as described herein in connection with Formula 1; and
wherein, in Formulae 7 and 8,
$L_1$ is a direct linkage, a substituted or unsubstituted arylene group having 6 to 30 carbon atoms for forming a ring, or a substituted or unsubstituted heteroarylene group having 5 to 30 carbon atoms for forming a ring,
$L_2$, $L_3$, and $Ar_1$ to $Ar_3$ are each independently the same as described herein in connection with Formula 1,
A is O, S or $CR_2R_3$, and
$R_2$ and $R_3$ are each independently the same as described herein in connection with Formula 4.

2. The monoamine compound of claim 1, wherein the monoamine compound is represented by Formula 4:

Formula 4

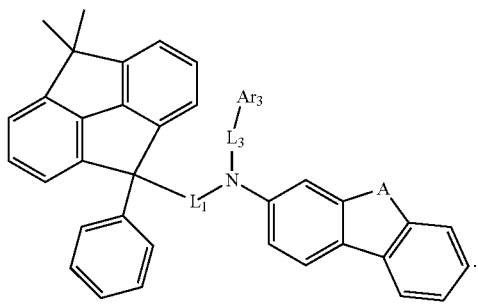

3. The monoamine compound of claim 1, wherein Formula 1 is represented by Formula 5:

Formula 5

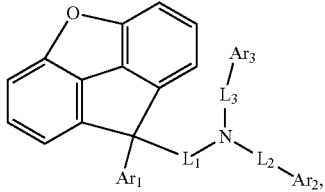

wherein $L_1$ to $L_3$ and $Ar_1$ to $Ar_3$ are each independently the same as described herein in connection with Formula 1.

4. The monoamine compound of claim 1, wherein Formula 1 is represented by Formula 6:

Formula 6

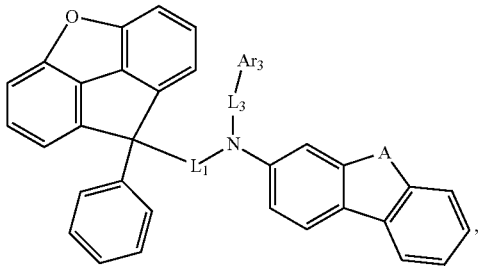

wherein A is O, S, or $CR_2R_3$,
$R_2$ and $R_3$ are each independently hydrogen, deuterium, an alkyl group having 1 to 20 carbon atoms, a substituted or unsubstituted aryl group having 6 to 30 carbon atoms for forming a ring, or a substituted or unsubstituted heteroaryl group having 5 to 30 carbon atoms for forming a ring, and $L_1$, $L_3$, and $Ar_3$ are each independently the same as described herein in connection with Formula 1.

5. The monoamine compound of claim 1, wherein the monoamine compound is represented by Formula 7:

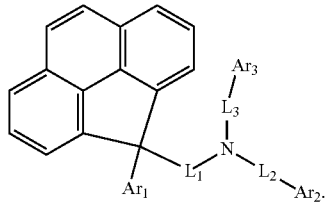

Formula 7

6. The monoamine compound of claim 1, wherein the monoamine compound is represented by Formula 8:

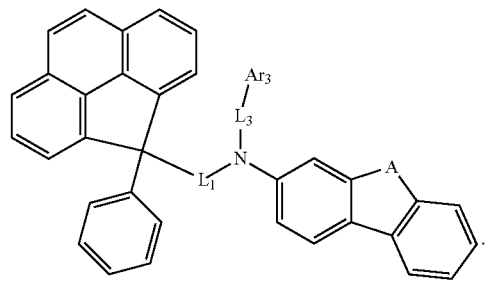

Formula 8

7. The monoamine compound of claim 1, wherein $L_1$ in Formulae 7 and 8 is a direct linkage, a substituted or unsubstituted divalent phenyl group, or a substituted or unsubstituted divalent biphenyl group.

8. The monoamine compound of claim 1, wherein $Ar_2$ is a substituted or unsubstituted phenyl group, a substituted or unsubstituted naphthyl group, a substituted or unsubstituted dibenzofuranyl group, a substituted or unsubstituted dibenzothiophene group, or a substituted or unsubstituted fluorene group.

9. The monoamine compound of claim 1, wherein $Ar_3$ is a substituted or unsubstituted phenyl group, a substituted or unsubstituted biphenyl group, or a substituted or unsubstituted naphthyl group.

10. A monoamine compound selected from the compounds represented by Compound Group 1:

Compound Group 1

33

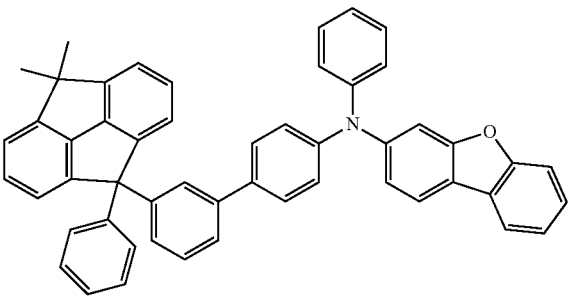

34

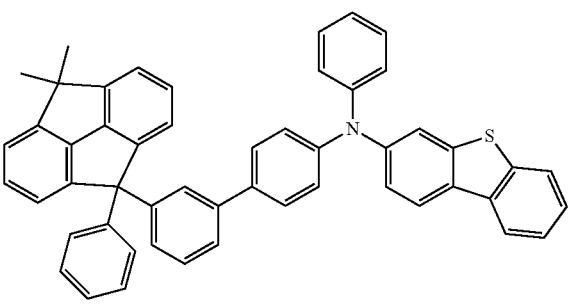

35

36

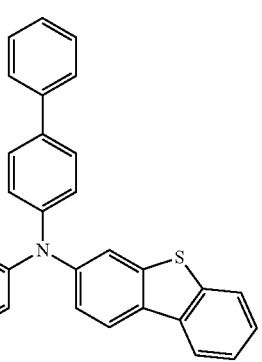

37
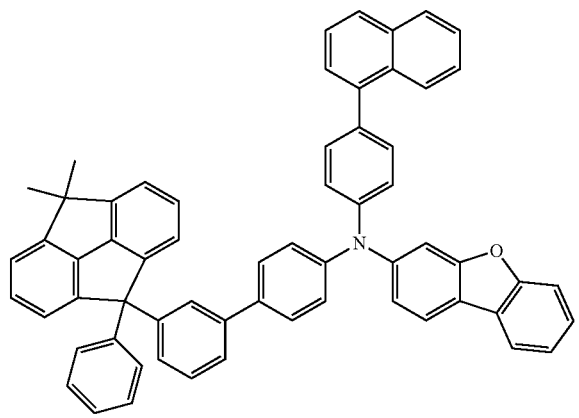
38
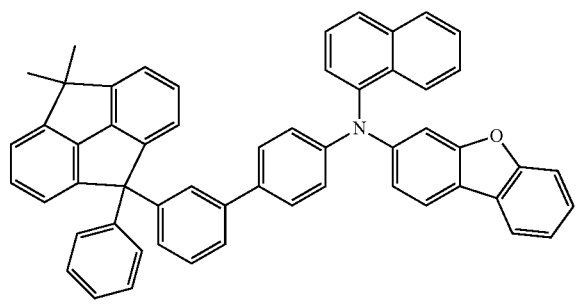
39
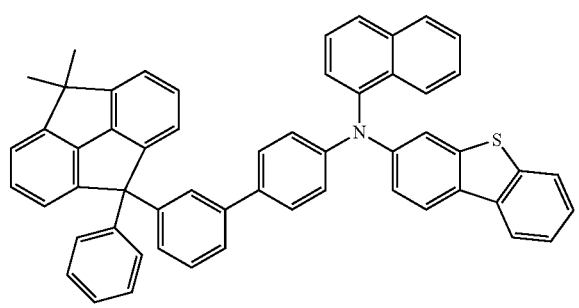
40
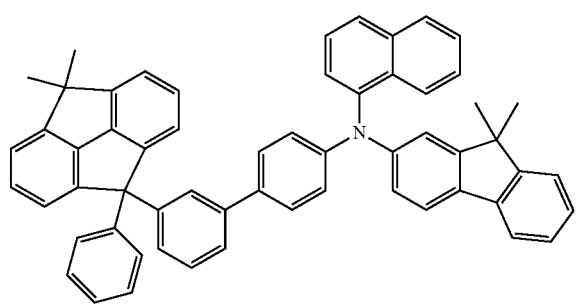
41
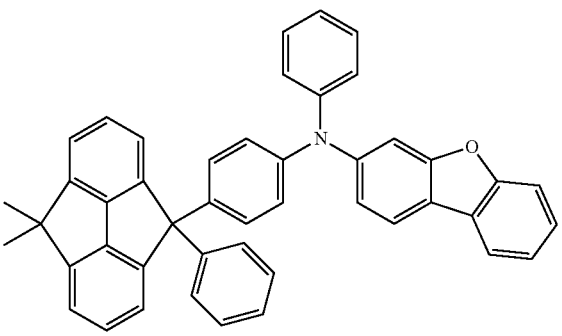
42
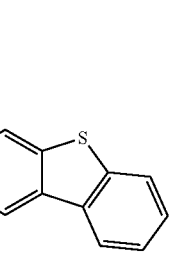
43
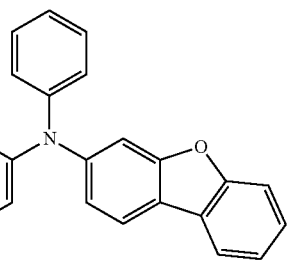

44
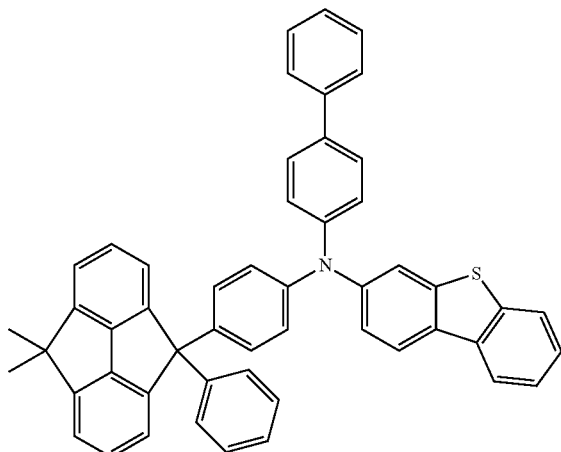
45
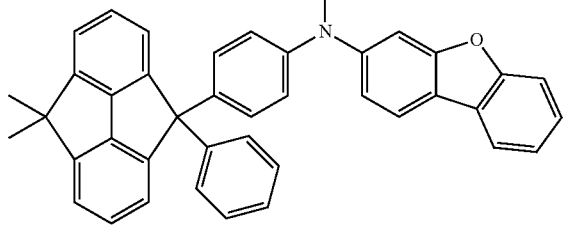
46
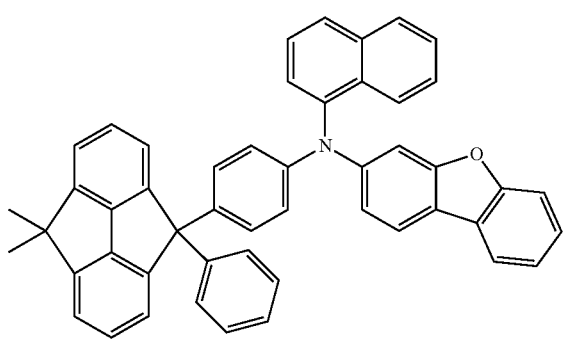
47
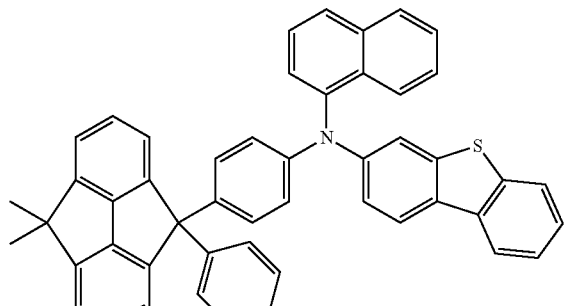
48
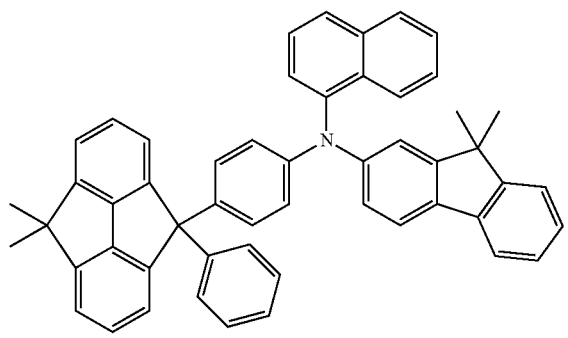
49
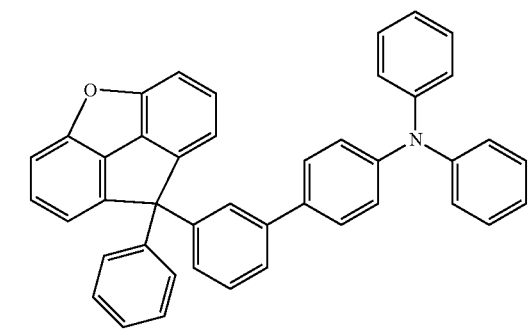
50
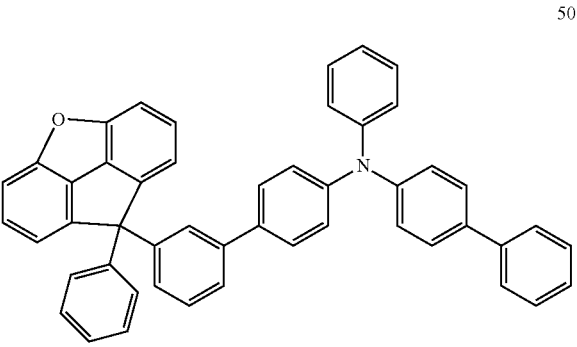

51
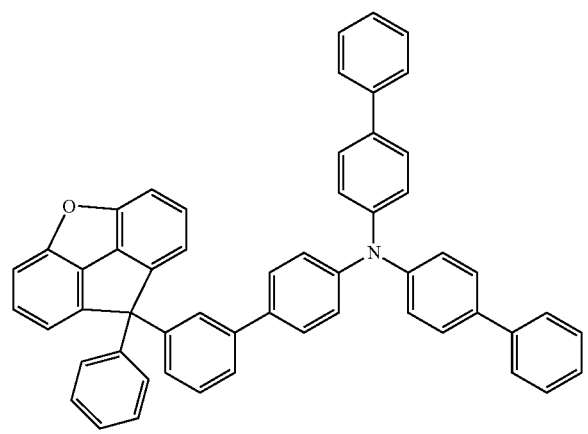
52
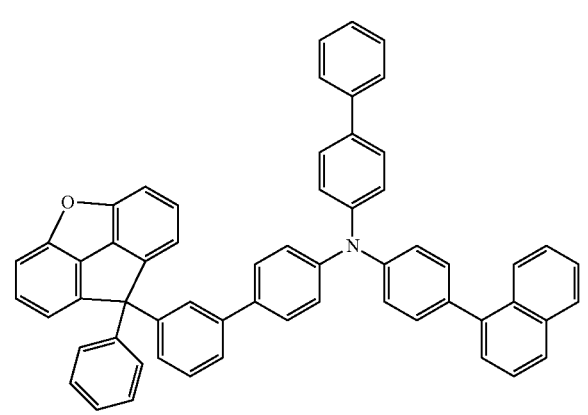
53
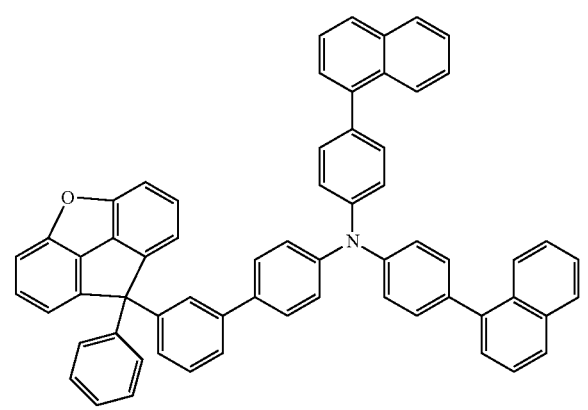
54
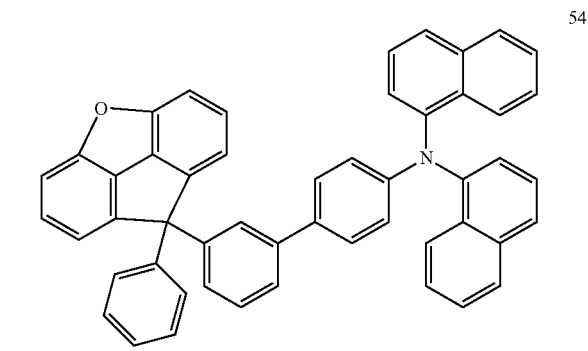
55
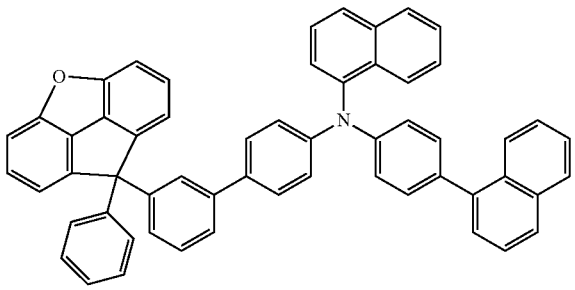
56
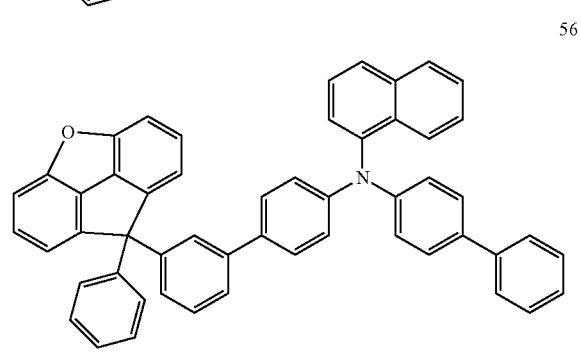
57
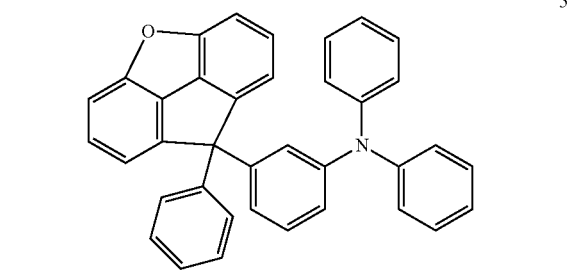
58
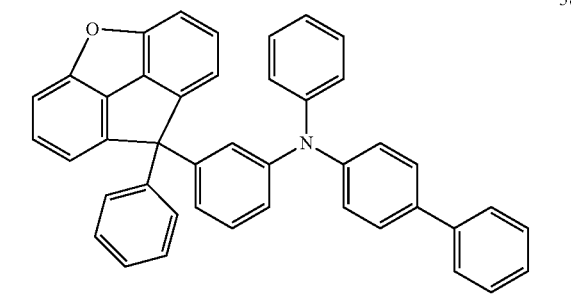
59
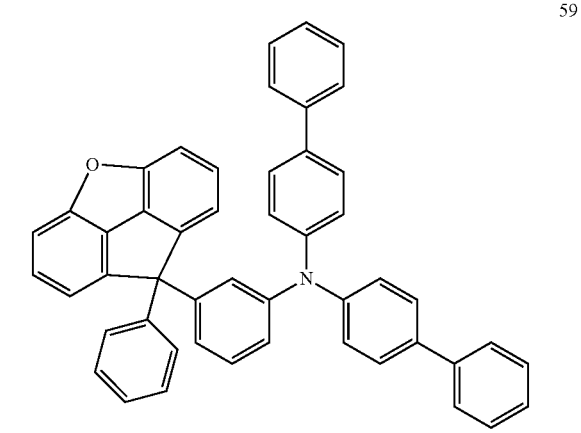

209
-continued
60
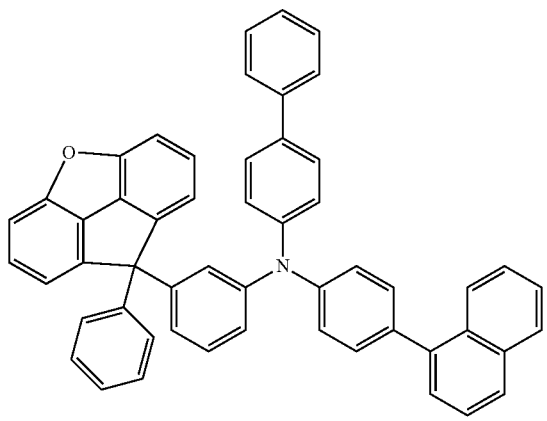
61
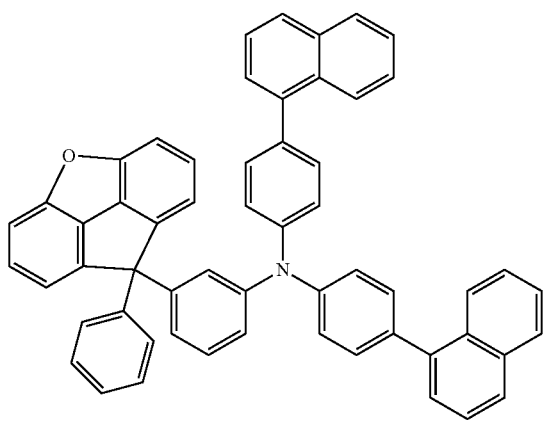
62
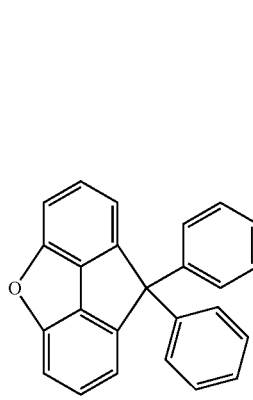
63
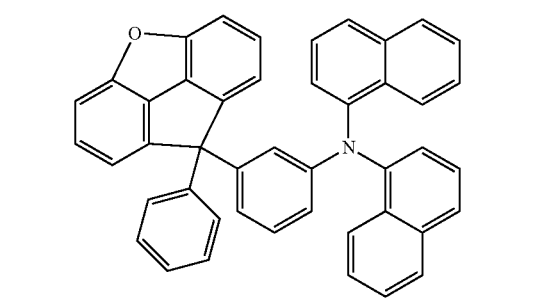
210
-continued
64
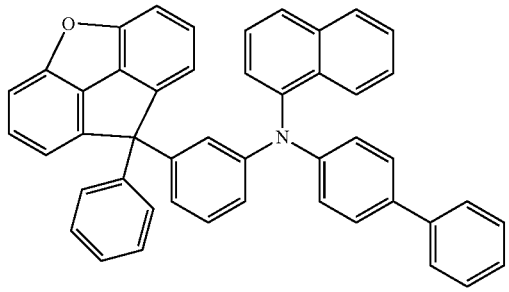
65
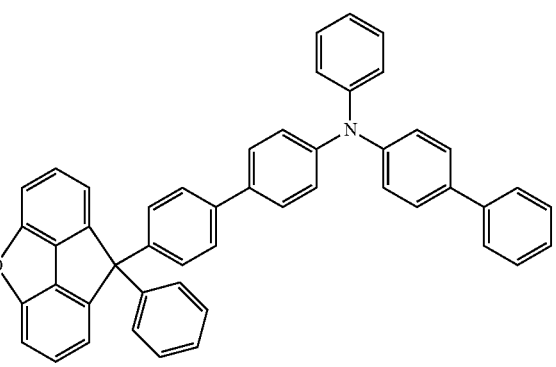
66
67
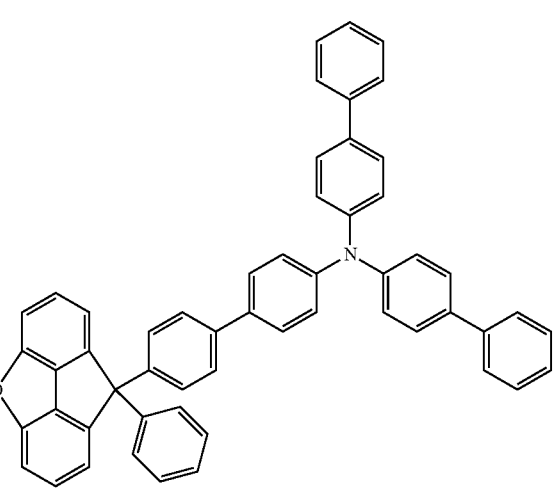

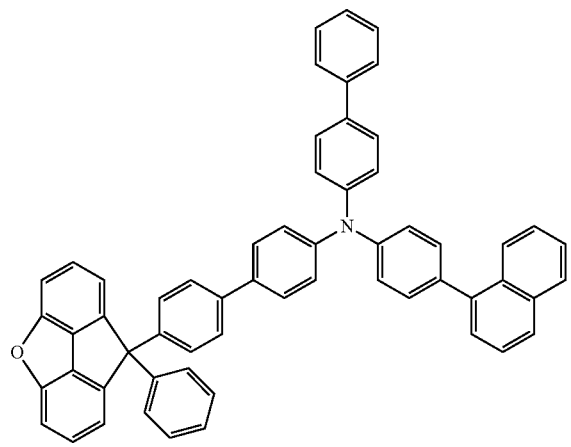
68
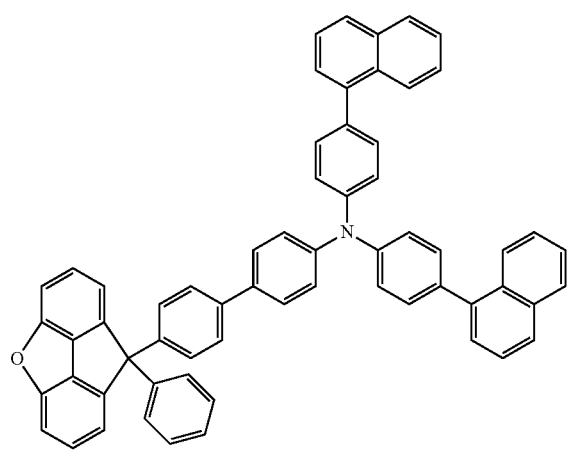
69
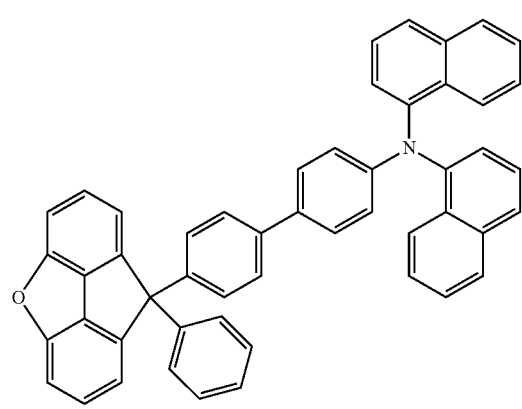
70
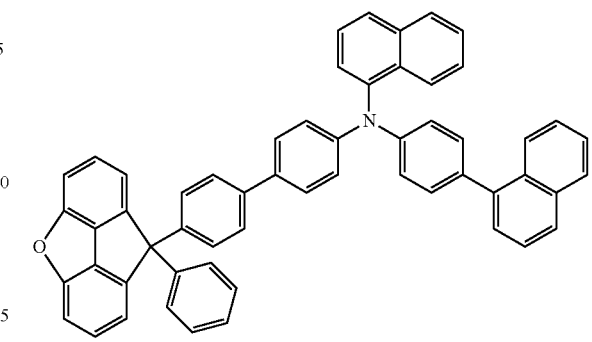
71
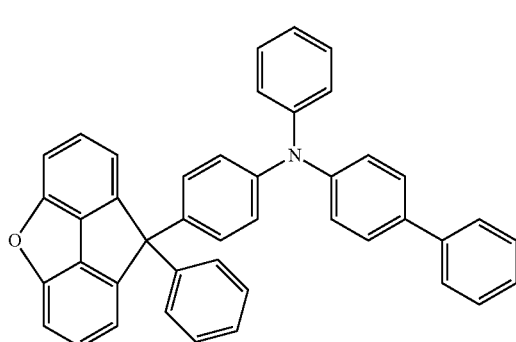
72
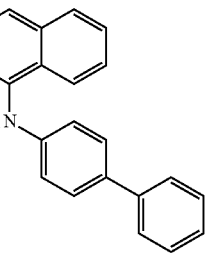
73
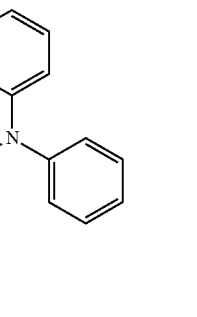
74

75
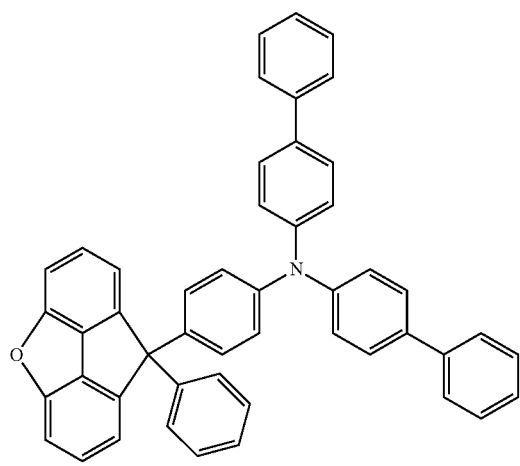
76
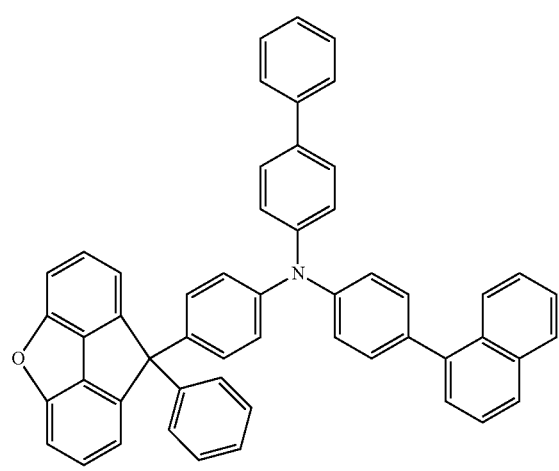
77
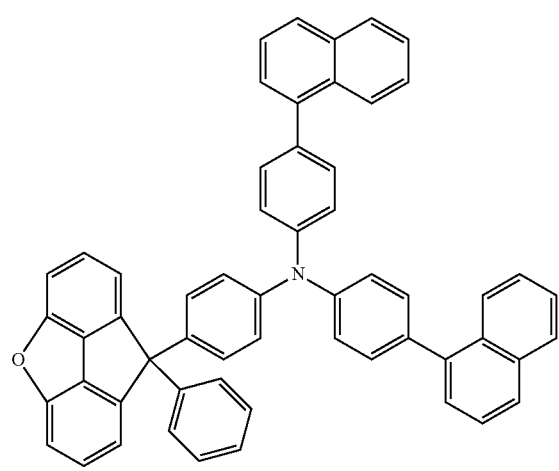
78
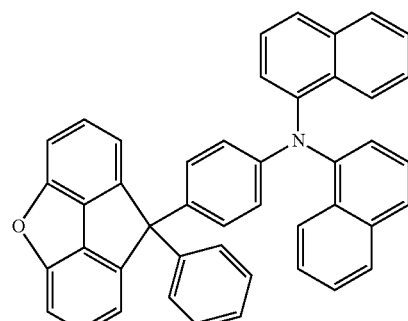
79
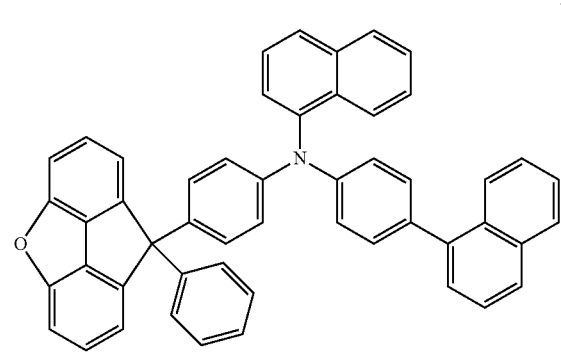
80
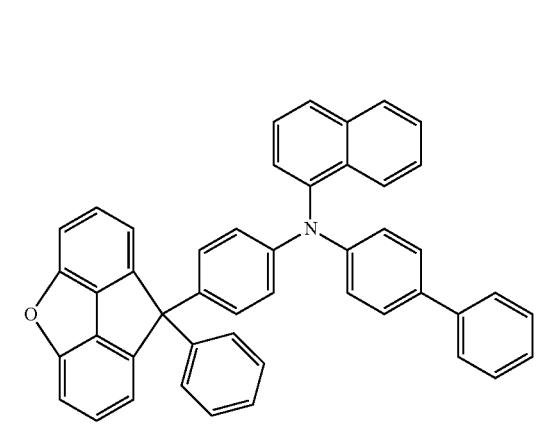
81
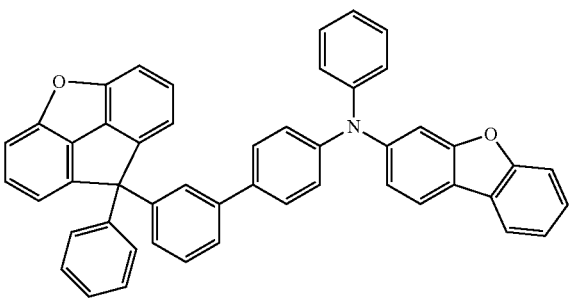

82
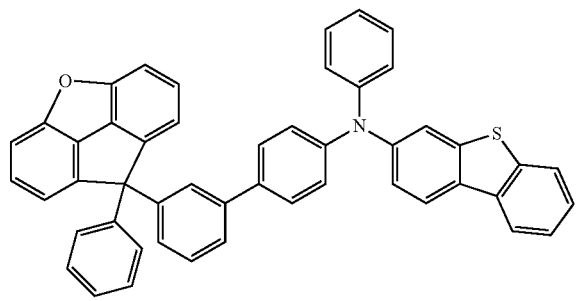
83
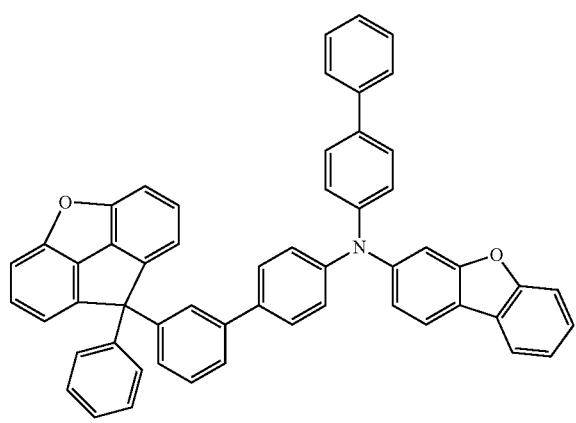
84
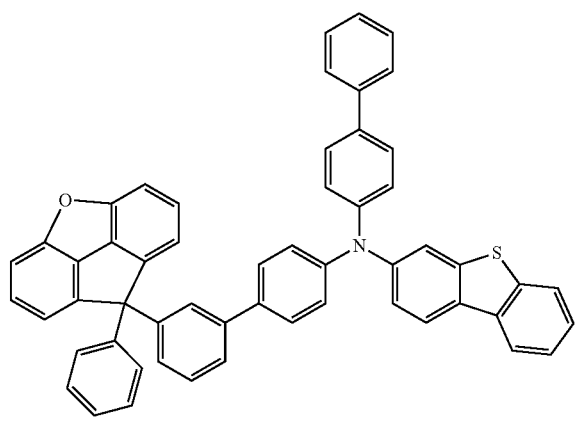
85
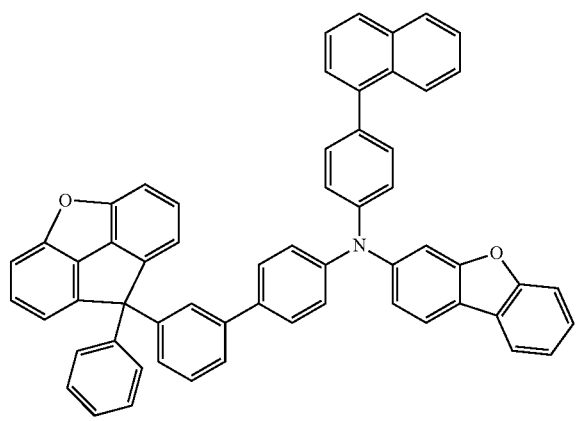
86
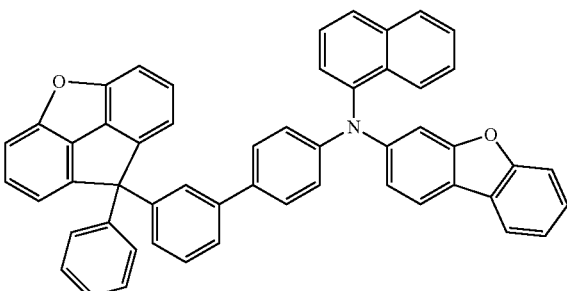
87
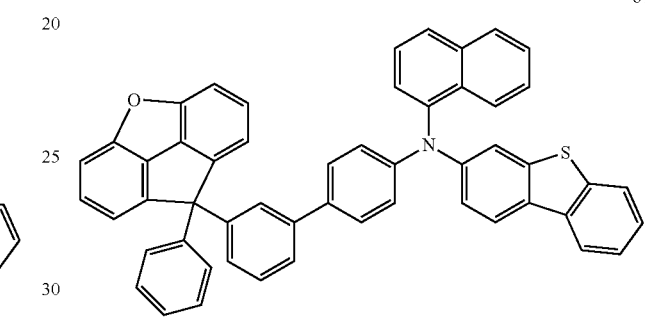
88
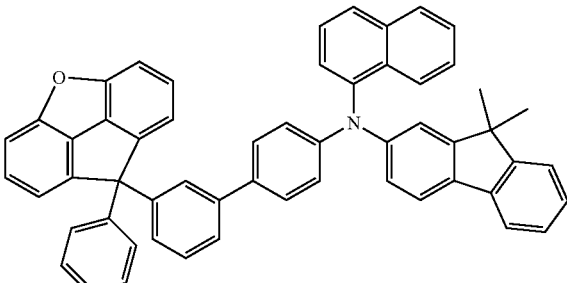
89
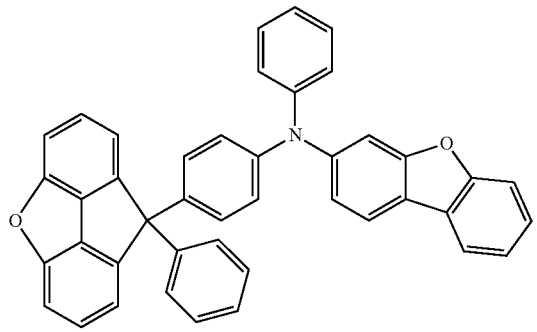

US 10,361,374 B2
217
-continued
90
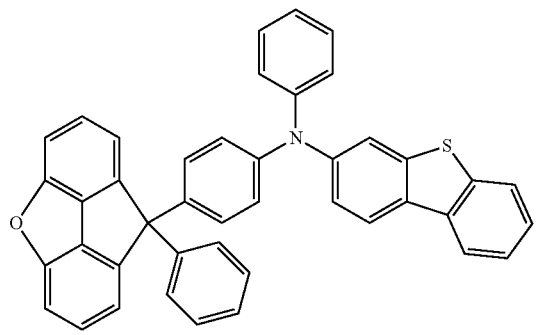
91
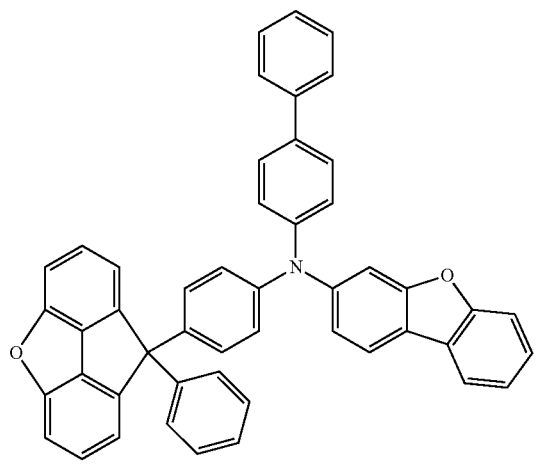
92
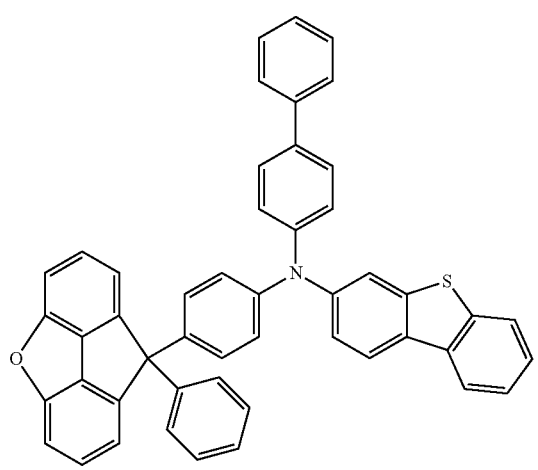
218
-continued
93
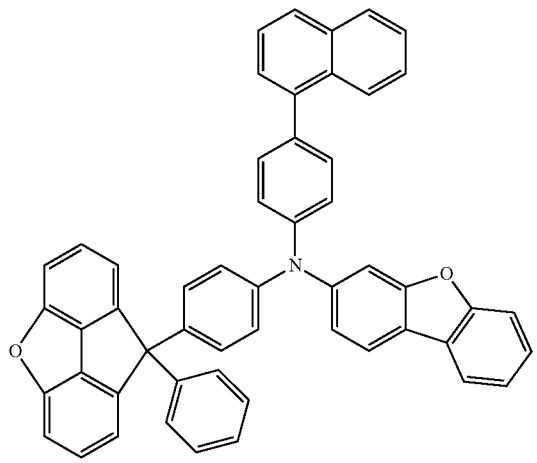
94
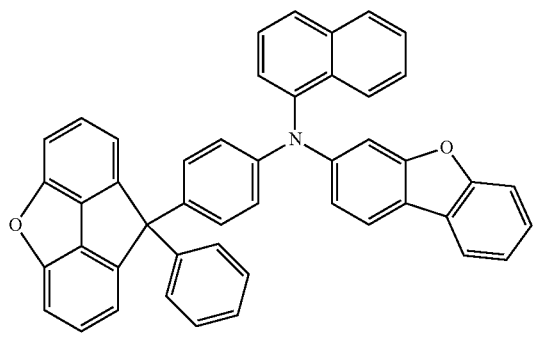
95
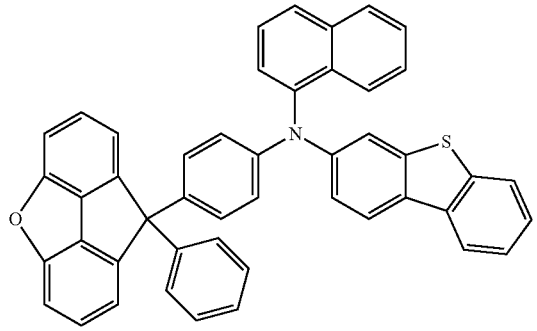
96
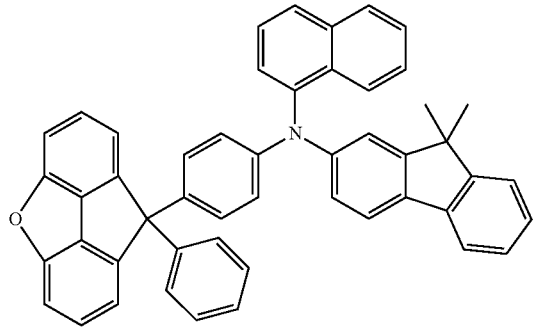

97
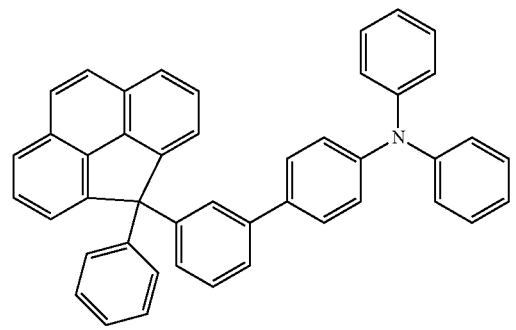
98
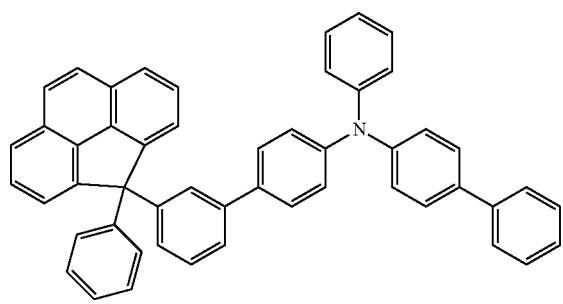
99
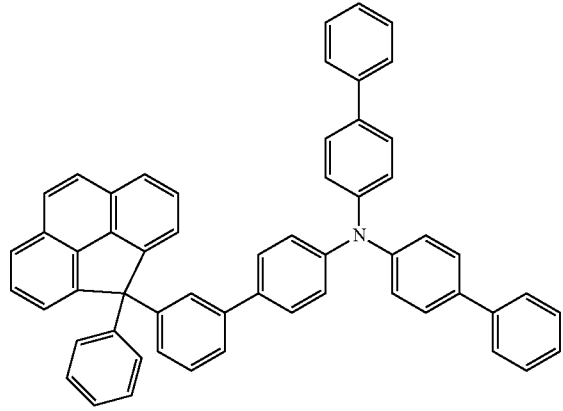
100
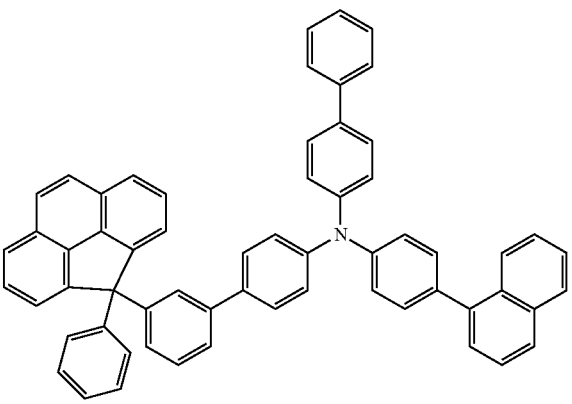
101
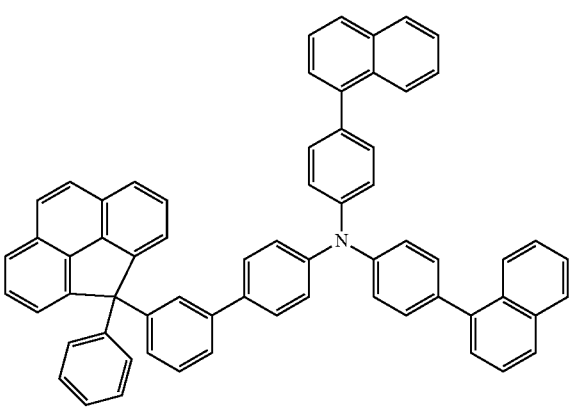
102
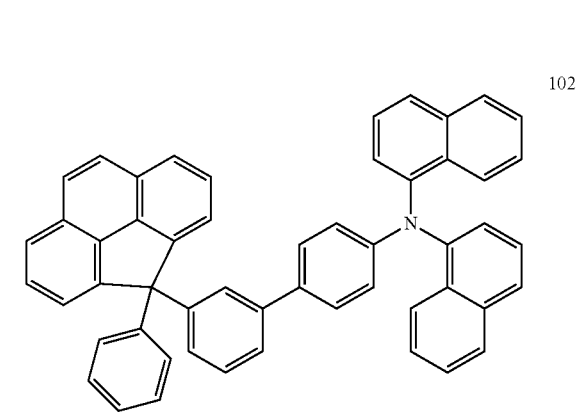
103
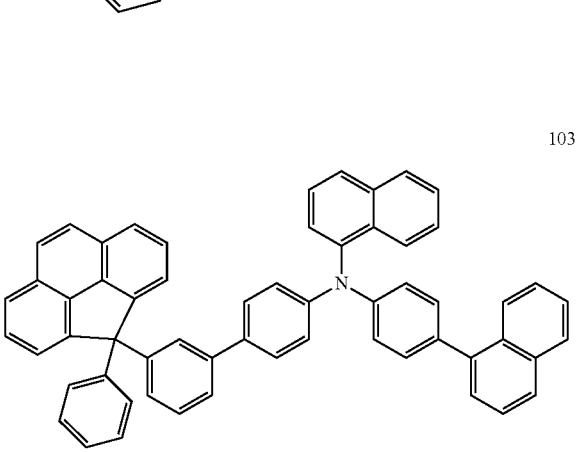
104
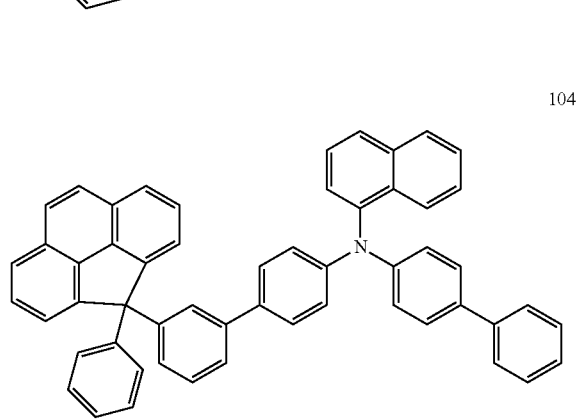

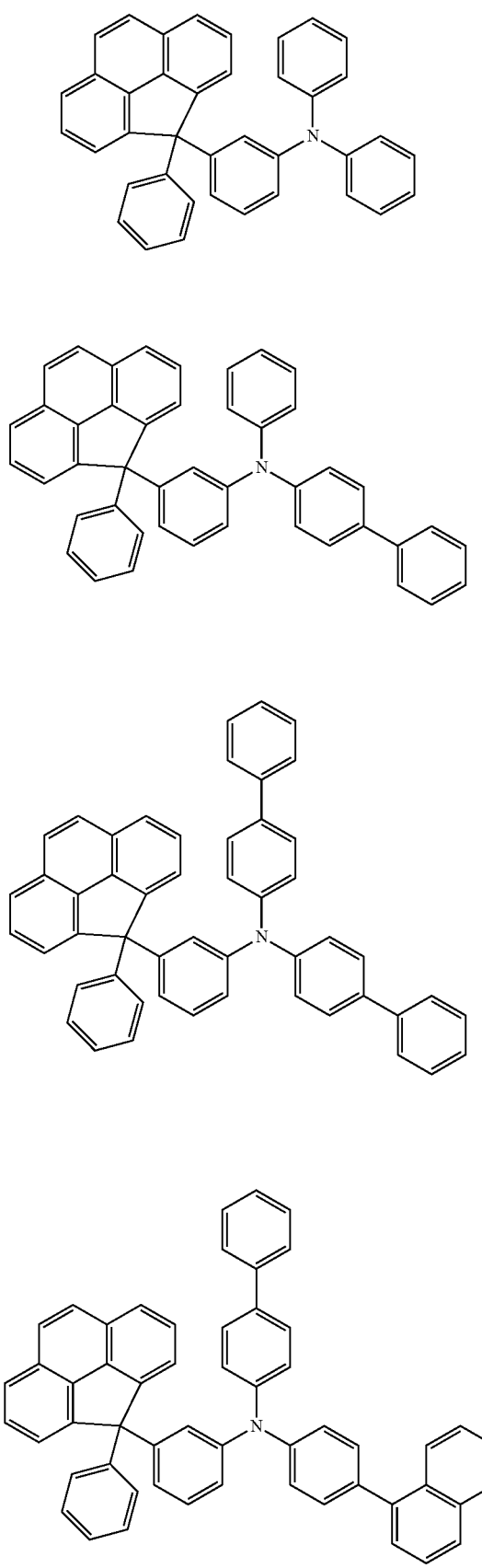

113
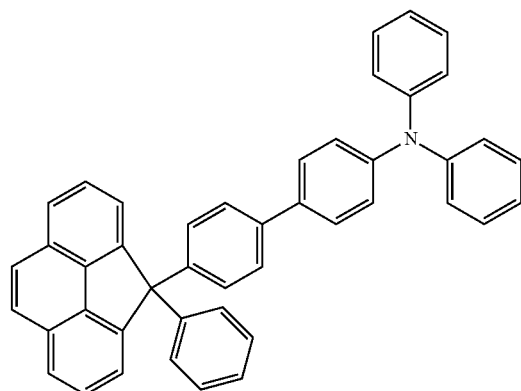
114
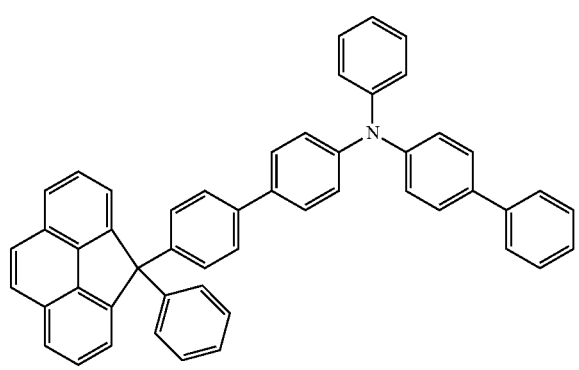
115
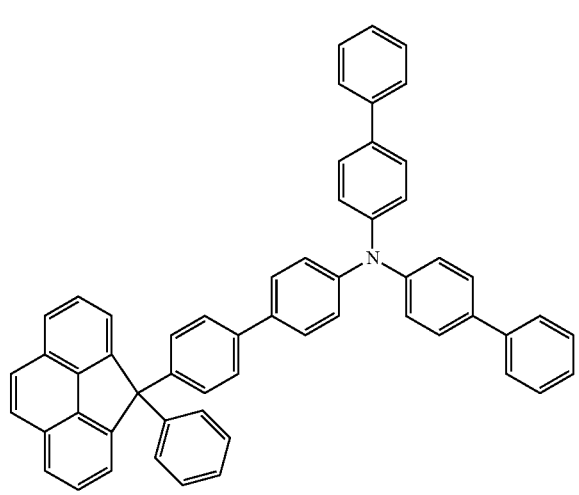
116
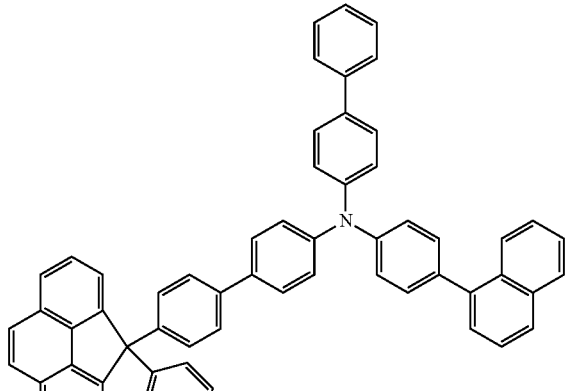
117
118
119
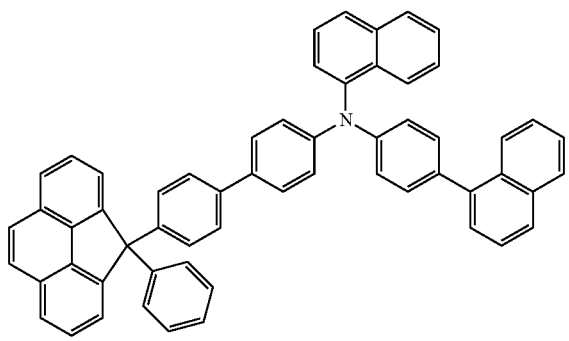

120
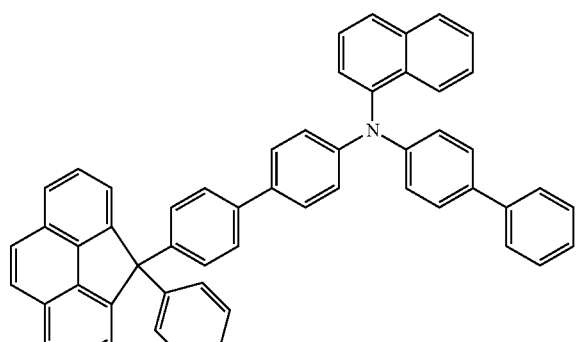
121
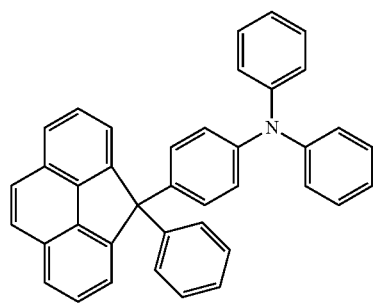
122
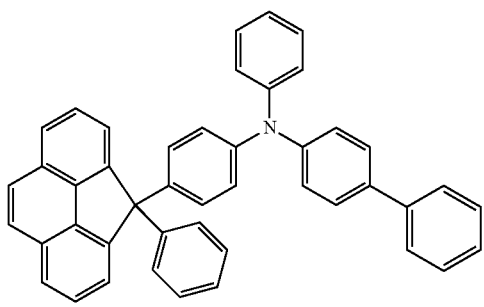
123
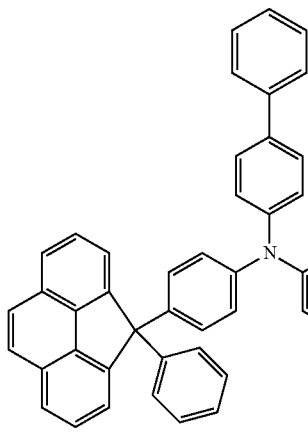
124
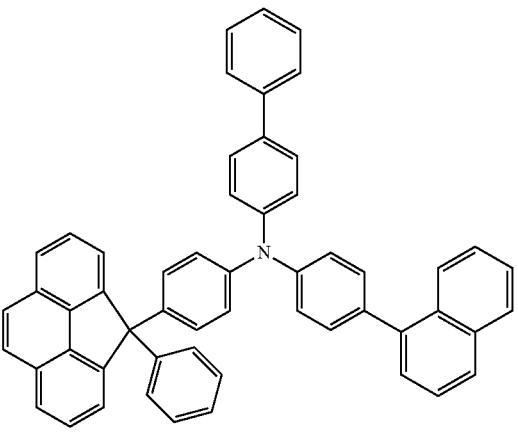
125
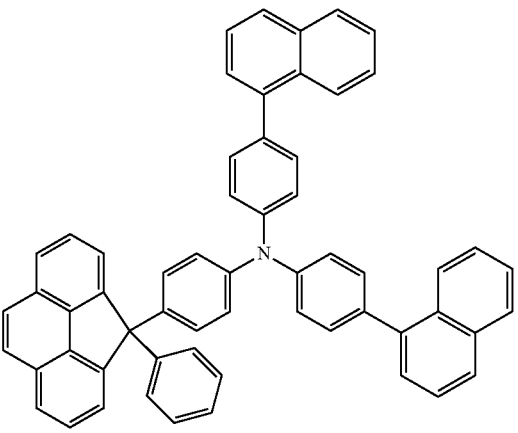
126
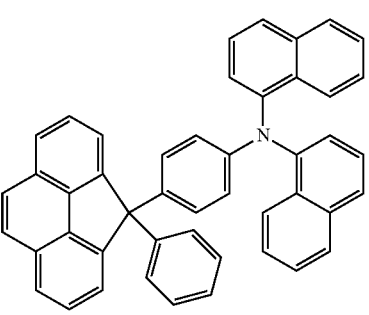
127
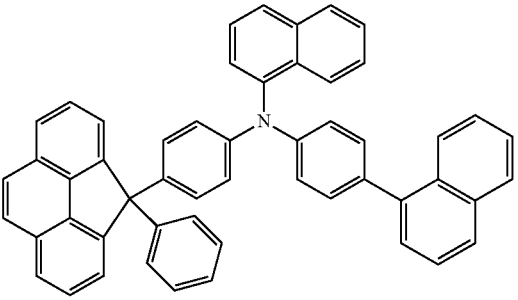

128
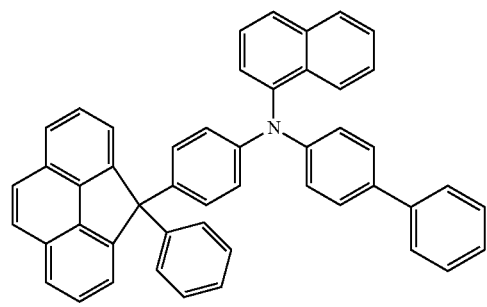
129
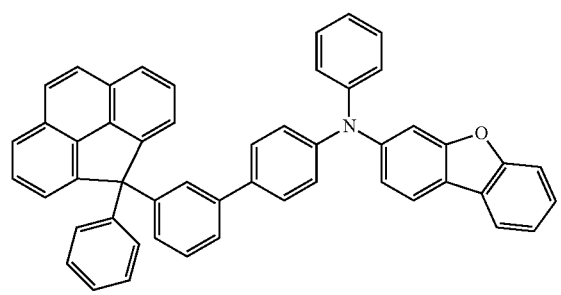
130
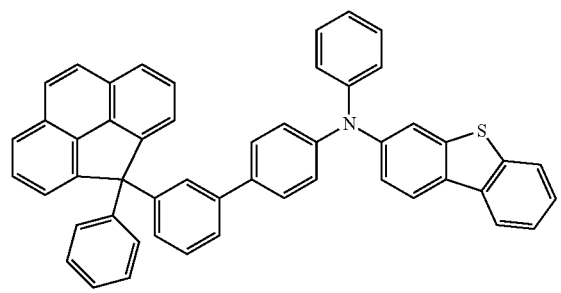
131
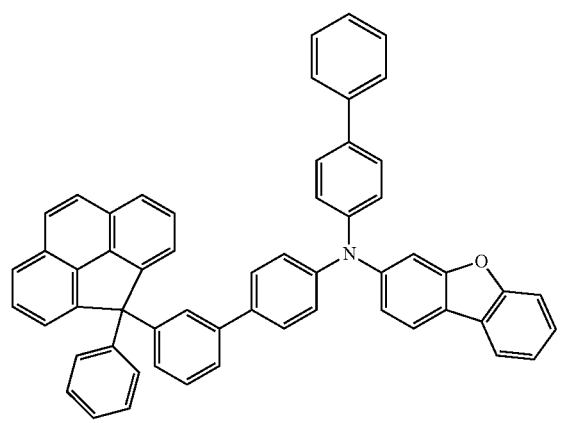
132
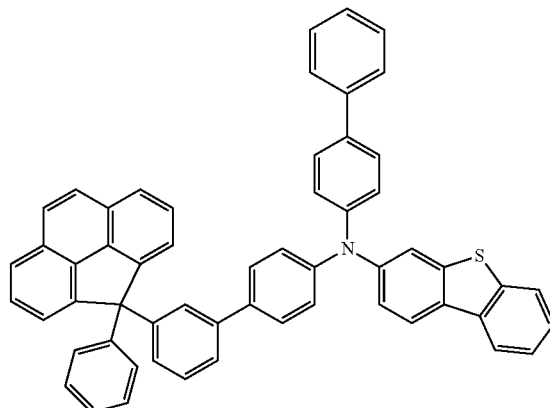
133
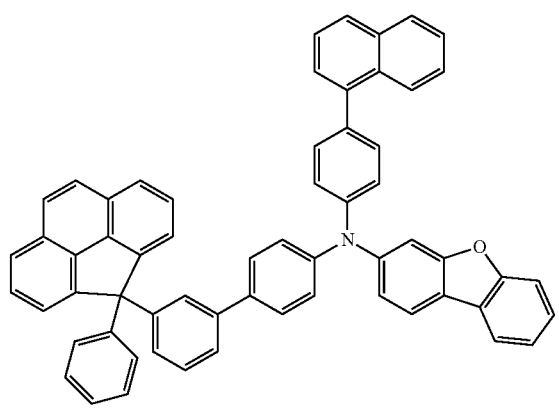
134
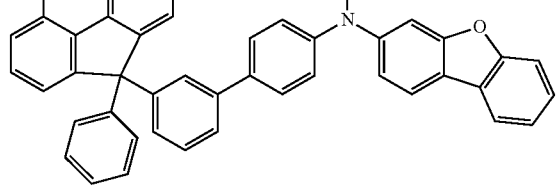
135
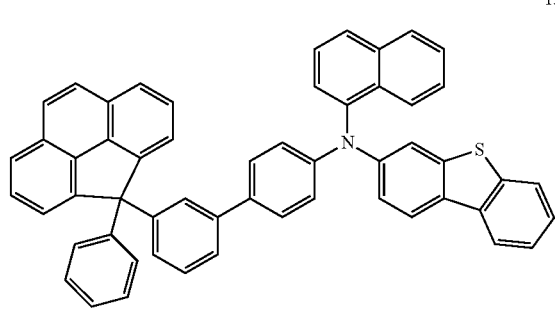

136
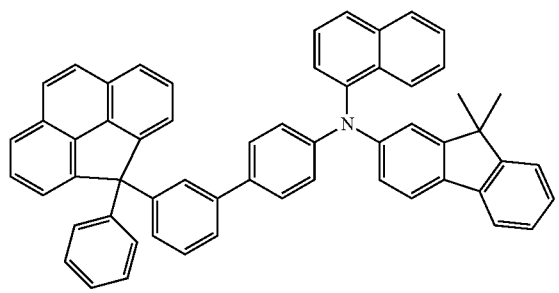
137
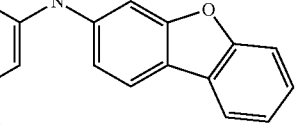
138
139
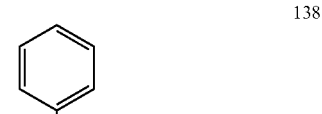
140
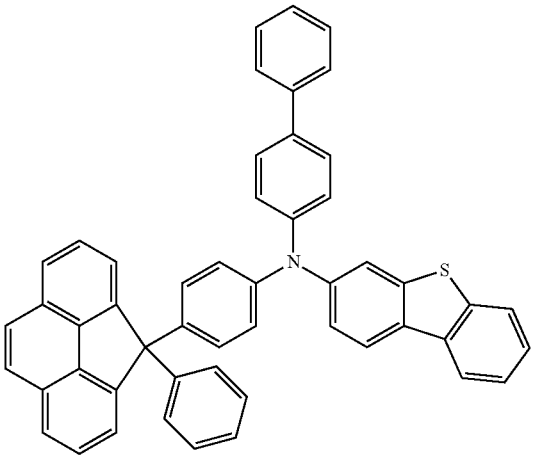
141
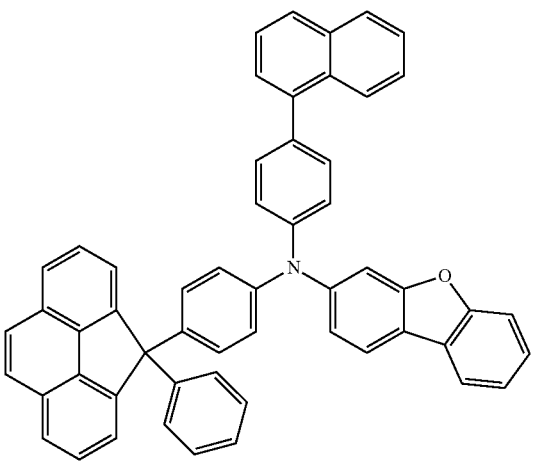
142
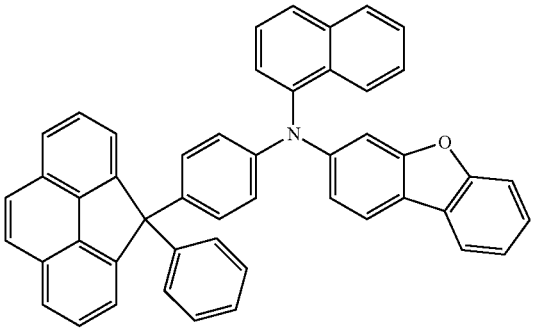
143
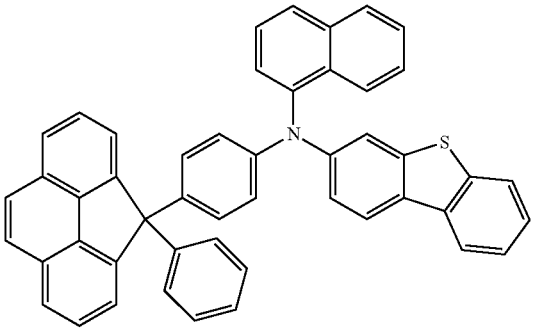

231
-continued
144
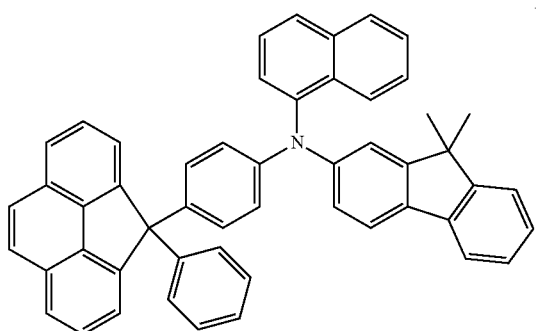
145
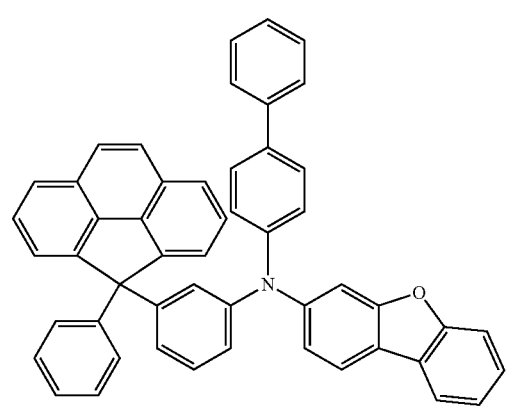
146
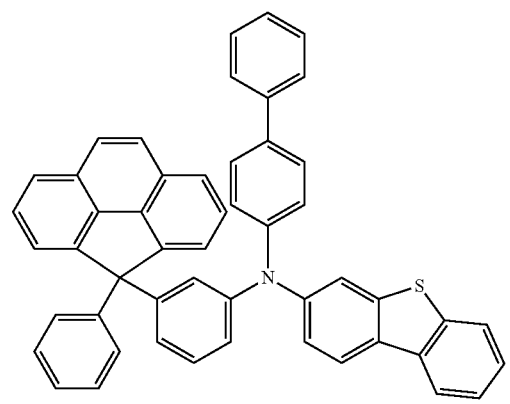
147
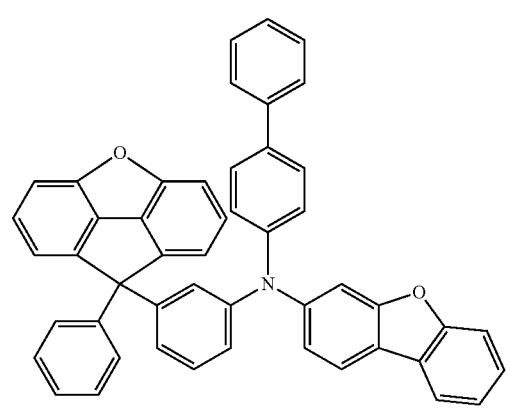
232
-continued
148
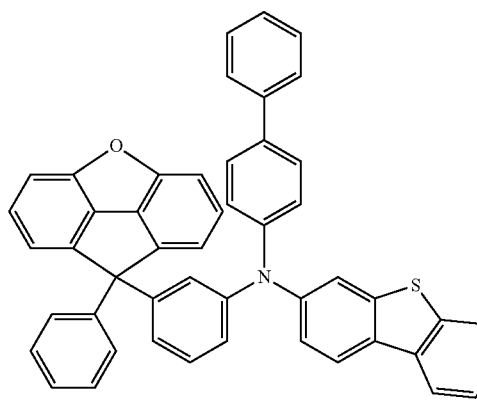
149
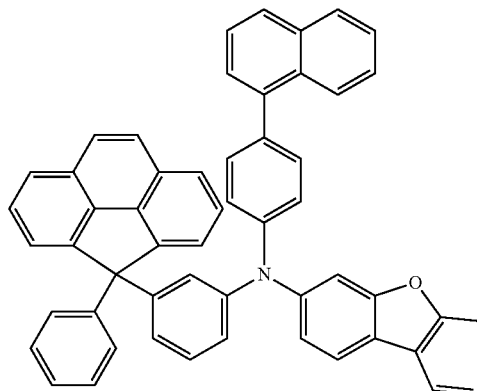
150
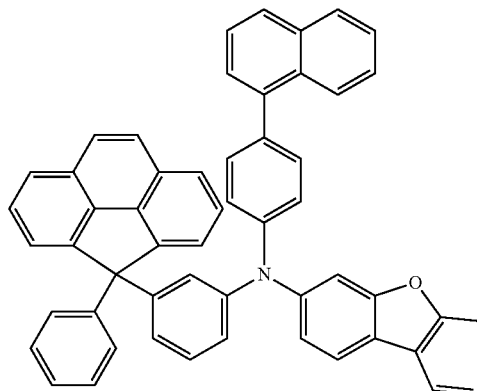
151
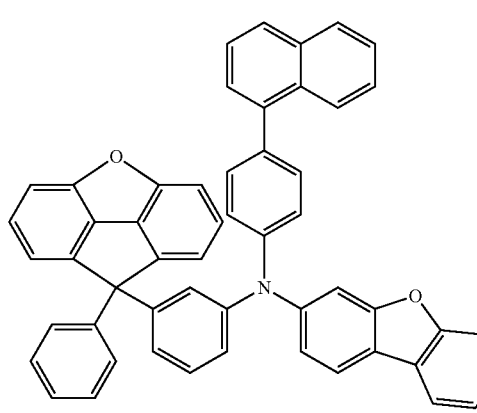

-continued

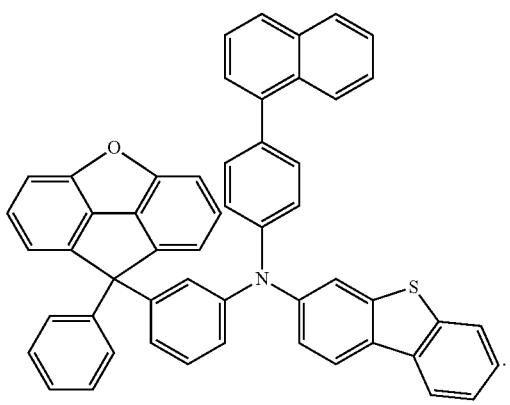
152

11. An organic light emitting device, comprising:
an anode;
a hole transport region on the anode;
an emission layer on the hole transport region;
an electron transport region on the emission layer; and
a cathode on the electron transport region,
the hole transport region comprising the monoamine compound of claim 1.

12. The organic light emitting device of claim 11, wherein the monoamine compound is represented by Formula 4:

Formula 4

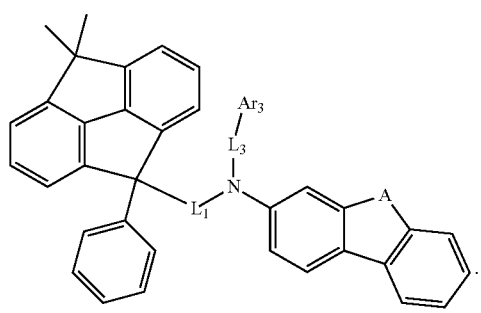

13. The organic light emitting device of claim 11, wherein Formula 1 is represented by Formula 5:

Formula 5

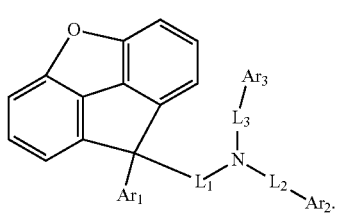

14. The organic light emitting device of claim 11, wherein Formula 1 is represented by Formula 6:

Formula 6

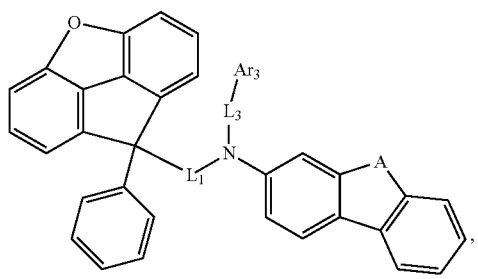

wherein A is O, S, or $CR_2R_3$,
$R_2$ and $R_3$ are each independently hydrogen, deuterium, an alkyl group having 1 to 20 carbon atoms, a substituted or unsubstituted aryl group having 6 to 30 carbon atoms for forming a ring, or a substituted or unsubstituted heteroaryl group having 5 to 30 carbon atoms for forming a ring, and
$L_1$, $L_3$, and $Ar_a$ are independently the same as described herein in connection with Formula 1.

15. The organic light emitting device of claim 11, wherein the monoamine compound is represented by Formula 7:

Formula 7

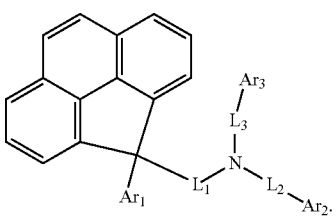

16. The organic light emitting device of claim 11, wherein the monoamine compound is represented by Formula 8:

Formula 8

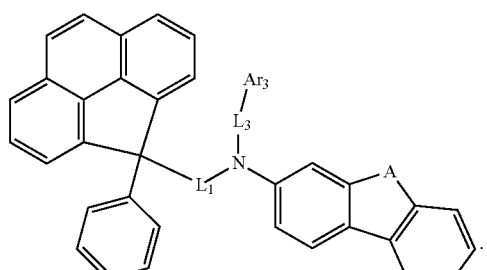

17. An organic light emitting device, comprising:
an anode;
a hole transport region on the anode;
an emission layer on the hole transport region;
an electron transport region on the emission layer; and
a cathode on the electron transport region,
the hole transport region comprising at least one selected from the compounds represented by Compound Group 1:

Compound Group 1
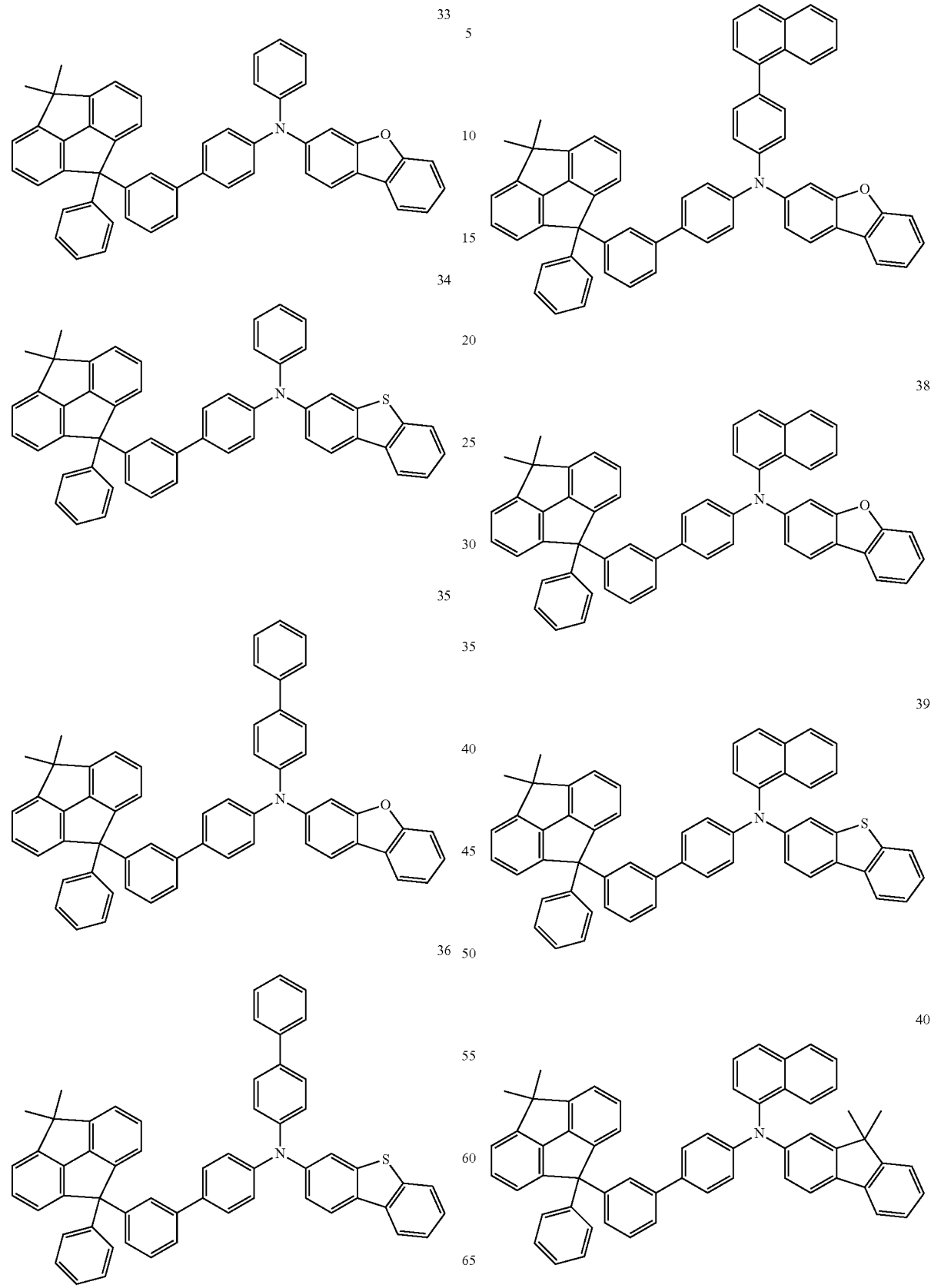

41
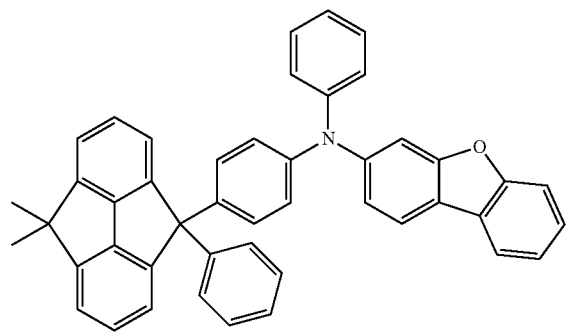
42
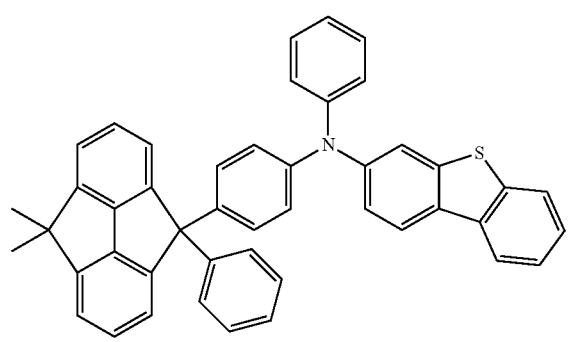
43
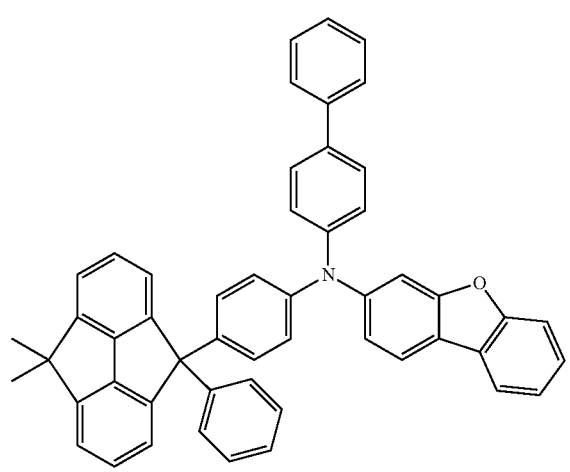
44
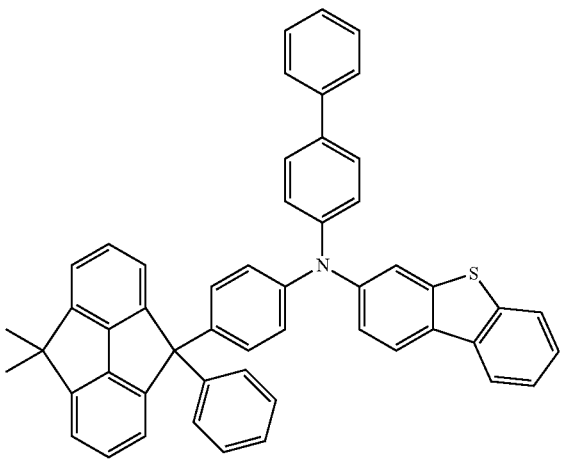
45
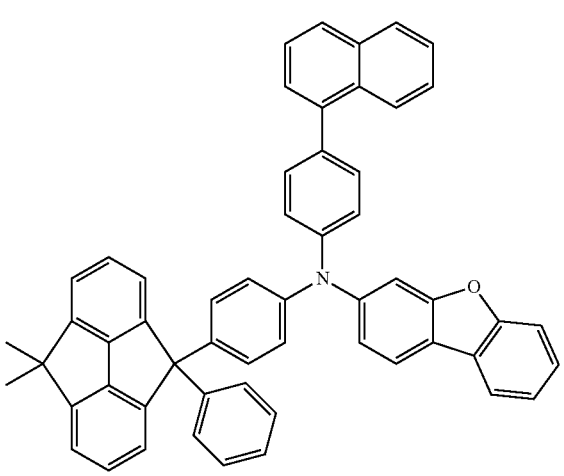
46
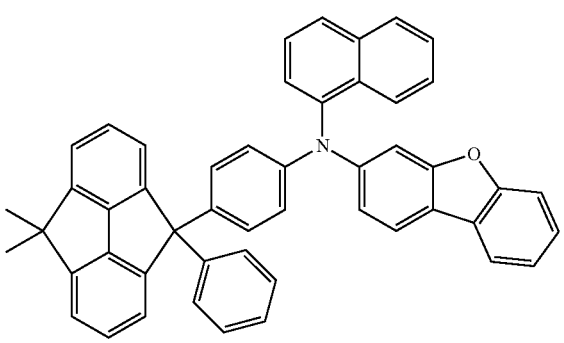

47
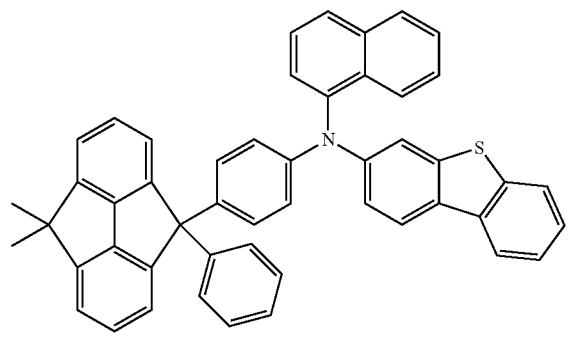
48
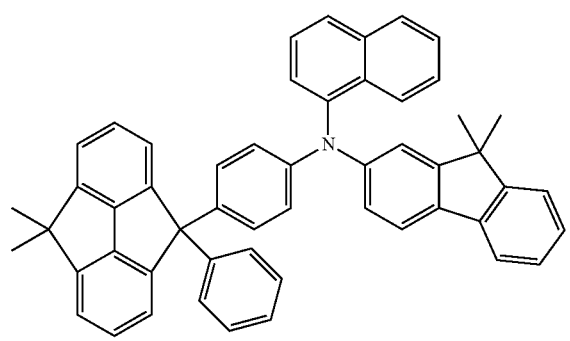
49
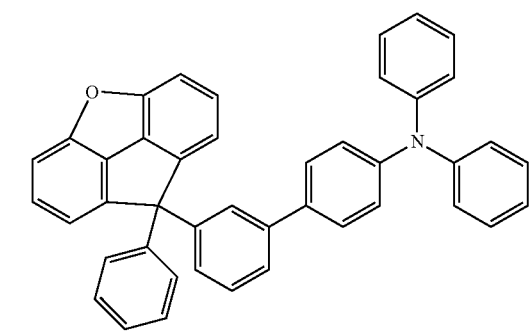
50
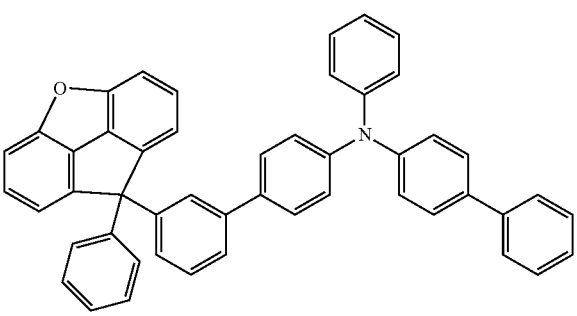
51
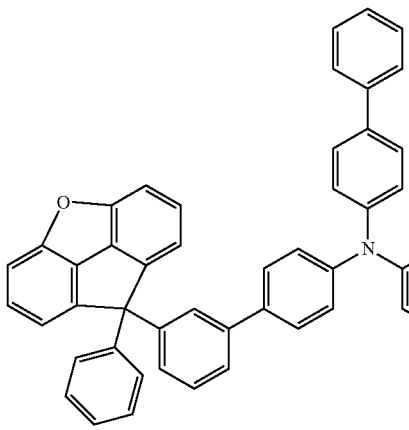
52
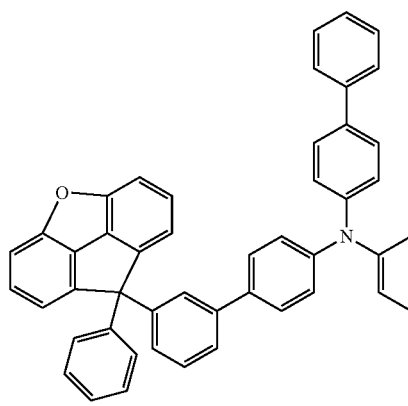
53
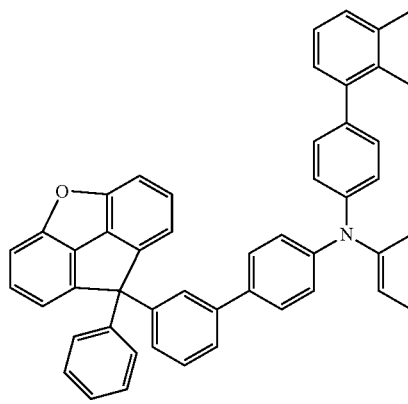
54
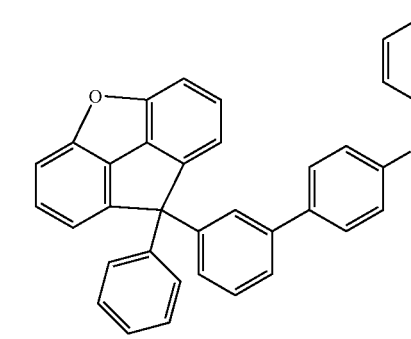

55
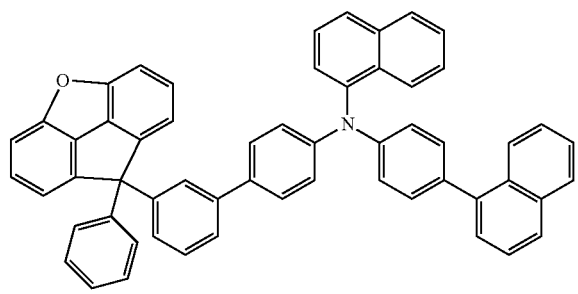
56
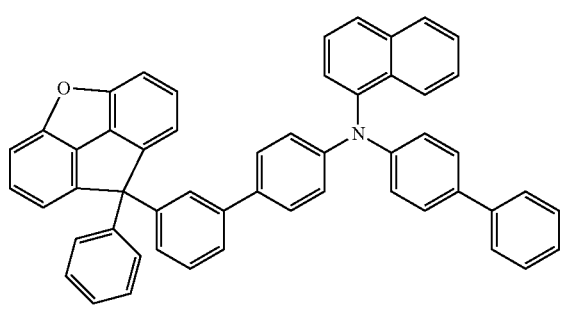
57
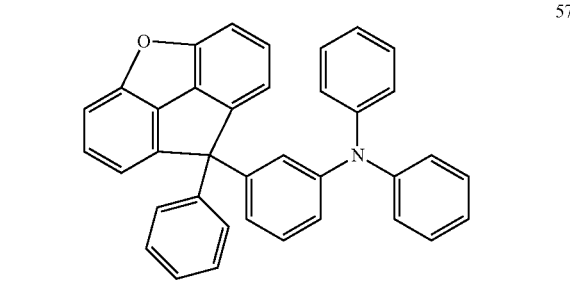
58
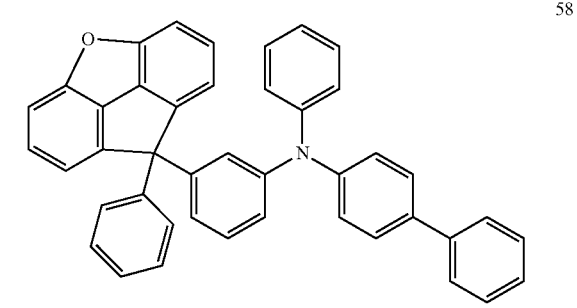
59
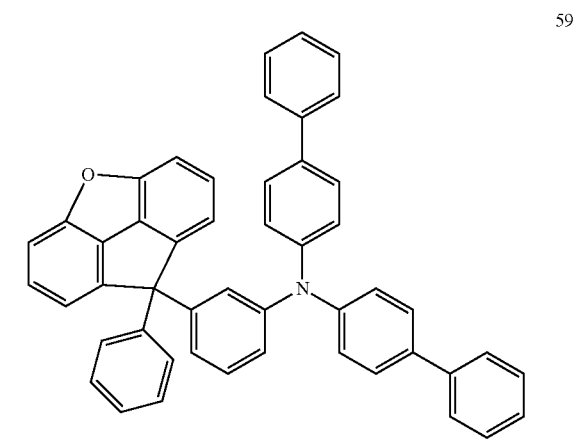
60
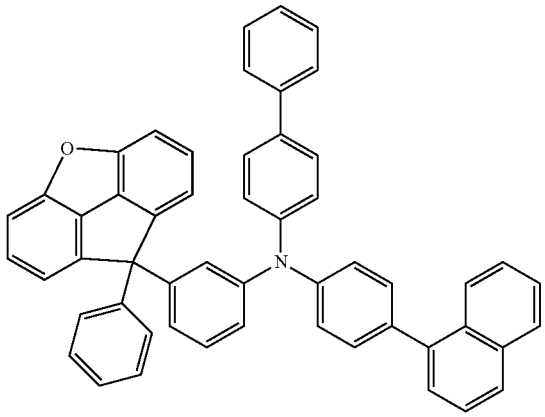
61
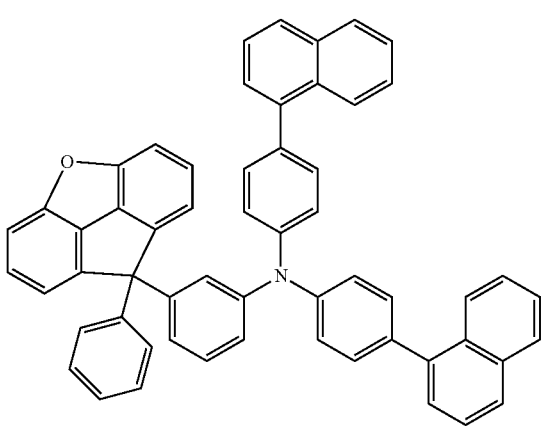
62
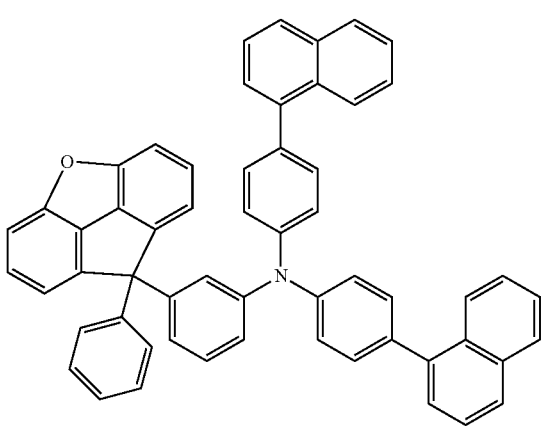
63
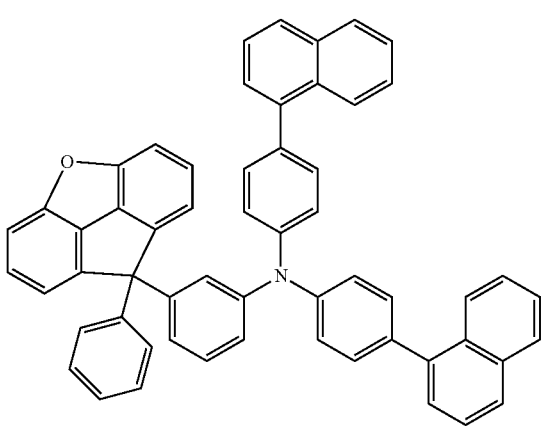

US 10,361,374 B2
243
-continued
244
-continued
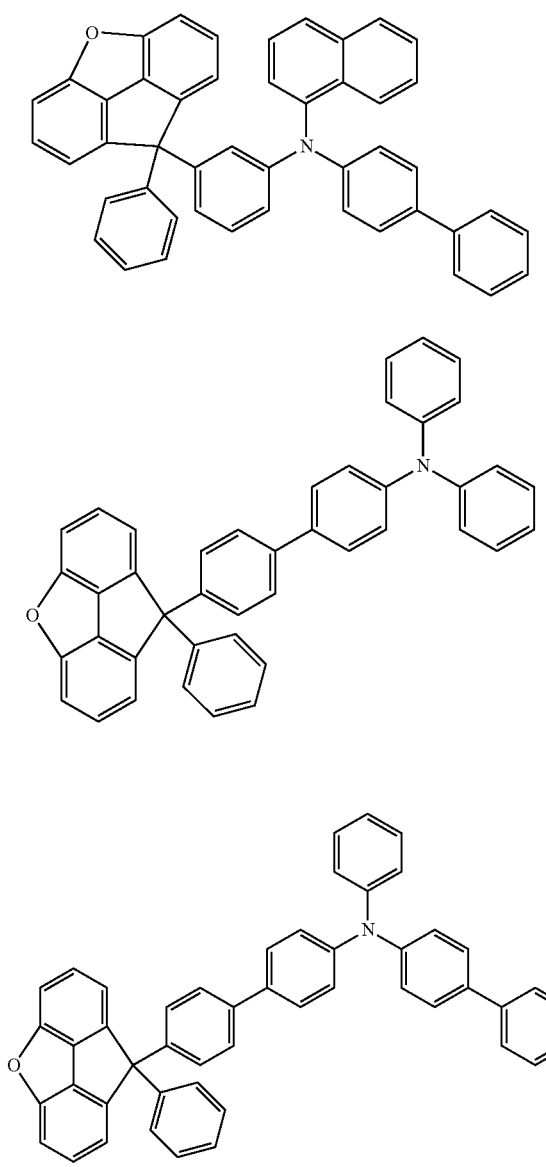
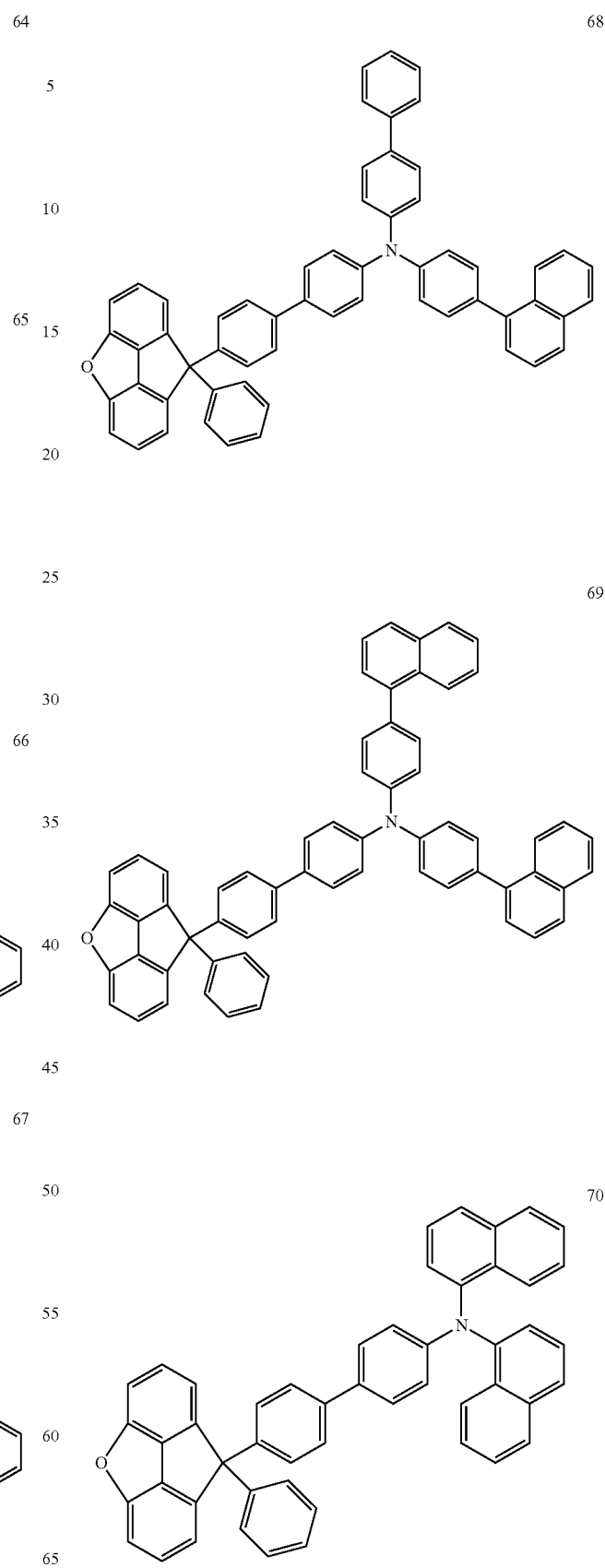

71
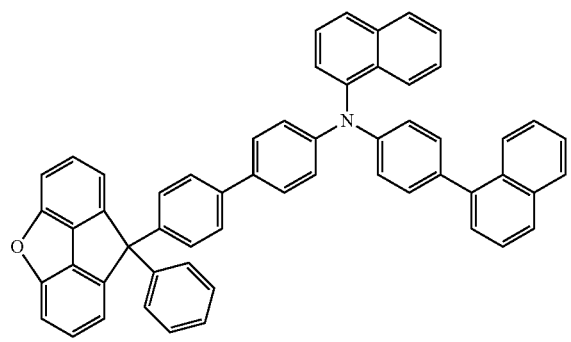
72
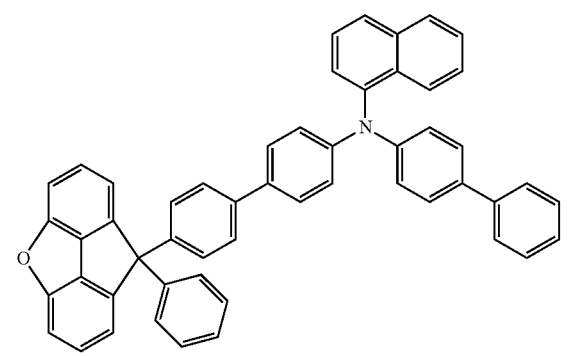
73
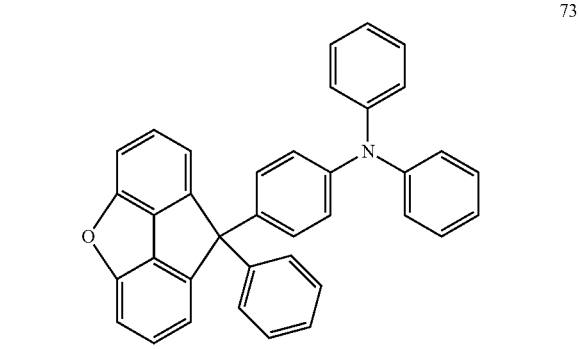
74
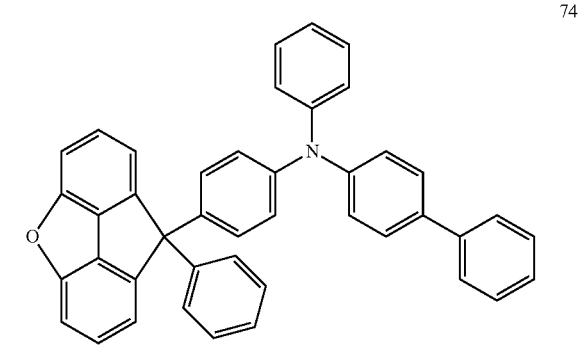
75
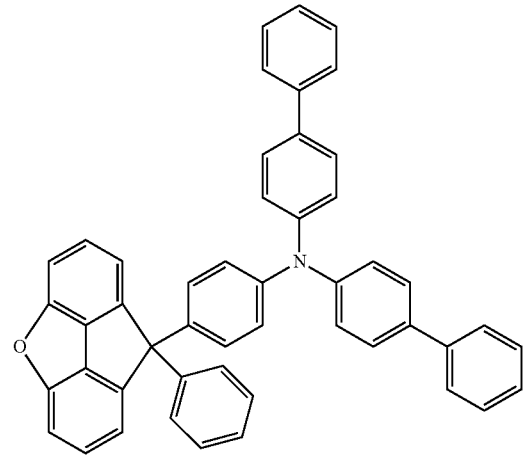
76
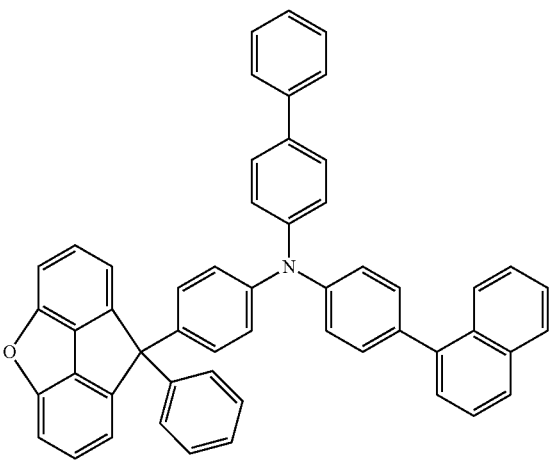
77
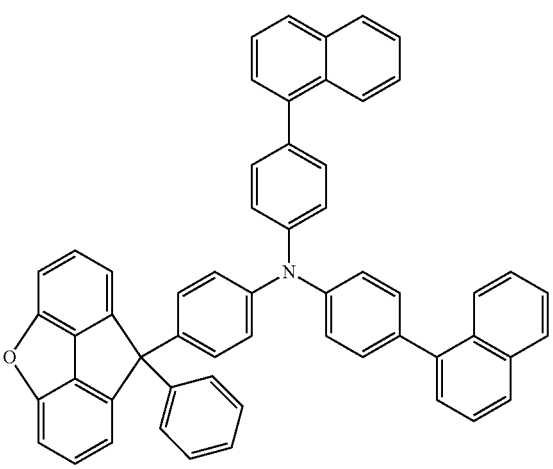

78
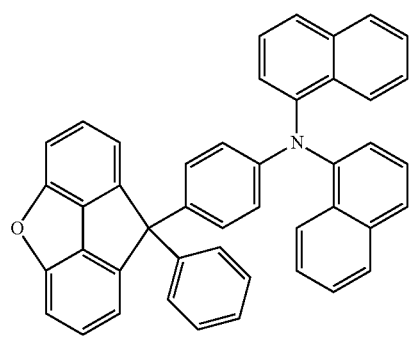
79
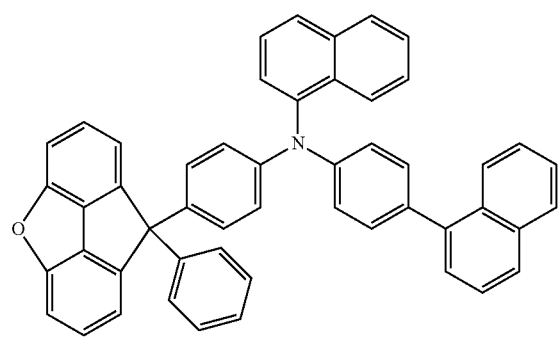
80
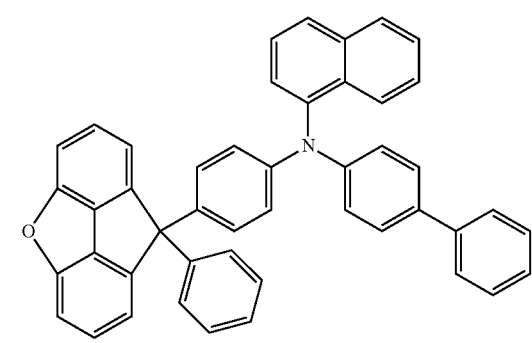
81
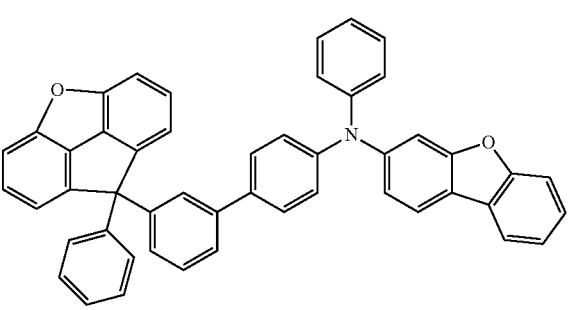
82
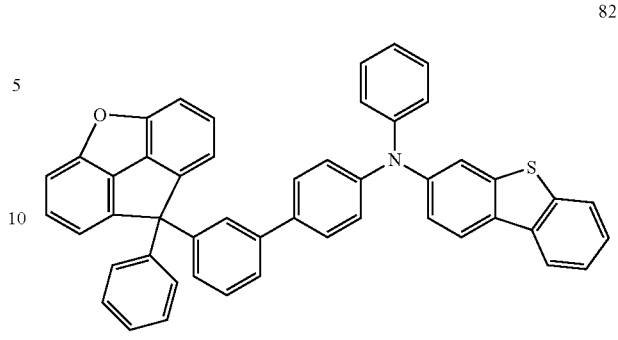
83
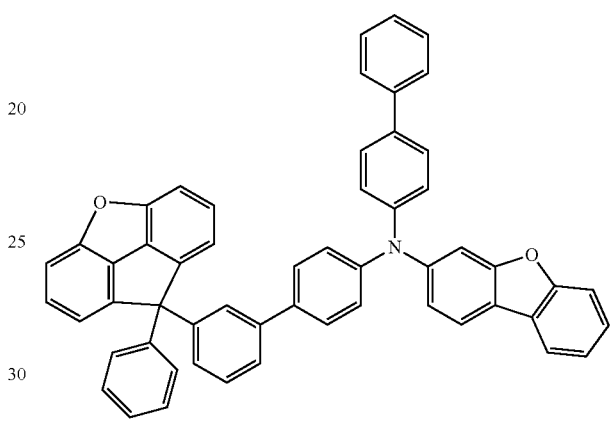
84
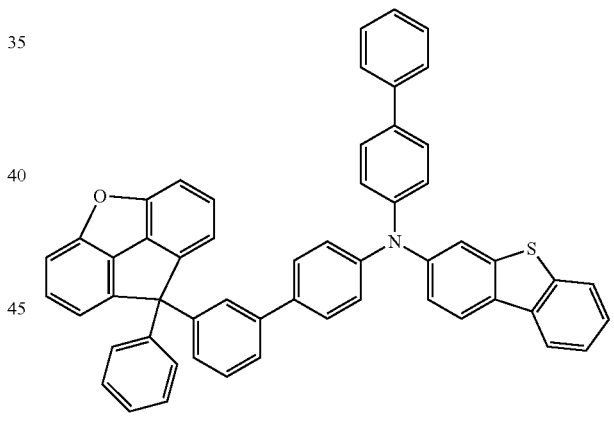
85
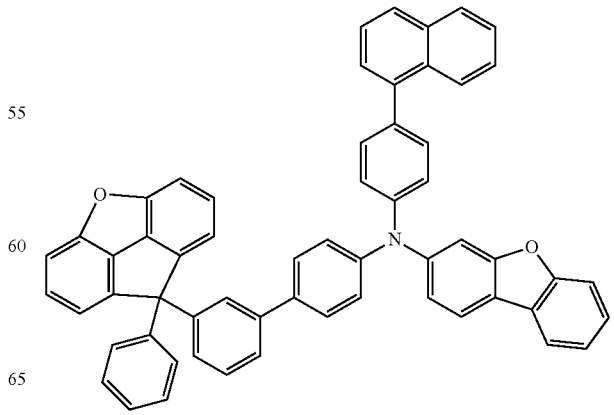

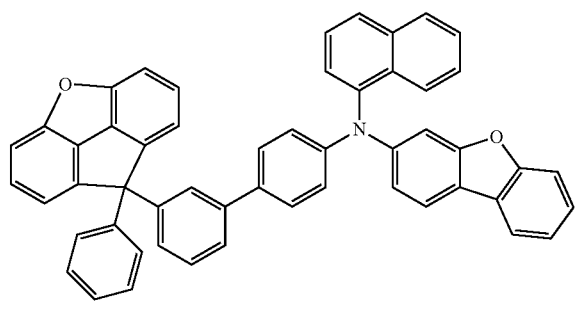
86
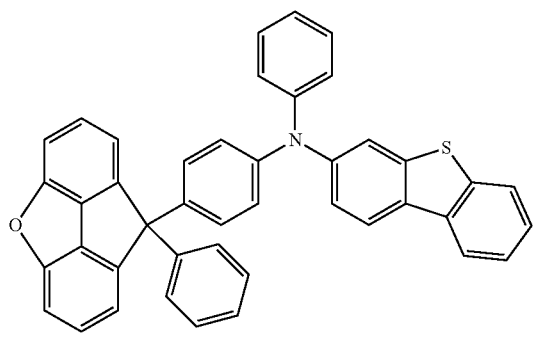
90
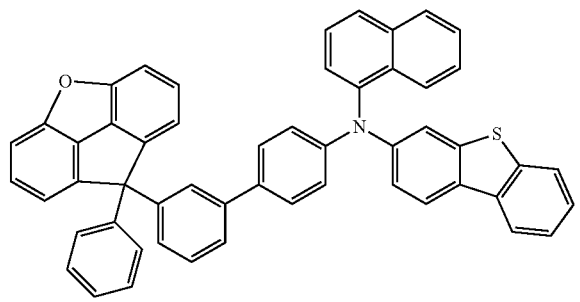
87
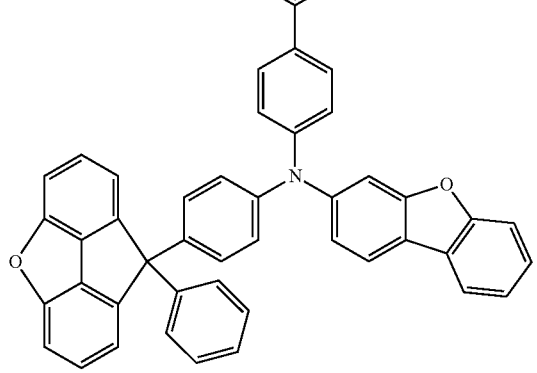
91
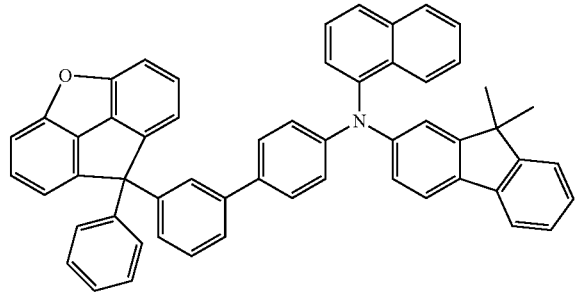
88
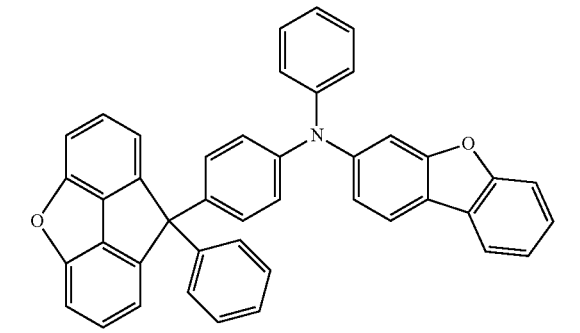
89
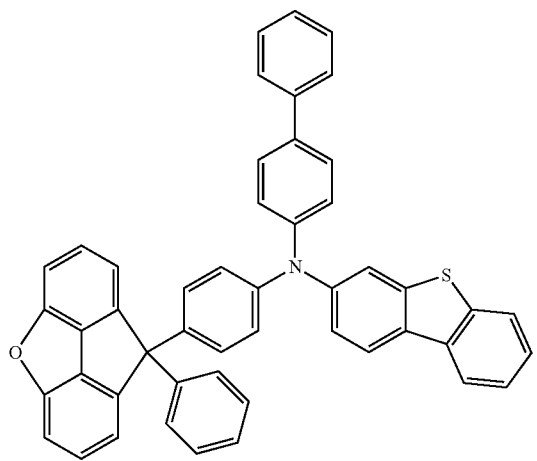
92

93
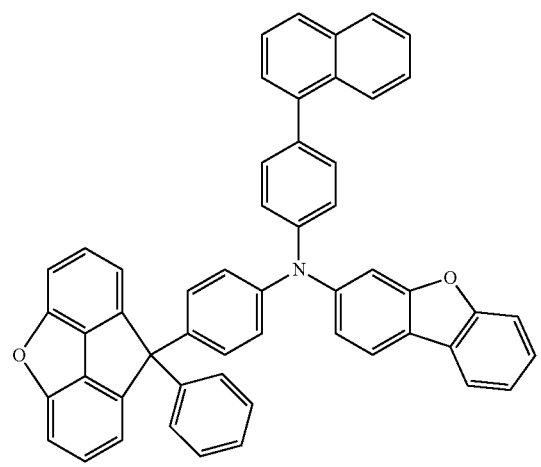
94
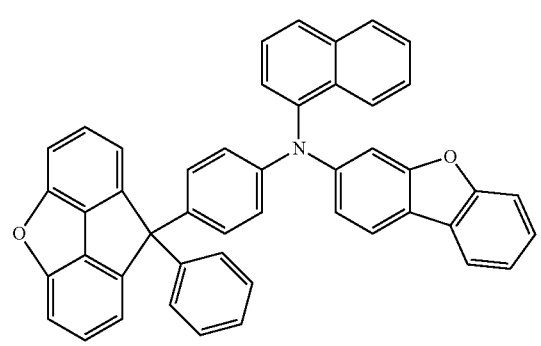
95
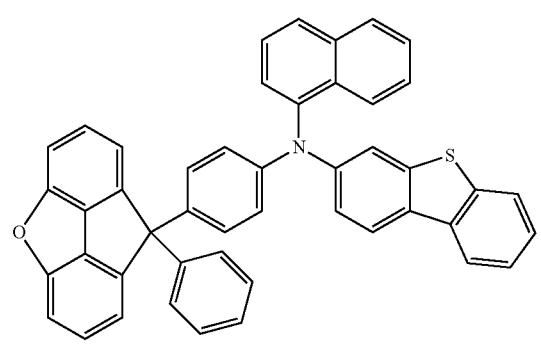
96
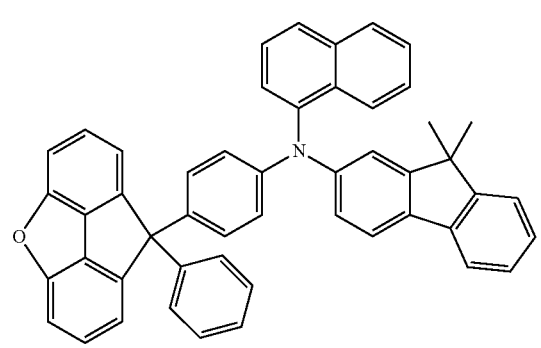
97
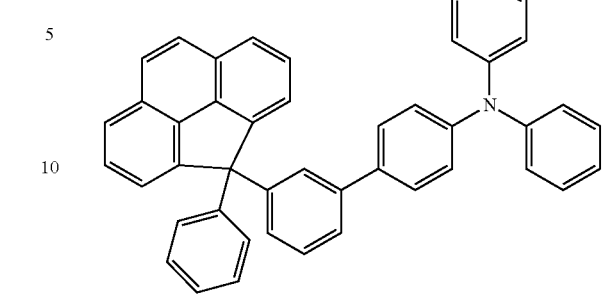
98
99
100
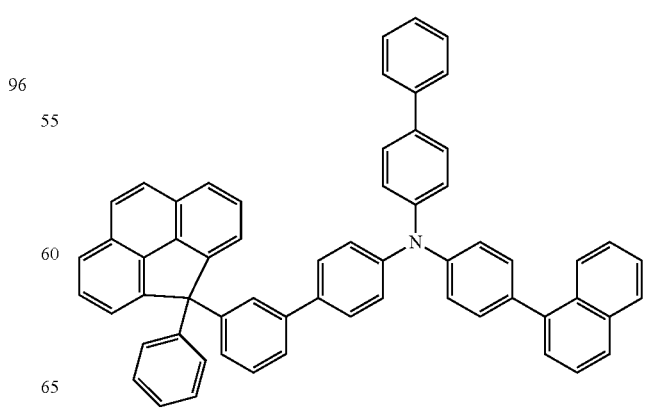

101
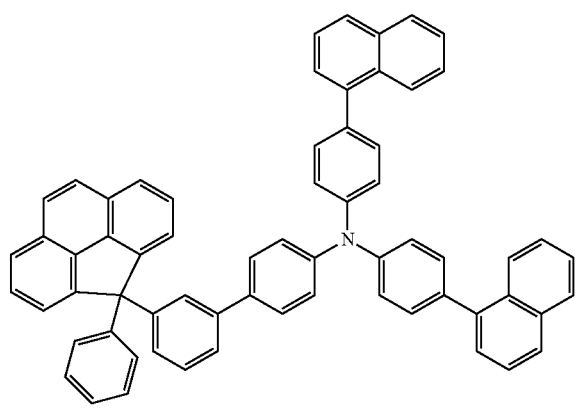
102
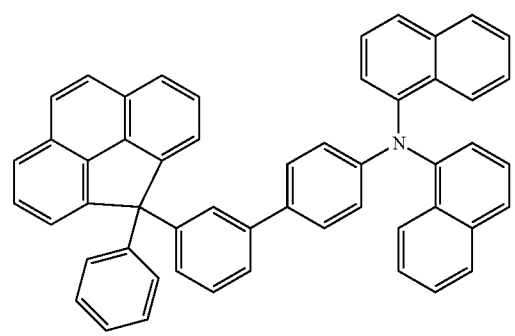
103
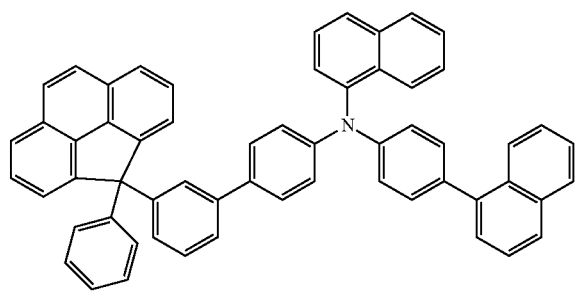
104
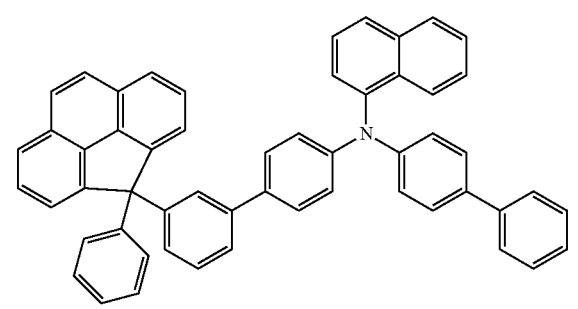
105
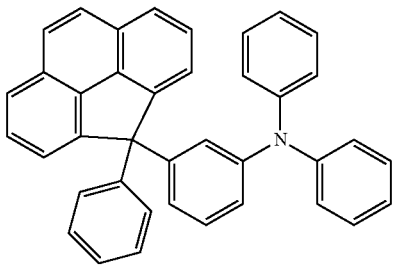
106
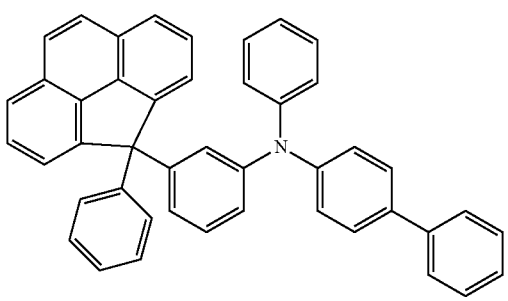
107
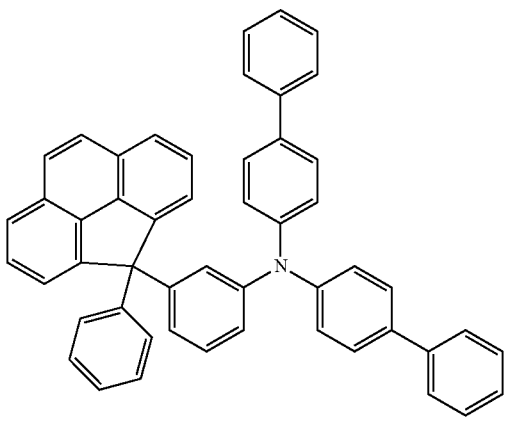
108
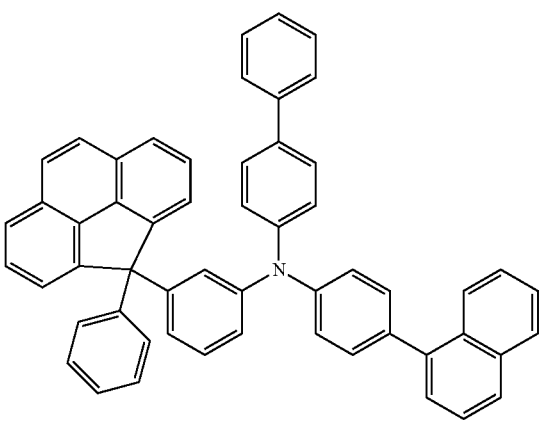

US 10,361,374 B2
255
-continued
109
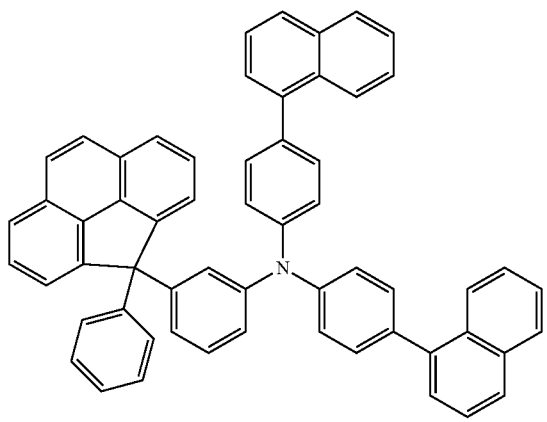
110
111
112
256
-continued
113
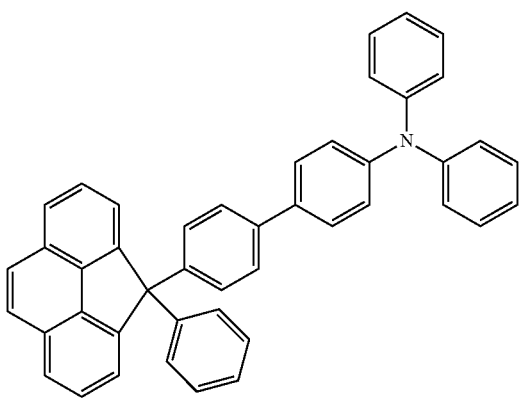
114
115

116
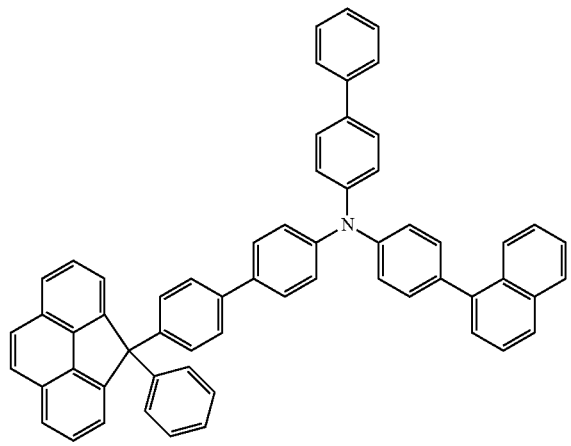
117
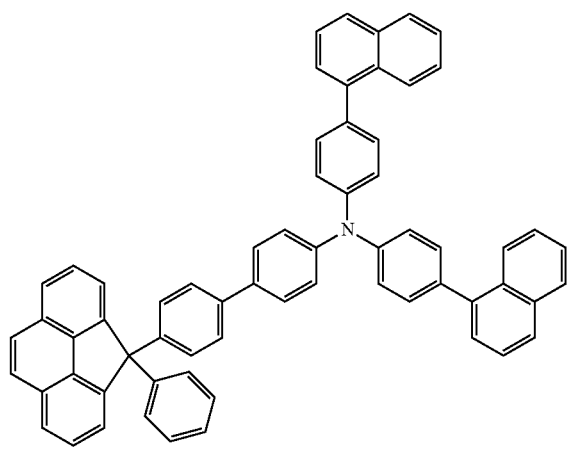
118
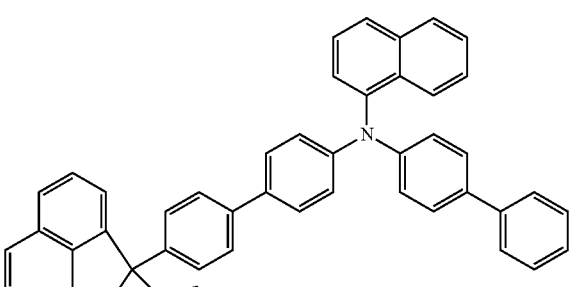
119
120
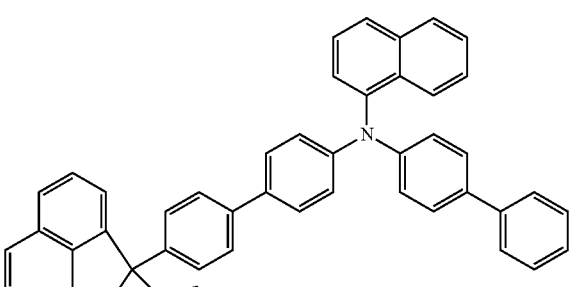
121
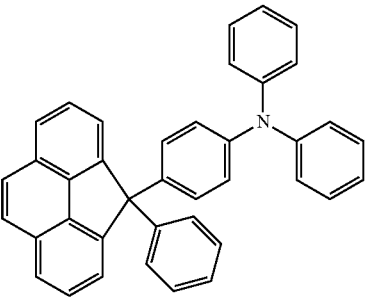
122
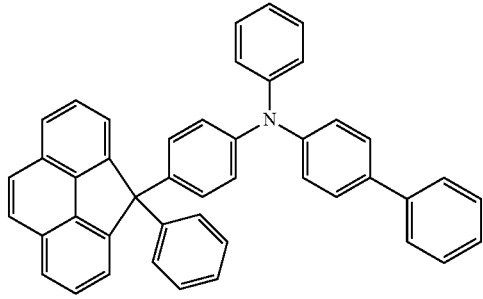
123
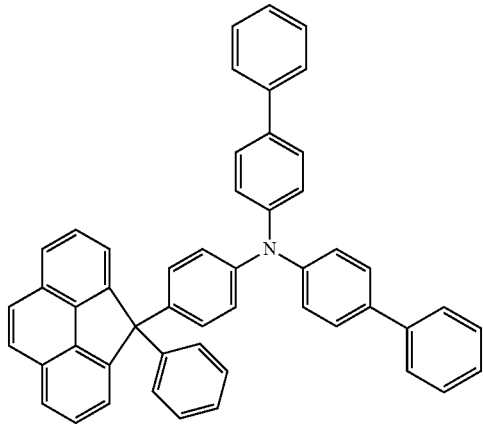

124
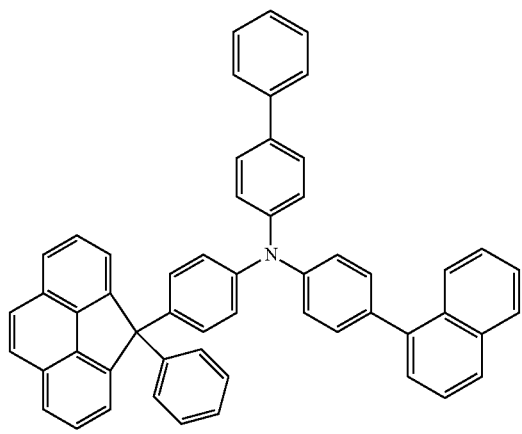
125
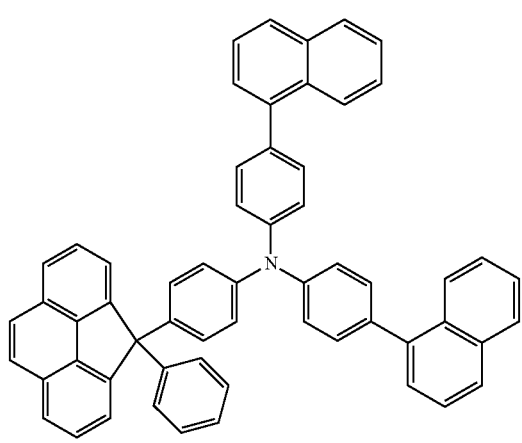
126
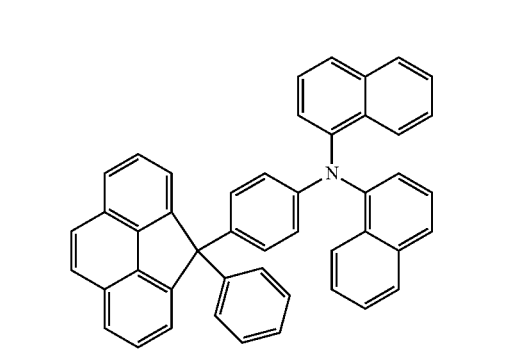
127
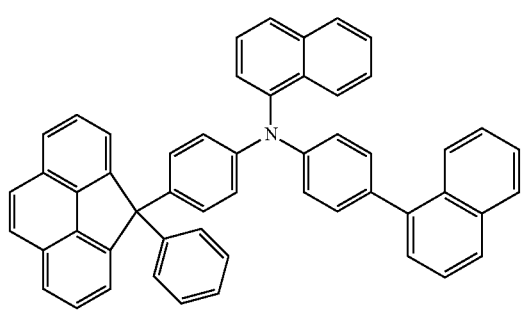
128
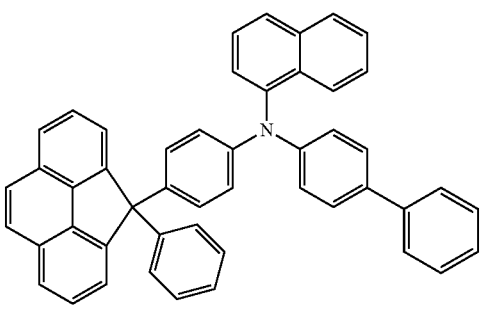
129
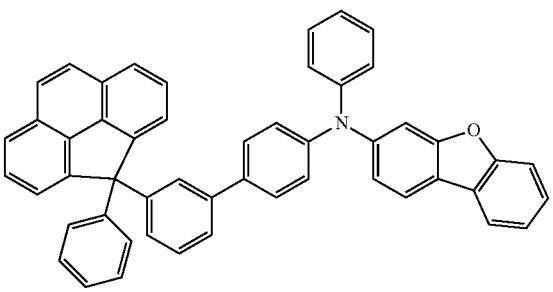
130
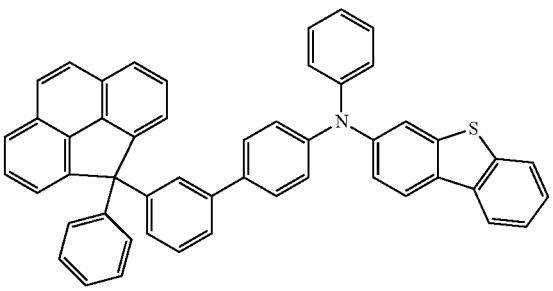
131
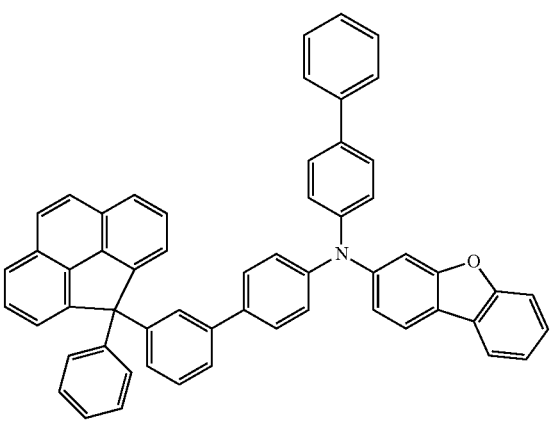

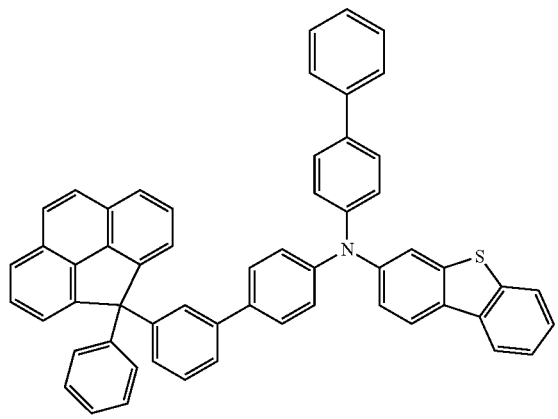
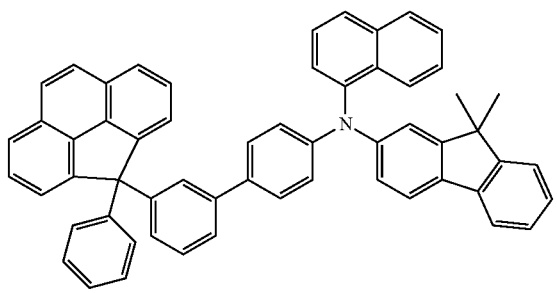
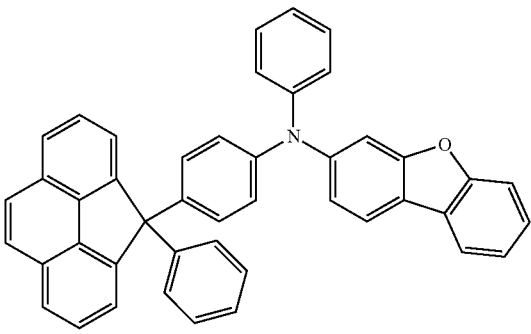
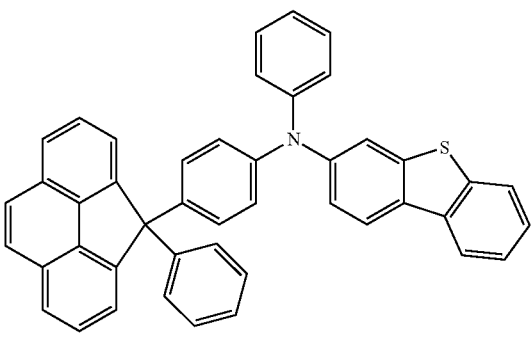
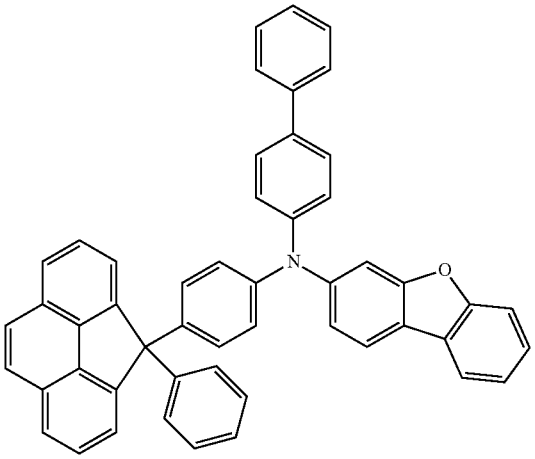

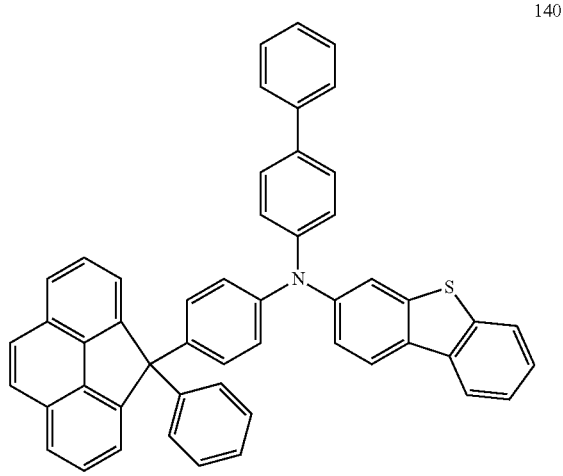
140
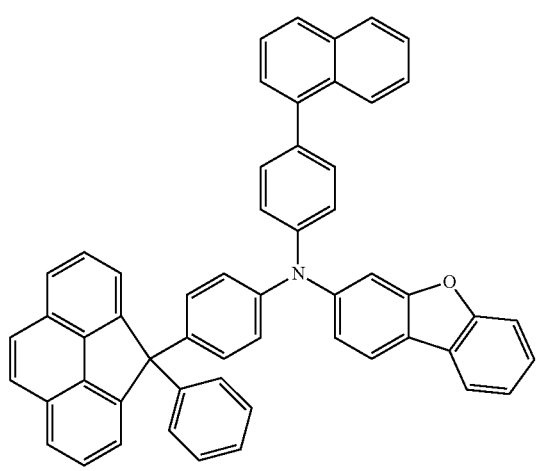
141
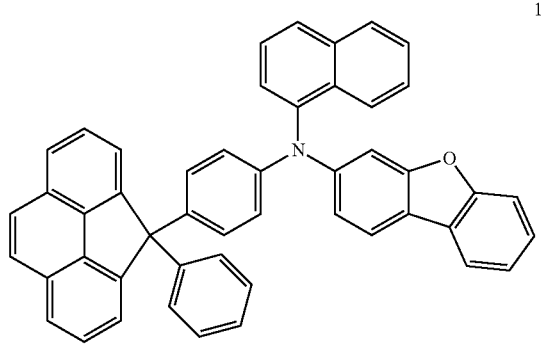
142
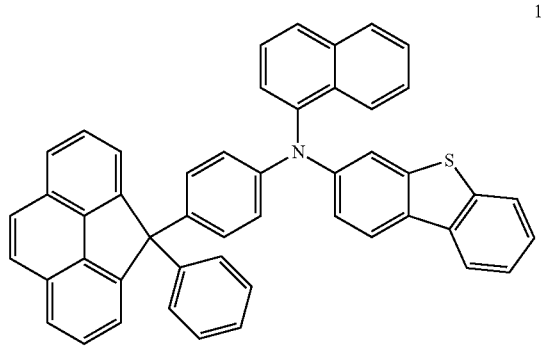
143
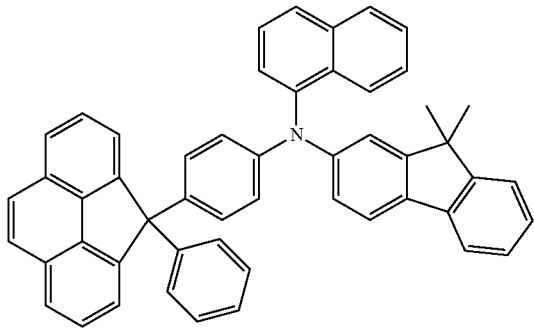
144
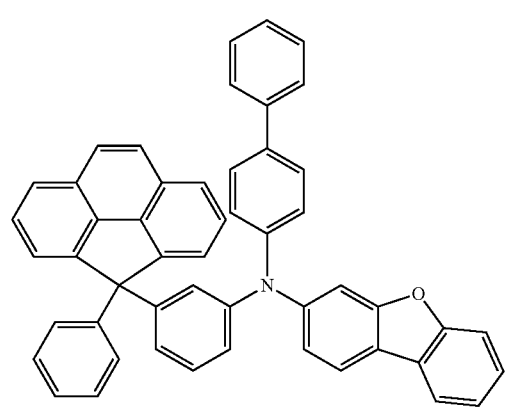
145
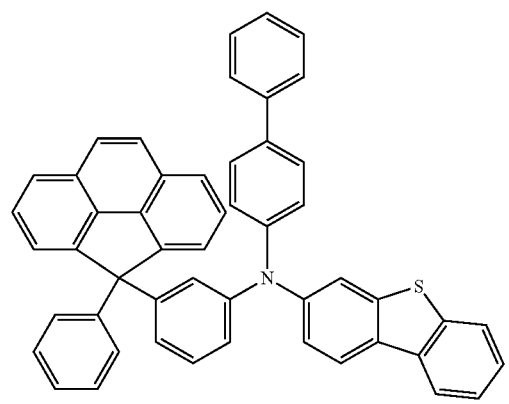
146
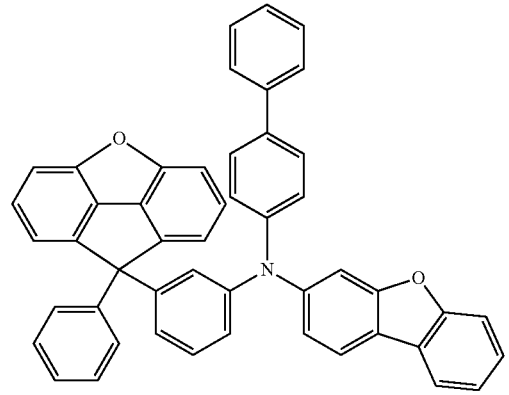
147

148
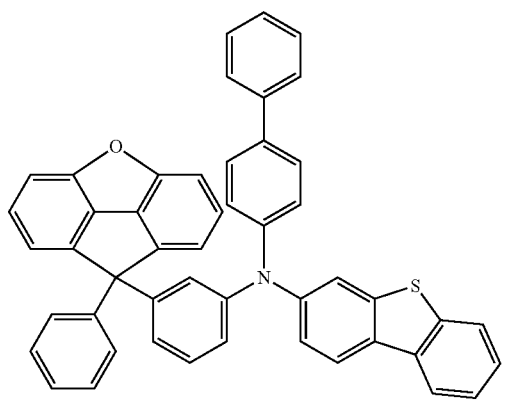
149
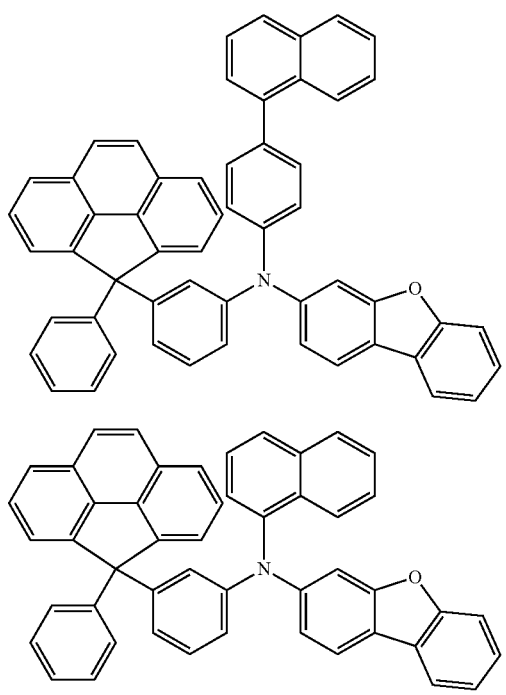
150
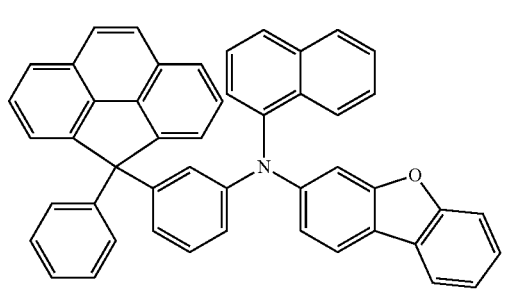
151
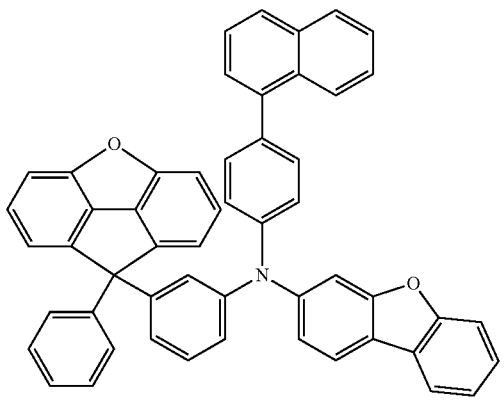
152
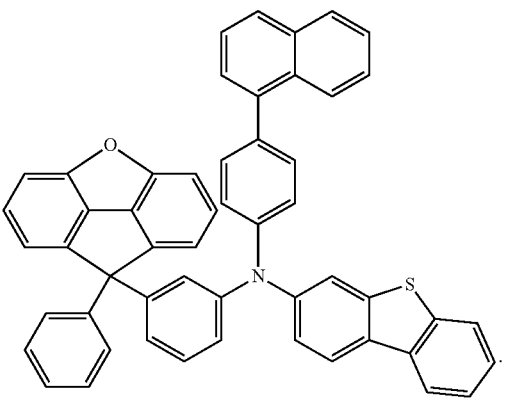
18. The monoamine compound of claim 1, wherein in Formulae 7 and 8, $L_1$ is a divalent phenyl group.
* * * * *

UNITED STATES PATENT AND TRADEMARK OFFICE
CERTIFICATE OF CORRECTION

PATENT NO. : 10,361,374 B2
APPLICATION NO. : 15/199764
DATED : July 23, 2019
INVENTOR(S) : Hiroaki Itoi Page 1 of 1

It is certified that error appears in the above-identified patent and that said Letters Patent is hereby corrected as shown below:

In the Claims

Column 234, Line 25 approx., Claim 14     delete "$Ar_a$" and insert -- $Ar_3$ --

Signed and Sealed this
Twenty-first Day of July, 2020

Andrei Iancu
*Director of the United States Patent and Trademark Office*